United States Patent
Lee et al.

(10) Patent No.: US 11,271,172 B2
(45) Date of Patent: Mar. 8, 2022

(54) COMPOUND FOR ORGANIC ELECTRONIC ELEMENT, ORGANIC ELECTRONIC ELEMENT USING SAME, AND ELECTRONIC DEVICE THEREOF

(71) Applicant: DUK SAN NEOLUX CO., LTD., Cheonan-si (KR)

(72) Inventors: Mun Jae Lee, Cheonan-si (KR); Soung Yun Mun, Cheonan-si (KR); Jae Taek Kwon, Cheonan-si (KR); Dae Sung Kim, Yongin-si (KR); Moo Jin Park, Cheonan-si (KR); Jin Bae Jeon, Cheonan-si (KR); Sun Hee Lee, Hwaseong-si (KR); Ho Young Jung, Cheonan-si (KR); Bum Sung Lee, Hwaseong-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 274 days.

(21) Appl. No.: 16/093,394

(22) PCT Filed: Apr. 10, 2017

(86) PCT No.: PCT/KR2017/003883
§ 371 (c)(1),
(2) Date: Oct. 12, 2018

(87) PCT Pub. No.: WO2017/179875
PCT Pub. Date: Oct. 19, 2017

(65) Prior Publication Data
US 2019/0131543 A1 May 2, 2019

(30) Foreign Application Priority Data

Apr. 14, 2016 (KR) .................. 10-2016-0045602

(51) Int. Cl.
| | | |
|---|---|---|
| *H01L 51/00* | (2006.01) | |
| *C09K 11/06* | (2006.01) | |
| *H01L 51/50* | (2006.01) | |
| *C07D 487/04* | (2006.01) | |
| *C07D 491/048* | (2006.01) | |
| *C07D 495/04* | (2006.01) | |
| *C07D 209/56* | (2006.01) | |
| *C07D 405/14* | (2006.01) | |
| *C07D 405/12* | (2006.01) | |
| *C07D 403/04* | (2006.01) | |
| *C07D 209/86* | (2006.01) | |
| *C07D 471/04* | (2006.01) | |
| *C07D 401/04* | (2006.01) | |

(Continued)

(52) U.S. Cl.
CPC ........ *H01L 51/0072* (2013.01); *C07D 209/56* (2013.01); *C07D 209/86* (2013.01); *C07D 209/88* (2013.01); *C07D 401/04* (2013.01); *C07D 401/10* (2013.01); *C07D 401/14* (2013.01); *C07D 403/04* (2013.01); *C07D 403/10* (2013.01); *C07D 403/12* (2013.01); *C07D 405/12* (2013.01); *C07D 405/14* (2013.01); *C07D 409/10* (2013.01); *C07D 409/12* (2013.01); *C07D 409/14* (2013.01); *C07D 471/04* (2013.01); *C07D 487/04* (2013.01); *C07D 491/048* (2013.01); *C07D 495/04* (2013.01); *C07D 519/00* (2013.01); *C09K 11/06* (2013.01); *H01L 51/004* (2013.01); *H01L 51/006* (2013.01); *H01L 51/0059* (2013.01); *H01L 51/0061* (2013.01); *H01L 51/0067* (2013.01); *H01L 51/0071* (2013.01); *H01L 51/0074* (2013.01); *H01L 51/5012* (2013.01); *H01L 51/5016* (2013.01); *H01L 2251/5384* (2013.01)

(58) Field of Classification Search
CPC .. C07D 209/56; C07D 209/86; C07D 209/88; C07D 401/04; C07D 401/10; C07D 401/14; C07D 403/04; C07D 403/10; C07D 403/12; C07D 405/12; C07D 405/14; C07D 409/10; C07D 409/12; C07D 409/14; C07D 471/04; C07D 487/04; C07D 491/048; C07D 495/04; C07D 519/00; C09K 11/06; C09K 2211/1029; H01L 2251/5384; H01L 51/004; H01L 51/0059; H01L 51/006; H01L 51/0061; H01L 51/0067; H01L 51/0071; H01L 51/0072; H01L 51/0074; H01L 51/5012; H01L 51/5016
See application file for complete search history.

(56) References Cited

U.S. PATENT DOCUMENTS

2008/0124572 A1* 5/2008 Mizuki ................ C07D 409/10
428/690
2012/0217492 A1* 8/2012 Kim ..................... C07D 209/80
257/40

FOREIGN PATENT DOCUMENTS

KR  10-2013-0057397 A  5/2013
KR  10-2013-0114785 A  10/2013
(Continued)

OTHER PUBLICATIONS

Lai et al., Advanced Functional Materials, (2015), vol. 25, pp. 5548-5556. (Year: 2015).*

*Primary Examiner* — Dawn L Garrett
(74) *Attorney, Agent, or Firm* — Vorys, Sater, Seymour & Pease LLP; Mih Suhn Koh

(57) ABSTRACT

Provided are a mixture of compounds used as a phosphorescent host material in an organic electronic element, an organic electronic element comprising the compounds to achieve high light-emitting efficiency, low driving voltage, and significantly improved lifespan, and an electronic device comprising the element.

22 Claims, 1 Drawing Sheet

(51) Int. Cl.
*C07D 403/10* (2006.01)
*C07D 409/12* (2006.01)
*C07D 401/10* (2006.01)
*C07D 401/14* (2006.01)
*C07D 409/10* (2006.01)
*C07D 403/12* (2006.01)
*C07D 409/14* (2006.01)
*C07D 519/00* (2006.01)
*C07D 209/88* (2006.01)

(56) References Cited

FOREIGN PATENT DOCUMENTS

| KR | 10-2014-0133572 A | 11/2014 |
|---|---|---|
| KR | 10-2015-0030660 A | 3/2015 |
| KR | 10-2015-0077513 A | 7/2015 |
| WO | WO 2015/099486 * | 7/2015 |

* cited by examiner

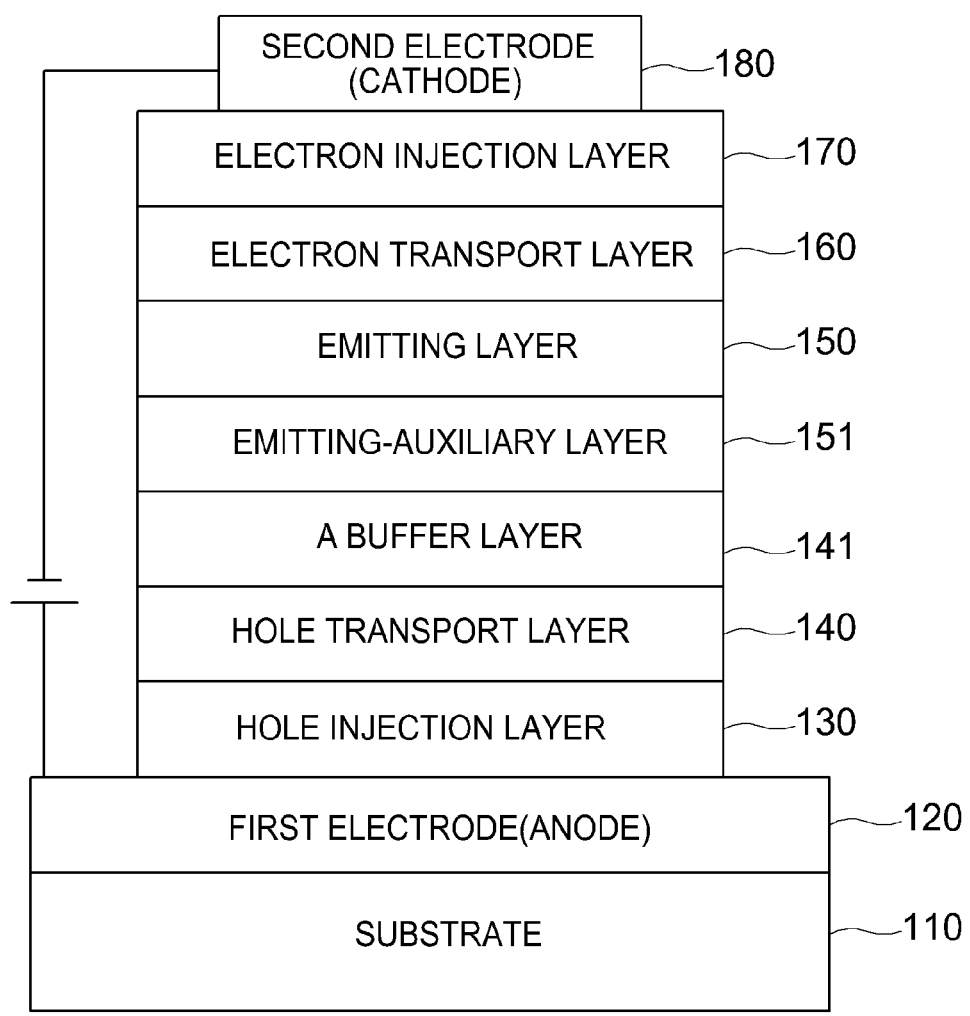

COMPOUND FOR ORGANIC ELECTRONIC ELEMENT, ORGANIC ELECTRONIC ELEMENT USING SAME, AND ELECTRONIC DEVICE THEREOF

BACKGROUND

Technical Field

The present invention relates to compound for organic electronic element, organic electronic element using the same, and an electronic device thereof.

Background Art

In general, organic light emitting phenomenon refers to a phenomenon that converts electronic energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the case of a polycyclic compound containing a heteroatom, the difference in properties according to the material structure is so large that it is applied to various layers as a material of an organic electronic element. In particular, it has characteristics of different band gaps (HOMO, LUMO), electronical characteristics, chemical properties, and physical properties depending on the number of rings, fused positions and the type and arrangement of heteroatoms, therefore application development for layers of various organic electronic elements using the same has been progressed.

As a representative example thereof, in the following Patent Documents 1 to 4, the performance of the 5-membered cyclic compound in the polycyclic compound has been reported depending on the hetero type, arrangement, substituent type, fused position, and the like.

[Patent Document 1]: U.S. Pat. No. 5,843,607
[Patent Document 2]: Japanese Laid-Open Patent Publication No. 1999-162650
[Patent Document 3]: Korean Published Patent Application No. 2008-0085000
[Patent Document 4]: US Patent Publication No. 2010-0187977
[Patent Document 5]: Korean Published Patent Application No. 2011-0018340
[Patent Document 6]: Korean Published Patent Application No. 2009-0057711

Patent Documents 1 and 2 disclose an embodiment in which the indolecarbazole core in which the hetero atom in the 5-membered cyclic compound is composed only of nitrogen (N) is used, and an aryl group substituted or unsubstituted in N of indolocarbazole is used. However, in the prior invention 1, there exists only a simple aryl group substituted or unsubstituted with an alkyl group, an amino group, an alkoxy group, or the like as a substituent, so that the effect of the substituents of the polycyclic compounds was very poor to prove, and only the use as a hole transport material is described, and the use thereof as a phosphorescent host material is not described.

Patent Documents 3 and 4 disclose a compound in which pyridine, pyrimidine, triazine or the like containing an aryl group and N, respectively, were substituted for an indolecarbazole core having a hetero atom N in the same 5-membered cyclic compound as in the above Patent Documents 1 and 2, however only the use examples for phosphorescent green host materials are described, and the performance for other heterocyclic compounds substituted for indolecarbazole core is not described.

In Patent Documents 5, Nitrogen (N), oxygen (O), sulfur (S), carbon and the like are described as heteroatom in the 5-membered cyclic compound, however there are only examples using the same heteroatom in the performance measurement data, the performance characteristics of a 5-membered cyclic compound containing a different heteroatom could not be confirmed.

Therefore, the patent document does not disclose solutions to low charge carrier mobility and low oxidation stability of a 5-membered cyclic compound containing same heteroatom.

When the 5-membered cyclic compound molecules are generally laminated, as the adjacent $\pi$-electrons increase, they have a strong electronical interaction, and this is closely related to the charge carrier mobility, particularly, the same 5-membered cyclic compound of N—N type has an edge-to-face morphology as an order of arrangement of molecules when molecules are laminated, otherwise a different 5-membered cyclic compound with different heteroatoms has an antiparallel cofacial r-stacking structure in which the packing structure of the molecules is opposite to each other, so that the arrangement order of the molecules becomes face-to-face morphology. It is reported that the steric effect of the substituent substituted on the asymmetrically arranged hetero atom N as the cause of this laminated structure causes relatively high carrier mobility and high oxidation stability (Org. Lett. 2008, 10, 1199).

In Patent Document 6, an example of using as a fluorescent host material for various polycyclic compounds having 7 or more membered cyclic compounds has been reported.

As described above, the fused positions, the number of rings, the arrangement of heteroatoms, and characteristic change by type of the polycyclic compounds have not yet been sufficiently developed.

Particularly, in a phosphorescent organic electronic element using a phosphorescent dopant material, the LUMO and HOMO levels of the host material have a great influence on the efficiency and life span of the organic electronic element, this is because the charge balance control in the emitting layer, the quenching of the dopant, and the reduction in efficiency and life span due to light emission at the interface of the hole transport layer can be prevented, depending on whether electron and hole injection in the emitting layer can be efficiently controlled.

For fluorescent and phosphorescent host materials, recently we have been studying the increase of efficiency and life span of organic electronic elements using TADF (thermal activated delayed fluorescent), exciplex, etc., particularly, and many studies have been carried out to identify the energy transfer method from the host material to the dopant material.

Although there are various methods for identifying the energy transfer in the emitting layer for TADF (thermally activated delayed fluorescent) and exciplex, it can be easily confirmed by the PL lifetime (TRTP) measurement method.

The TRTP (Time Resolved Transient PL) measurement method is a method of observing a decay time over time after irradiating the host thin film with a pulsed light source, and therefore it is possible to identify the energy transfer method by observing the energy transfer and the lag time. The TRTP measurement can distinguish between fluorescence and phosphorescence, an energy transfer method in a mixed host material, an exciplex energy transfer method, and a TADF energy transfer method.

There are various factors affecting the efficiency and life span depending on the manner in which the energy is transferred from the host material to the dopant material, and the energy transfer method differs depending on the material, so that the development of stable and efficient host material for organic electronic element has not yet been sufficiently developed. Therefore, development of new materials is continuously required, and especially development of a host material for an emitting layer is urgently required.

DETAILED DESCRIPTION OF THE INVENTION

Summary

The present invention has been proposed in order to solve the problems of the phosphorescent host material, and an object of the present invention is, by controlling the HOMO level of a host material of a phosphorescent emitting organic electronic element including a phosphorescent dopant, to provide a compound capable of controlling charge balance and of improving efficiency and life span in an emitting layer, and an organic electronic element using the same and an electronic device thereof.

Technical Solution

In order to control the efficient hole injection in the emitting layer of the phosphorescence emitting organic electronic element, by containing a specific second host material in combination with a specific first host material as a main component, it is possible to reduce the energy barrier of the emitting layer and the adjacent layer, the charge balance in the emitting layer is maximized, thereby providing high efficiency and high life of the organic electronic device.

The present invention provides an organic electronic element comprising a first electrode, a second electrode, and an organic material layer formed between the first electrode and the second electrode, wherein the organic material layer includes an emitting layer, wherein the emitting layer includes a first host compound represented by the following Formula (1) and a second host compound represented by the following Formula (2).

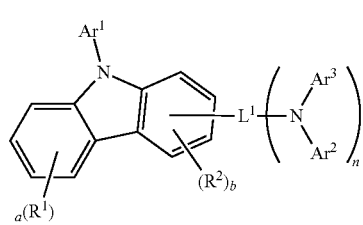

Formula 1

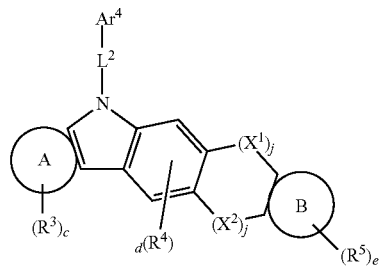

Formula 2

The present invention also provides an organic electronic element using the compound represented by the above Formulas and an electronic device thereof.

Effects of the Invention

By using the mixture according to the present invention as a phosphorescent host material, it is possible to achieve a high luminous efficiency and a low driving voltage of an organic electric element, and the life span of the device can be greatly improved.

BRIEF DESCRIPTION OF THE DRAWINGS

The FIGURE is an illustration of an organic electroluminescent device according to the present invention.

| | |
|---|---|
| 100 : organic electric element, | 110 : substrate |
| 120 : the first electrode(anode), | 130 : the hole injection layer |
| 140 : the hole transport layer, | 141 : a buffer layer |
| 150 : the emitting layer, | 151 : the emitting auxiliary layer |
| 160 : the electron transport layer, | 170 : the electron injection layer |
| 180 : the second electrode(cathode) | |

DETAILED DESCRIPTION

Hereinafter, some embodiments of the present invention will be described in detail.

Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

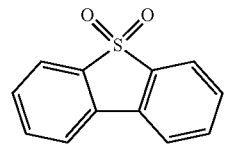 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

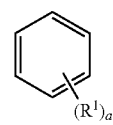

Wherein, when a is an integer of zero, the substituent $R^1$ is absent, when a is an integer of 1, the sole substituent $R^1$ is linked to any one of the carbon constituting the benzene ring, when a is an integer of 2 or 3, they are respectively combined as follows, in which $R^1$ are the same or different from each other, and when a is an integer of 4 to 6, and it is bonded to the carbon of the benzene ring in a similar manner, whereas the indication of hydrogen bonded to the carbon forming the benzene ring is omitted.

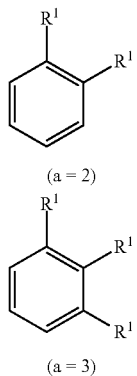

(a = 2)

(a = 3)

Hereinafter, a compound according to an aspect of the present invention and an organic electric element comprising the same will be described.

The present invention provides an organic electric element comprising a first electrode, a second electrode, and an organic material layer formed between the first electrode and the second electrode, wherein the organic material layer comprises an emitting layer, wherein the emitting layer comprises a first host compound represented by Formula 1 and a second host compound represented by Formula 2.

Formula 1

Formula 2

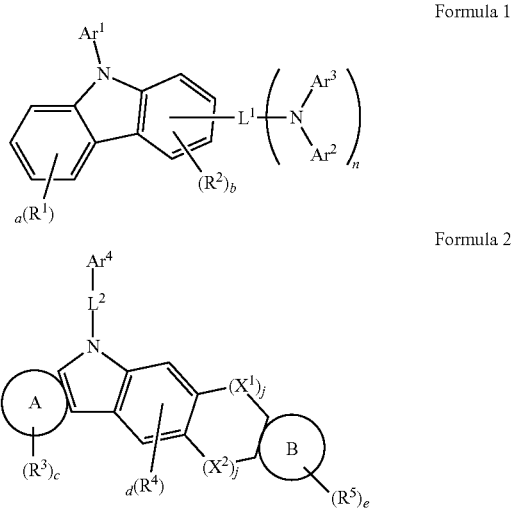

{In Formulas 1 and 2,

1) $Ar^1$, $Ar^2$, $Ar^3$, and $Ar^4$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic; and $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P), wherein $Ar^2$ and $Ar^3$ may combine to each other to form a ring, 2) a is an of 0 to 4, and b is an integer of 0 to 3, and c and e are each independently integer of 0 to 10, and d is an integer of 0 to 2, 3) $R^1$, $R^2$, $R^3$, $R^4$ and $R^5$ are the same or different from each other, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b, c, and e are 2 or more, and d is 2, and $R^1$, $R^2$, $R^3$, $R^4$ and $R^5$ are each in plural being the same or different, and a plurality of $R^1$ or a plurality of $R^2$ or a plurality of $R^3$ or a plurality of $R^4$ or a plurality of $R^5$ combine to each other to form a ring.

4) $L^1$ and $L^2$ are each independently selected from the group consisting of a single bond, a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group;

5) A and B are each independently a $C_6$-$C_{60}$ aryl group or a $C_2$-$C_{20}$ heterocyclic group, 6) i and j are independently 0 or 1, with the proviso that i+j is 1 or more, and when i or j is 0, it means a direct bond, 7) $X^1$ and $X^2$ are independently NR', O, S, or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; wherein R' and R" may combine to each other to form a spiro, 8) n is an integer of 1 or 2, when n is 2, two $Ar^2$ are the same or different from each other, and two $Ar^3$ are the same or different from each other.

(wherein, the aryl group, fluorenyl group, arylene group, heterocyclic group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of thereof.)}

The present invention also provides a compound represented by Formula 2

In a specific aspect of the invention, the first host compound represented by Formula 1 includes a compound represented by the following Formula 3 or 4.

Formula 3
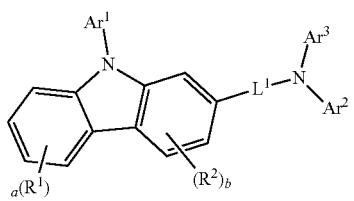
Formula 4
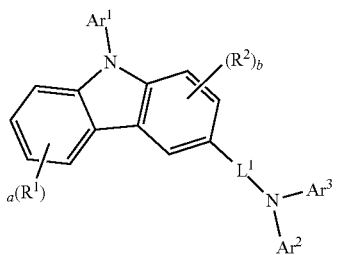
{In Formulas 3 and 4,
wherein $R^1$, $R^2$, $L^1$, $Ar^1$, $Ar^2$, $Ar^3$, a and b are the same as defined above.}
In Formula 1 of the present invention, $L^1$ and $L^2$ are selected from the group consisting of the following Formulas (A-1) to (A-12).
(A-1)
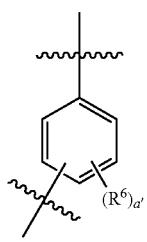
(A-2)
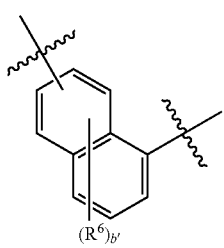
(A-3)
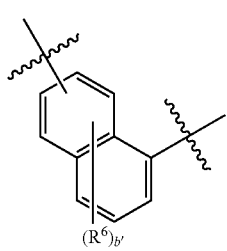
(A-4)
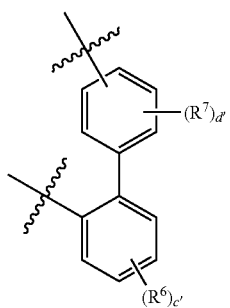
(A-5)
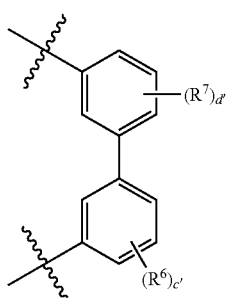
(A-6)
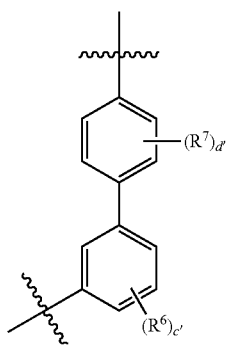
(A-7)
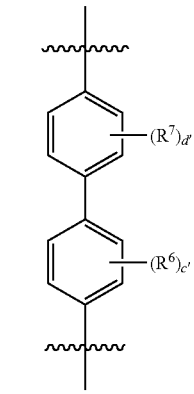
(A-8)
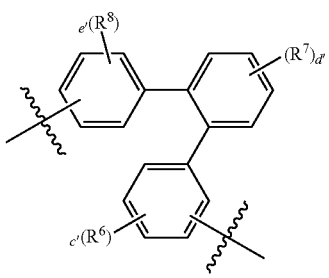

-continued

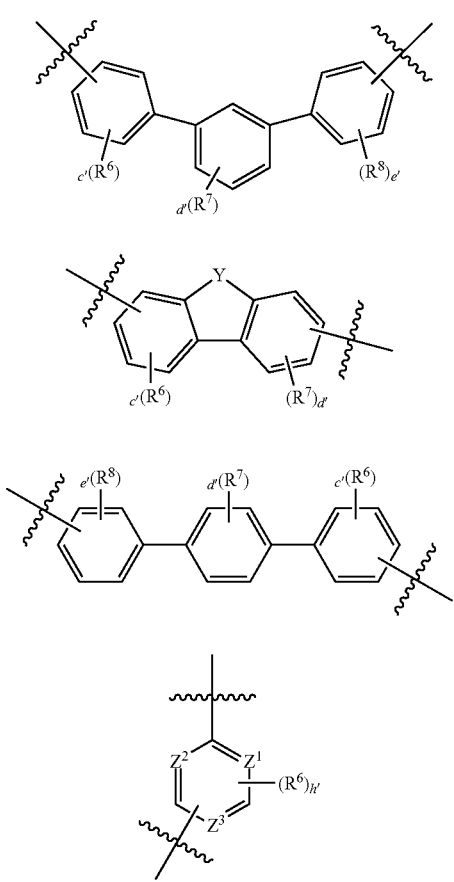

{In Formulas (A-1) to (A-12), 1) a', c', d' and e' are an integer of 0 to 4, and b' is an integer of 0 to 5, and f' and g' are integer of 0 to 3, and h' is an integer of 0 to 1, 2) $R^6$, $R^7$ and $R^8$ are the same or different from each other, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$);

wherein f' and g' are 2 or more, $R^6$, $R^7$ and $R^8$ are each in plural being the same or different, and a plurality of $R^6$ or a plurality of $R^7$ or a plurality of $R^8$ may combine to each other to form an aromatic or a heteroaromatic ring, wherein two adjacent $R^6$ and $R^7$, or $R^7$ and $R^8$ may combine to form an aromatic or heteroaromatic ring, 3) Y is NR', O, S or CR'R"

4) R' and R" are the same as defined above,

5) $Z^1$, $Z^2$ and $Z^3$ are independently of each other CR' or N and at least one is N.}

Also, the present invention provides a compound wherein the first host compound represented by Formula 1 is represented by any of the following Formulas 5 to 8.

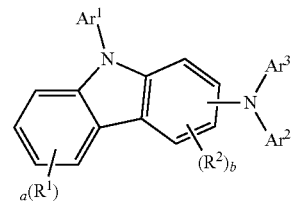

Formula 5

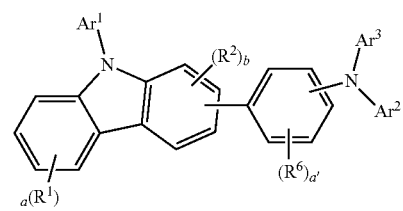

Formula 6

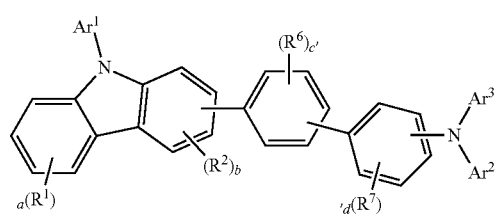

Formula 7

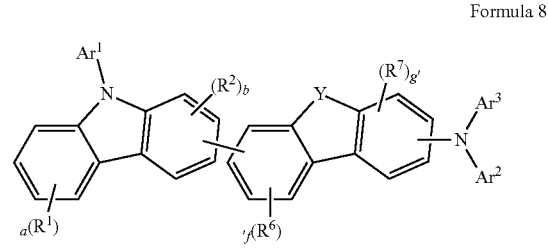

Formula 8

{In Formulas 5 to 8, 1) wherein $R^1$, $R^2$, $Ar^1$, $Ar^2$, $Ar^3$, a, b, R' and R" are the same as defined above, 2) $R^6$ and $R^7$ are the same or different from each other, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case f' and g' are two or more, $R^6$ and $R^7$ are each in plural being the same or different, and a plurality of $R^6$ or a plurality of $R^7$ or a plurality of $R^8$ or adjacent $R^6$ and $R^7$, or adjacent $R^7$ and $R^8$ may combine to each other to form an aromatic or a heteroaromatic ring, 3) a', c' and d' are integer of 0 to 4, and f' and g' are integer of 0 to 3, 4) Y is NR', O, S or CR'R".}

The present invention also provides an organic electric element wherein the first host compound represented by Formula 1 is represented by any of the following Formulas 9 to 20.

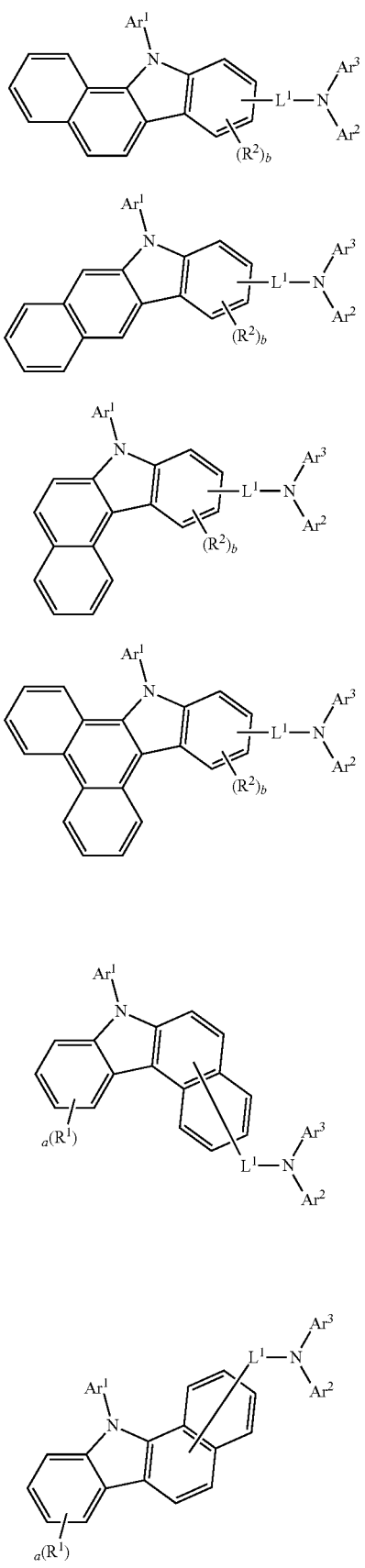
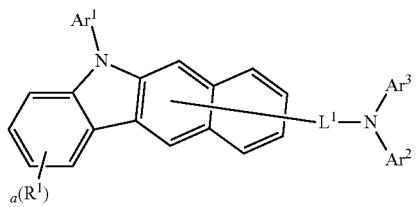
Formula 9
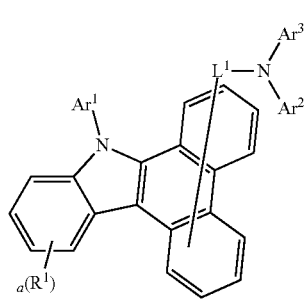
Formula 15
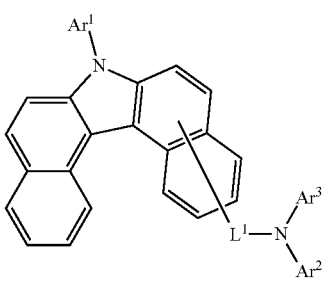
Formula 16
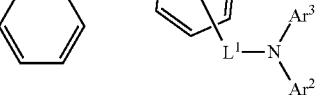
Formula 17
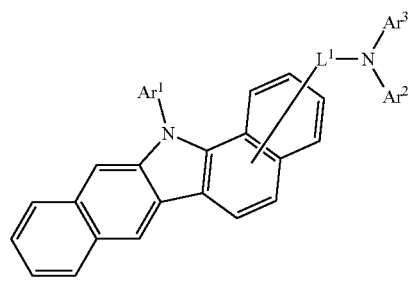
Formula 18
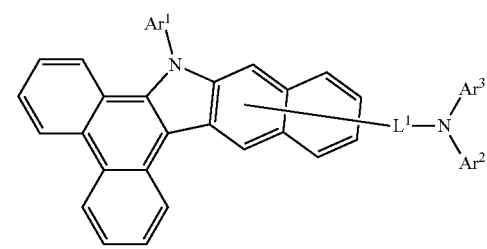
Formula 19
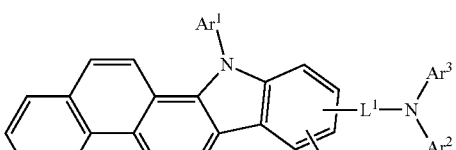
Formula 20
{In Formulas 9 to 20,
wherein R¹, R², L¹, Ar¹, Ar², Ar³, a and b are the same as defined above.}

Also, the first host compound represented by Formula 1 includes a compound represented by the following Formula 21 to 22.

Formula 21

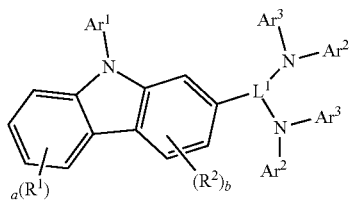

Formula 22

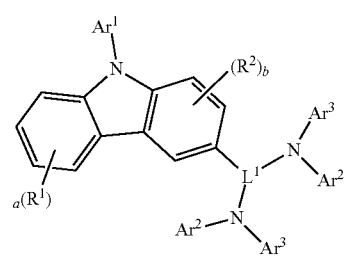

{In Formulas 21 to 22,
wherein $R^1$, $R^2$, $L^1$, $Ar^1$, $Ar^2$, $Ar^3$, a and b are the same as defined above.}

The present invention also provides an organic electric element wherein n is 1 in Formula 1 and n is 2 in Formula 2.

The present invention provides an organic electric element wherein the first host compound represented by Formula 1 comprises a compound represented by the following Formula 23.

Formula 23

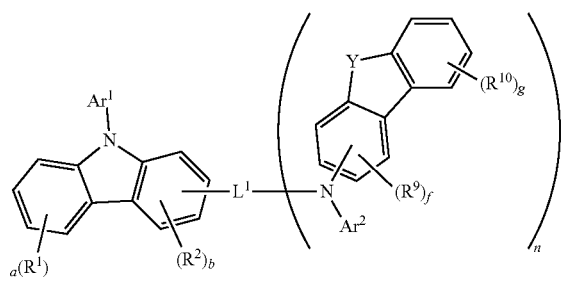

{In Formula 23,
1) $R^1$, $R^2$, $L^1$, $Ar^1$, $Ar^2$, a, b and n are the same as defined above,
2) f is an integer of 0 to 3, and g is an integer of 0 to 4,
3) $R^9$ and $R^{10}$ are the same or different from each other, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case f and g are 2 or more, $R^9$ and $R^{10}$ are each in plural being the same as or different, and a plurality of $R^9$ or a plurality of $R^{10}$ or adjacent $R^9$ and $R^{10}$ may combine to each other to form an aromatic or a heteroaromatic ring, 4) Y is NR', O, S or CR'R",
5) R' and R" are the same as defined above.}

The present invention provides an organic electric element wherein the second host compound represented by Formula 2 comprises a compound represented by the following Formula 24 or 25.

Formula 24

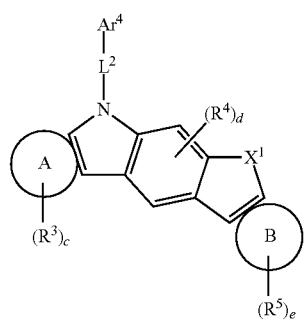

Formula 25

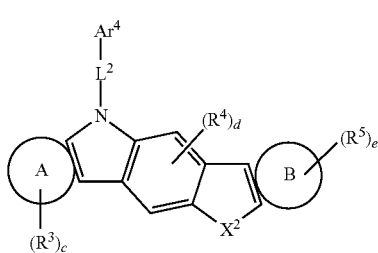

{In Formulas 24 to 25,
wherein $R^3$, $R^4$, $R^5$, $Ar^4$, $L^2$, c, d, e, A, B, $X^1$ and $X^2$ are the same as defined above.}

The present invention also provides an organic electric element comprising a compound wherein A and B in Formula 2 are selected from the group consisting of the following Formulas (B-1) to (B-7).

(B-1)

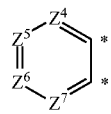

(B-2)

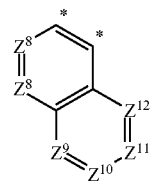

(B-3)

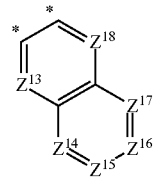

(B-4) 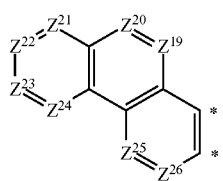

(B-5) 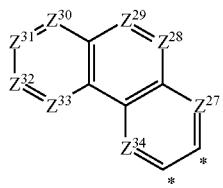

(B-6) 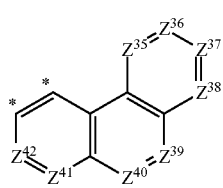

(B-7) 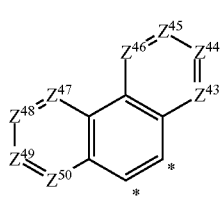

{In Formulas (B-1) to (B-7),
1) $Z^4$ to $Z^{50}$ are CR' or N,
2) R' is the same as defined above,
3) * indicates the position to be condensed.}

As a specific example of the present invention, $R^4$ in Formula 2 includes a compound necessarily forming an aromatic ring or a heteroaromatic ring.

As another example, the present invention provides a compound wherein the second host compound represented by Formula 2 includes a compound represented by any of the following Formulas 26 to 45.

Formula 26
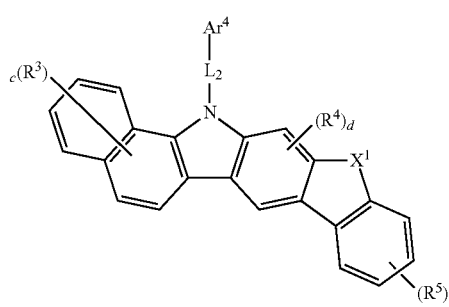

Formula 27
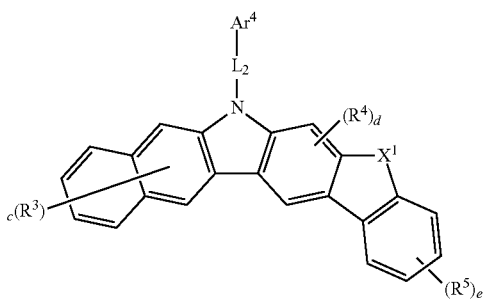

Formula 28
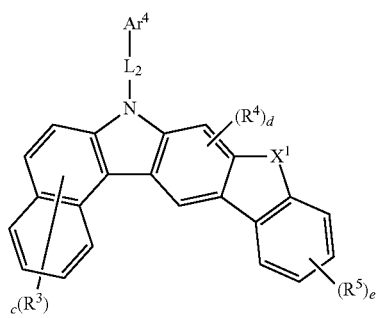

Formula 29
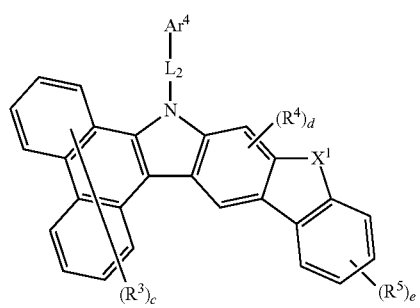

Formula 30
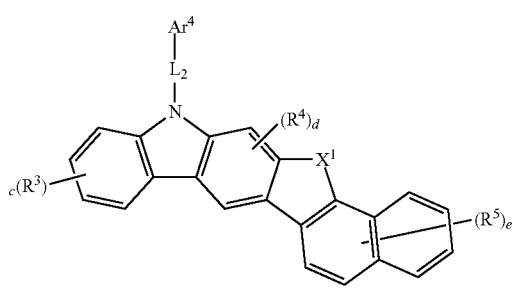

Formula 31
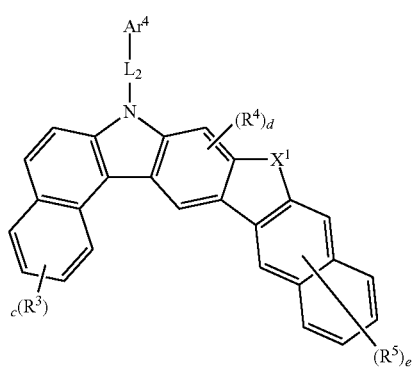

Formula 32
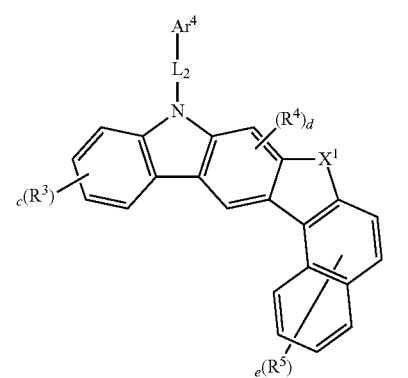
Formula 33
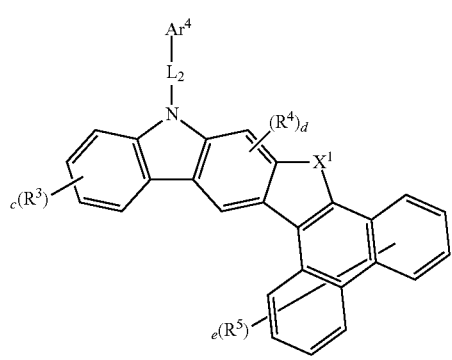
Formula 34
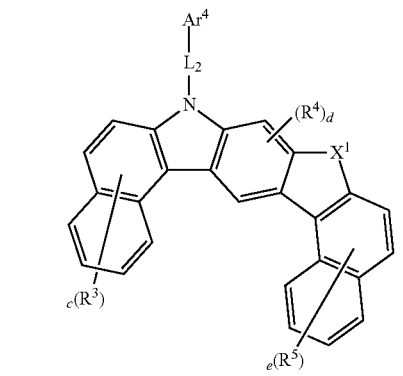
Formula 35
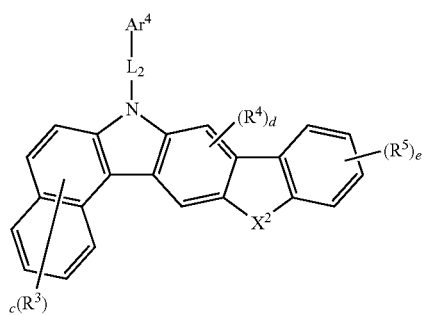
Formula 36
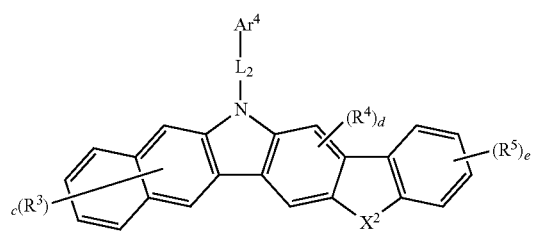
Formula 37
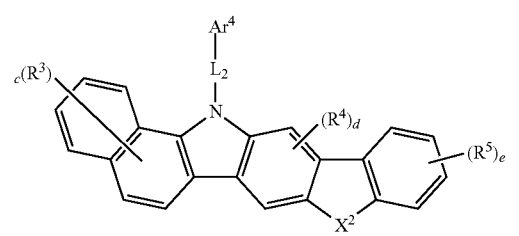
Formula 38
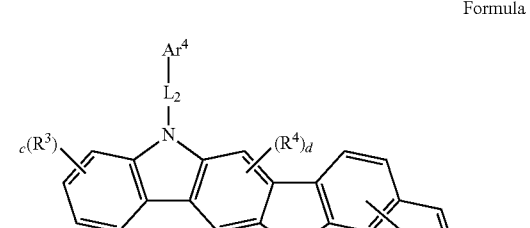
Formula 39
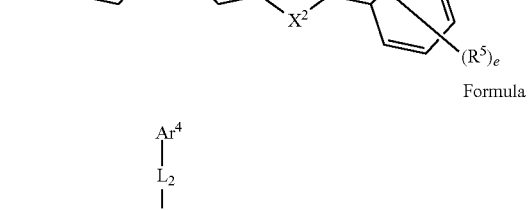
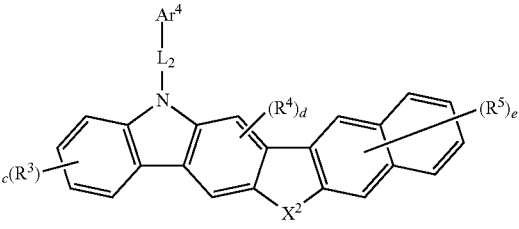
Formula 40
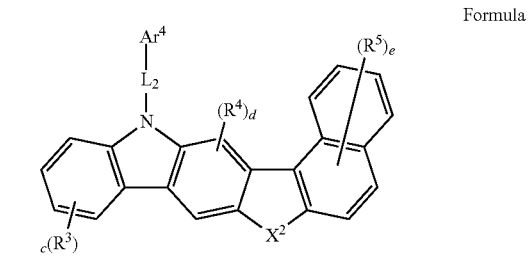
Formula 41
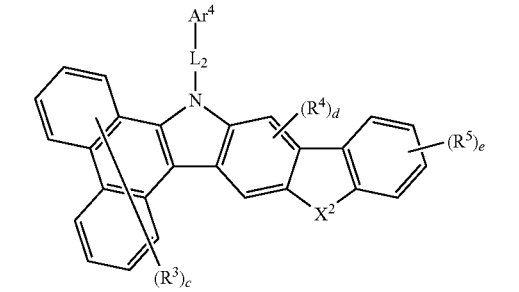

Formula 42
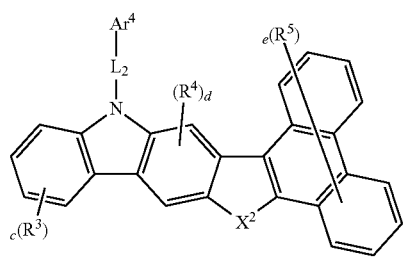
Formula 43
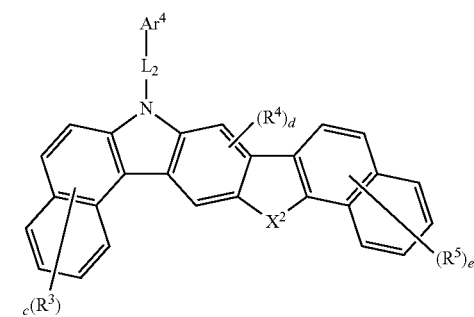
Formula 44
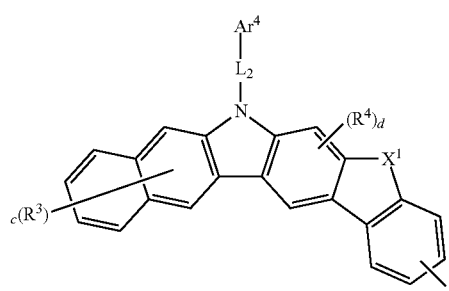
Formula 45
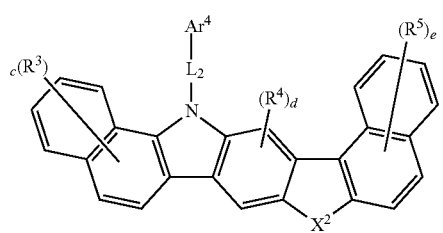
{In Formulas 26 to 45,
$Ar^4$, $X^1$, $X^2$, $R^3$, $R^4$, $R^5$, $L^2$, c, d, and e are the same as defined above.}
In the present invention, the second host compound represented by Formula 2 comprises any of compounds represented by the following Formulas 46 to 53.
Formula 46
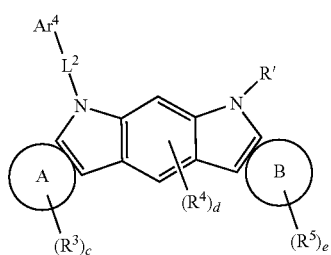
Formula 47
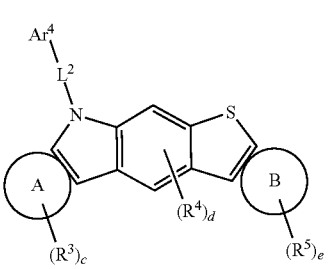
Formula 48
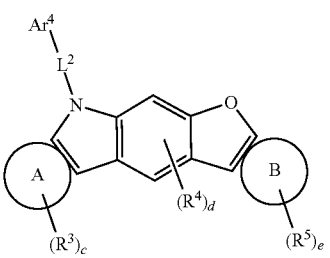
Formula 49
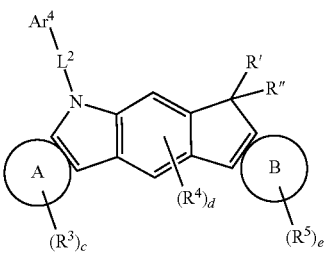
Formula 50
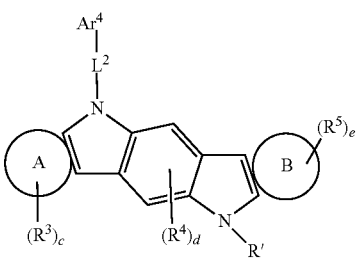
Formula 51
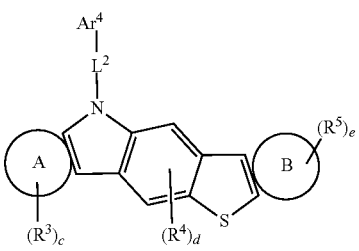
Formula 52
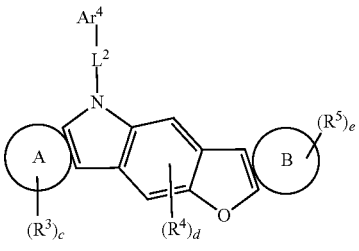

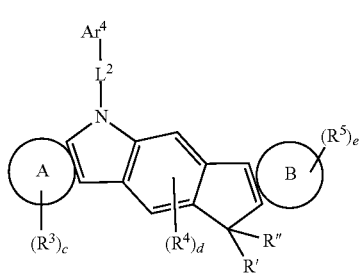
Formula 53
{In Formulas 46 to 53,
$R^3$, $R^4$, $R^5$, $Ar^4$, $L^2$, c, d, e, A, B, R' and R" are the same as defined above.}
As a specific example of the present invention, the first host compound represented by Formula 1 is one of the following Compounds 1-1 to 1-68 and Compounds 2-1 to 2-68.
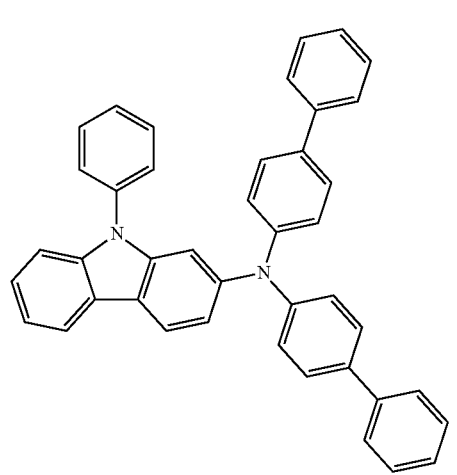
1-1
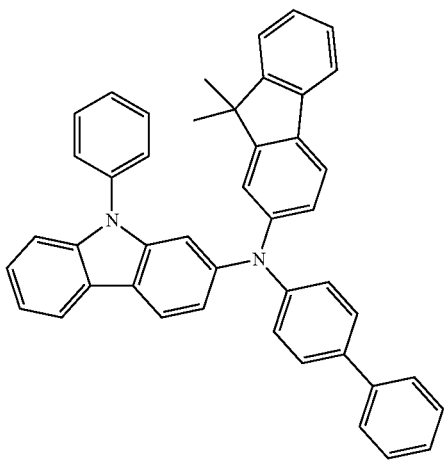
1-2
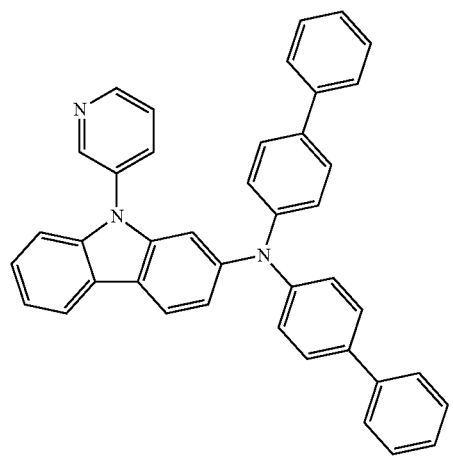
1-3
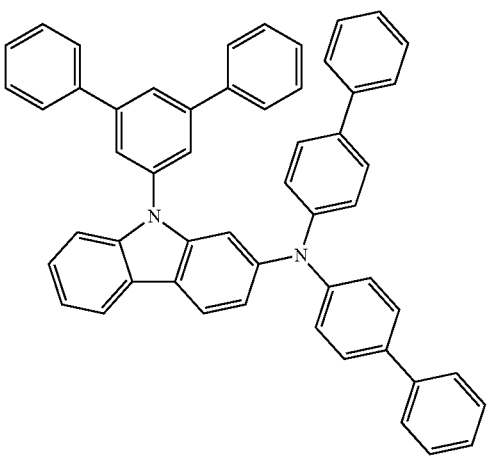
1-4

-continued
1-5
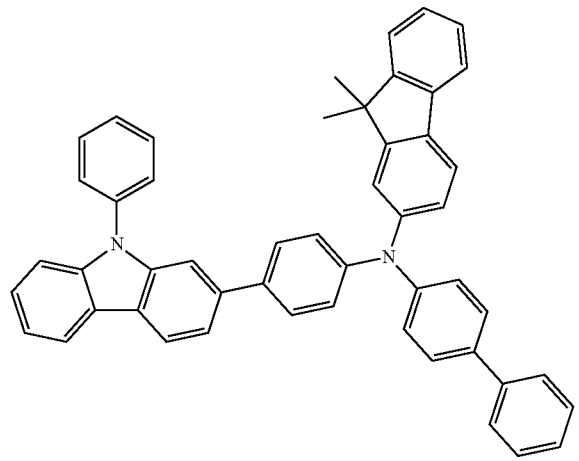
1-6
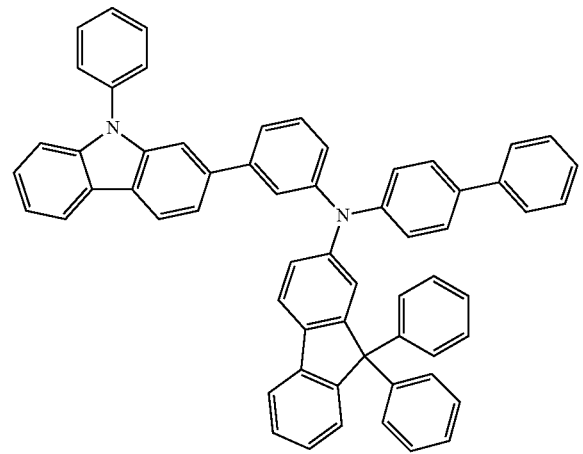
1-7
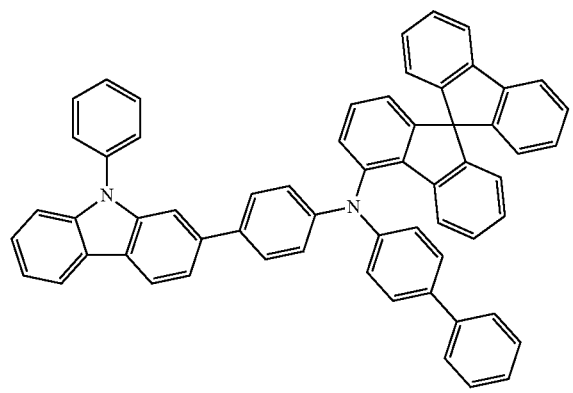
1-8
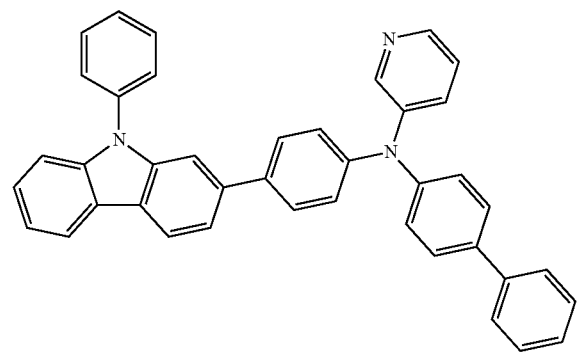
1-9
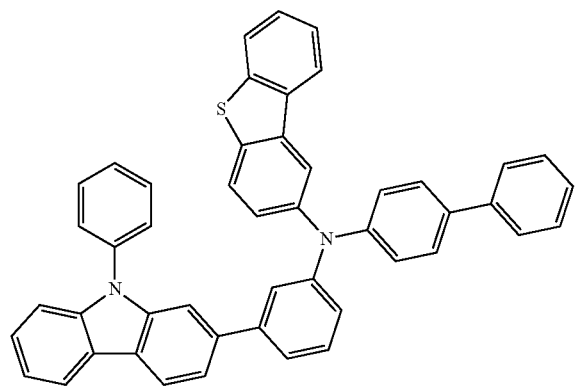
1-10
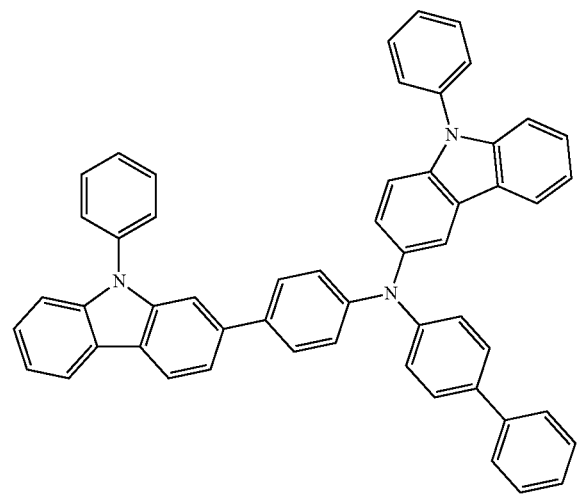

-continued
1-11
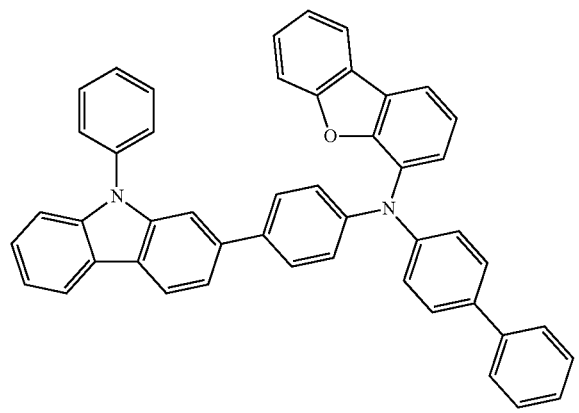
1-12
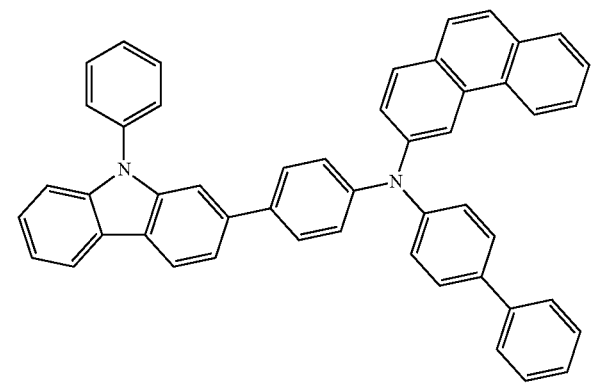
1-13
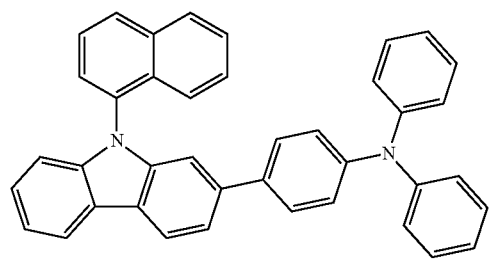
1-14
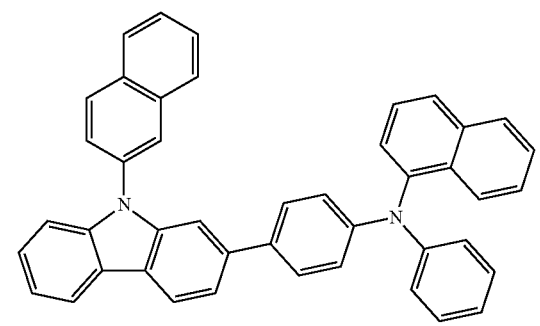
1-15
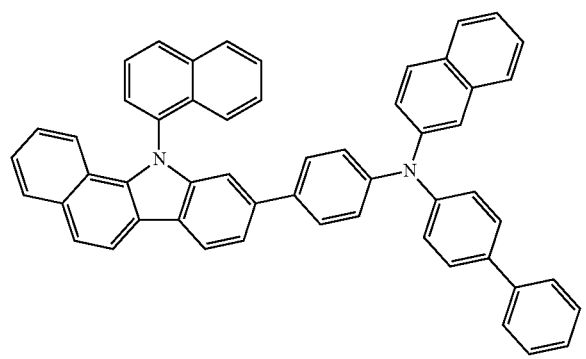
1-16
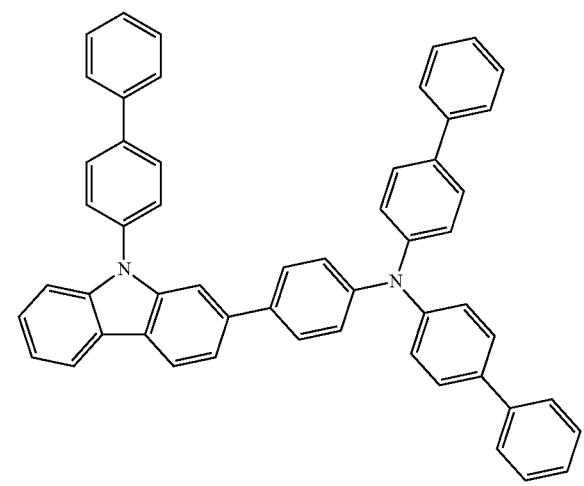

-continued
1-17
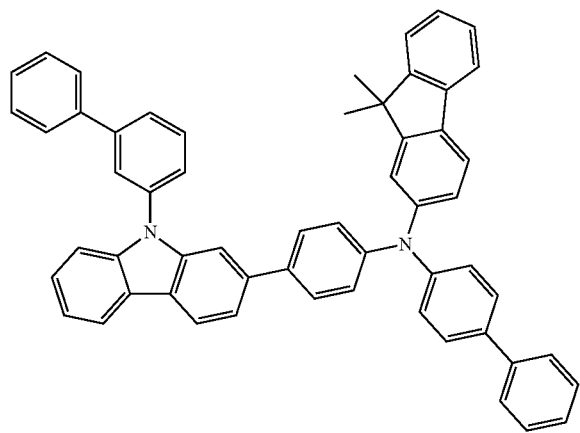
1-18
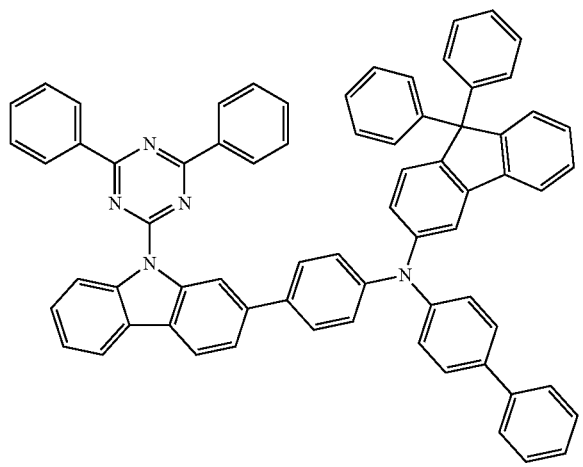
1-19
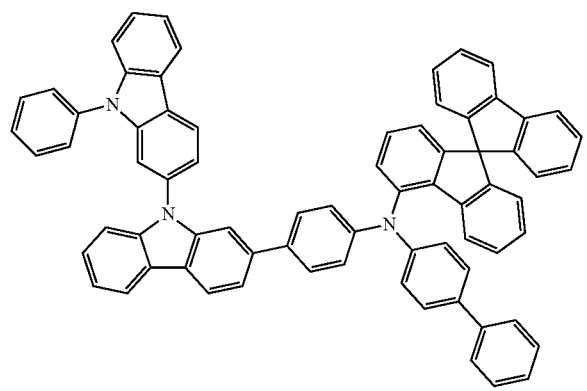
1-20
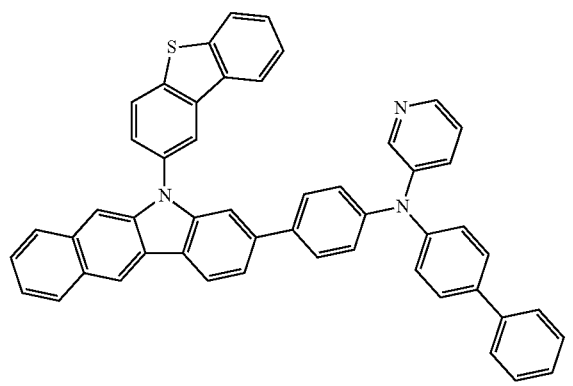
1-21
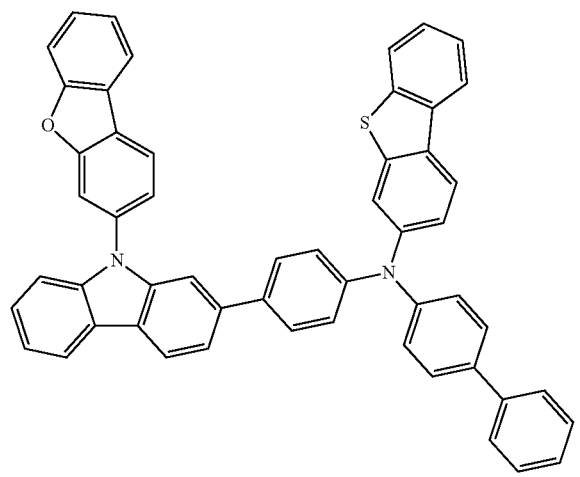
1-22
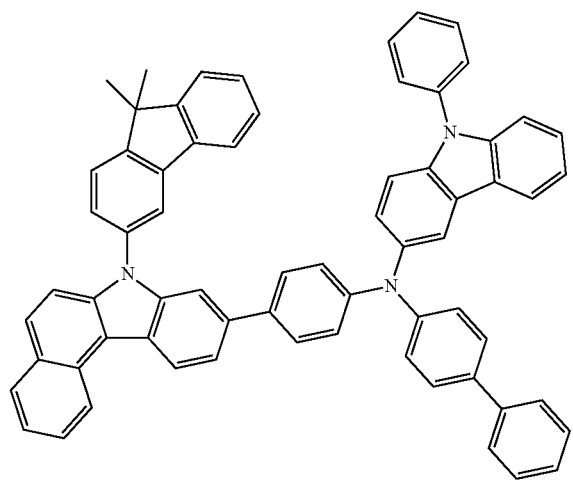

-continued
1-23
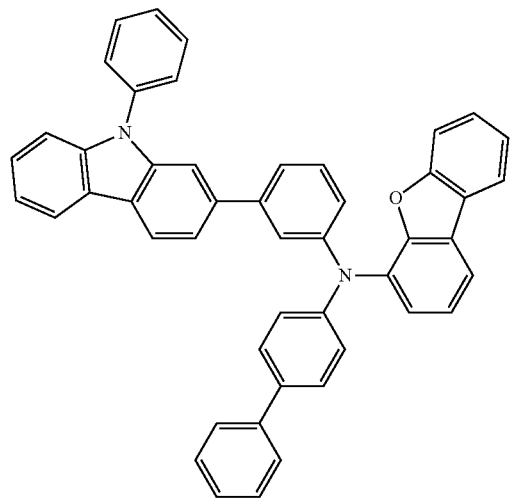
1-24
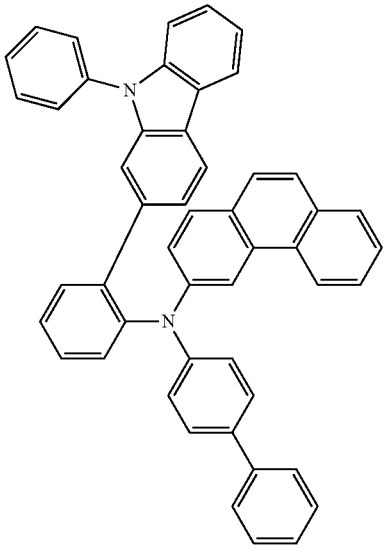
1-25
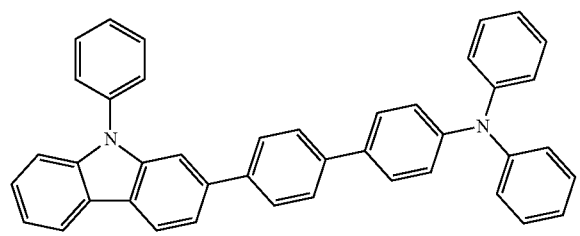
1-26
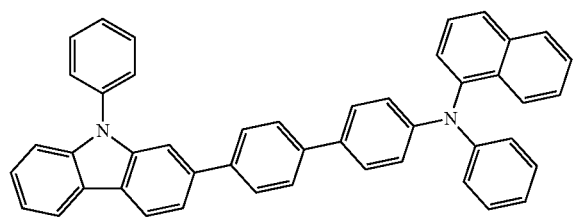
1-27
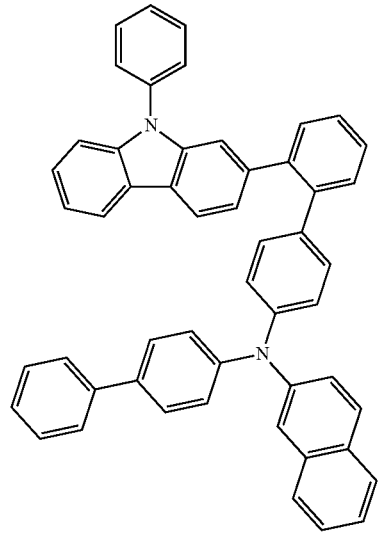
1-28
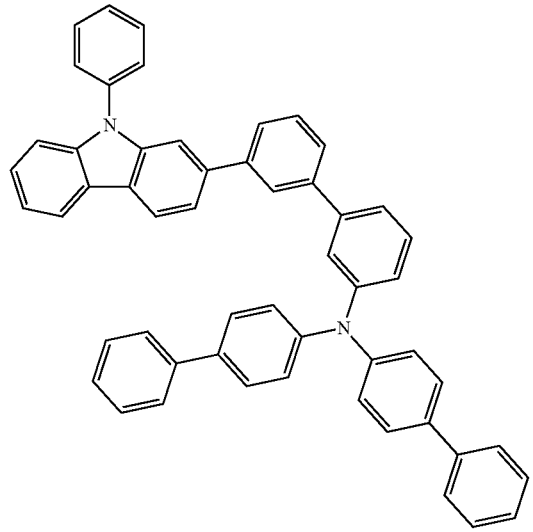

-continued
1-29
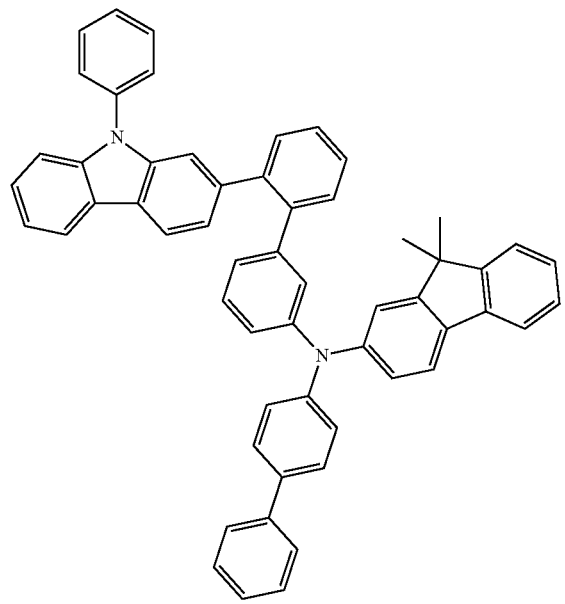
1-30
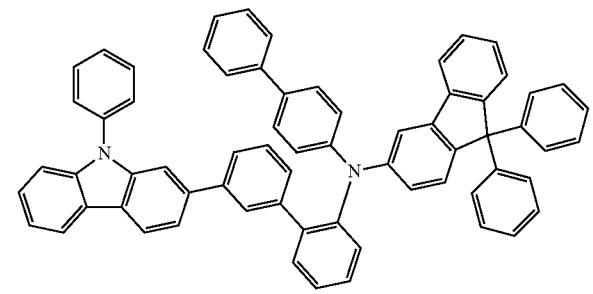
1-31
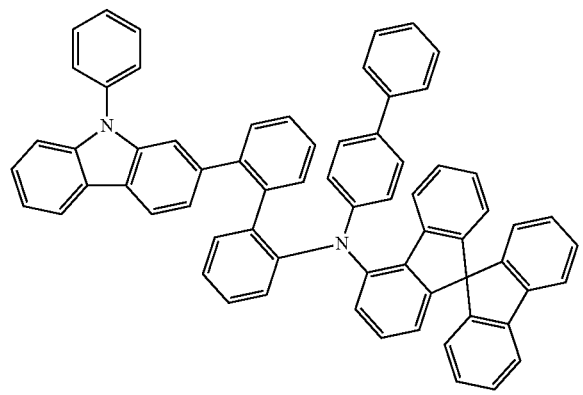
1-32
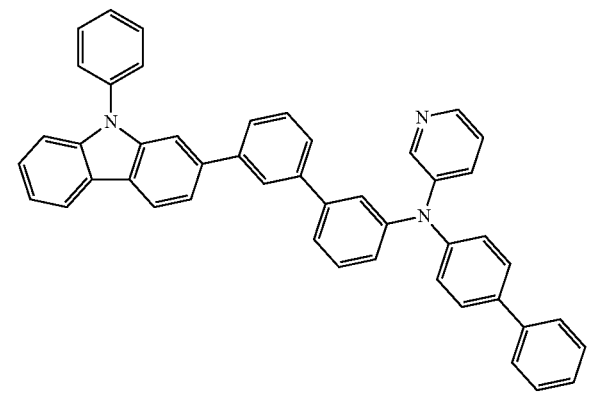
1-33
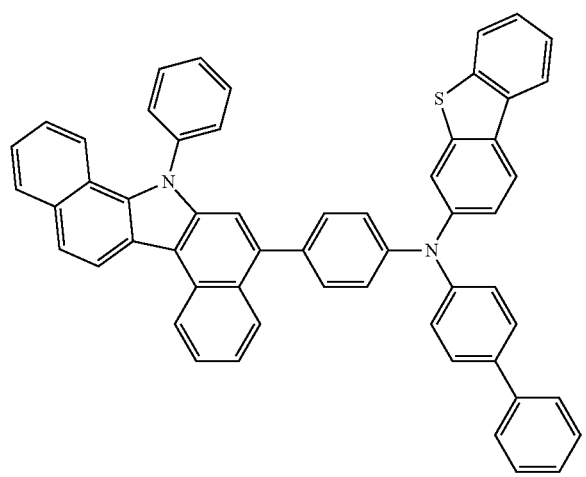
1-34
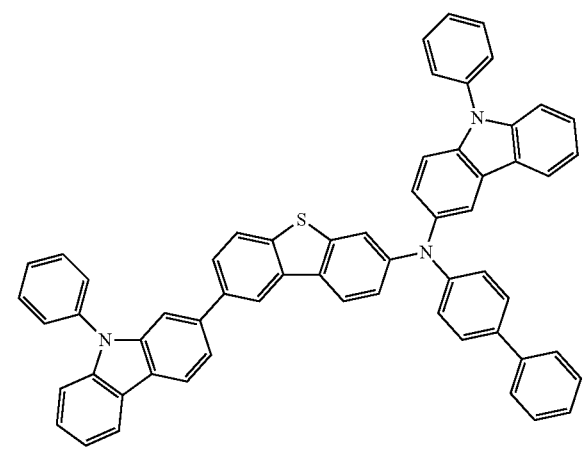

-continued
1-35
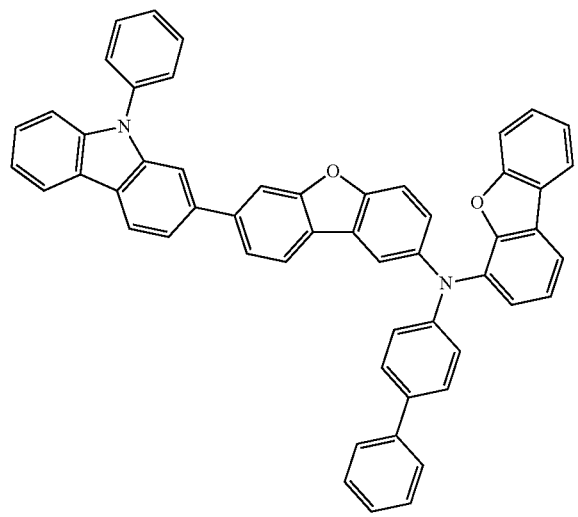
1-36
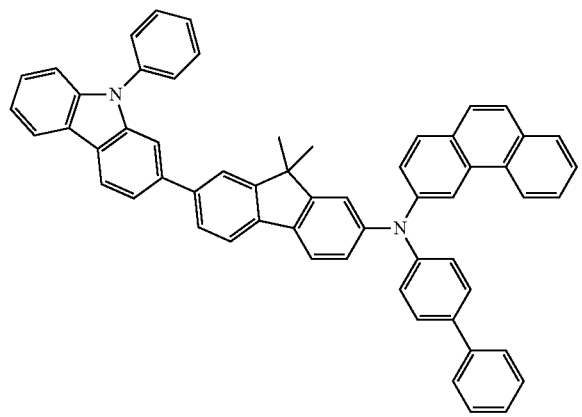
1-37
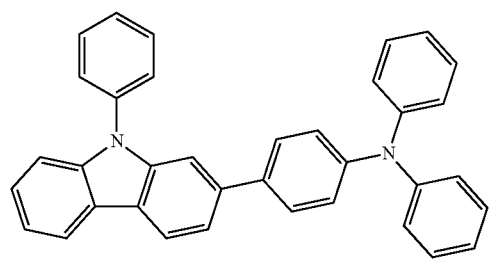
1-38
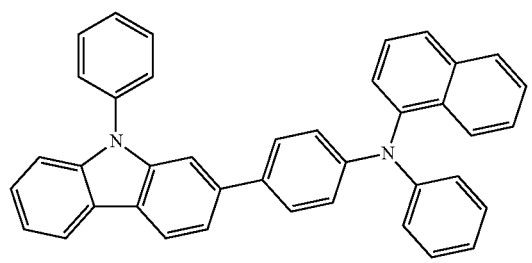
1-39
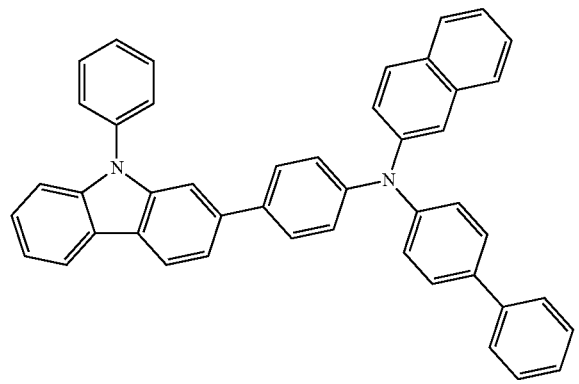
1-40
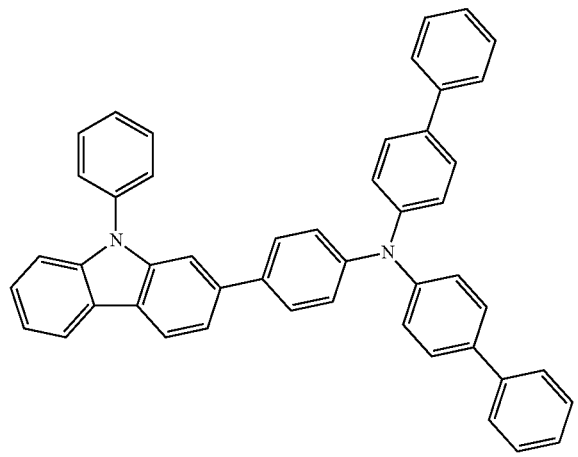
1-41
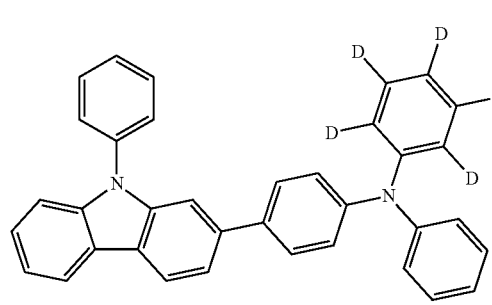
1-42
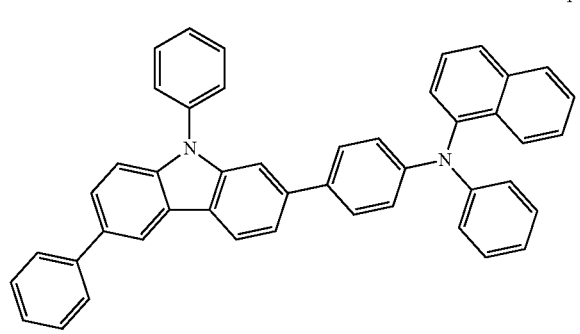

-continued
1-43
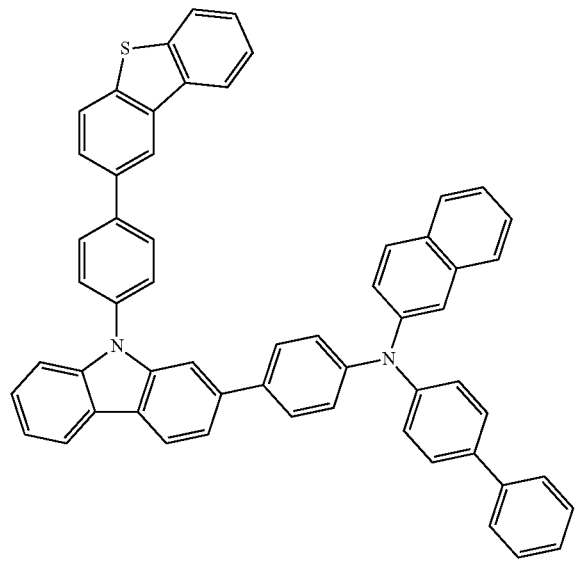
1-44
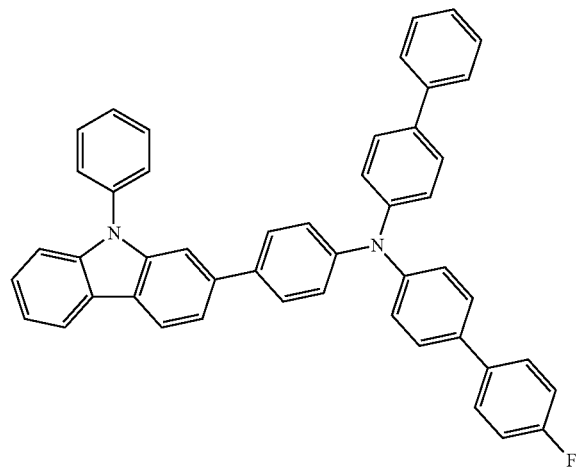
1-45
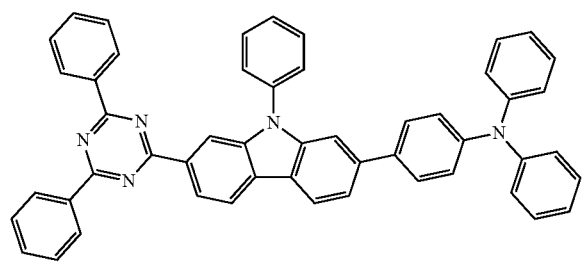
1-46
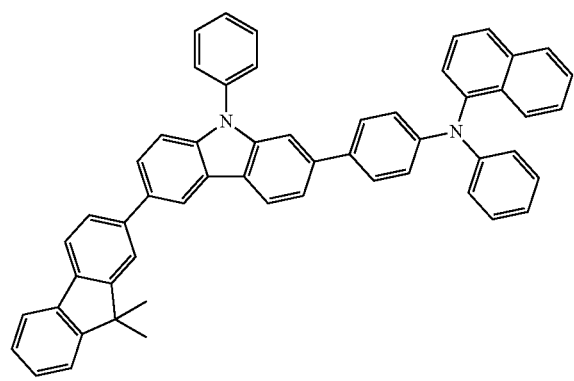
1-47
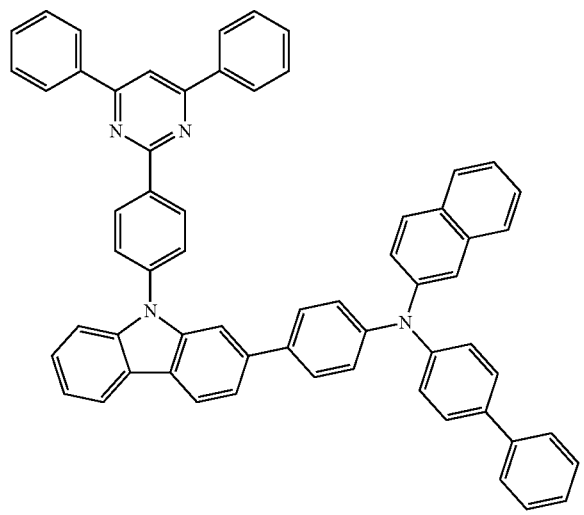
1-48
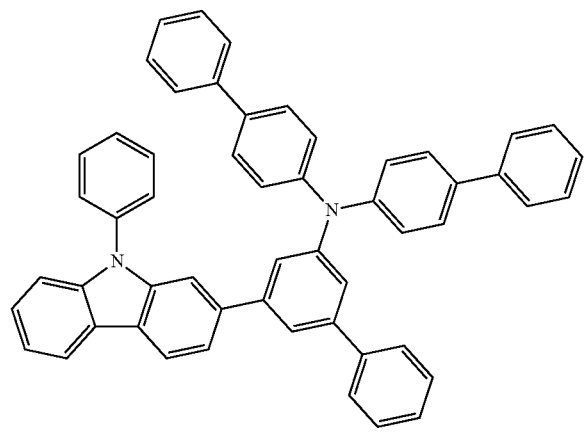

1-49
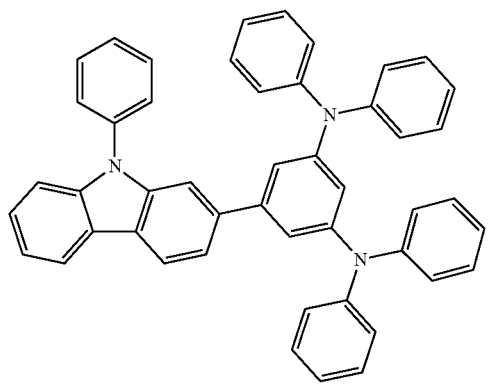
1-50
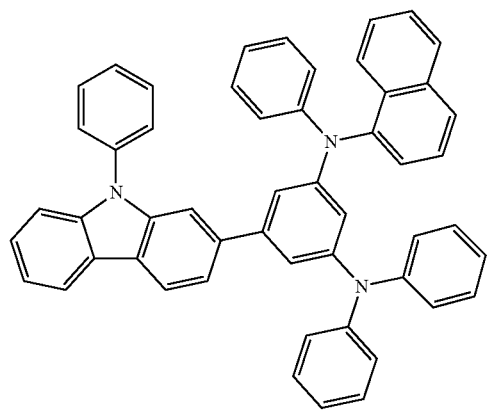
1-51
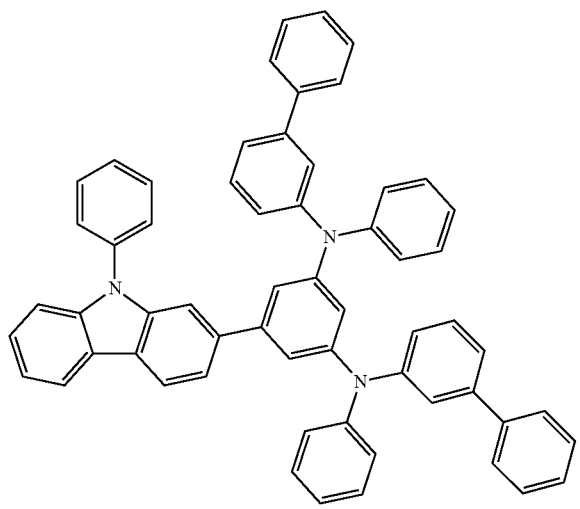
1-52
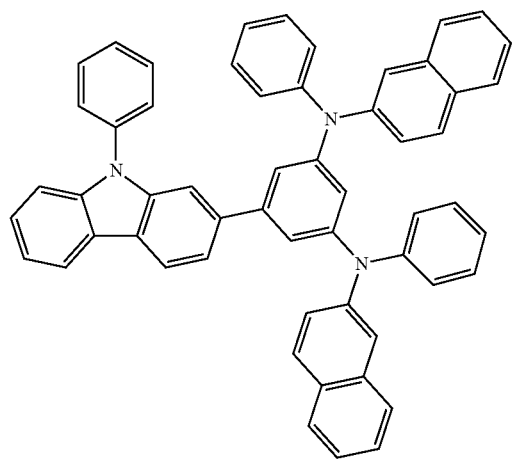
1-53
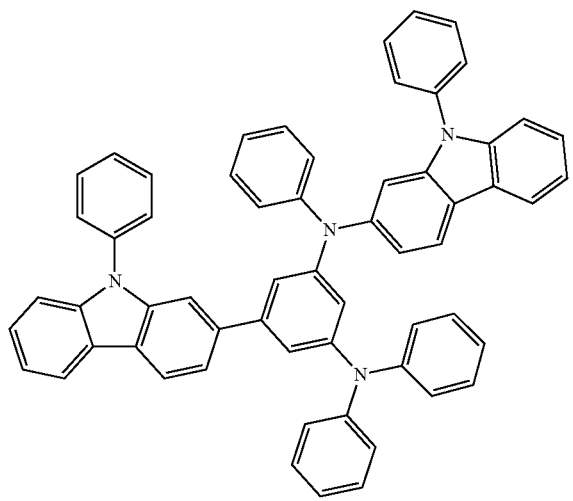
1-54
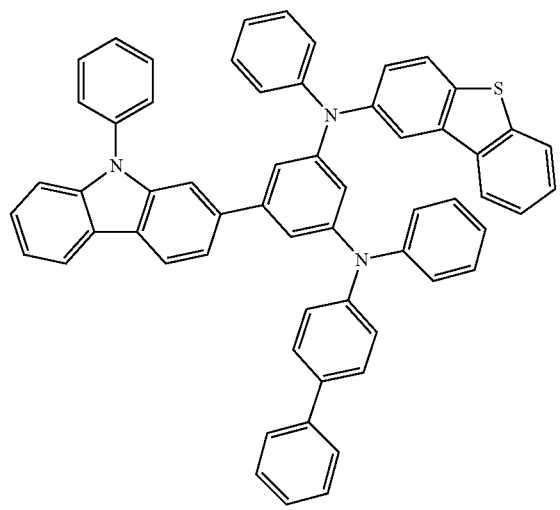

-continued
1-55
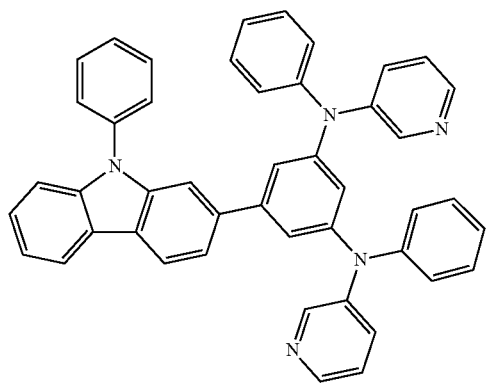
1-56
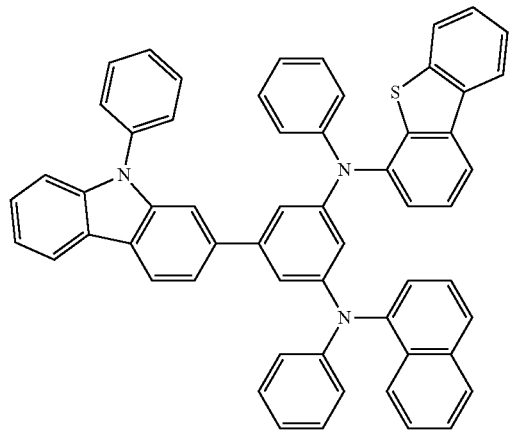
1-57
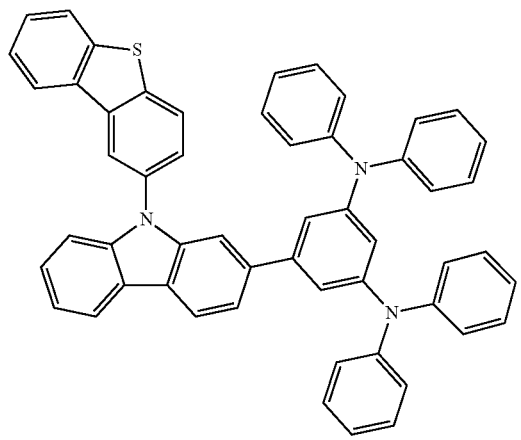
1-58
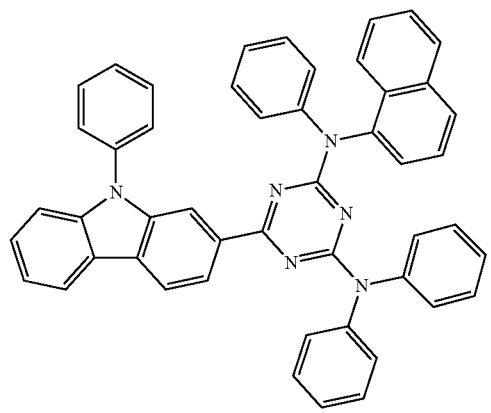
1-59
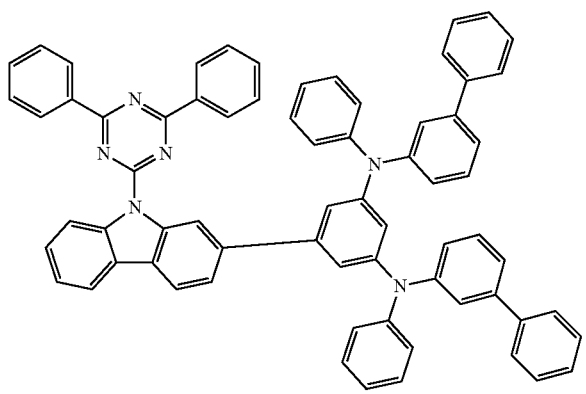
1-60
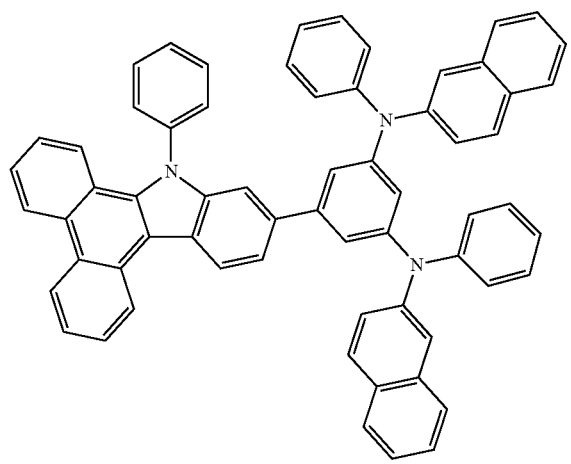

1-61
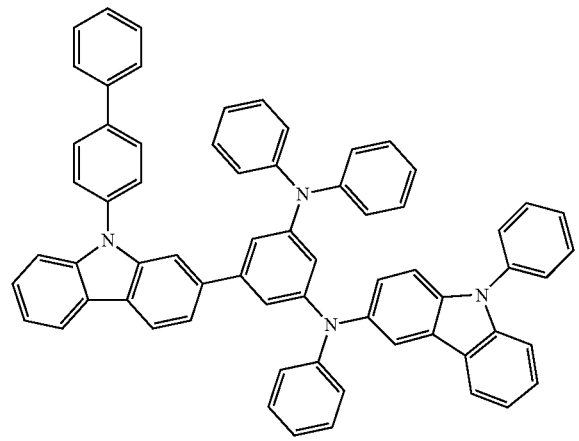
1-62
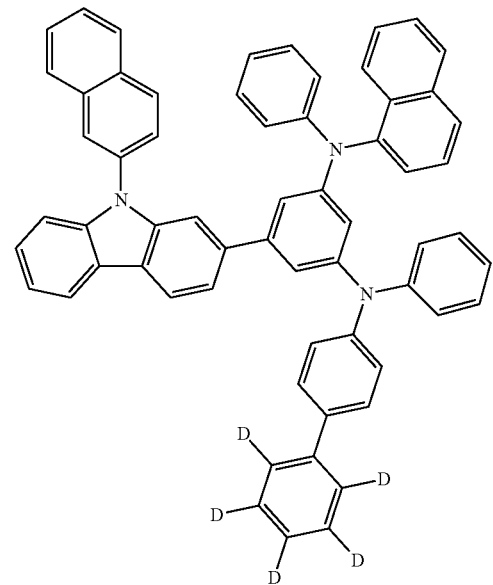
1-63
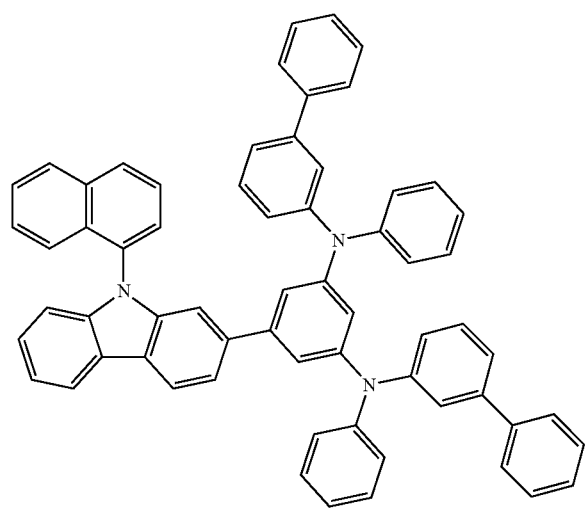
1-64
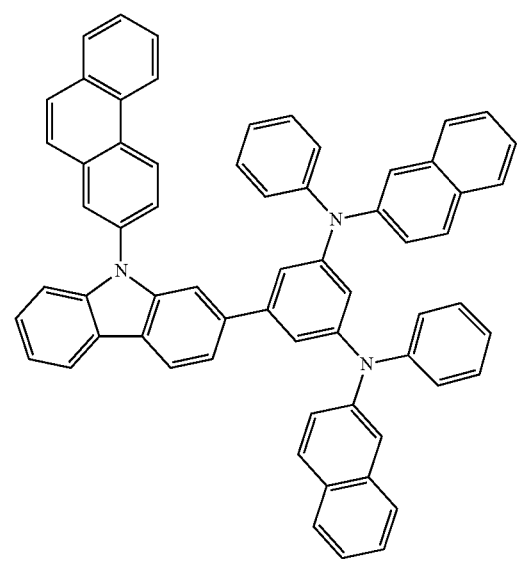
1-65
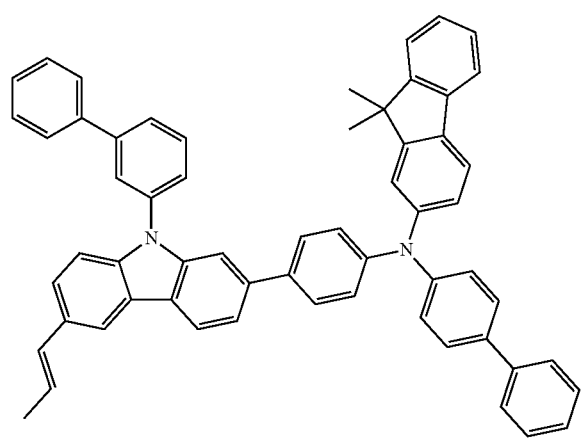
1-66
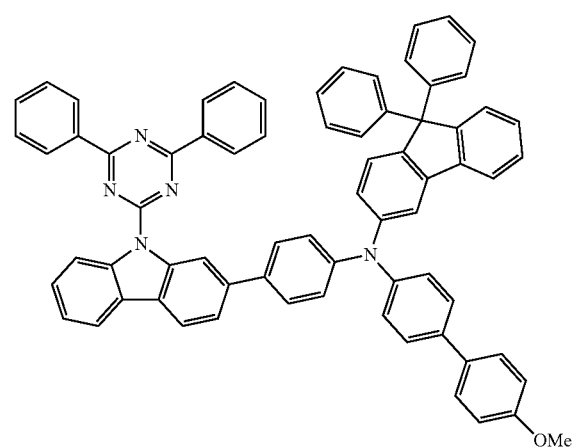

1-67
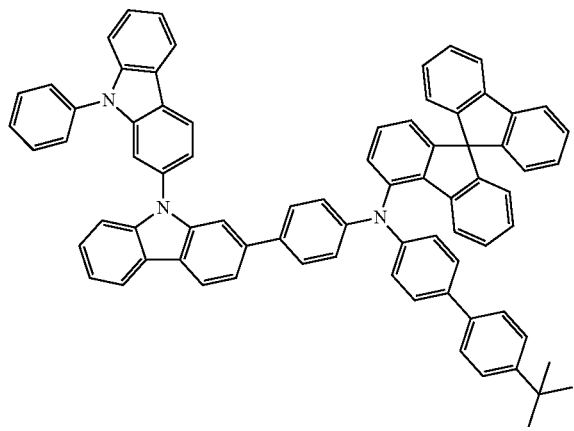
1-68
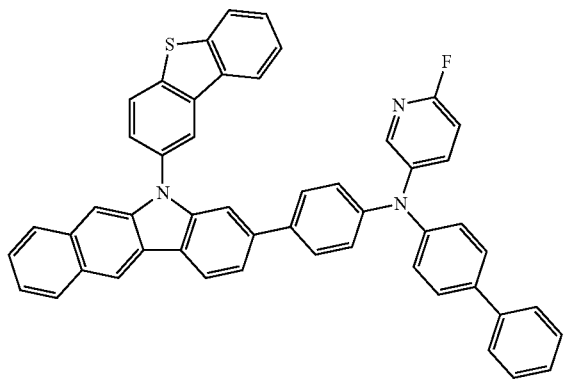
2-1
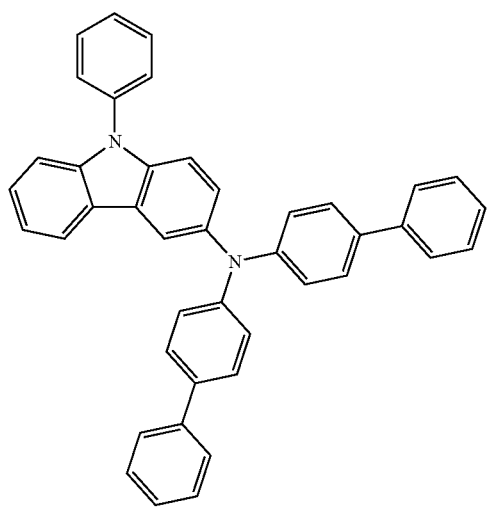
2-2
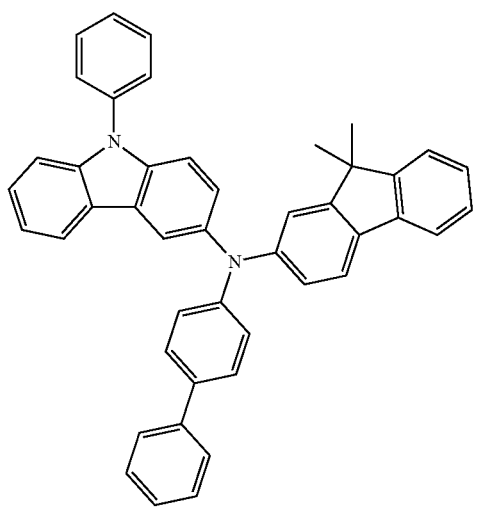
2-3
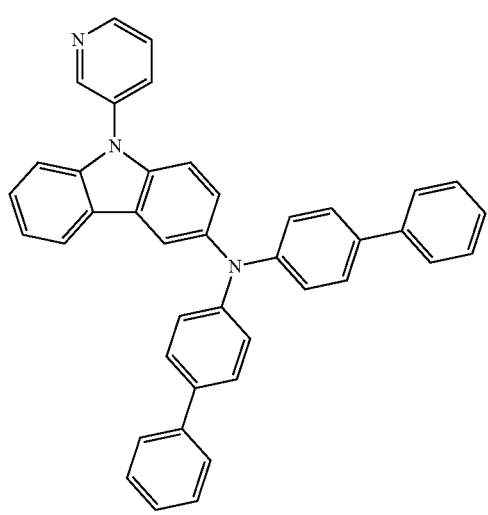
2-4
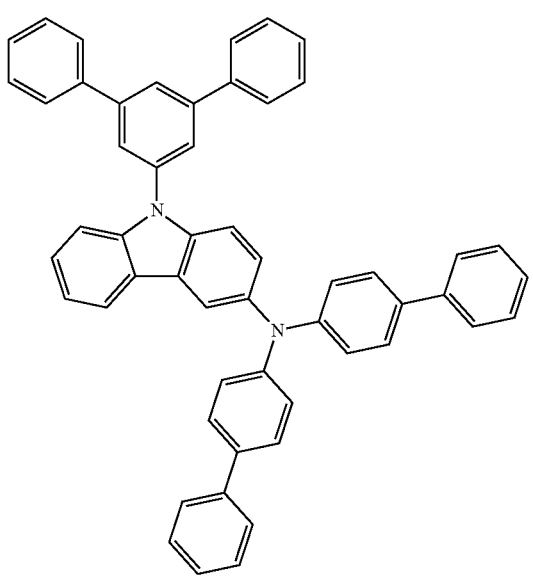

2-5
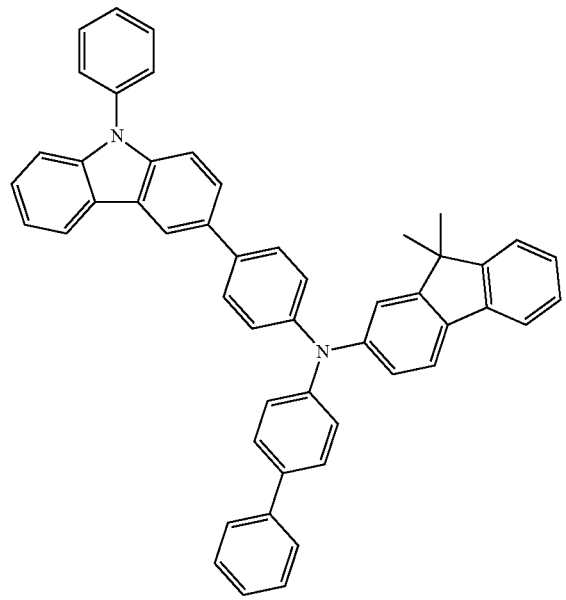
2-6
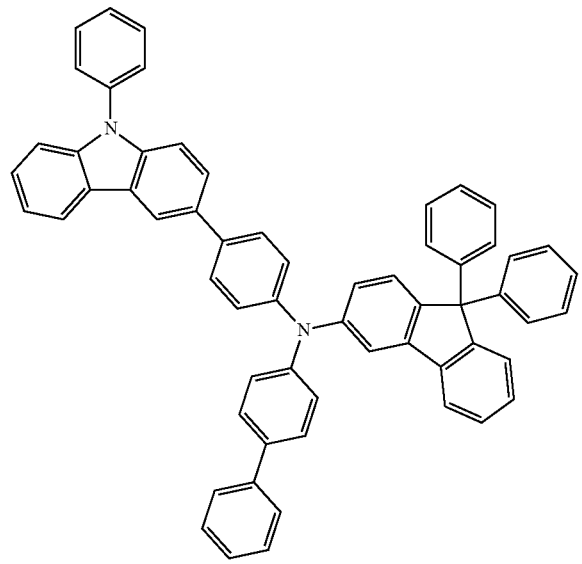
2-7
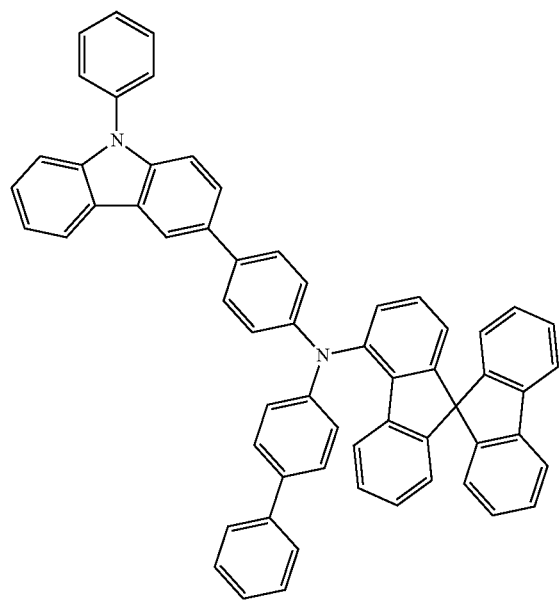
2-8
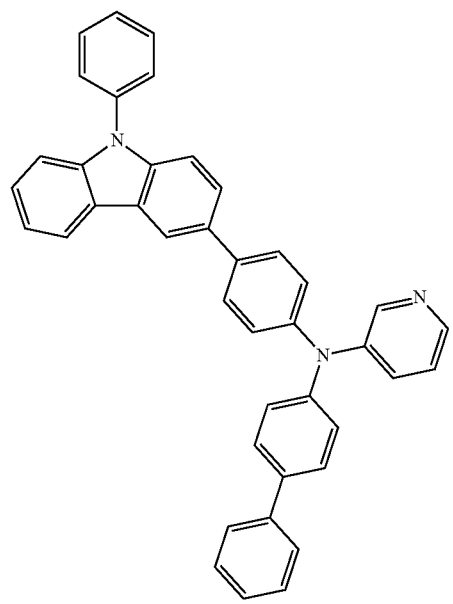

-continued
2-9
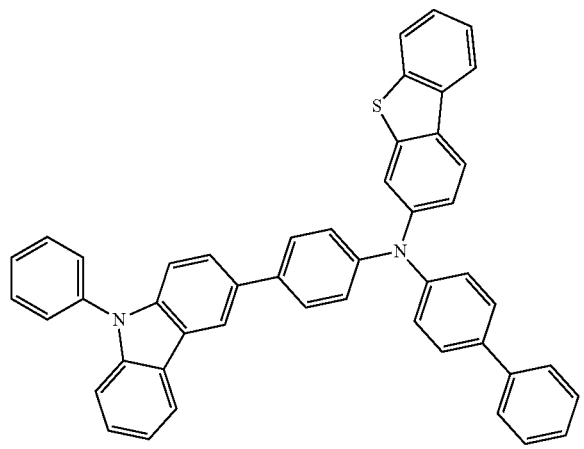
2-10
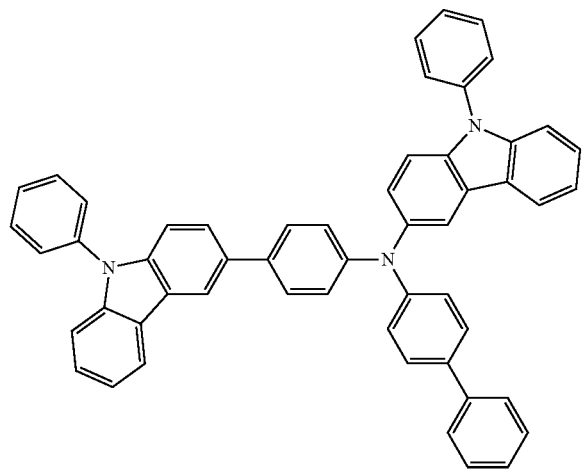
2-11
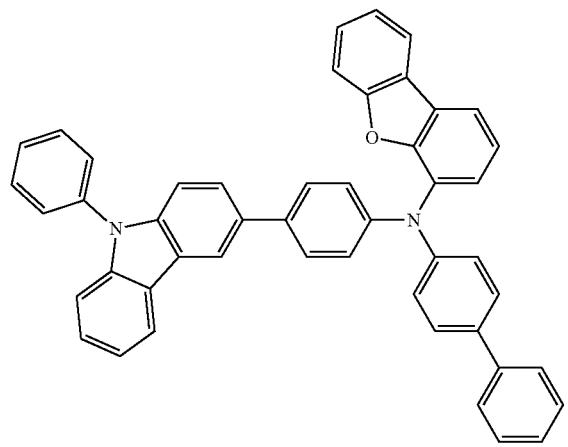
2-12
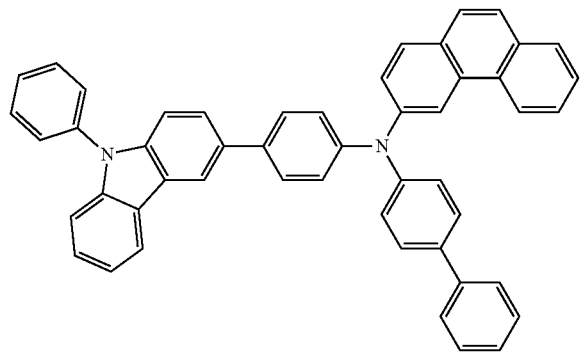
2-13
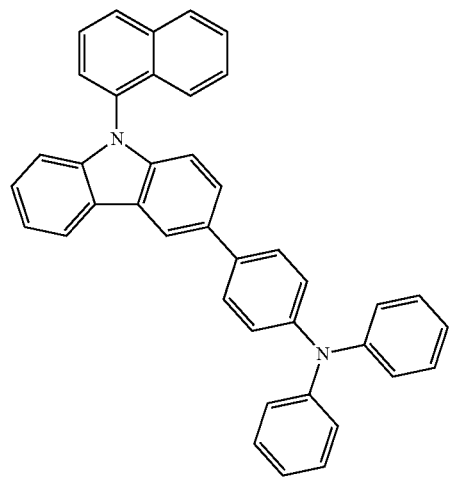
2-14
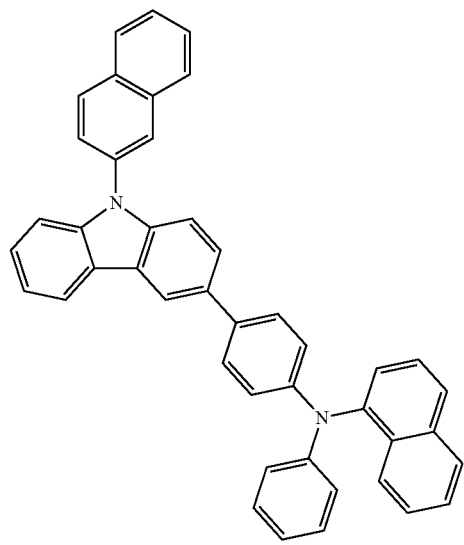

-continued
2-15
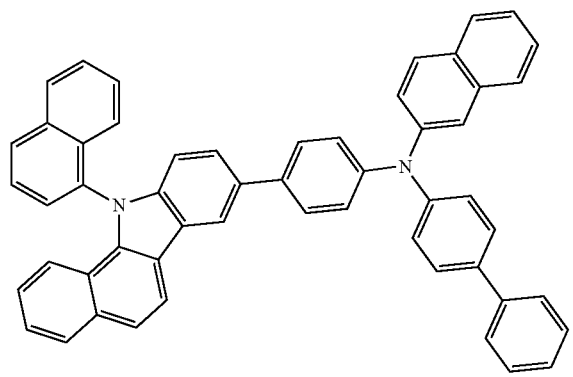
2-16
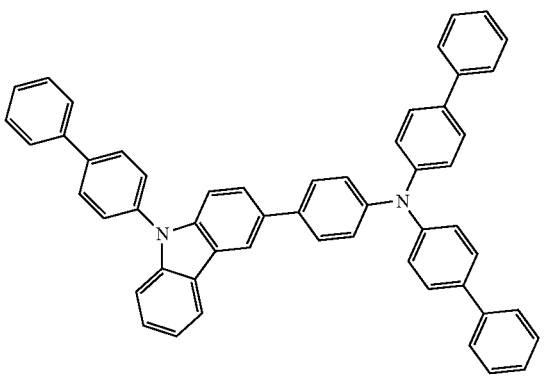
2-17
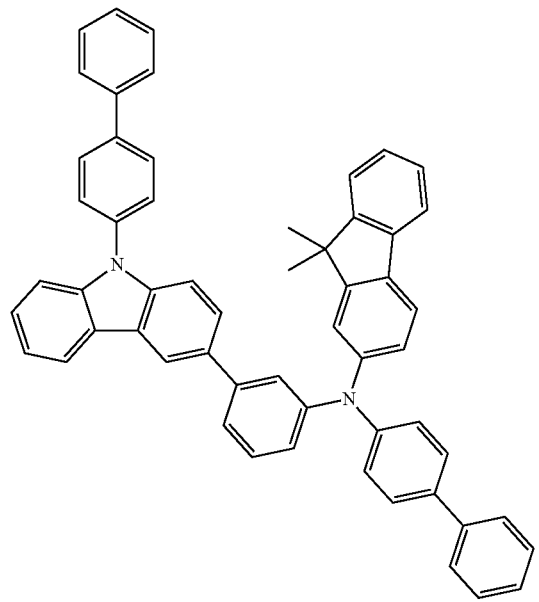
2-18
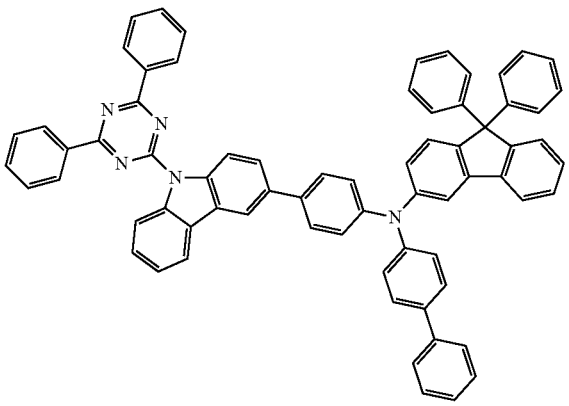
2-19
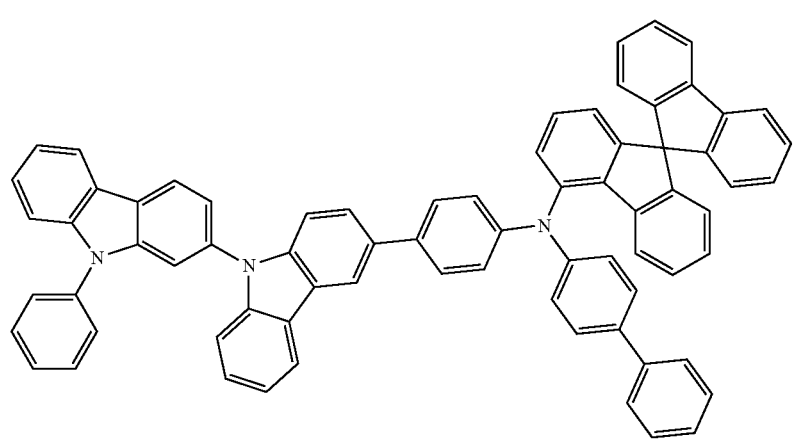

-continued
2-20
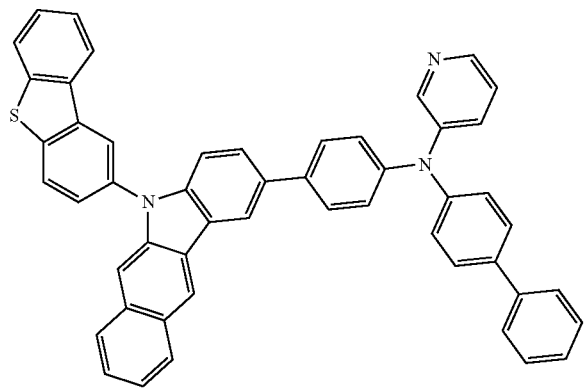
2-21
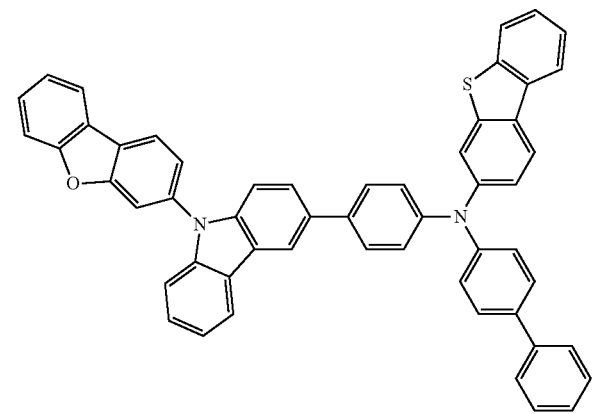
2-22
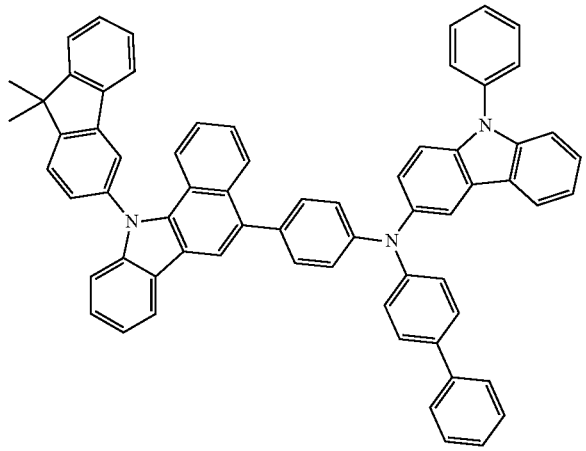
2-23
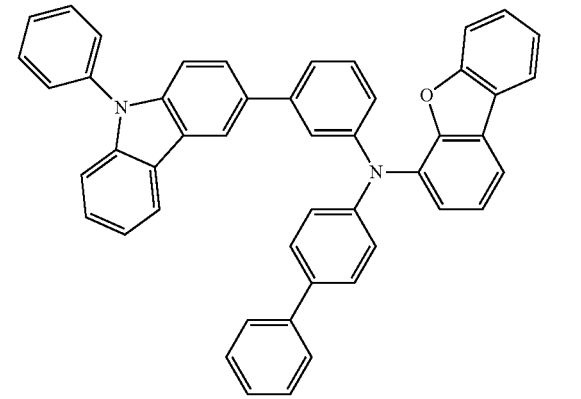
2-24
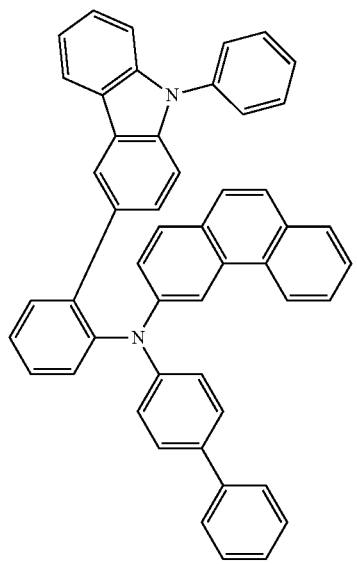
2-25
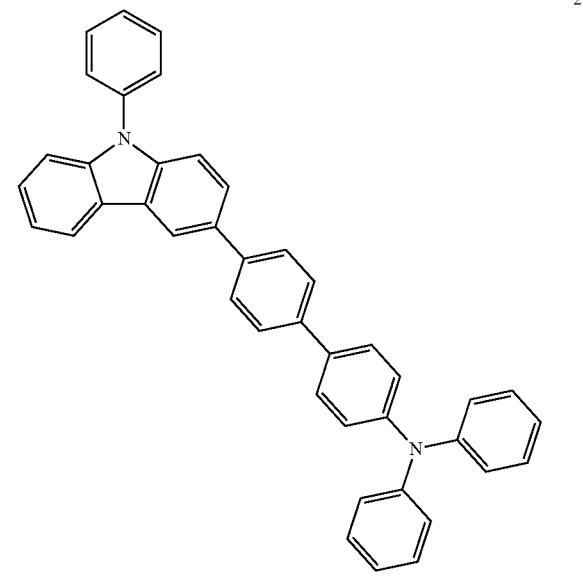

2-26
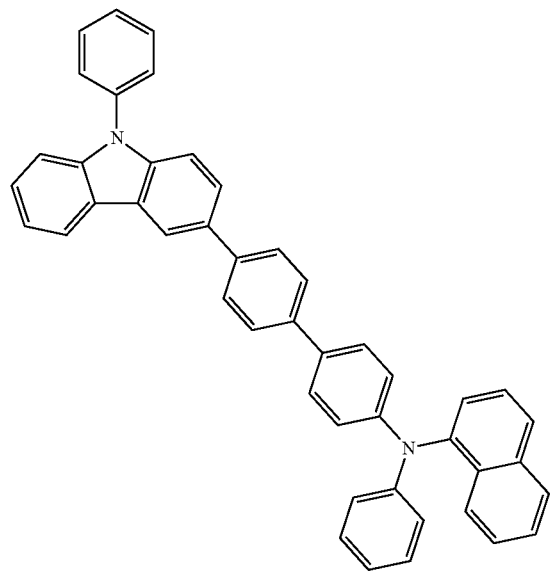
2-27
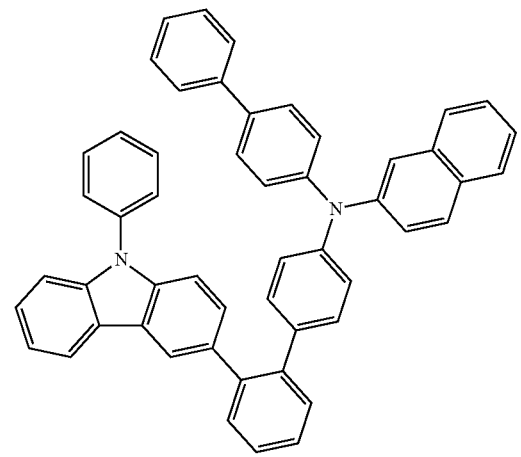
2-28
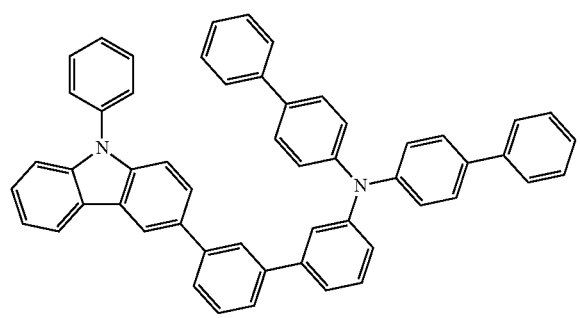
2-29
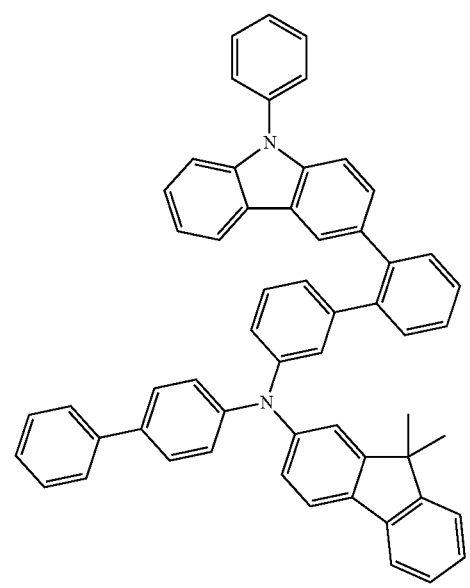

2-30
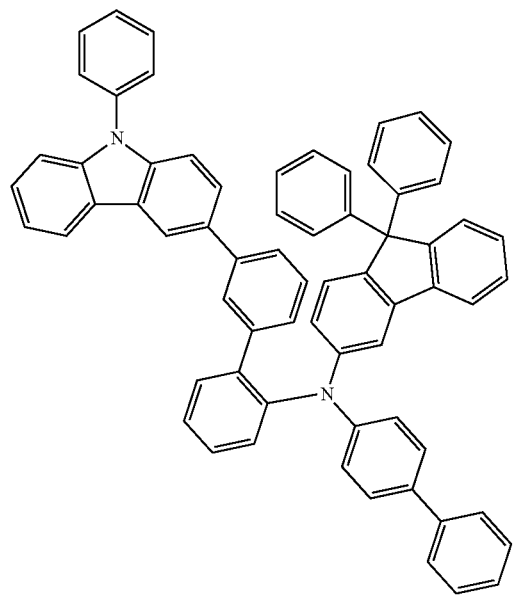
2-31
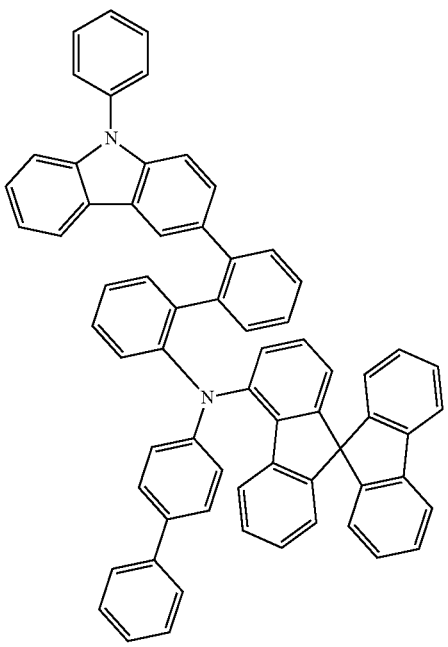
2-32
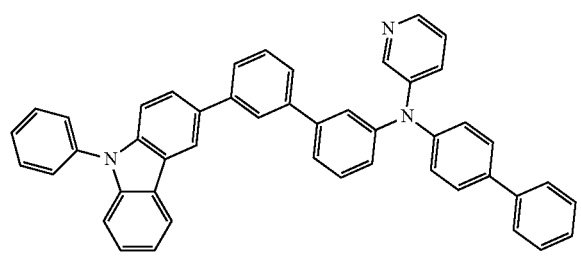
2-33
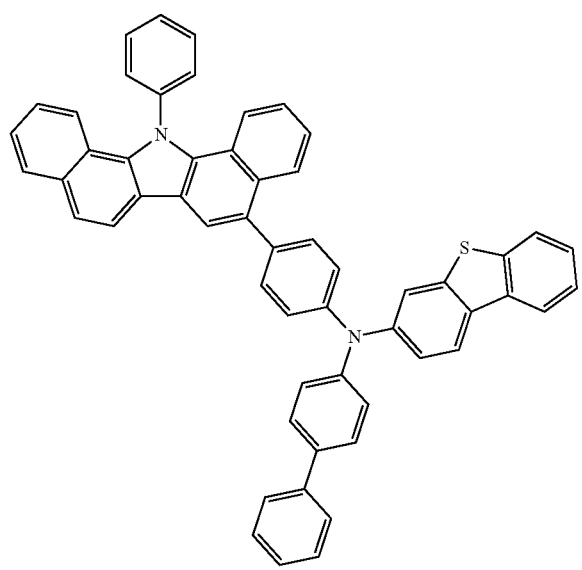

-continued
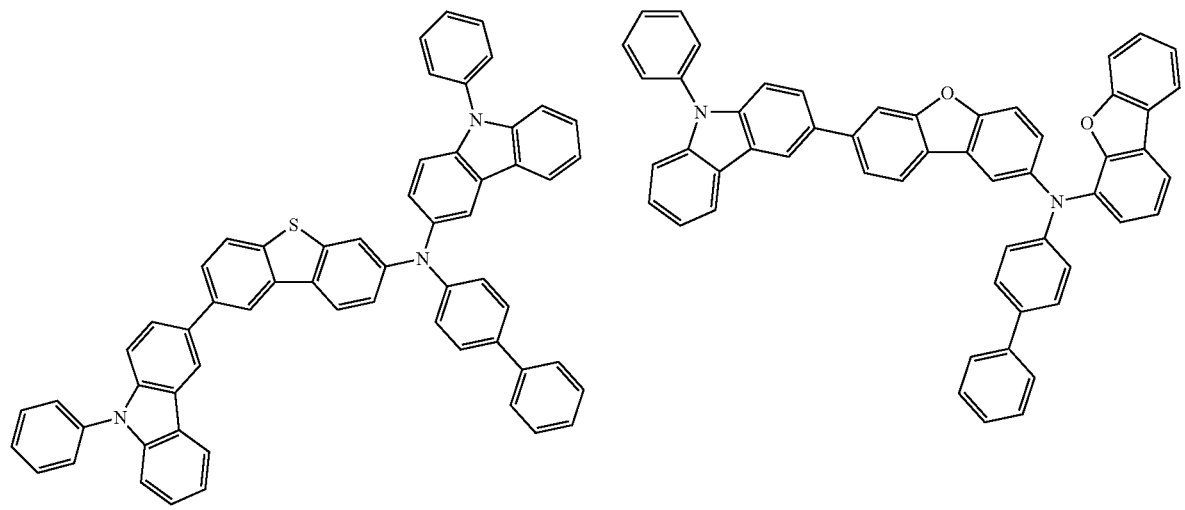
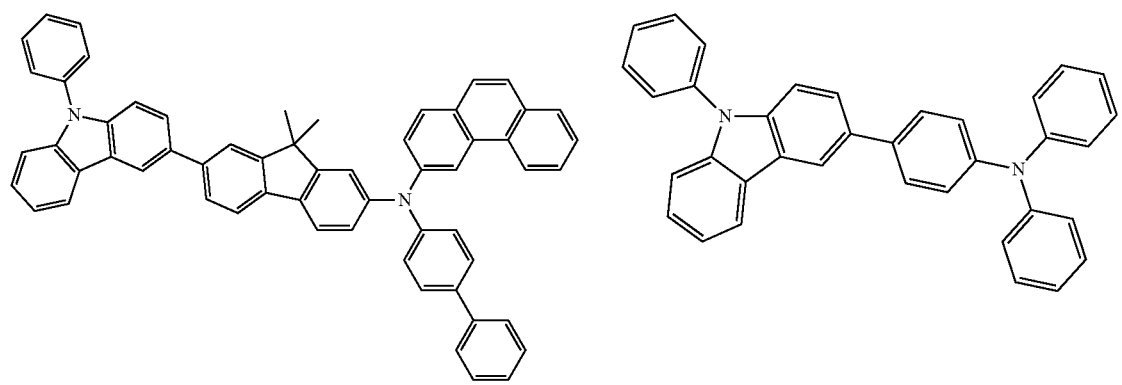
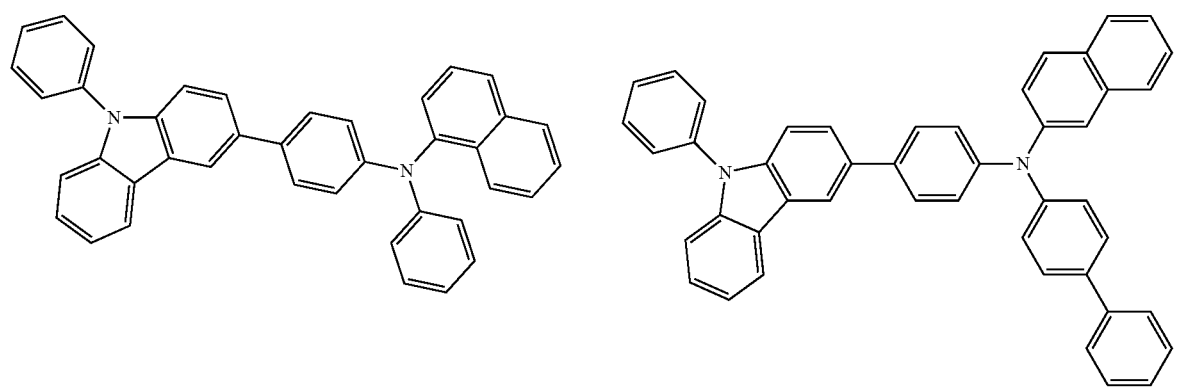

2-40
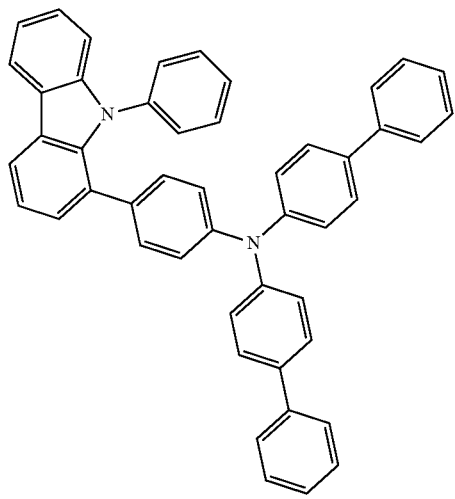
2-41
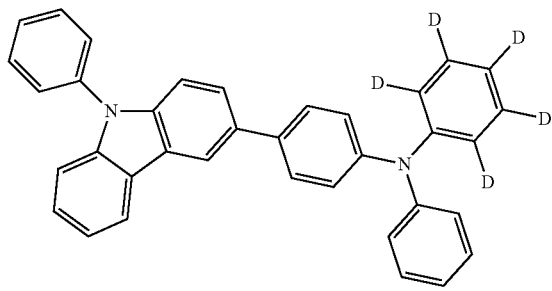
2-42
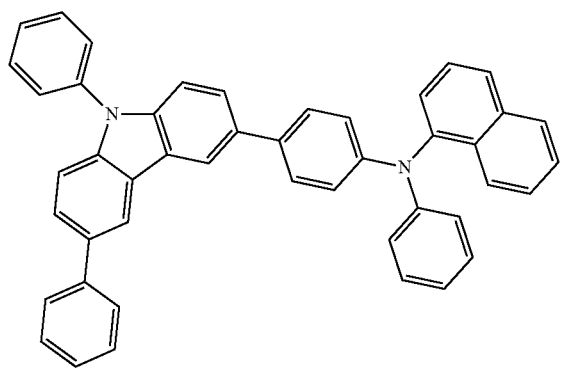
2-43
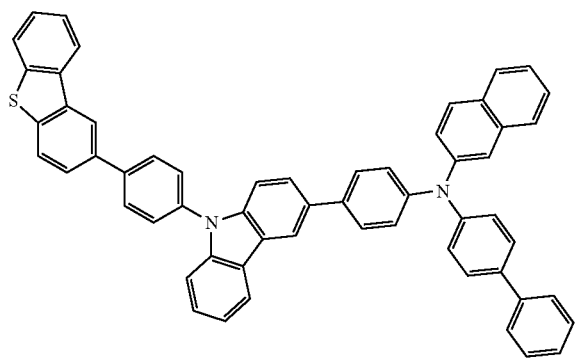
2-44
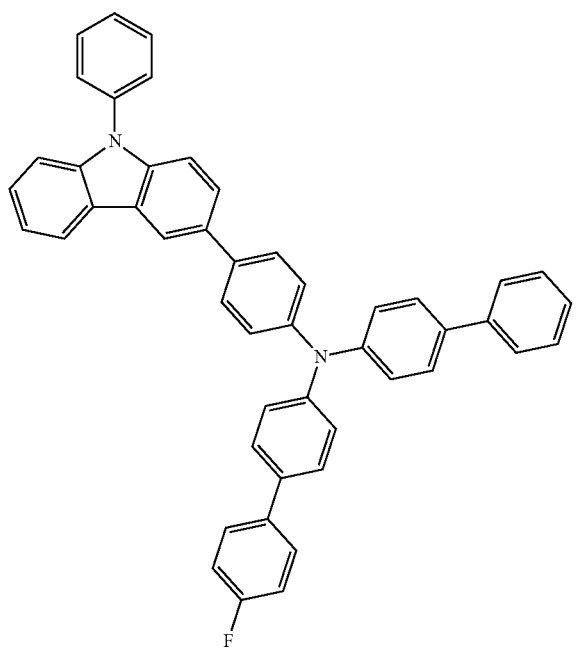
2-45
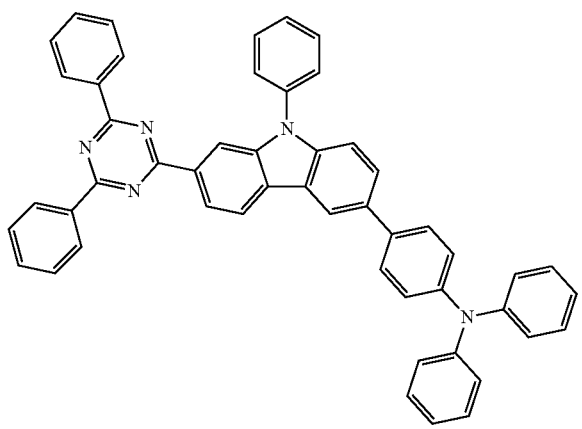

2-46
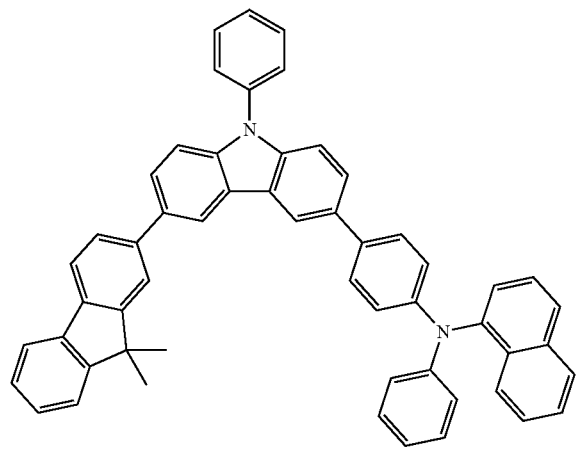
2-47
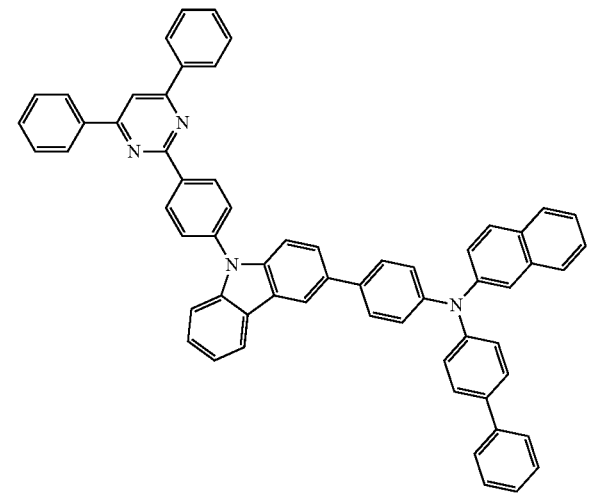
2-48
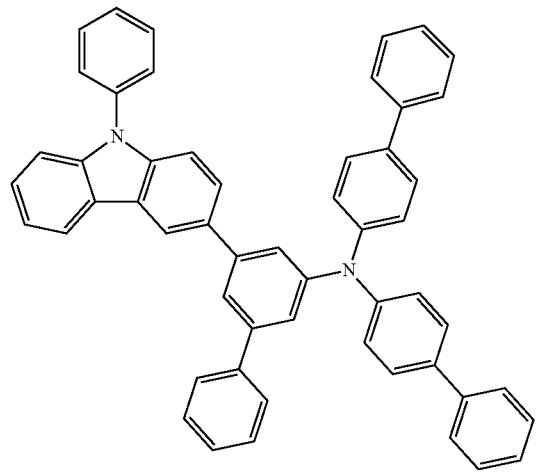
2-49
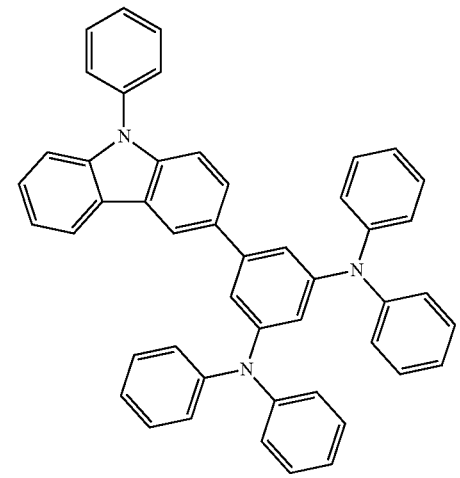
2-50
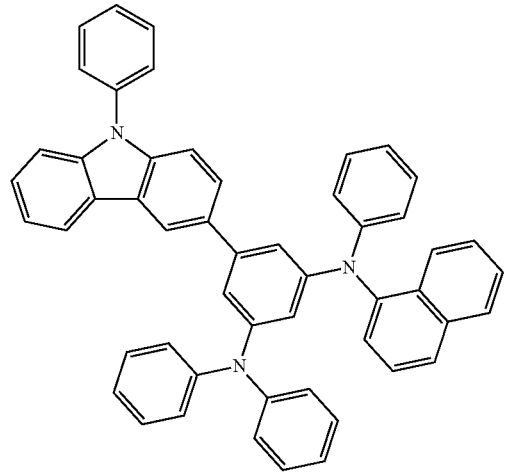
2-51
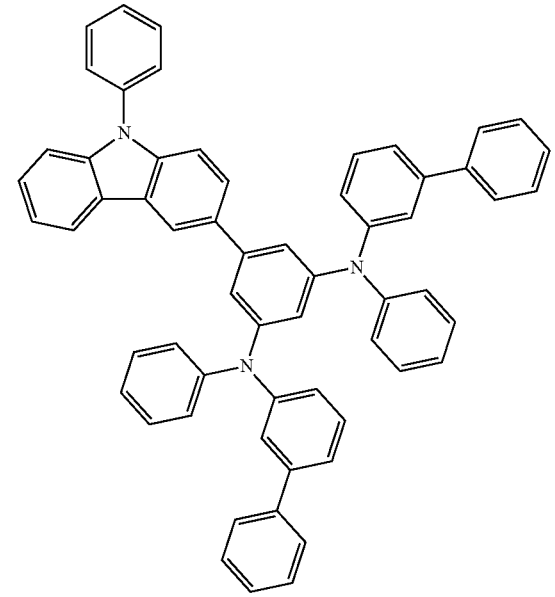

-continued
2-52
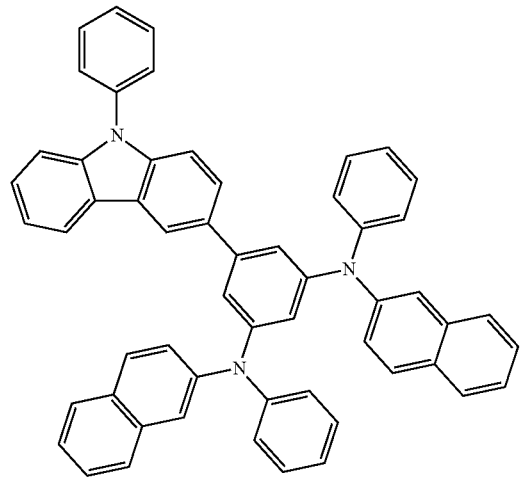
5-53
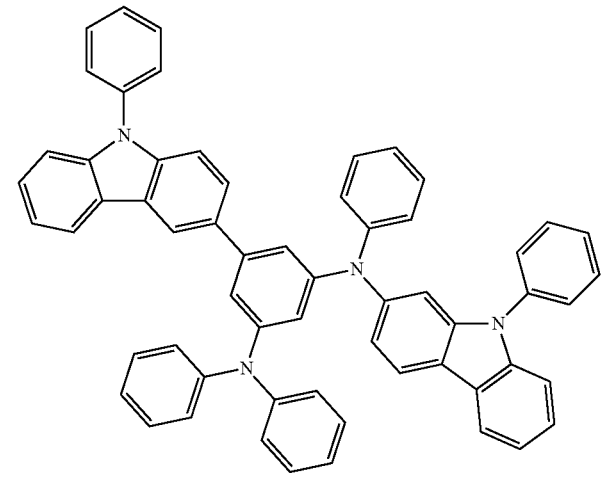
2-54
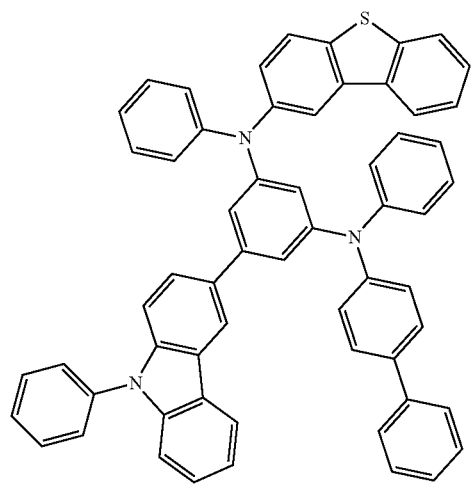
2-55
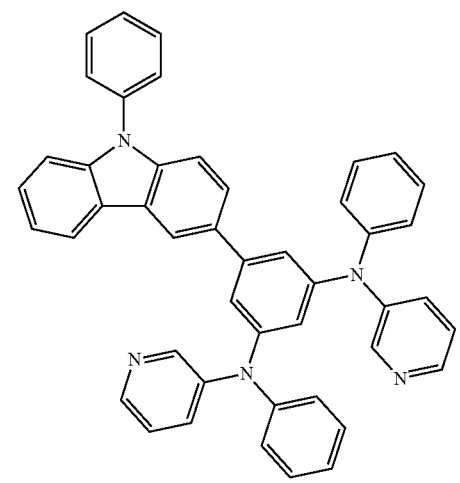
2-56
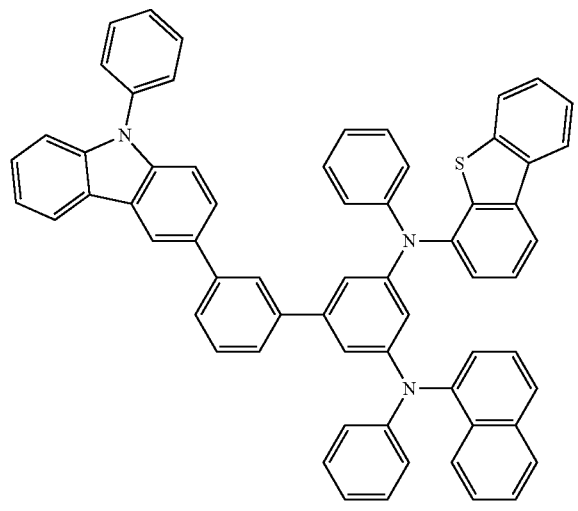
2-57
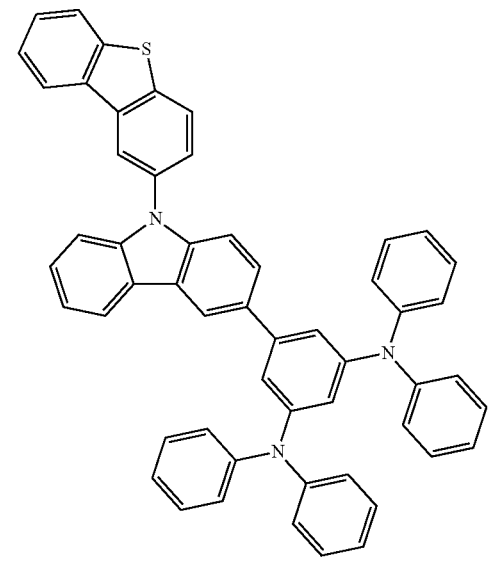

2-58
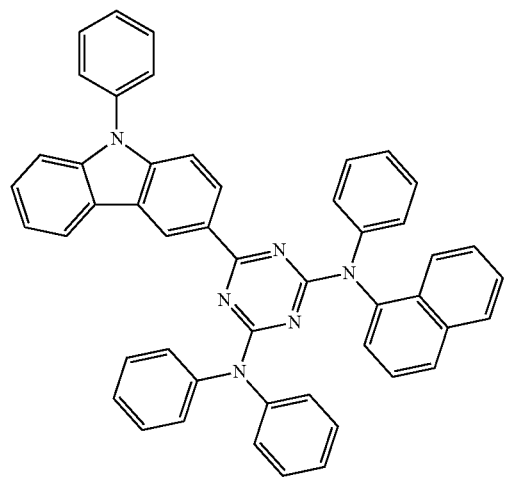
2-59
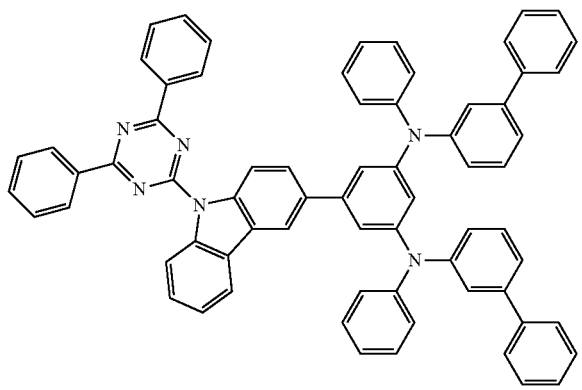
2-60
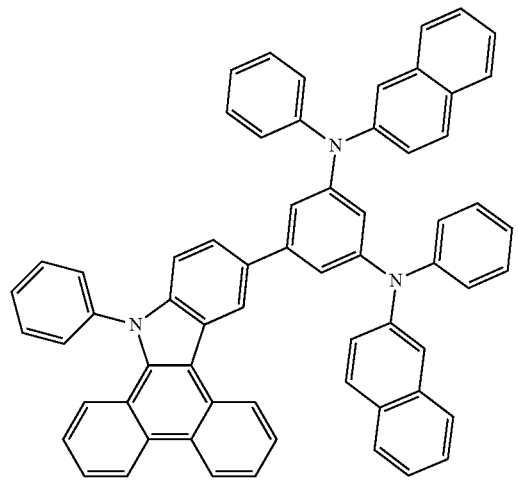
2-61
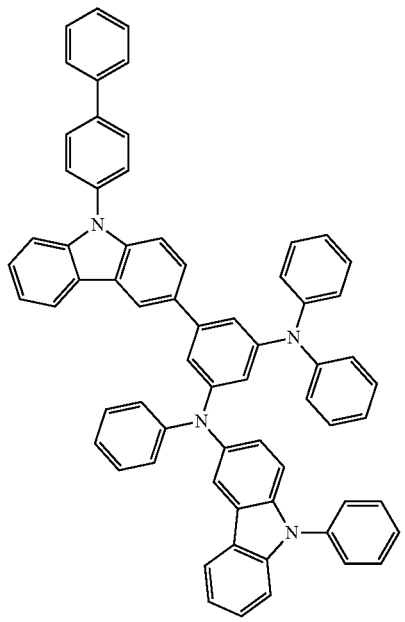

-continued
2-62
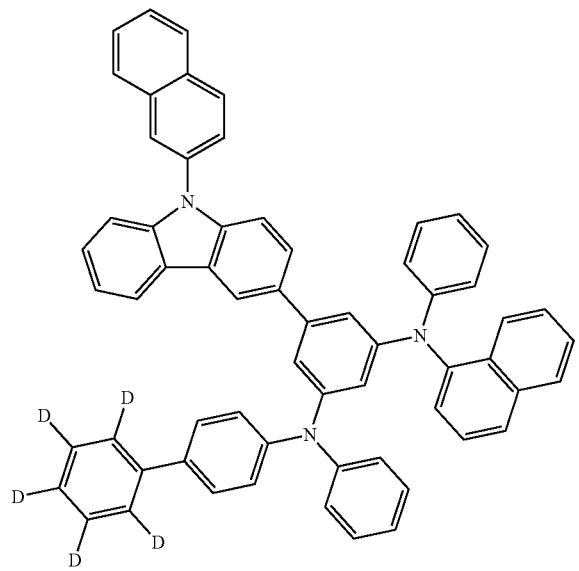
2-63
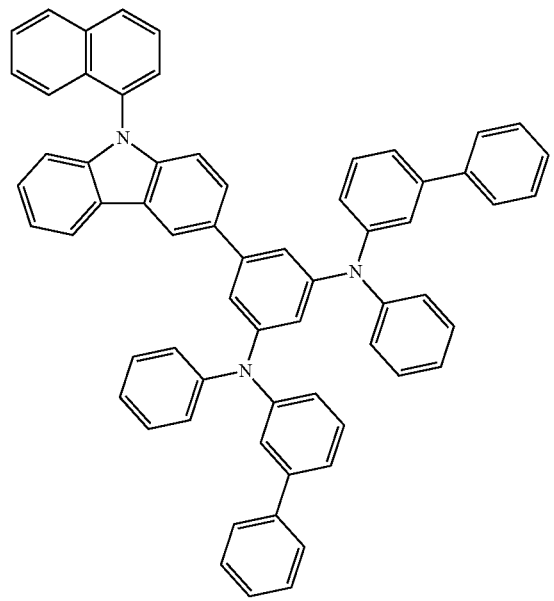
2-64
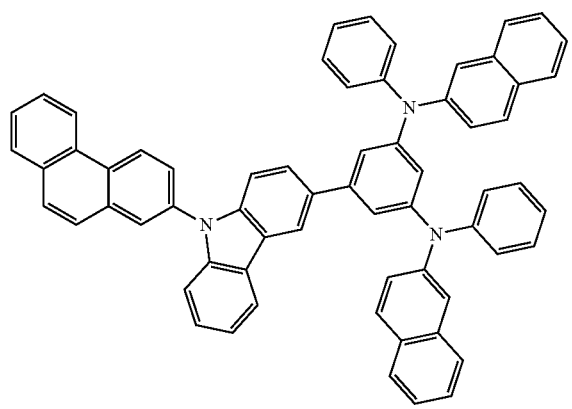
2-65
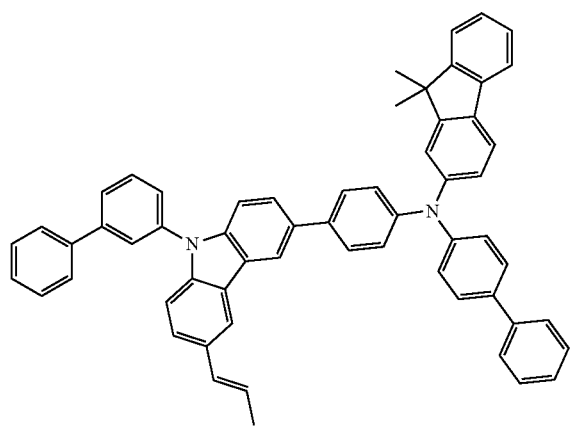
2-66
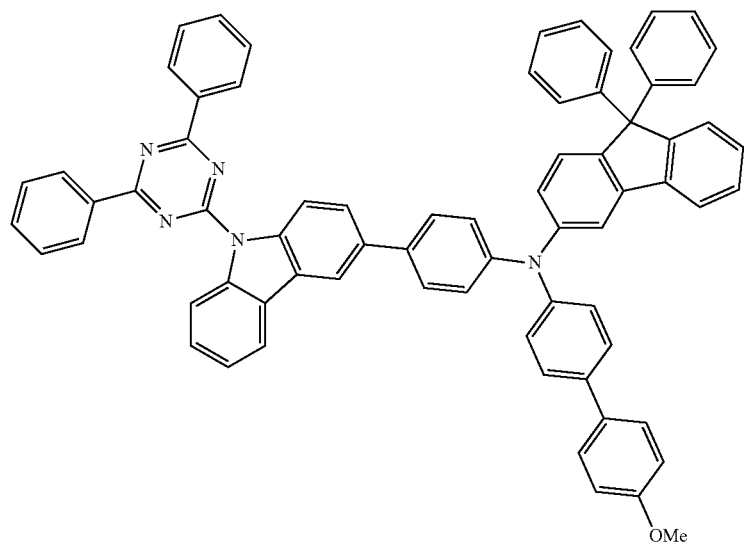

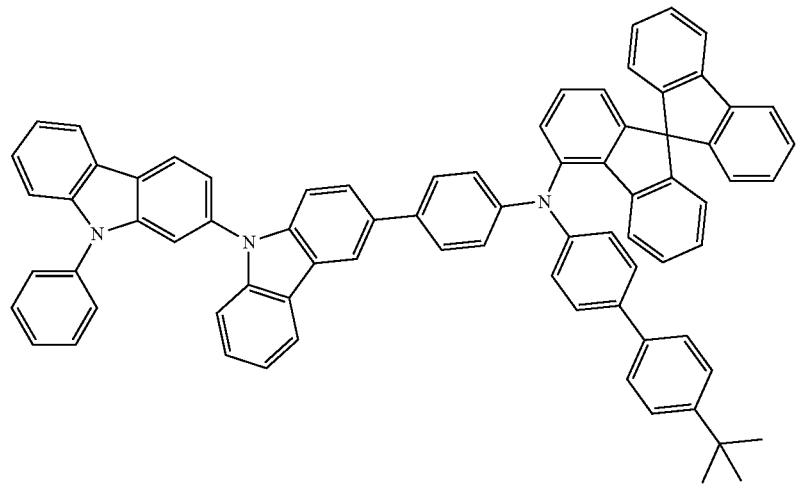
2-67
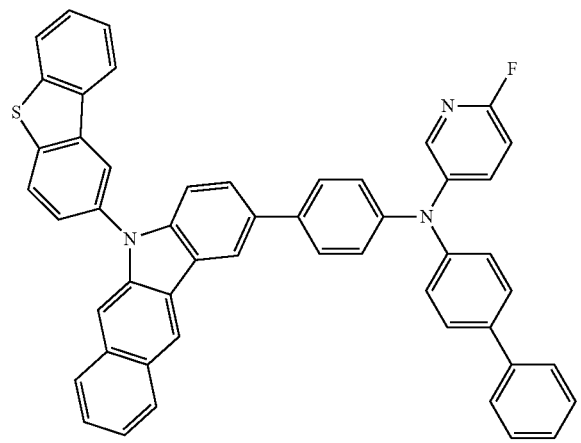
2-68
Further, in the present invention, the second host compound represented by Formula 2 includes one of the following Compounds 3-1 to 3-100.
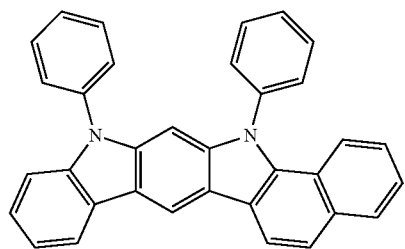
3-1
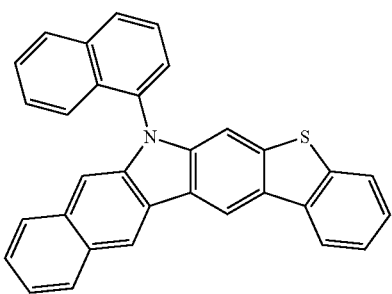
3-2

3-3
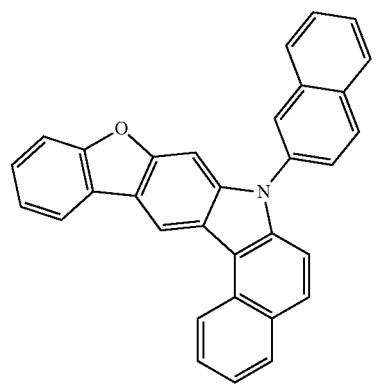
3-4
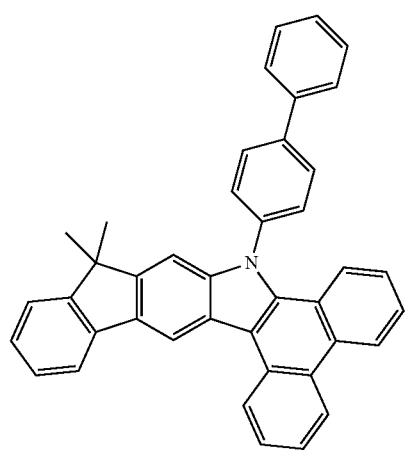
3-5
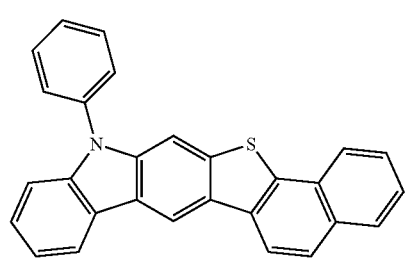
3-6
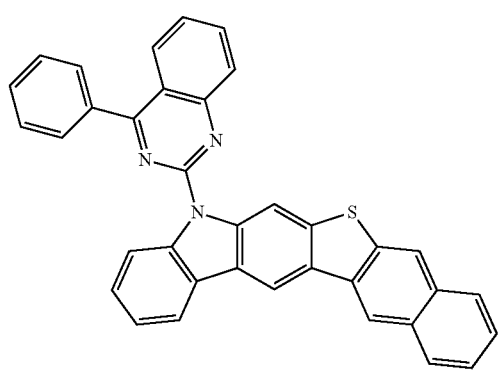
3-7
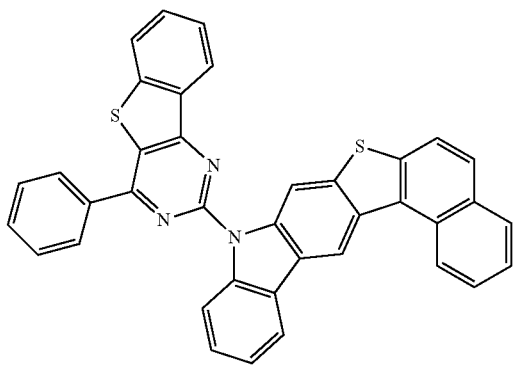
3-8
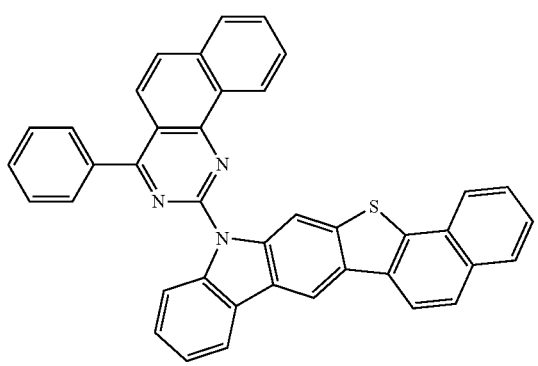
3-9
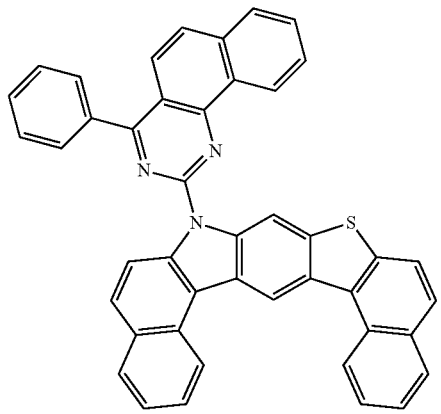
3-10
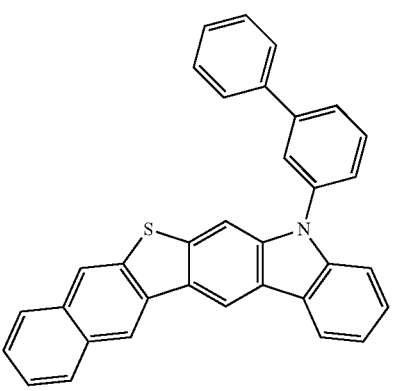

75
-continued
3-11
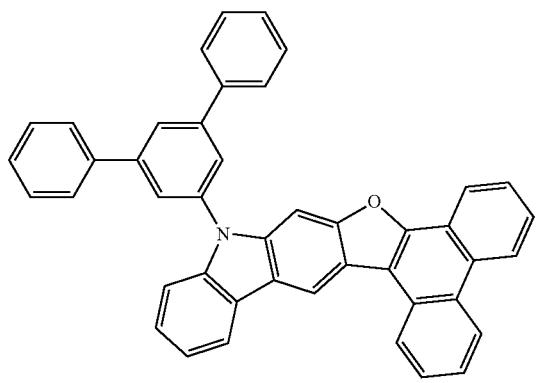
3-12
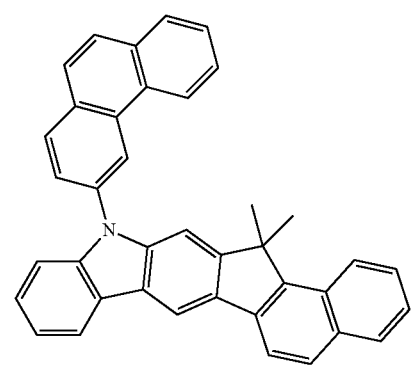
3-13
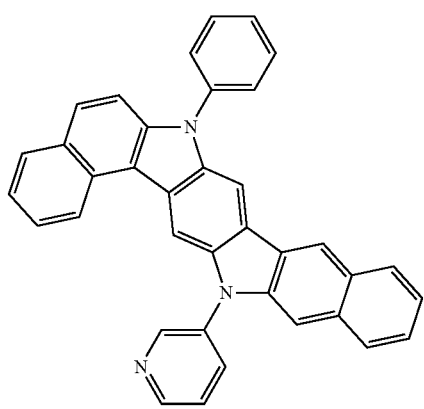
3-14
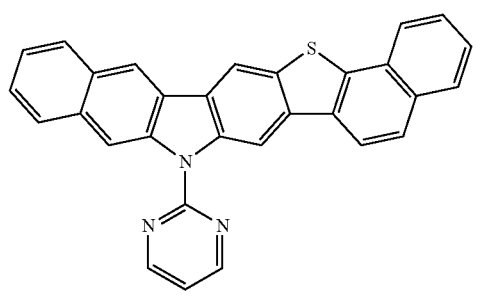
76
-continued
3-15
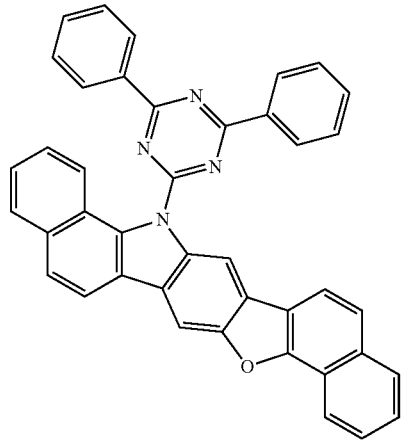
3-16
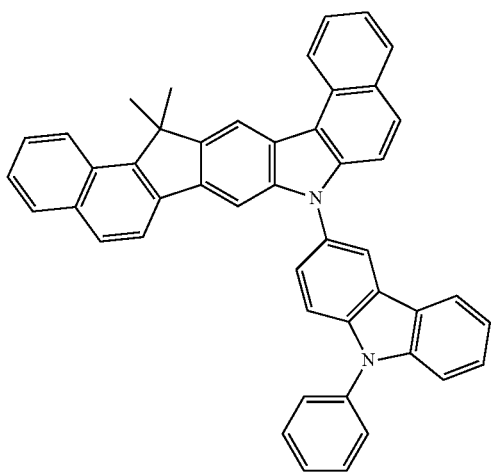
3-17
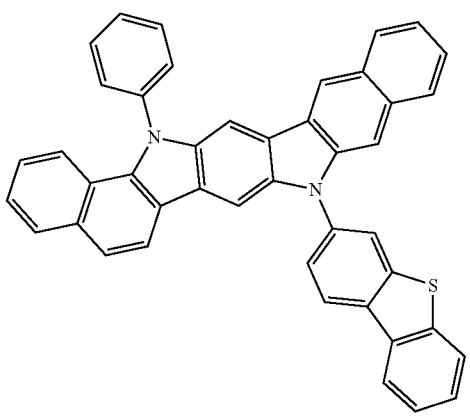
3-18
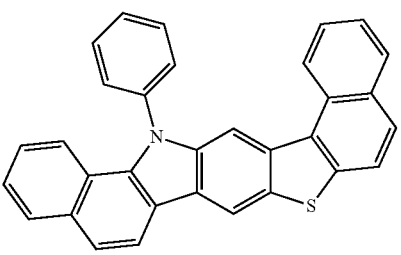

77
-continued
3-19
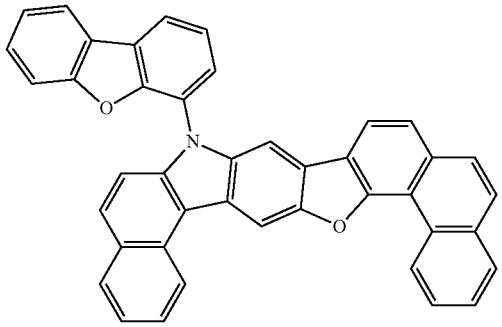
3-20
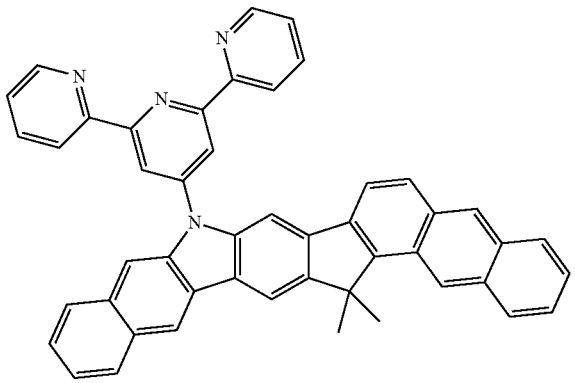
3-21
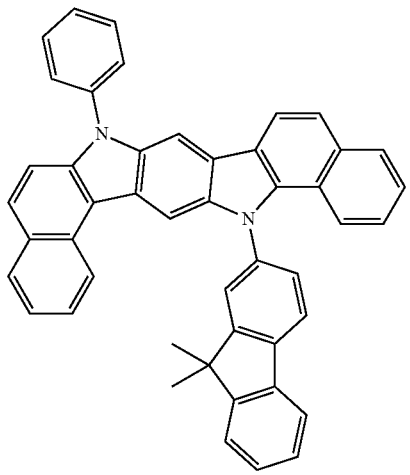
3-22
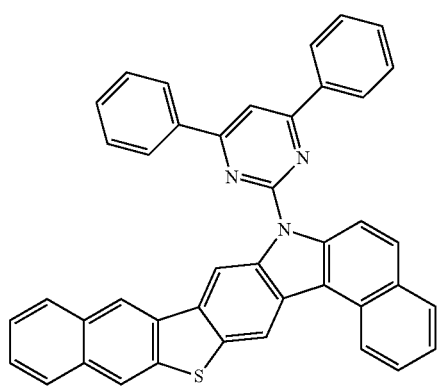
78
-continued
3-23
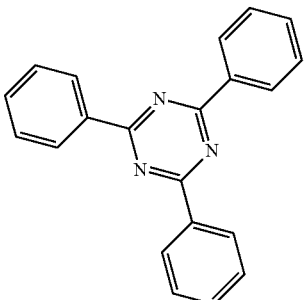
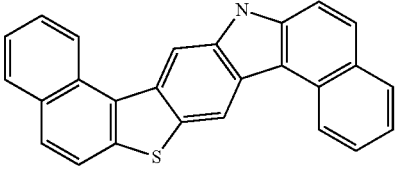
3-24
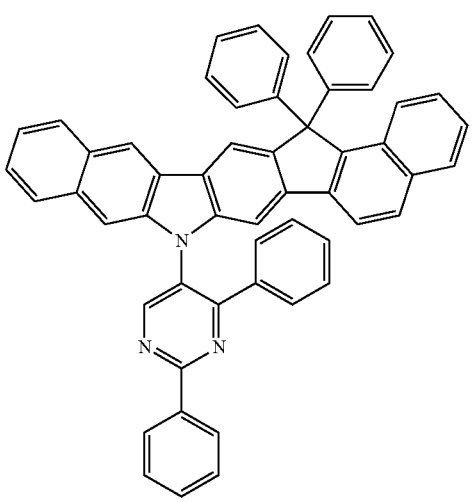
3-25
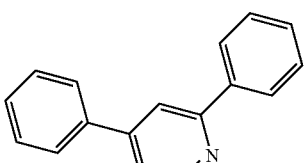
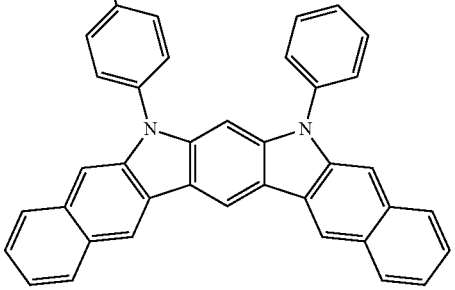

-continued
3-26
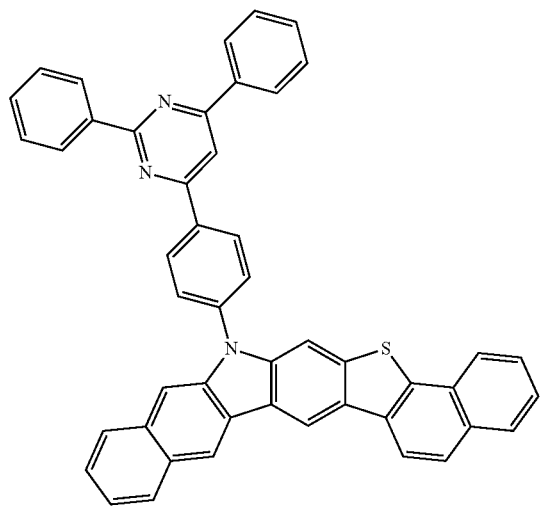
3-27
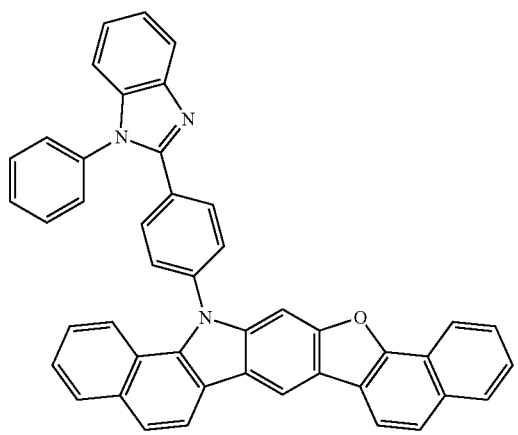
3-28
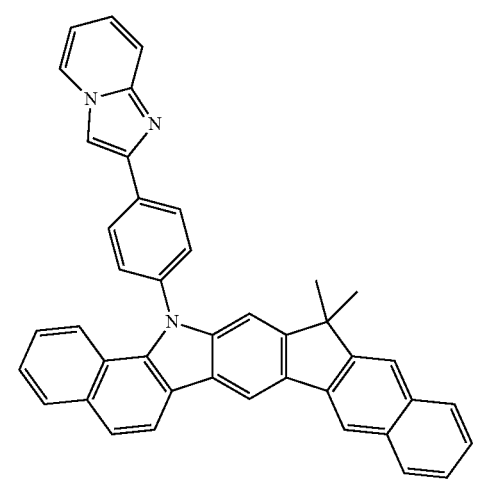
-continued
3-29
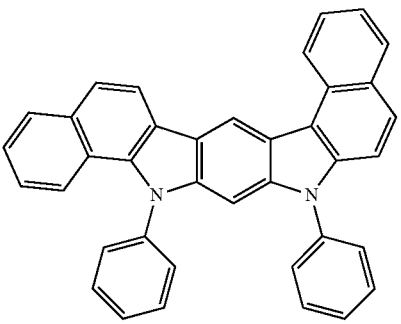
3-30
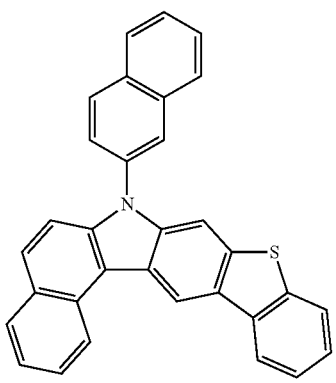
3-31
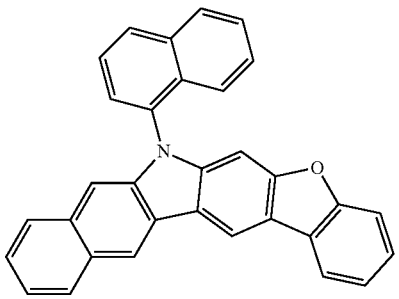
3-32
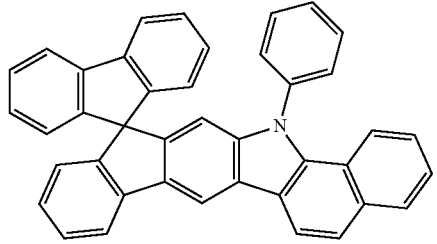
3-33
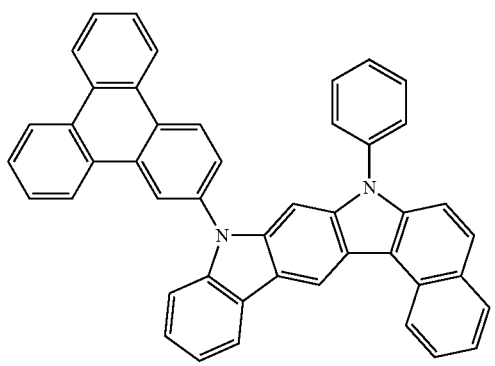

3-34
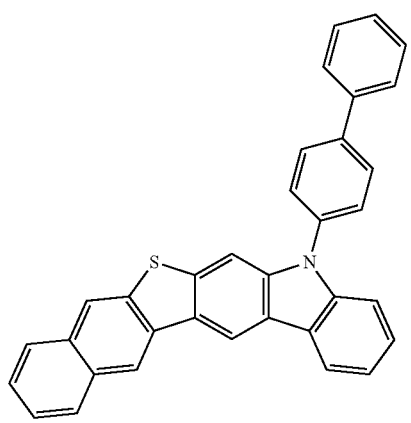
3-35
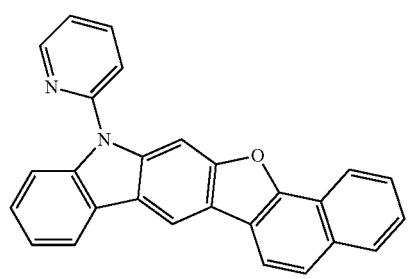
3-36
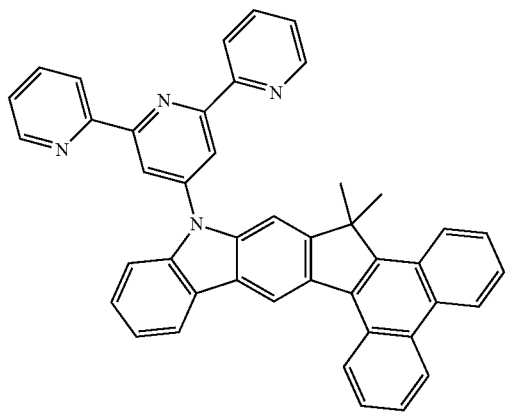
3-37
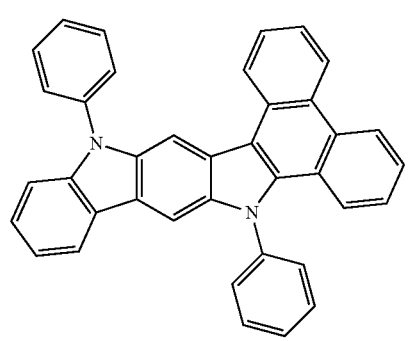
3-38
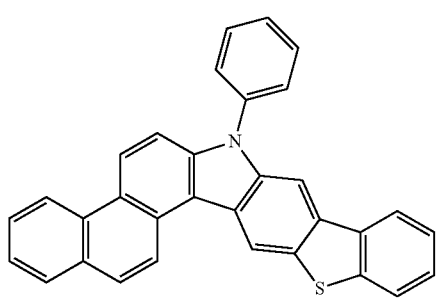
3-39
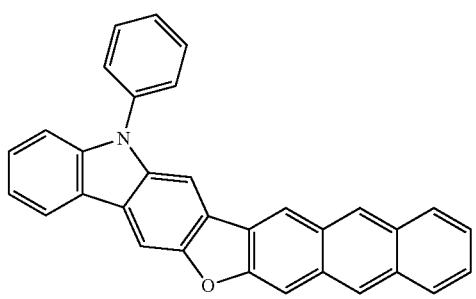
3-40
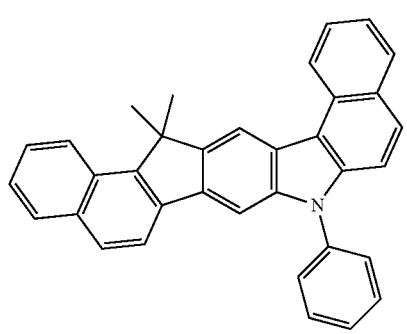
3-41
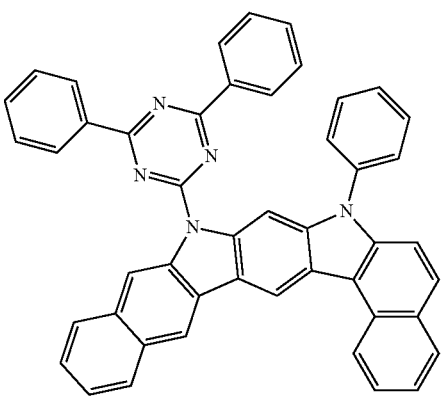

3-42
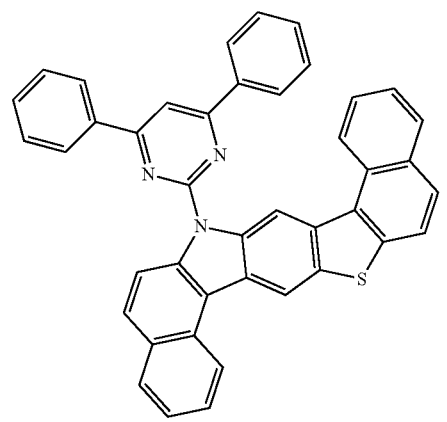
3-43
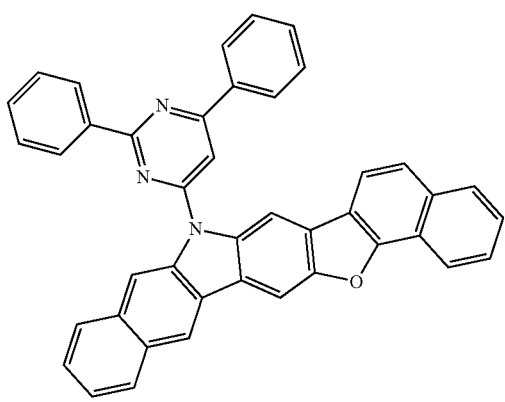
3-44
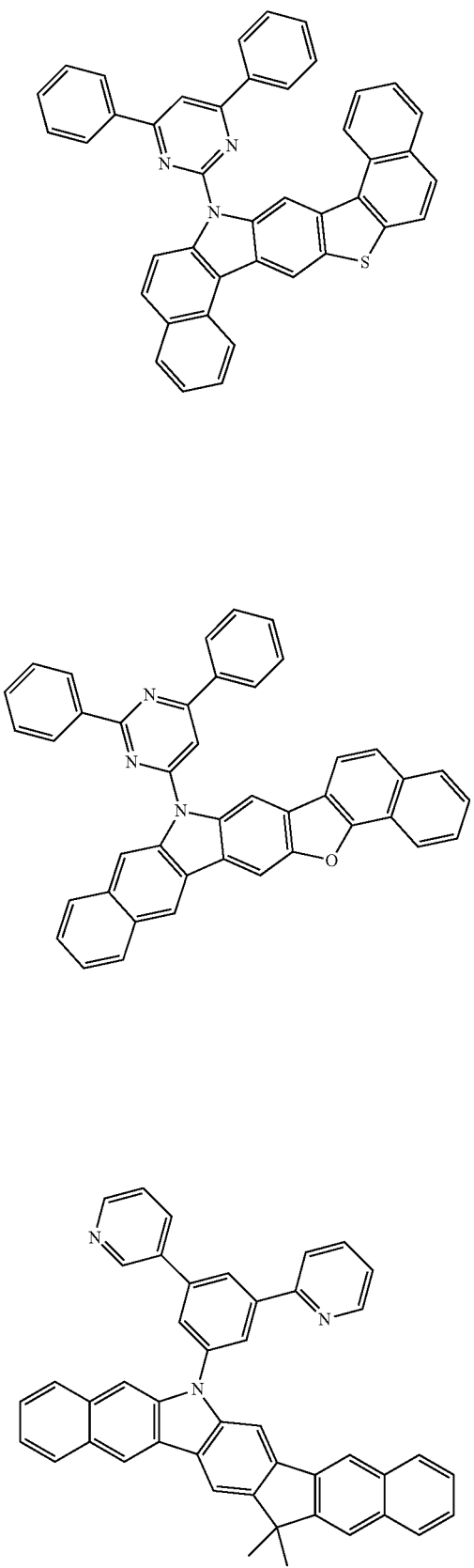
3-45
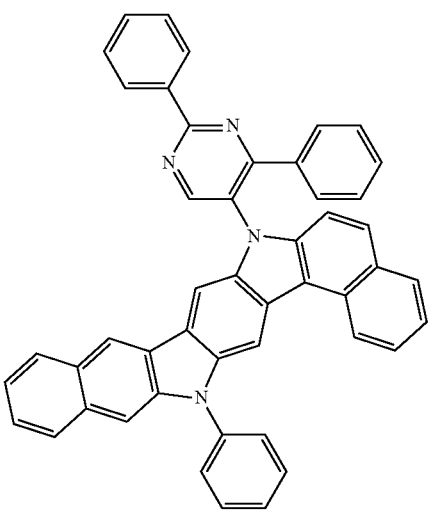
3-46
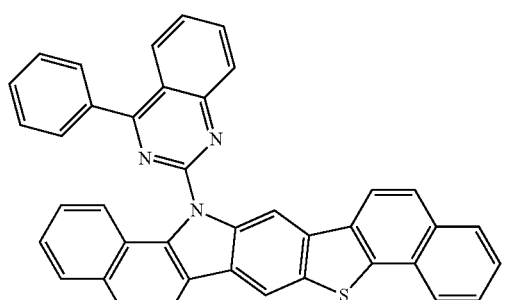
3-47
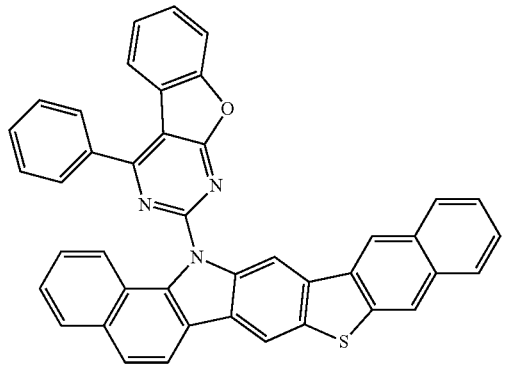
3-48
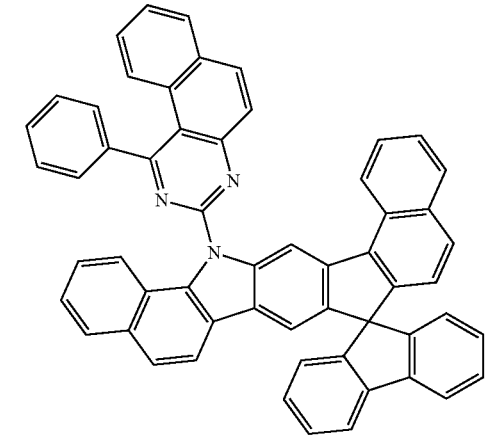

3-49
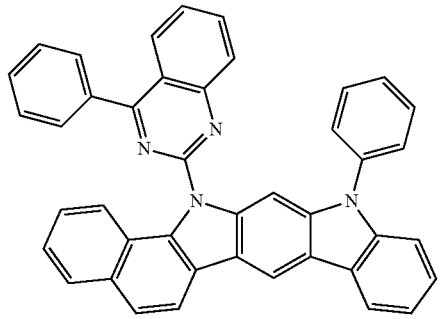
3-50
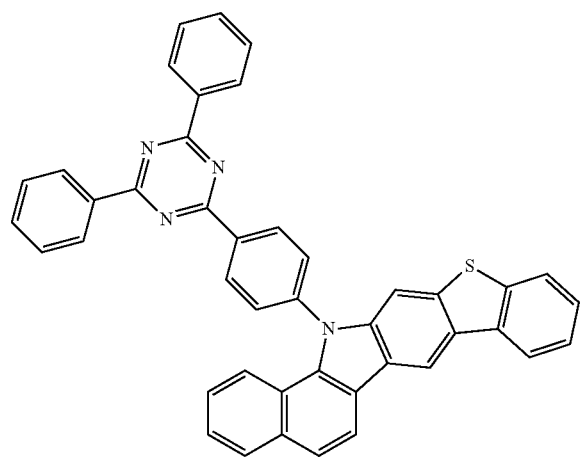
3-51
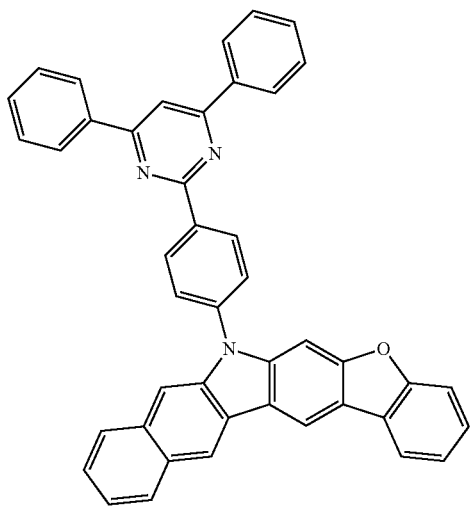
3-52
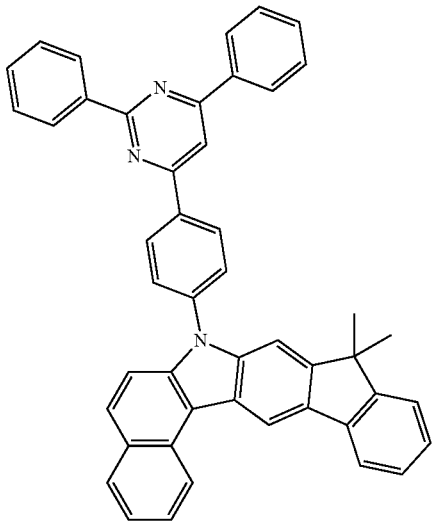
3-53
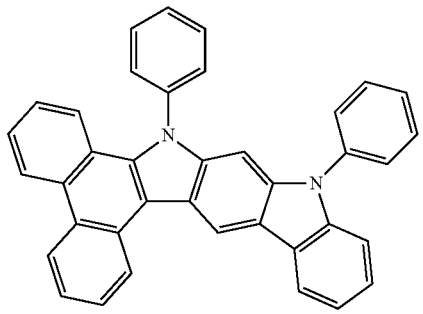
3-54
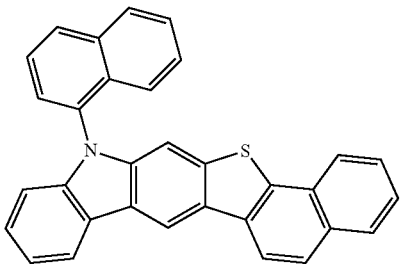
3-55
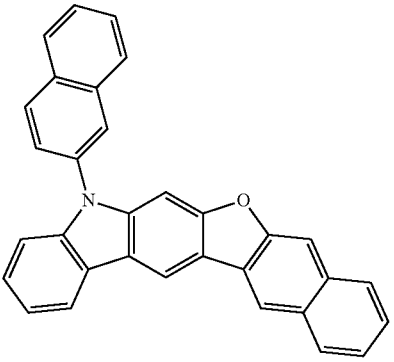

-continued
3-56
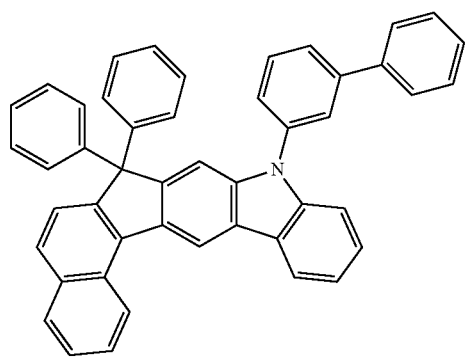
3-57
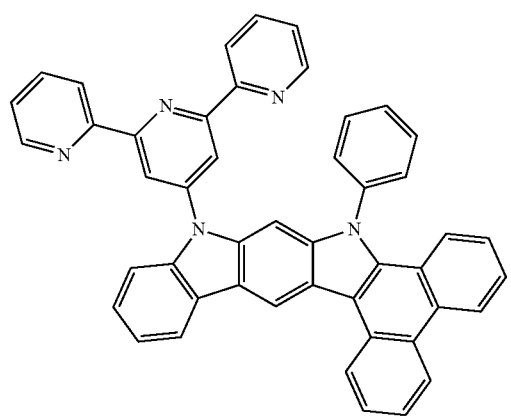
3-58
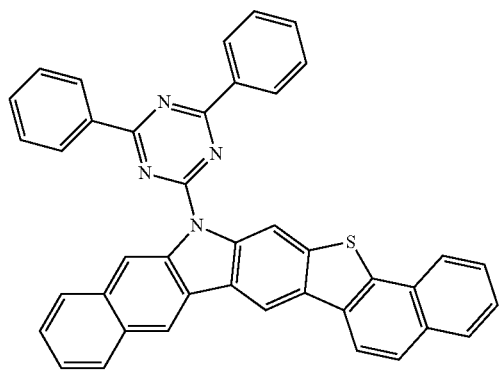
3-59
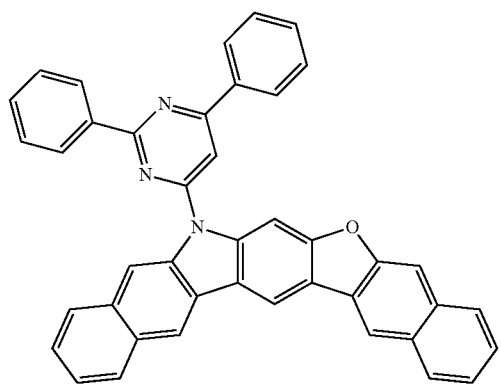
-continued
3-60
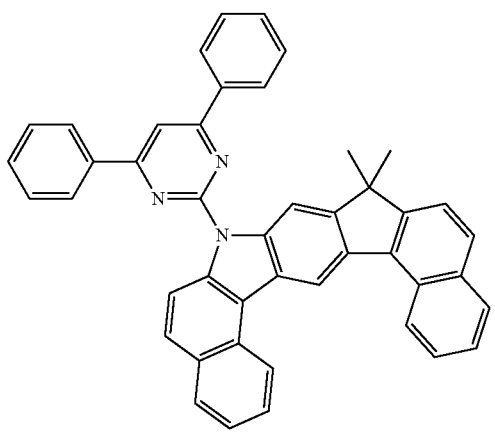
3-61
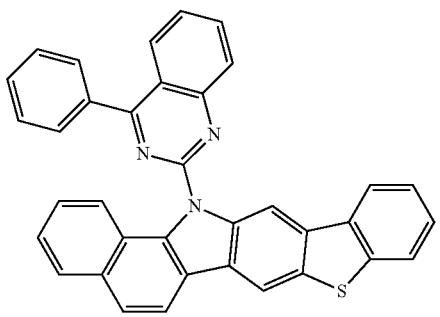
3-62
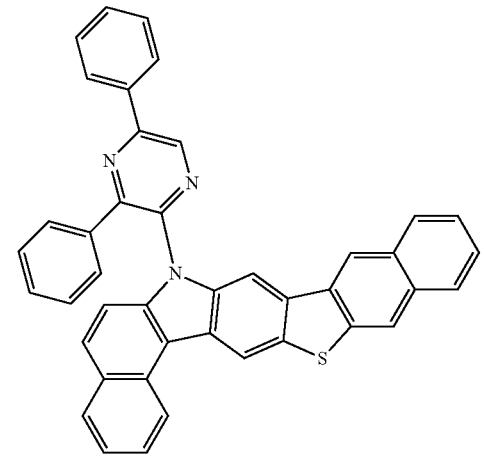
3-63
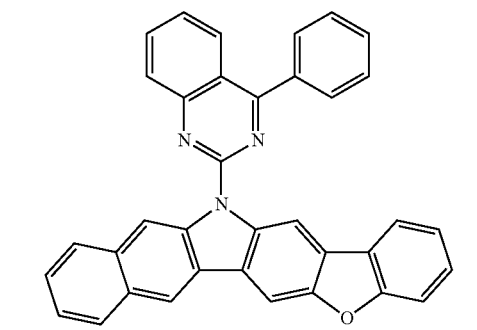

-continued
3-64
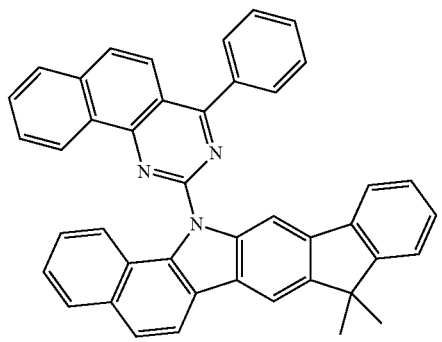
3-65
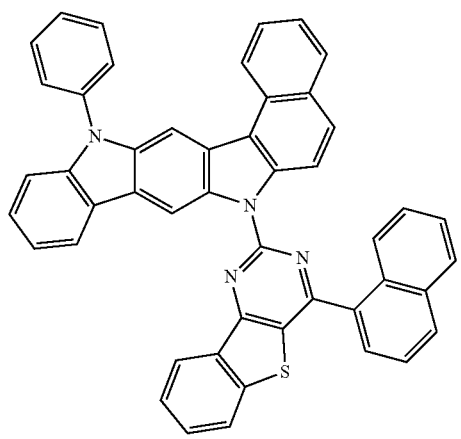
3-66
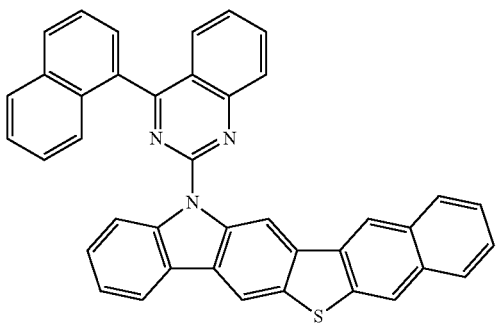
3-67
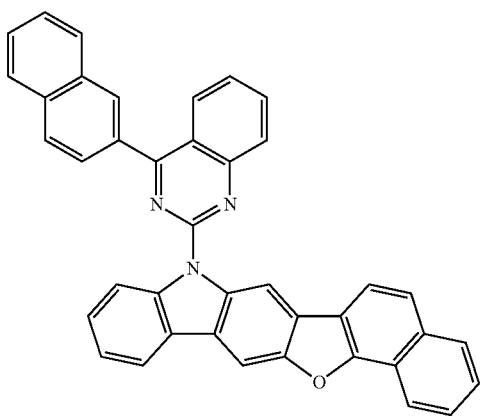
-continued
3-68
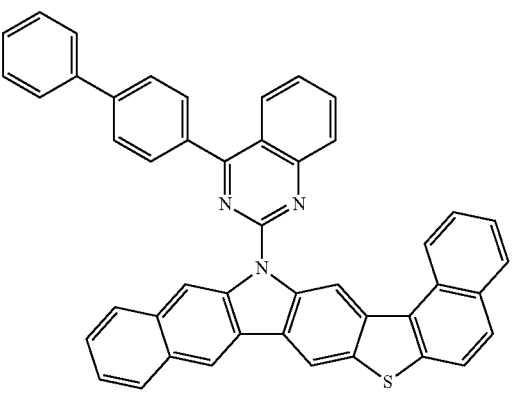
3-69
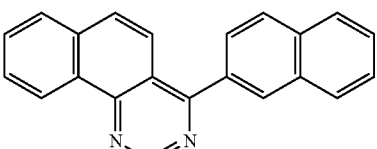
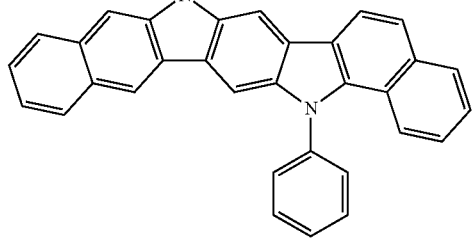
3-70
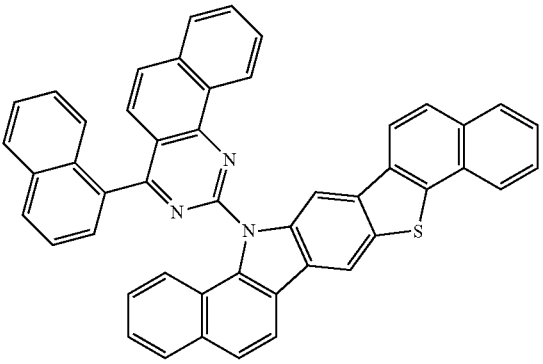

-continued
3-71
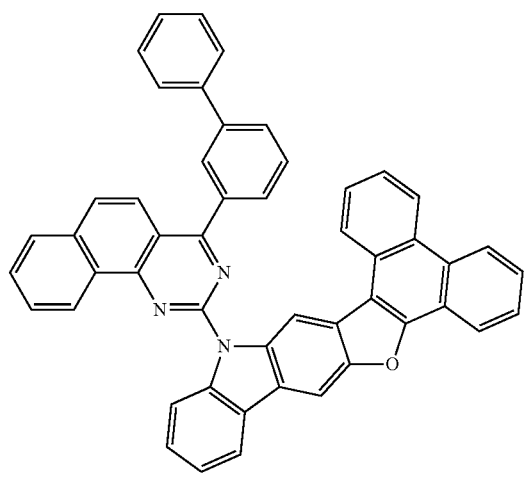
3-72
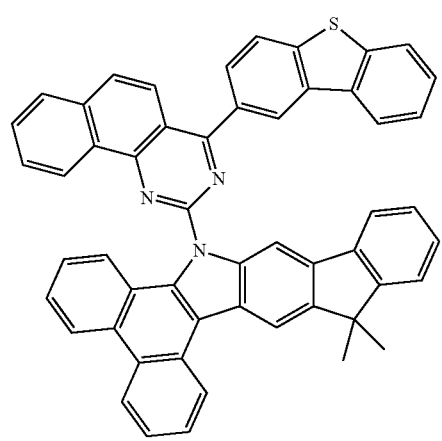
3-73
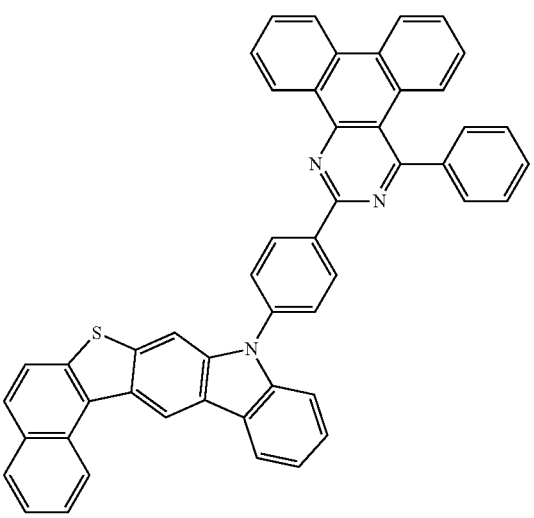
-continued
3-74
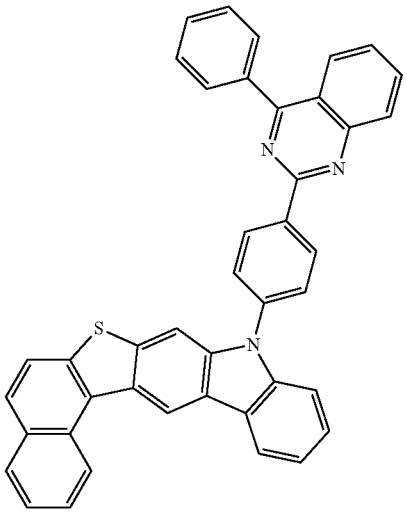
3-75
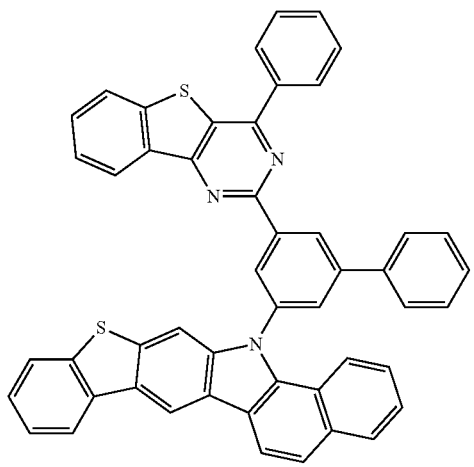
3-76
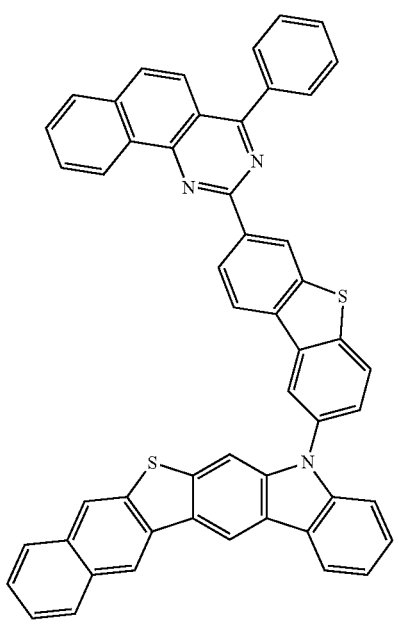

3-77
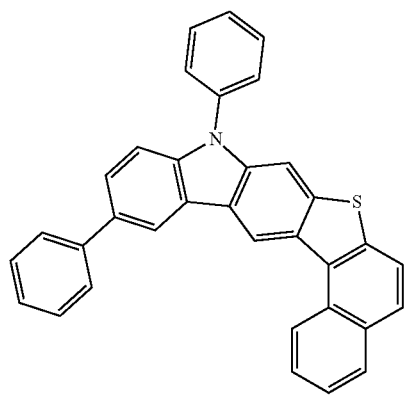
3-78
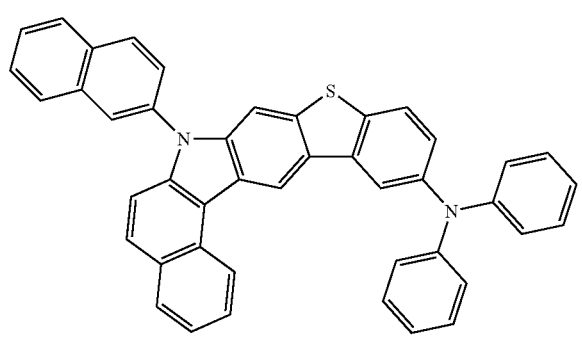
3-79
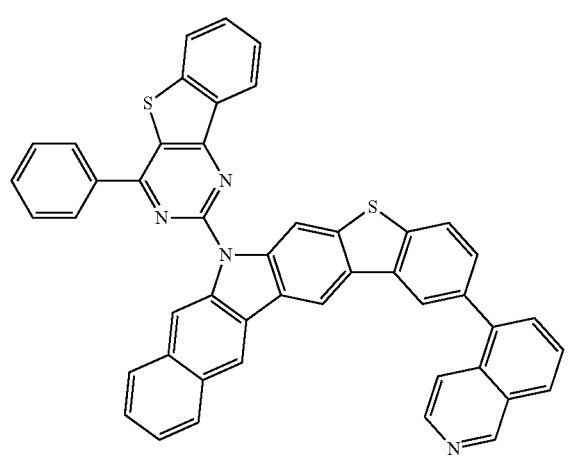
3-80
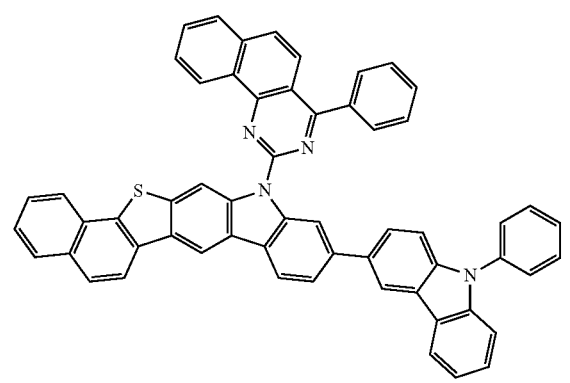
3-81
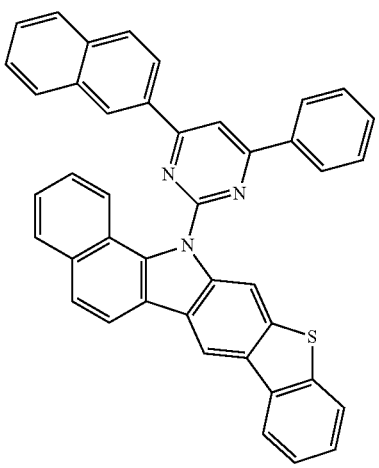
3-82
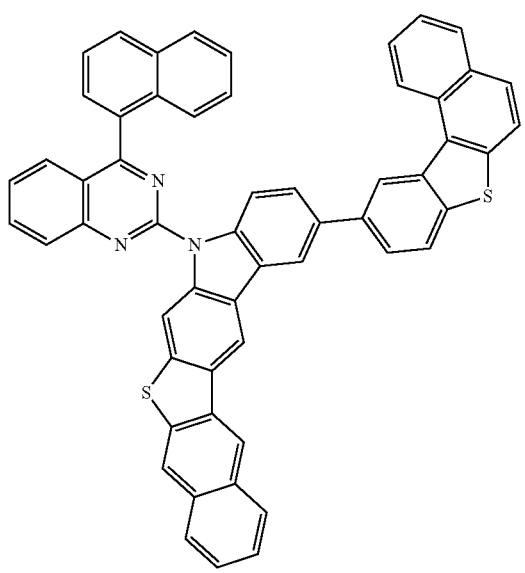
3-83
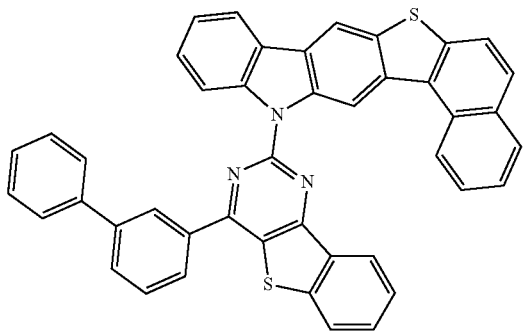

3-84
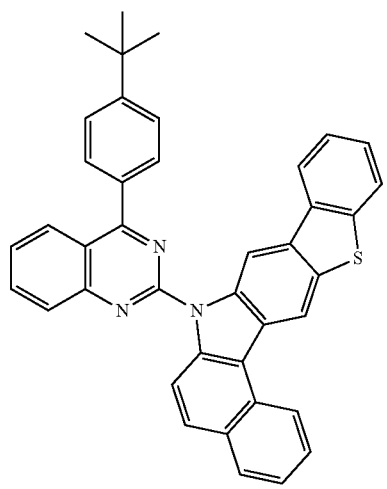
3-85
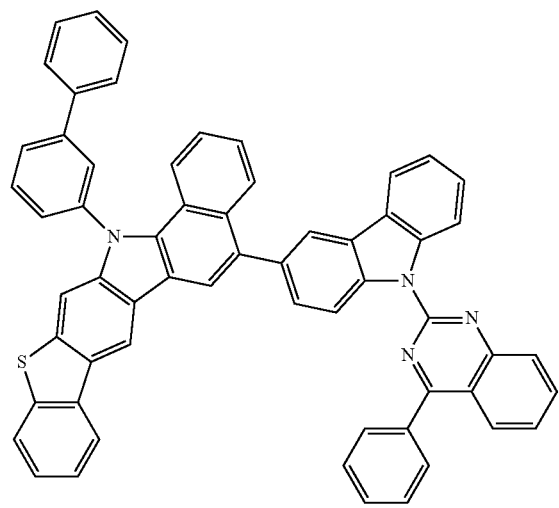
3-86
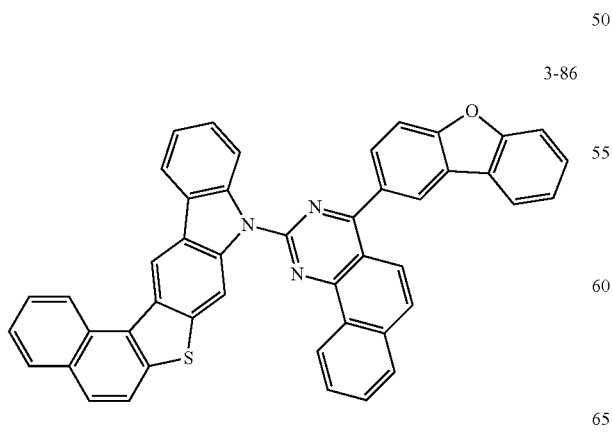
3-87
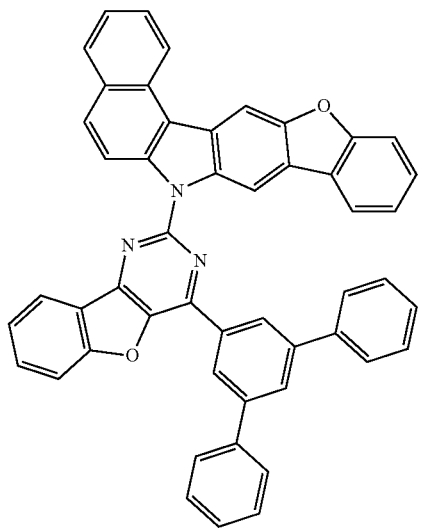
3-88
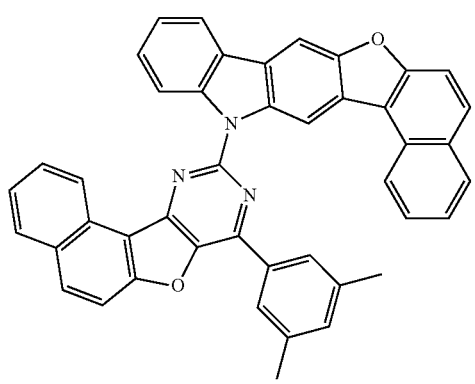
3-89
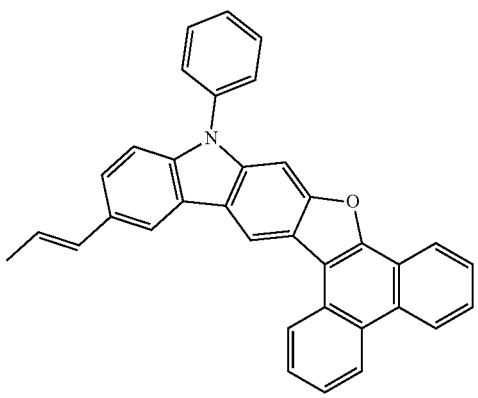

3-90
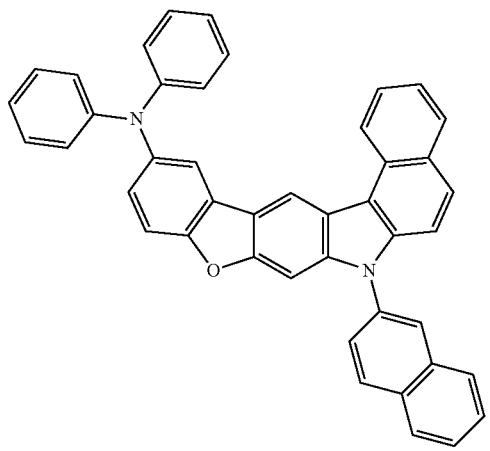
3-91
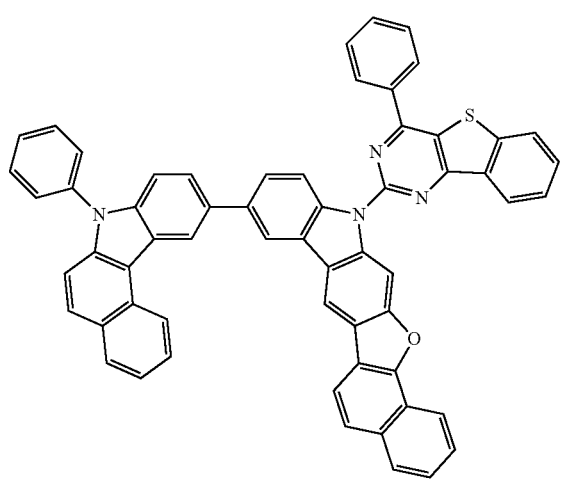
3-92
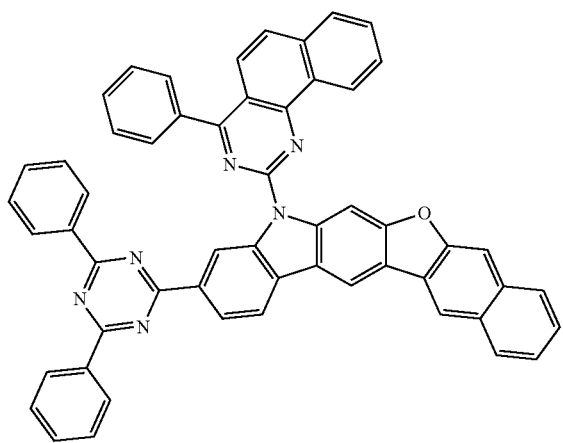
3-93
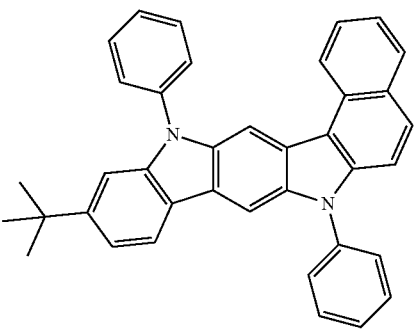
3-94
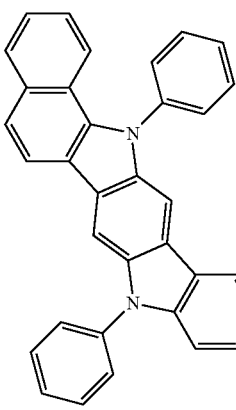
3-95
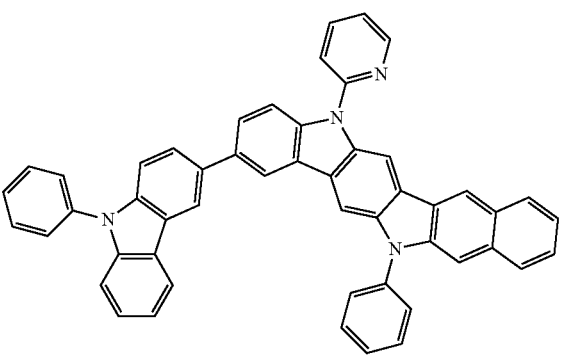
3-96
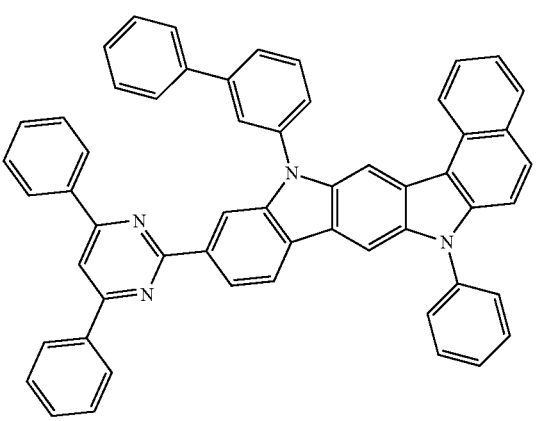

3-97 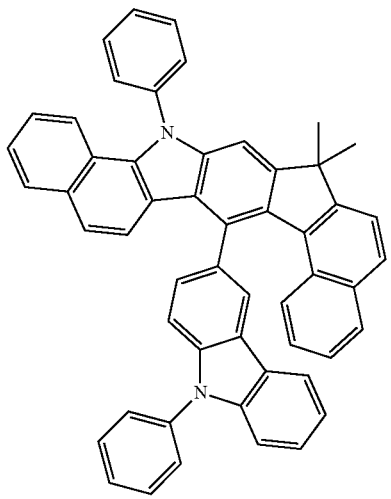

3-98 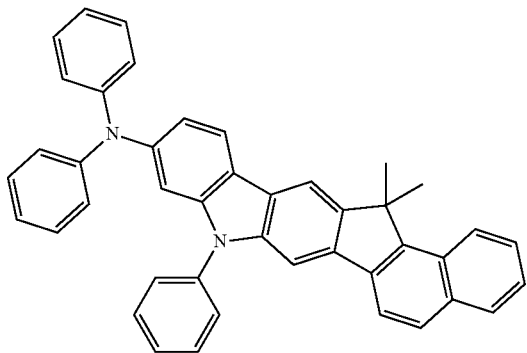

3-99 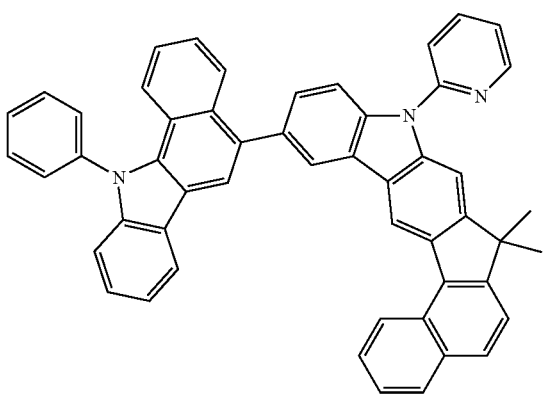

3-100 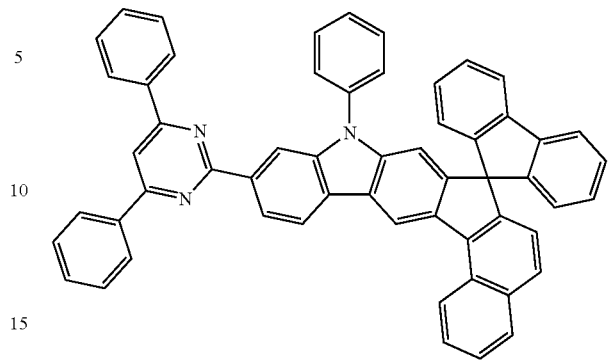

Referring to the FIGURE, the organic electric element (100) according to the present invention includes a first electrode (120) formed on a substrate (110), a second electrode (180), and an organic material layer including the compound represented by Formula 1 between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further include a hole blocking layer, an electron blocking layer, an emitting-auxiliary layer (151), an electron transport auxiliary layer, a buffer layer (141), etc., and the electron transport layer (160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and Ti values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emission auxiliary layer (151) may be further formed between the hole transport layer (140) and the emitting layer (150), and an electron transport auxiliary layer may be further formed between the emitting layer (150) and the electron transport layer (160).

The present invention may further include a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

As another specific example, the present invention provides an organic electric element wherein the emitting layer in the organic material layer is a phosphorescent light emitting layer.

The compounds represented by Formula 1 and 2 are mixed in a ratio of any one of 1:9 to 9:1 to be included in the emitting layer of the organic material layer.

The compound represented by Formula 1 and 2 are mixed in a ratio of any one of 1:9 to 5:5 to be included in the emitting layer of the organic material layer. More preferably, the mixing ratio of the compound represented by Formula 1 and 2 is 2:8 or 3:7 to be included in the emitting layer.

The organic electric element according to an embodiment of the present invention may be a front emission type, a back emission type, or a both-sided emission type, depending on the material used.

WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the radiation part of the R (red), G (green) and B (blue), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an display device wherein the organic electric element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula 1 of the present invention and preparation examples of the organic electric element of the present invention will be described in detail by way of example, but are not limited to the following examples.

Synthesis Example 1

The final products 1 represented by Formula 1 of the present invention can be synthesized by reaction between Sub 1 and Sub 2 as illustrated in the following Reaction Scheme 1.

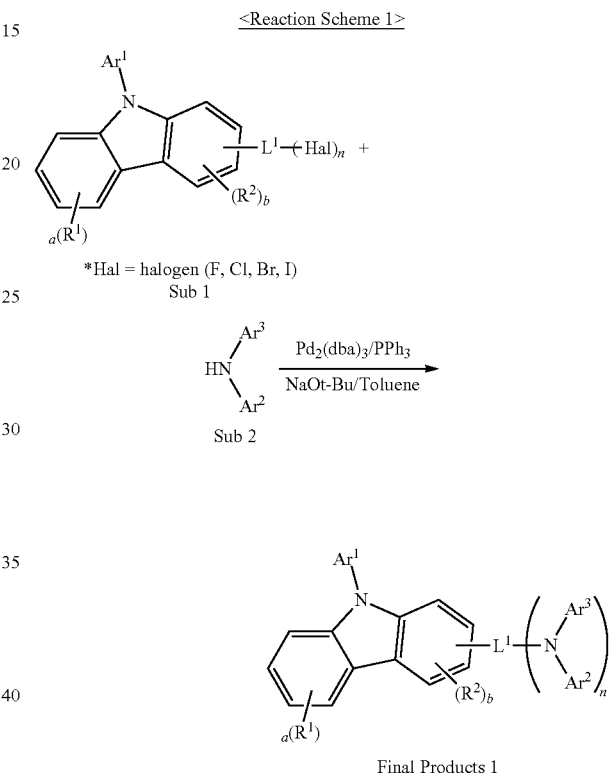

<Reaction Scheme 1>

*Hal = halogen (F, Cl, Br, I)
Sub 1

Sub 2

Final Products 1

Synthesis Examples of Sub 1

When $L^1$ in Sub 1 of Reaction Scheme 1 is not a single bond, it can be synthesized by the reaction path of the following Reaction Scheme 2, but is not limited thereto.

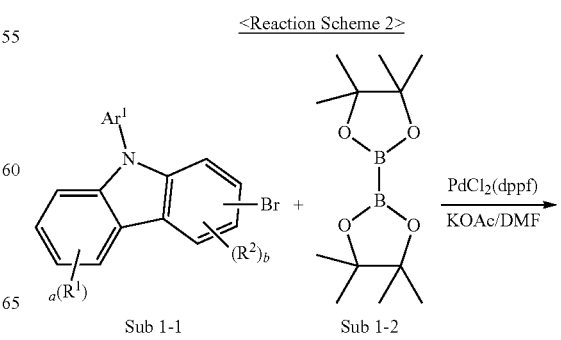

<Reaction Scheme 2>

Sub 1-1     Sub 1-2

Synthesis Examples of Sub 1-3(1)

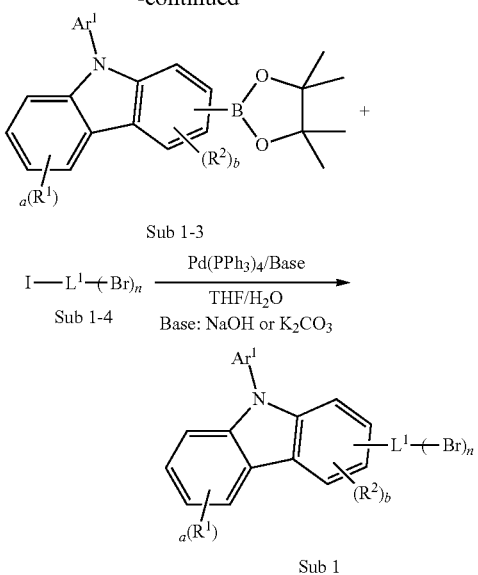

Sub 1-3

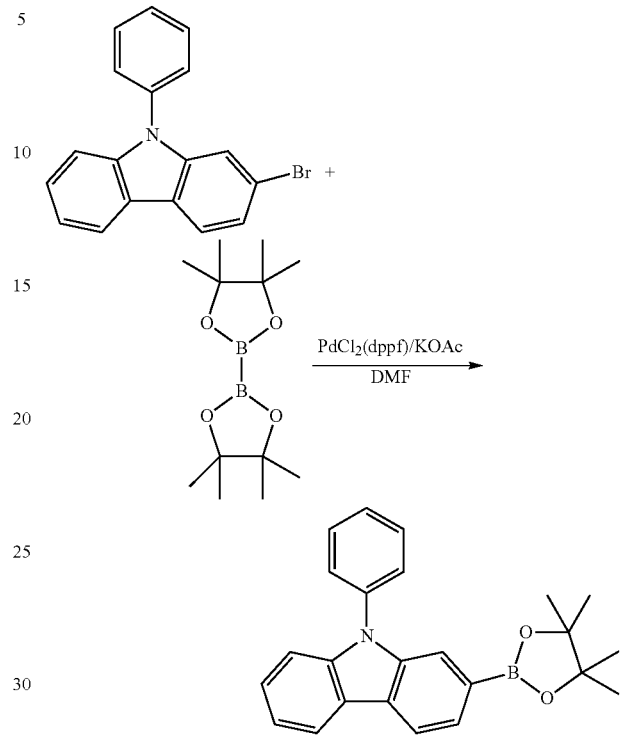

Sub 1

Synthesis Examples of Sub 1-3(1)

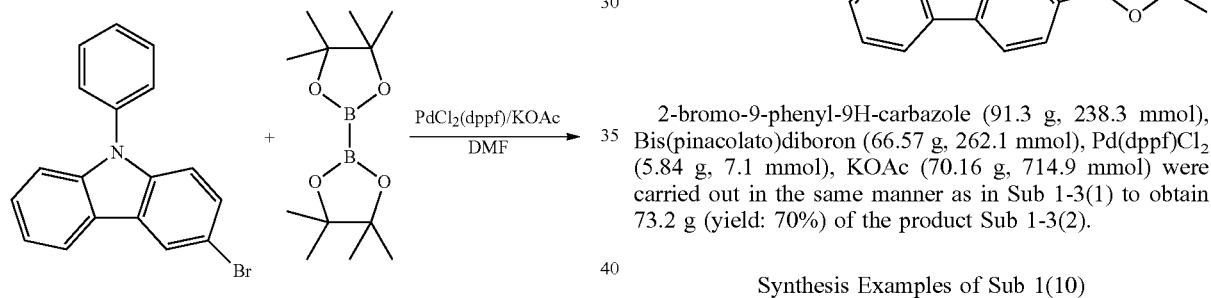

3-bromo-9-phenyl-9H-carbazole (45.1 g, 140 mmol) was dissolved in DMF 980 mL, Bispinacolborate (39.1 g, 154 mmol), PdCl$_2$(dppf) catalyst (3.43 g, 4.2 mmol), KOAc (41.3 g, 420 mmol) were added in order and stirred for 24 hours and then after synthesizing the borate compound, the obtained compound was separated over a silicagel column and recrystallization to give 35.2 g of the borate compound (yield: 68%).

Synthesis Examples of Sub 1-3(2)

2-bromo-9-phenyl-9H-carbazole (91.3 g, 238.3 mmol), Bis(pinacolato)diboron (66.57 g, 262.1 mmol), Pd(dppf)Cl$_2$ (5.84 g, 7.1 mmol), KOAc (70.16 g, 714.9 mmol) were carried out in the same manner as in Sub 1-3(1) to obtain 73.2 g (yield: 70%) of the product Sub 1-3(2).

Synthesis Examples of Sub 1(10)

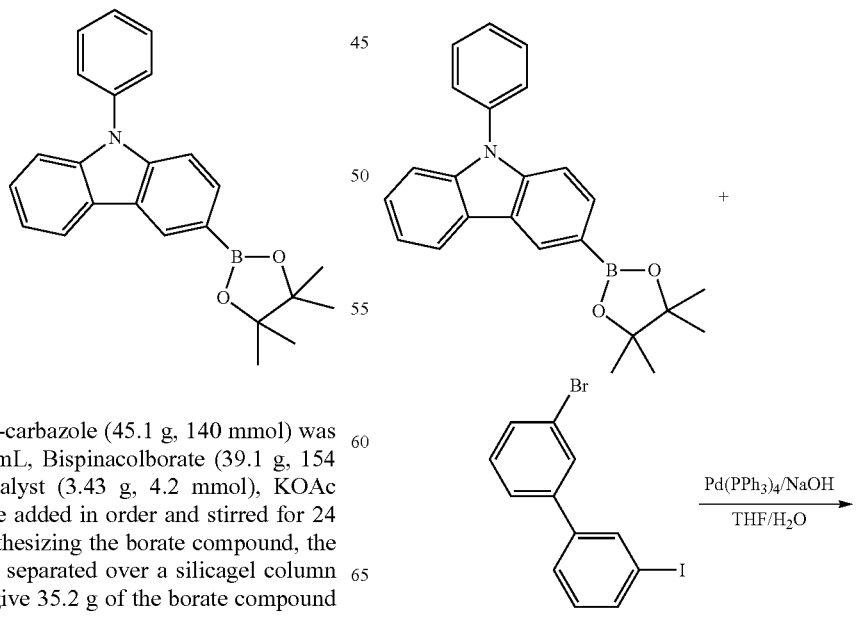

-continued

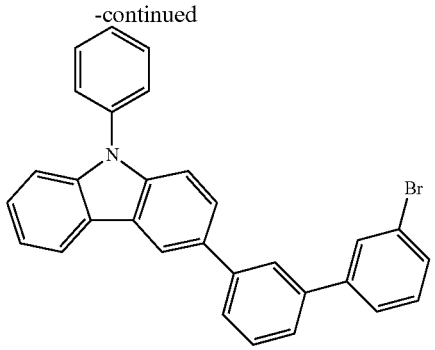

9-phenyl-3-(4,4,5,5-tetramethyl-1,3,2-dioxaborolan-2-yl)-9H-carbazole (29.5 g, 80 mmol) were dissolved in THF 360 mL, 3-bromo-3'-iodo-1,1'-biphenyl (30.16 g, 84 mmol), Pd(PPh$_3$)$_4$(2.8 g, 2.4 mmol), NaOH (9.6 g, 240 mmol), 180 mL of water were added and were refluxed with stirring. After the reaction was completed, the reaction mixture was extracted with ether and water. The organic layer was dried over MgSO$_4$ and concentrated. The resulting organic material was separated by silicagel column chromatography and recrystallization to obtain 26.56 g (yield: 70%) of the product.

Synthesis Examples of Sub 1(3)

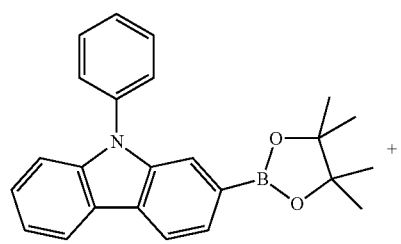

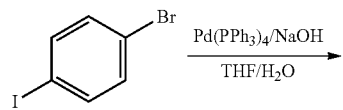

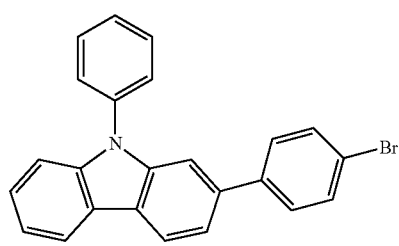

9-phenyl-2-(4,4,5,5-tetramethyl-1,3,2-dioxaborolan-2-yl)-9H-carbazole (29.5 g, 80 mmol), THF 360 mL, 1-bromo-4-iodobenzene (23.8 g, 84 mmol), Pd(PPh$_3$)$_4$(2.8 g, 2.4 mmol), NaOH (9.6 g, 240 mmol), and 180 mL of water were carried out in the same manner as in Sub 1(10) to obtain 22.9 g of the product Sub 1(3) (yield: 72%).

Synthesis Examples of Sub 1(5)

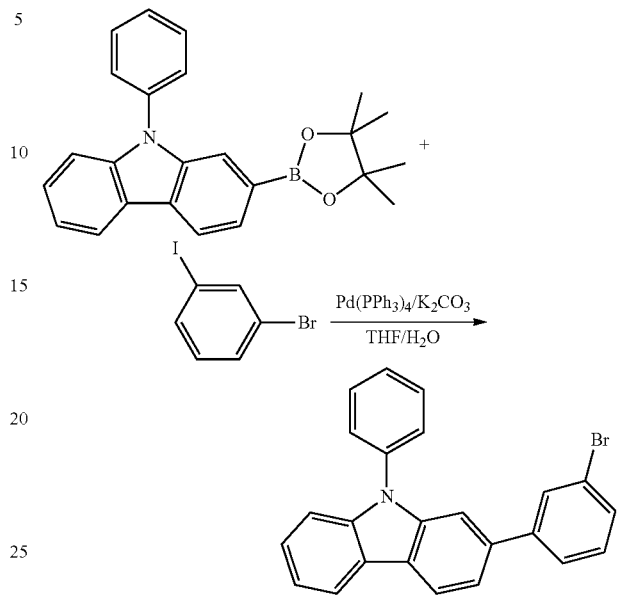

9-phenyl-2-(4,4,5,5-tetramethyl-1,3,2-dioxaborolan-2-yl)-9H-carbazole (73.92 g, 200.2 mmol) were dissolved in THF 880 mL in a round bottom flask, 1-bromo-2-iodobenzene (85.0 g, 300.3 mmol), Pd(PPh$_3$)$_4$(11.6 g, 10 mmol), K$_2$CO$_3$ (83 g, 600.6 mmol), and 440 mL of water were carried out in the same manner as in Sub 1(10) to obtain 55.8 g of the product Sub 1(5) (yield: 70%).

Synthesis Examples of Sub 1(15)

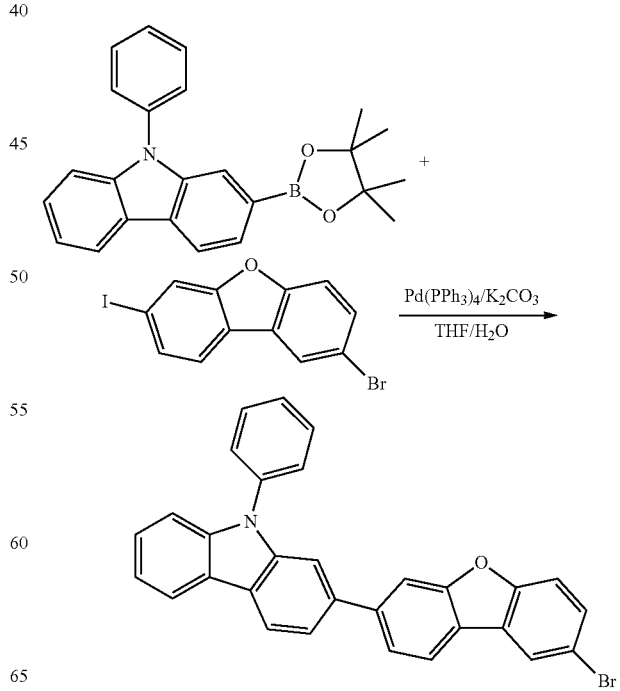

9-phenyl-2-(4,4,5,5-tetramethyl-1,3,2-dioxaborolan-2-yl)-9H-carbazole (73.92 g, 200.2 mmol) were dissolved in THF 880 mL in a round bottom flask, 2-bromo-7-iodod-ibenzo[b,d]furan (112.0 g, 300.3 mmol), Pd(PPh₃)₄(11.6 g, 10 mmol), K₂CO₃ (83 g, 600.6 mmol), and 440 mL of water were carried out in the same manner as in Sub 1(10) to obtain 72.4 g of the product Sub 1(15) (yield: 74%).

Synthesis Examples of Sub 1(22)

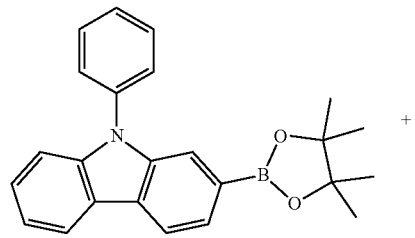

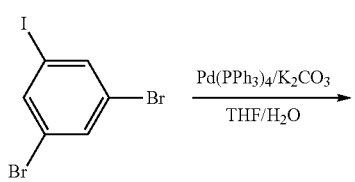

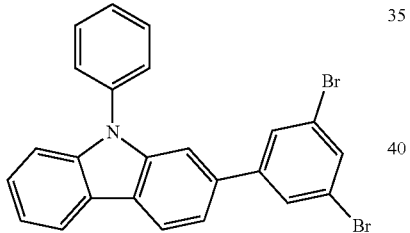

9-phenyl-2-(4,4,5,5-tetramethyl-1,3,2-dioxaborolan-2-yl)-9H-carbazole (73.92 g, 200.2 mmol) were dissolved in THF 880 mL in a round bottom flask, 1,3-dibromo-5-iodobenzene (108.65 g, 300.3 mmol), Pd(PPh₃)₄(11.6 g, 10 mmol), K₂CO₃ (83 g, 600.6 mmol), and 440 mL of water were carried out in the same manner as in Sub 1(10) to obtain 69.7 g of the product Sub 1(22) (yield: 73%).

Examples of Sub 1 are as follows, but are not limited thereto.

Sub1(1)

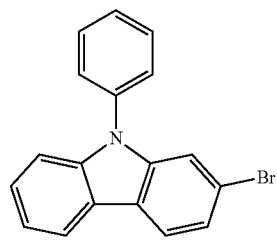

Sub1(2)

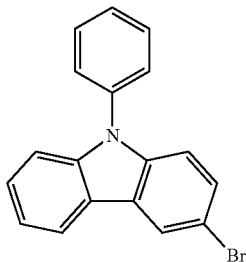

Sub1(3)

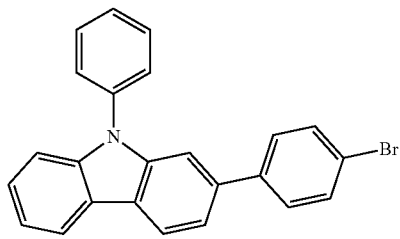

Sub1(4)

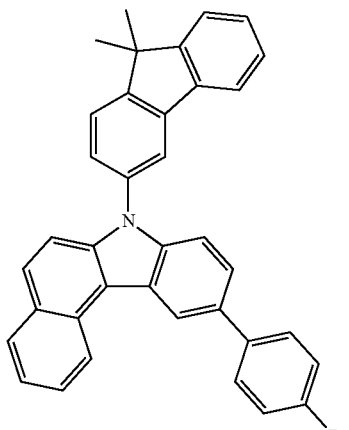

Sub1(5)

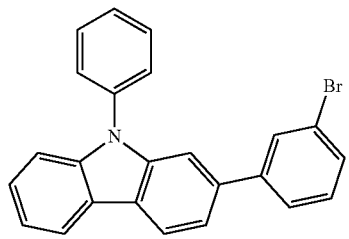

Sub1(6)

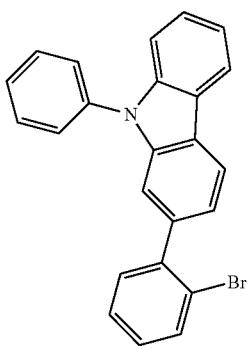

Sub1(7)
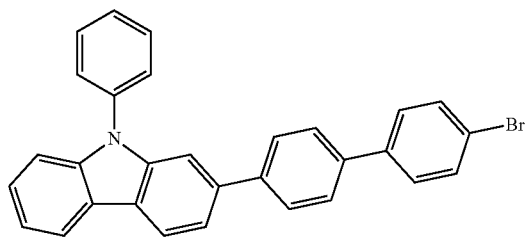
Sub1(8)
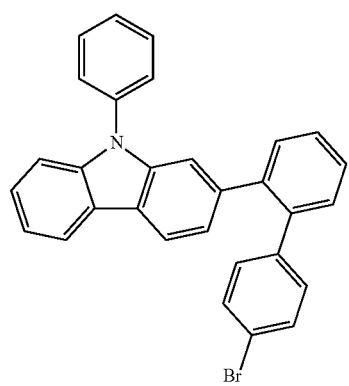
Sub1(9)
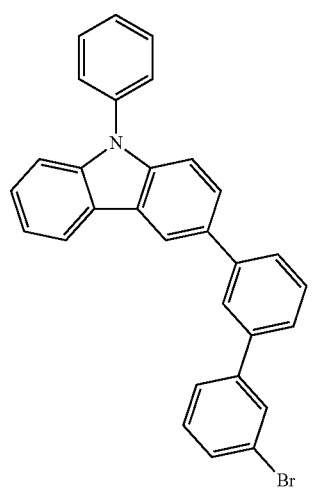
Sub1(10)
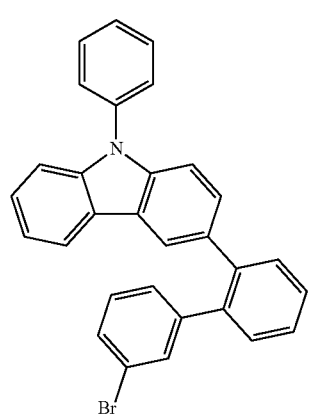
Sub1(11)
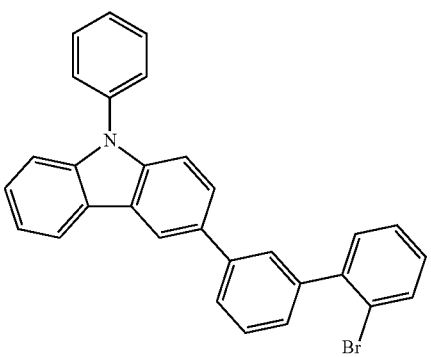
Sub1(12)
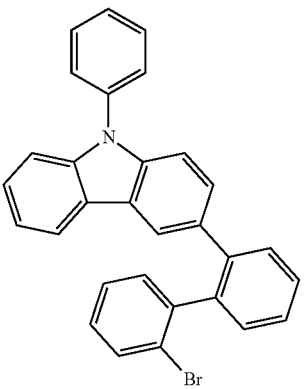
Sub1(13)
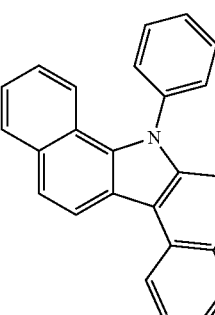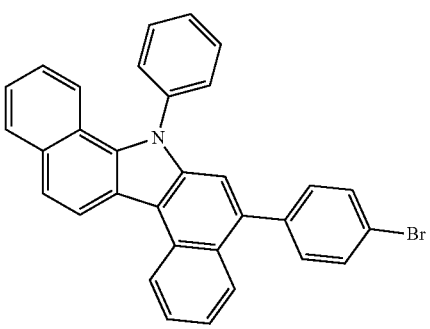
Sub1(14)
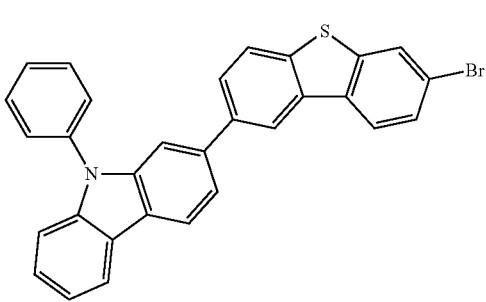

Sub1(15)
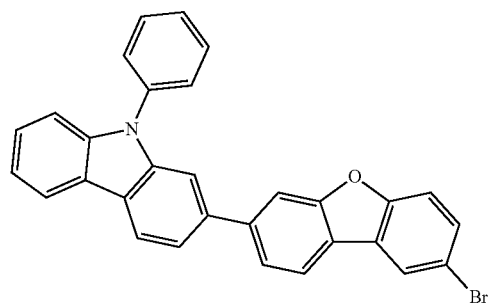
Sub1(16)
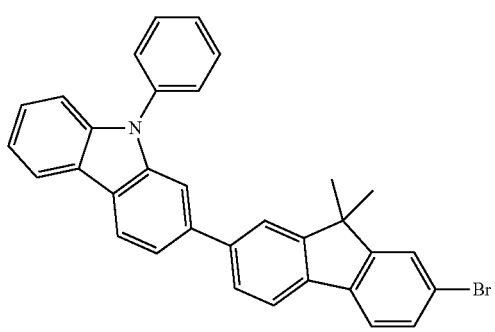
Sub1(17)
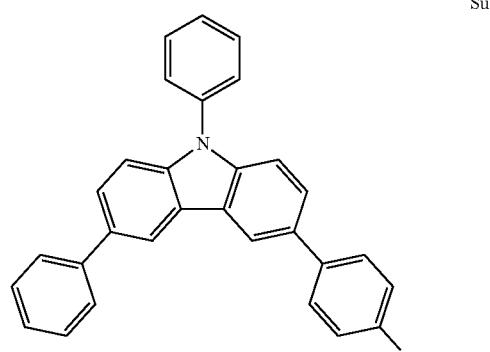
Sub1(18)
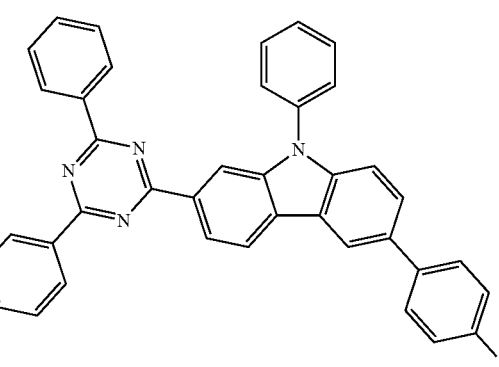
Sub1(19)
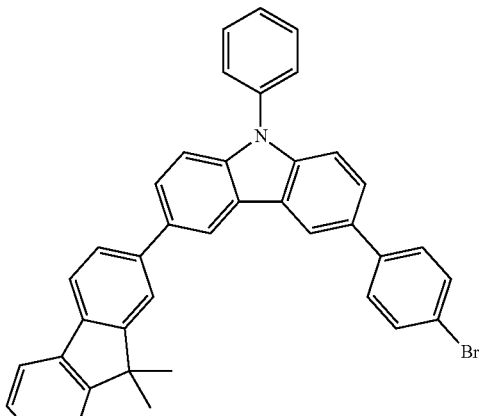
Sub1(20)
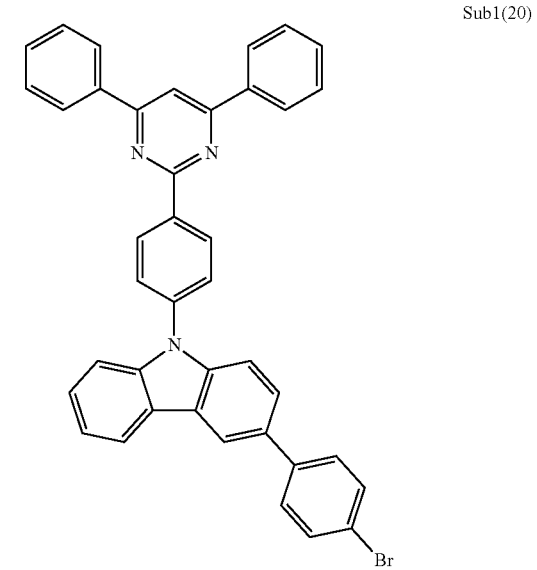
Sub1(21)
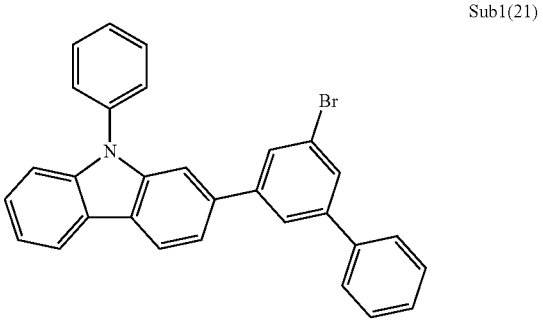
Sub1(22)
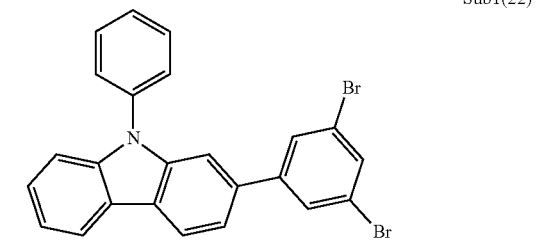

Sub1(23)
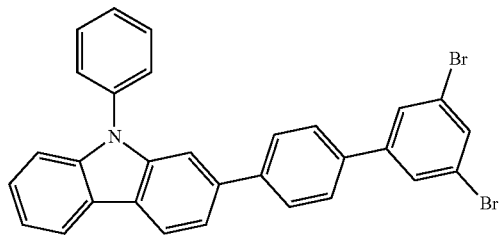
Sub1(24)
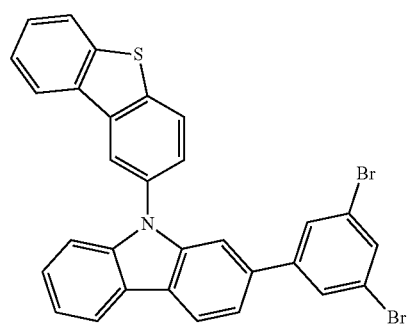
Sub1(25)
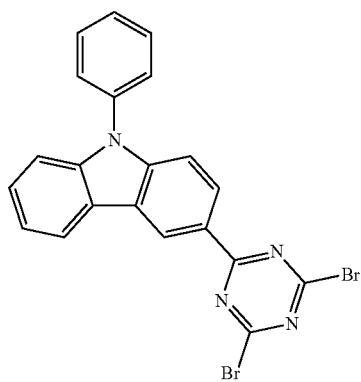
Sub1(26)
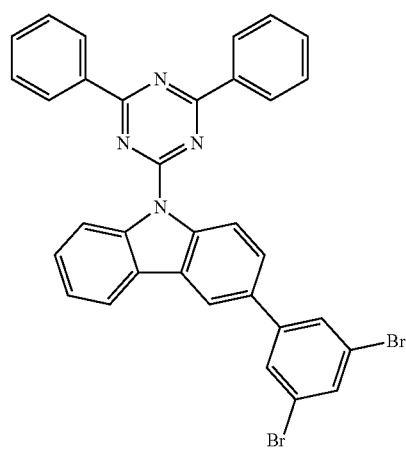
Sub1(27)
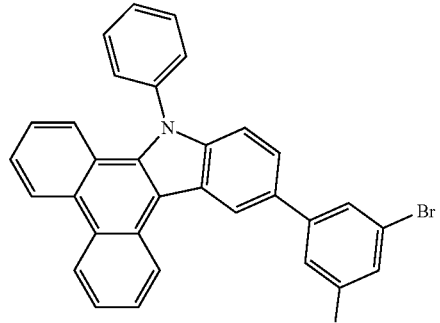
Sub1(28)
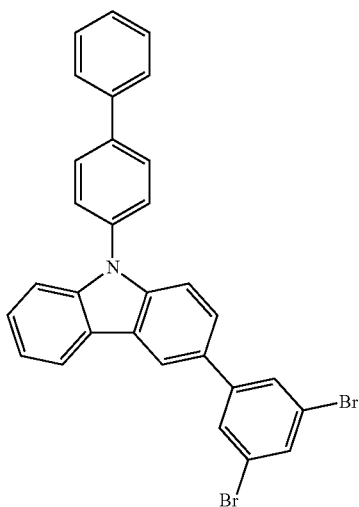
Sub1(29)
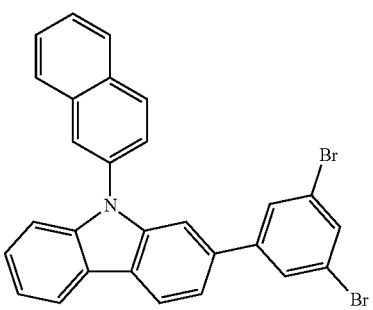
Sub1(30)
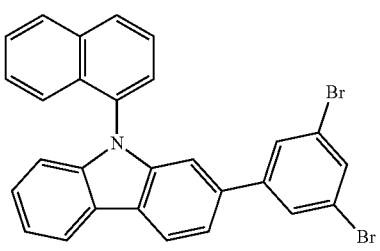

Sub1(31)

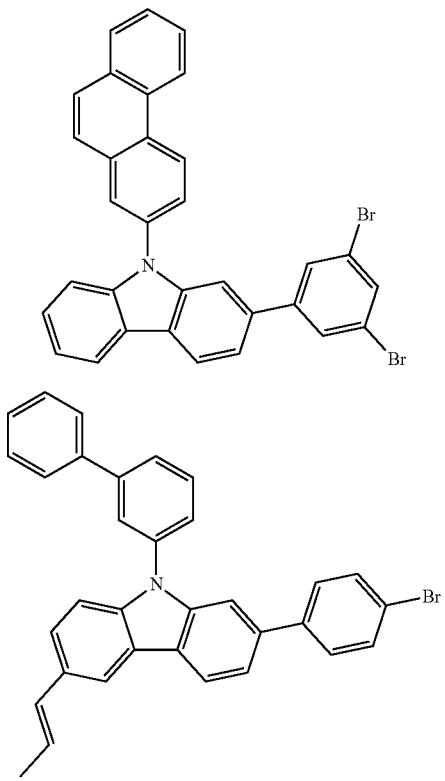

Sub1(32)

Synthesis Examples of Sub 2-1

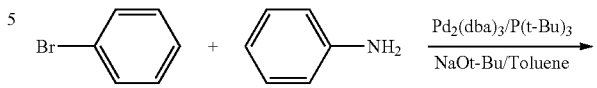

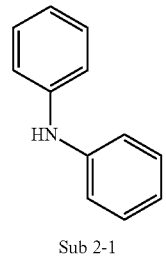

Sub 2-1

Bromobenzene (37.1 g, 236.2 mmol) was added to a round bottom flask and dissolved in toluene (2200 mL), aniline (20 g, 214.8 mmol), Pd$_2$(dba)$_3$ (9.83 g, 10.7 mmol), P(t-Bu)$_3$ (4.34 g, 21.5 mmol), NaOt-Bu (62 g, 644.3 mmol) were added in the order and stirred at 100° C. After the reaction was completed, the reaction mixture was extracted with ether and water. The organic layer was dried over MgSO$_4$ and concentrated. The resulting compound was separated by silicagel column chromatography and recrystallized to obtain 28 g of the product. (yield: 77%)

TABLE 1

| compound | FD-MS | compound | FD-MS |
|---|---|---|---|
| Sub 1(1) | m/z = 321.02(C$_{18}$H$_{12}$BrN = 322.21) | Sub 1(2) | m/z = 321.02(C$_{18}$H$_{12}$BrN = 322.21) |
| Sub 1(3) | m/z = 397.05(C$_{24}$H$_{16}$BrN = 398.30) | Sub 1(4) | m/z = 563.12(C$_{37}$H$_{26}$BrN = 564.53) |
| Sub 1(5) | m/z = 397.05(C$_{24}$H$_{16}$BrN = 398.30) | Sub 1(6) | m/z = 397.05(C$_{24}$H$_{16}$BrN = 398.30) |
| Sub 1(7) | m/z = 473.08(C$_{30}$H$_{20}$BrN = 474.40) | Sub 1(8) | m/z = 473.08(C$_{30}$H$_{20}$BrN = 474.40) |
| Sub 1(9) | m/z = 473.08(C$_{30}$H$_{20}$BrN = 474.40) | Sub 1(10) | m/z = 473.08(C$_{30}$H$_{20}$BrN = 474.40) |
| Sub 1(11) | m/z = 473.08(C$_{30}$H$_{20}$BrN = 474.40) | Sub 1(12) | m/z = 473.08(C$_{30}$H$_{20}$BrN = 474.40) |
| Sub 1(13) | m/z = 497.08(C$_{32}$H$_{20}$BrN = 498.42) | Sub 1(14) | m/z = 503.03(C$_{30}$H$_{18}$BrNS = 504.45) |
| Sub 1(15) | m/z = 487.06(C$_{30}$H$_{18}$BrNO = 488.38) | Sub 1(16) | m/z = 513.11(C$_{33}$H$_{24}$BrN = 514.47) |
| Sub 1(17) | m/z = 473.08(C$_{30}$H$_{20}$BrN = 474.40) | Sub 1(18) | m/z = 628.13(C$_{39}$H$_{25}$BrN$_4$ = 629.56) |
| Sub 1(19) | m/z = 589.14(C$_{39}$H$_{28}$BrN = 590.56) | Sub 1(20) | m/z = 627.13(C$_{40}$H$_{26}$BrN$_3$ = 628.57) |
| Sub 1(21) | m/z = 473.08(C$_{30}$H$_{20}$BrN = 474.40) | Sub 1(22) | m/z = 474.96(C$_{24}$H$_{15}$Br$_2$N = 477.20) |
| Sub 1(23) | m/z = 550.99(C$_{30}$H$_{19}$Br$_2$N = 553.30) | Sub 1(24) | m/z = 580.94(C$_{30}$H$_{17}$Br$_2$N = 580.34) |
| Sub 1(25) | m/z = 477.94(C$_{21}$H$_{12}$Br$_2$N$_4$ = 480.16) | Sub 1(26) | m/z = 630.01(C$_{33}$H$_{20}$Br$_2$N$_4$ = 632.36) |
| Sub 1(27) | m/z = 574.99(C$_{32}$H$_{19}$Br$_2$N = 577.32) | Sub 1(28) | m/z = 550.99(C$_{30}$H$_{19}$Br$_2$N = 553.30) |
| Sub 1(29) | m/z = 524.97(C$_{28}$H$_{17}$Br$_2$N = 527.26) | Sub 1(30) | m/z = 524.97(C$_{28}$H$_{17}$Br$_2$N = 527.26) |
| Sub 1(31) | m/z = 574.99(C$_{32}$H$_{19}$Br$_2$N = 577.32) | Sub 1(32) | m/z = 513.11(C$_{33}$H$_{24}$BrN = 514.47) |

Synthesis Examples of Sub 2

Sub 2 of reaction scheme 1 can be synthesized by the reaction path of the following reaction scheme 3, but is not limited thereto.

Synthesis Examples of Sub 2-13

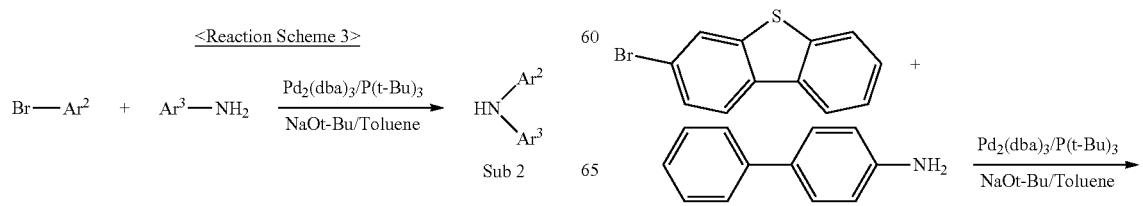

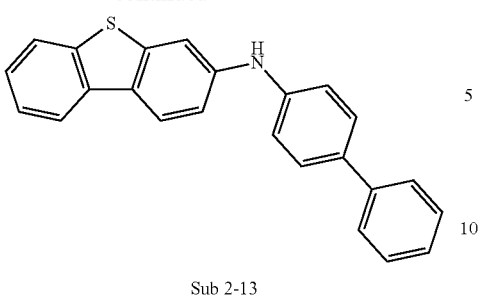
Sub 2-13
3-bromodibenzo[b,d]thiophene (42.8 g, 162.5 mmol), toluene (1550 mL), [1,1'-biphenyl]-4-amine (25 g, 147.7 mmol), Pd$_2$(dba)$_3$ (6.76 g, 7.4 mmol), P(t-Bu)$_3$ (3 g, 14.8 mmol), NaOt-Bu (42.6 g, 443.2 mmol) were added, the same procedure as described in the synthesis method of the 2-1 was carried out to obtain 37.9 g of the product. (yield: 73%).
Examples of Sub 2 include, but are not limited to, the followings.
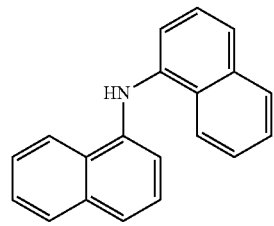
Sub 2-1
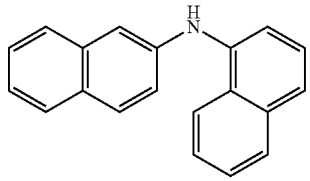
Sub 2-2
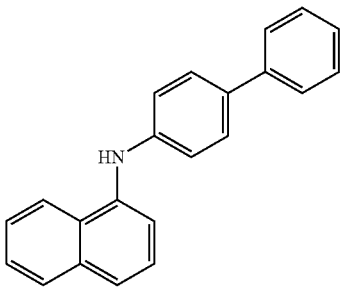
Sub 2-3, Sub 2-4, Sub 2-5
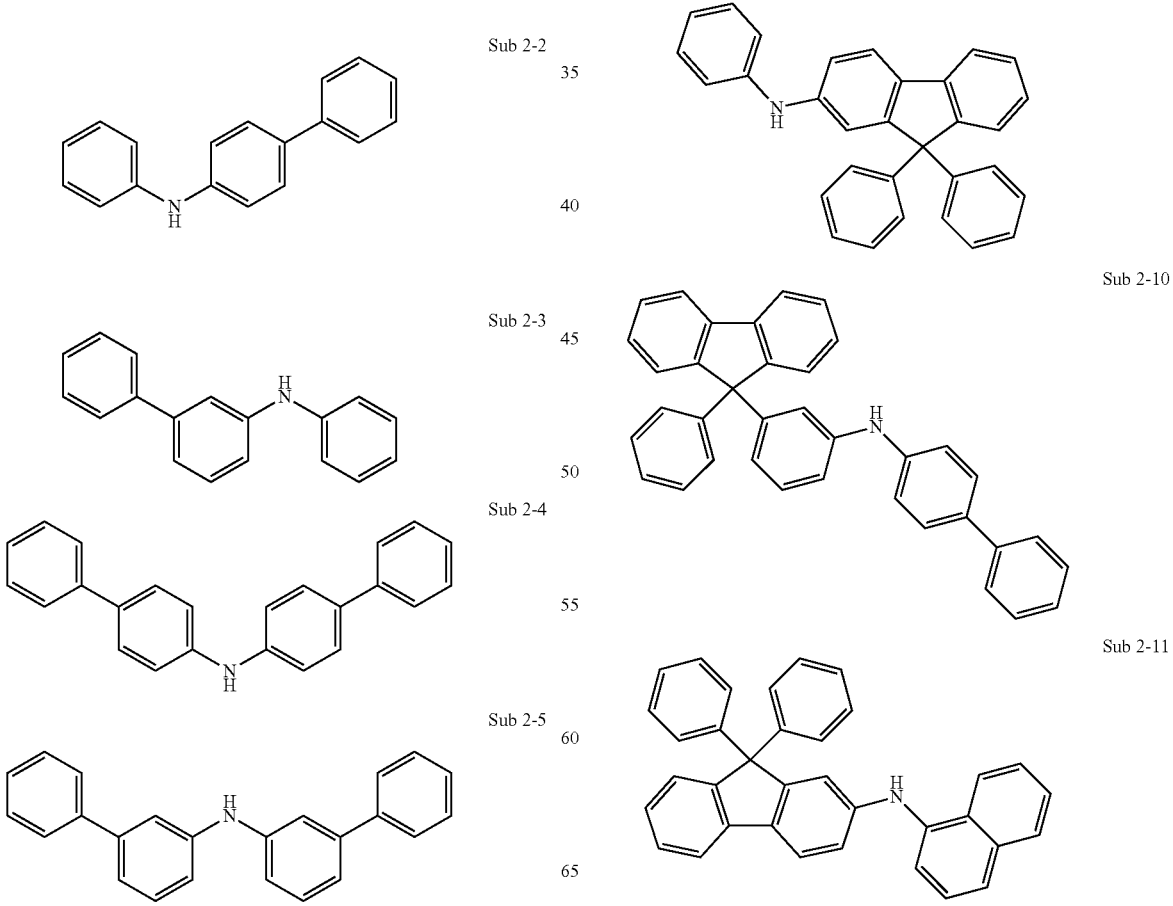
Sub 2-6, Sub 2-7, Sub 2-8, Sub 2-9, Sub 2-10, Sub 2-11

-continued
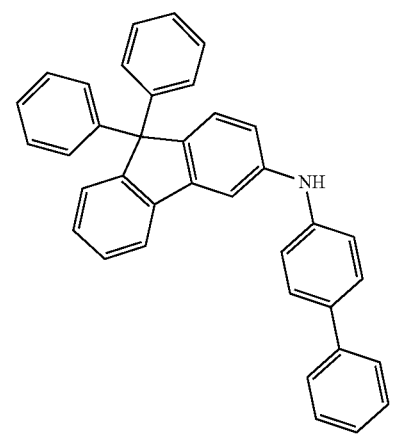
Sub 2-12
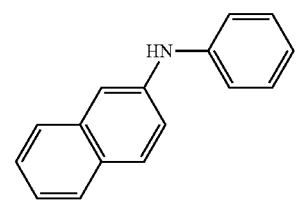
Sub 2-13
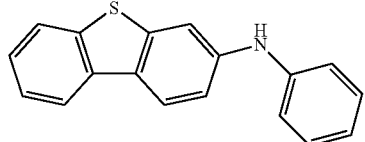
Sub 2-14
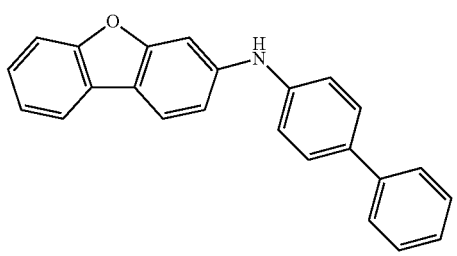
Sub 2-15
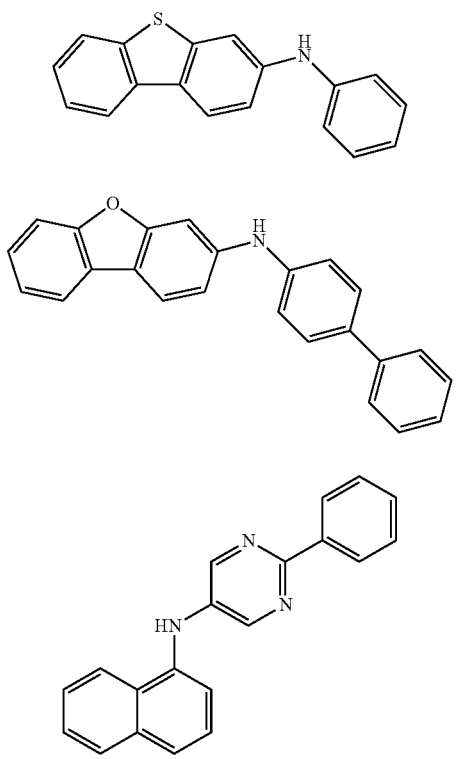
Sub 2-16
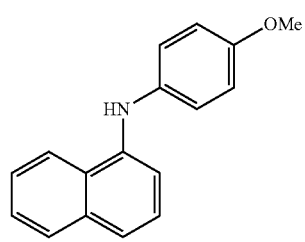
Sub 2-17
-continued
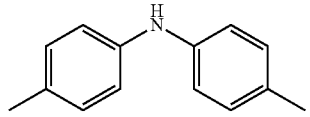
Sub 2-18
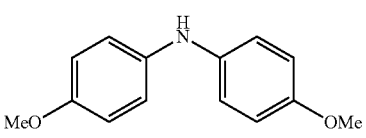
Sub 2-19
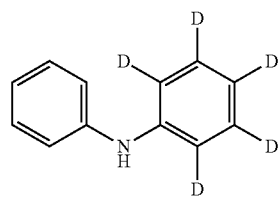
Sub 2-20
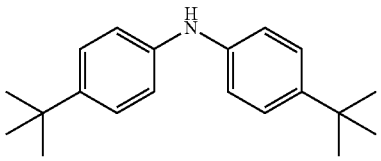
Sub 2-21
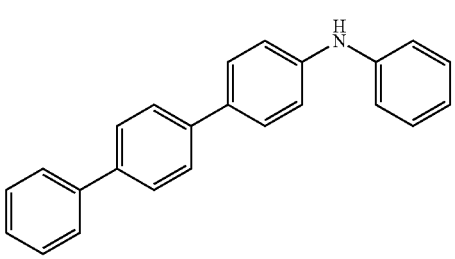
Sub 2-22
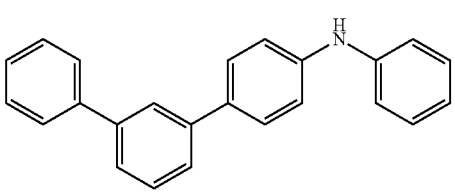
Sub 2-23
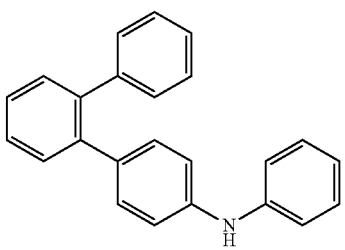
Sub 2-24
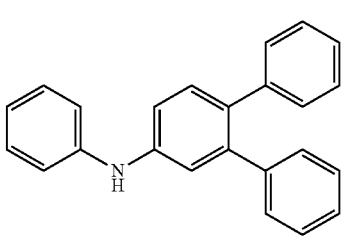
Sub 2-25

Sub 2-26
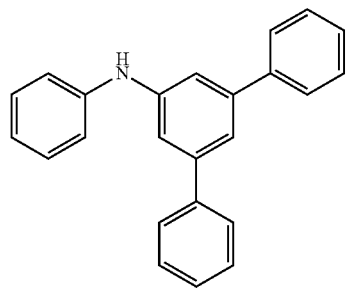
Sub 2-27
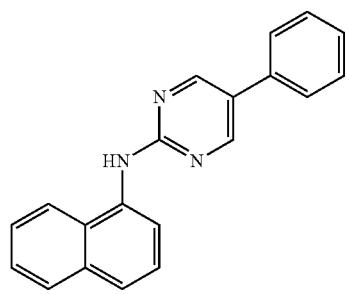
Sub 2-28
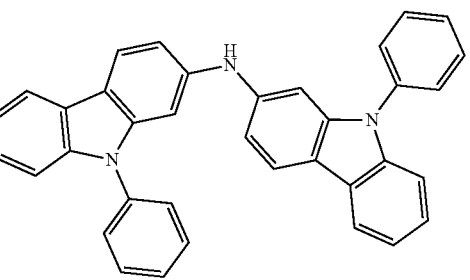
Sub 2-29
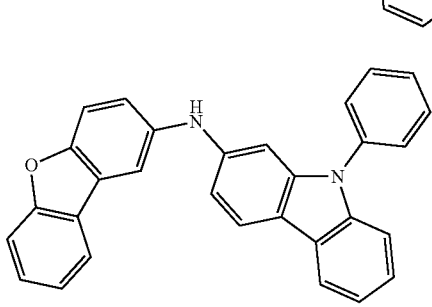
Sub 2-30
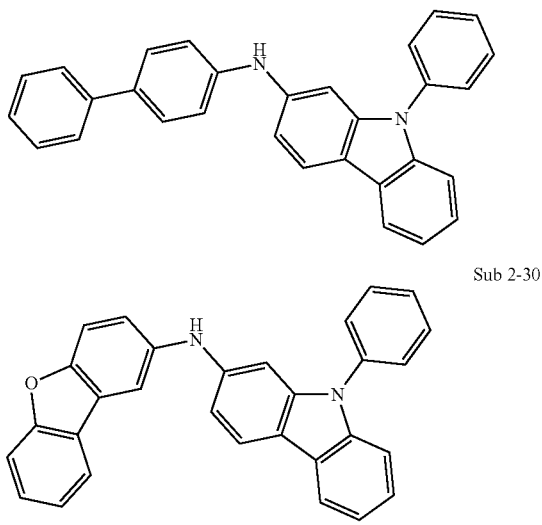
Sub 2-31
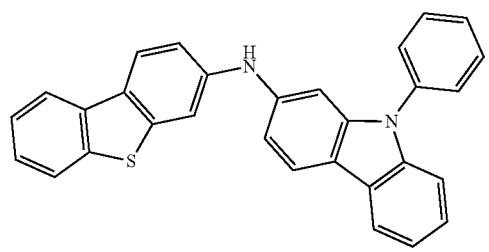
Sub 2-32
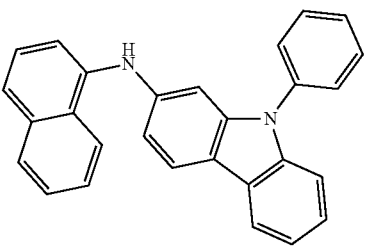
Sub 2-33
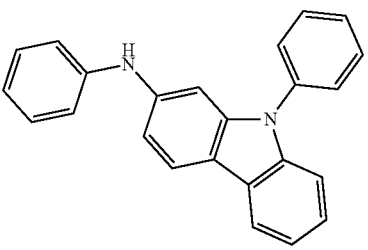
Sub 2-34
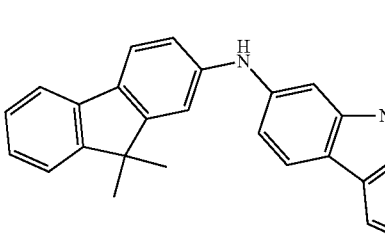
Sub 2-35
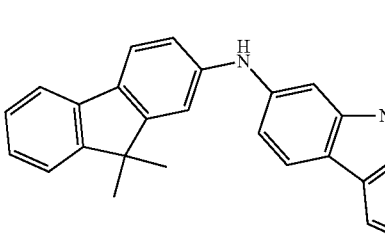

Sub 2-36
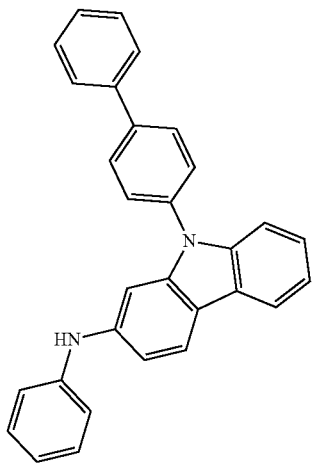
Sub 2-39
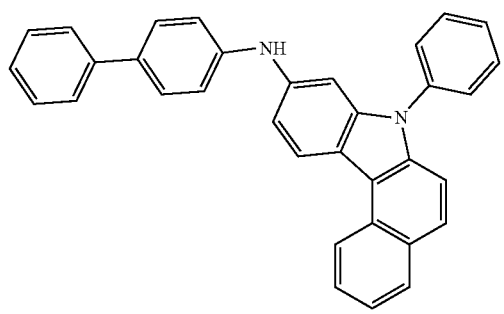
Sub 2-37
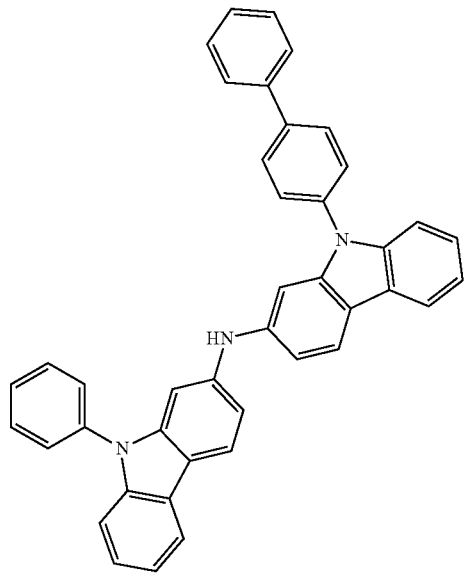
Sub 2-40
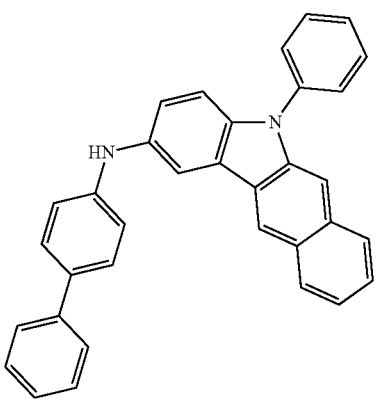
Sub 2-38
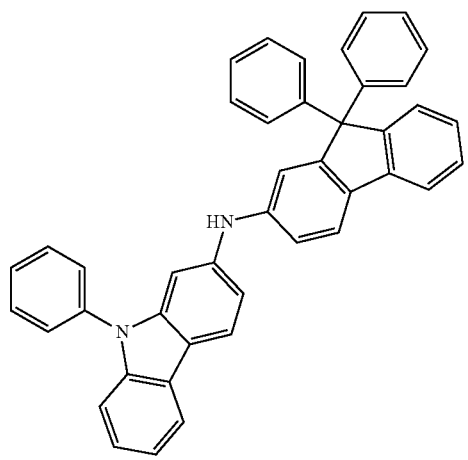
Sub 2-41
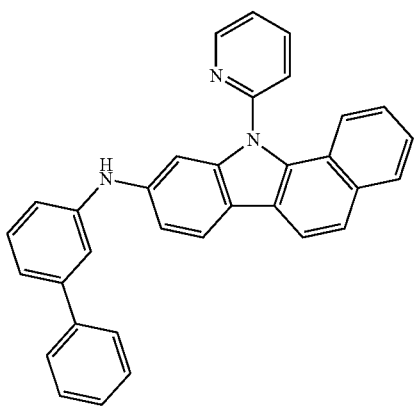

Sub 2-42

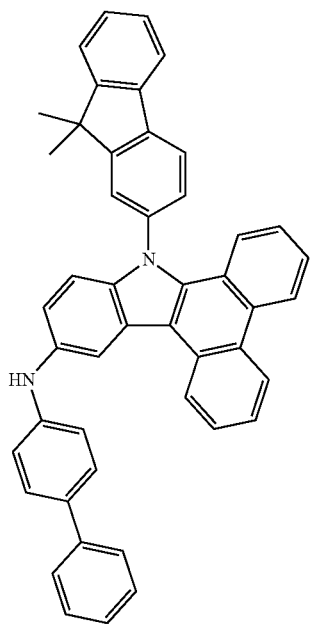

Sub 2-43

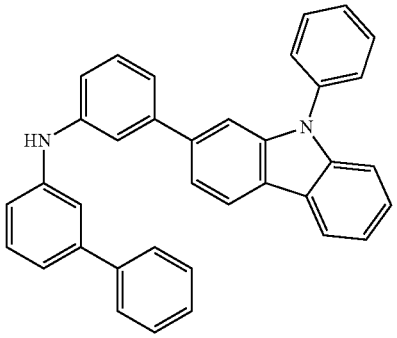

Sub 2-44

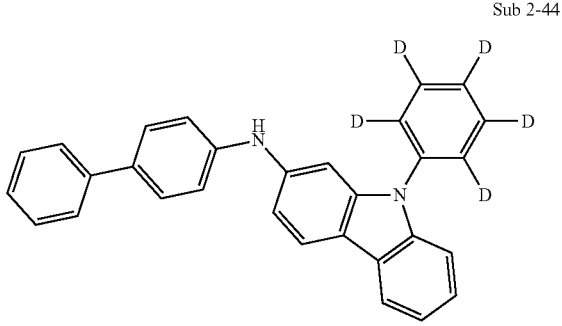

Sub 2-45

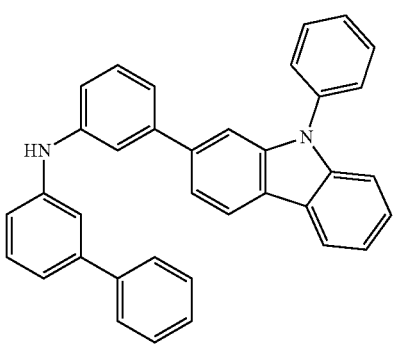

Sub 2-46

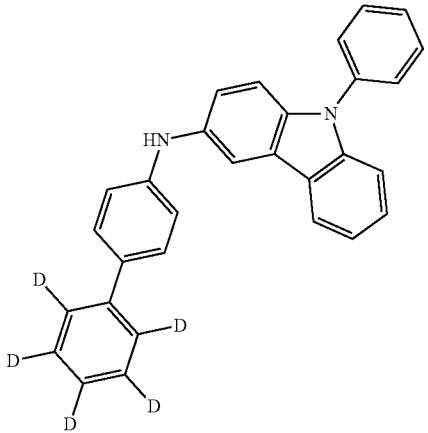

TABLE 2

| compound | FD-MS | compound | FD-MS |
| --- | --- | --- | --- |
| Sub 2-1 | m/z = 169.09($C_{12}H_{11}N$ = 169.22) | Sub 2-2 | m/z = 245.12($C_{18}H_{15}N$ = 245.32) |
| Sub 2-3 | m/z = 245.12($C_{18}H_{15}N$ = 245.32) | Sub 2-4 | m/z = 321.15($C_{24}H_{19}N$ = 321.41) |
| Sub 2-5 | m/z = 321.15($C_{24}H_{19}N$ = 321.41) | Sub 2-6 | m/z = 269.12($C_{20}H_{15}N$ = 269.34) |
| Sub 2-7 | m/z = 269.12($C_{20}H_{15}N$ = 269.34) | Sub 2-8 | m/z = 295.14($C_{22}H_{17}N$ = 295.38) |
| Sub 2-9 | m/z = 409.18($C_{31}H_{23}N$ = 409.52) | Sub 2-10 | m/z = 483.20($C_{37}H_{25}N$ = 483.60) |
| Sub 2-11 | m/z = 459.20($C_{35}H_{25}N$ = 459.58) | Sub 2-12 | m/z = 485.21($C_{37}H_{27}N$ = 485.62) |
| Sub 2-13 | m/z = 275.08($C_{18}H_{13}NS$ = 275.37) | Sub 2-14 | m/z = 335.13($C_{24}H_{17}NO$ = 335.40) |
| Sub 2-15 | m/z = 297.13($C_{20}H_{15}N_3$ = 297.35) | Sub 2-16 | m/z = 219.10($C_{16}H_{13}N$ = 219.28) |
| Sub 2-17 | m/z = 249.12($C_{17}H_{15}NO$ = 249.31) | Sub 2-18 | m/z = 197.12($C_{14}H_{15}N$ = 197.28) |
| Sub 2-19 | m/z = 229.11($C_{14}H_{15}NO_2$ = 229.27) | Sub 2-20 | m/z = 174.12($C_{12}H_6D_5N$ = 174.25) |
| Sub 2-21 | m/z = 281.21($C_{20}H_{27}N$ = 281.44) | Sub 2-22 | m/z = 321.15($C_{24}H_{19}N$ = 321.41) |
| Sub 2-23 | m/z = 321.15($C_{24}H_{19}N$ = 321.41) | Sub 2-24 | m/z = 321.15($C_{24}H_{19}N$ = 321.41) |
| Sub 2-25 | m/z = 321.15($C_{24}H_{19}N$ = 321.41) | Sub 2-26 | m/z = 321.15($C_{24}H_{19}N$ = 321.41) |
| Sub 2-27 | m/z = 297.13($C_{20}H_{15}N_3$ = 297.35) | Sub 2-28 | m/z = 499.20($C_{36}H_{25}N_3$ = 499.60) |
| Sub 2-29 | m/z = 499.20($C_{36}H_{22}N_2$ = 410.51) | Sub 2-30 | m/z = 424.16($C_{30}H_{20}N_2O$ = 424.49) |
| Sub 2-31 | m/z = 440.13($C_{30}H_{20}N_2S$ = 440.56) | Sub 2-32 | m/z = 384.16($C_{28}H_{20}N_2$ = 384.47) |
| Sub 2-33 | m/z = 334.15($C_{24}H_{18}N_2$ = 334.41) | Sub 2-34 | m/z = 450.21($C_{33}H_{26}N_2$ = 450.57) |
| Sub 2-35 | m/z = 410.18($C_{30}H_{22}N_2$ = 410.51) | Sub 2-36 | m/z = 410.18($C_{30}H_{22}N_2$ = 410.51) |
| Sub 2-37 | m/z = 575.24($C_{42}H_{29}N_3$ = 575.70) | Sub 2-38 | m/z = 574.24($C_{43}H_{30}N_2$ = 574.71) |
| Sub 2-39 | m/z = 460.19($C_{34}H_{24}N_2$ = 460.57) | Sub 2-40 | m/z = 460.19($C_{34}H_{24}N_2$ = 460.57) |

TABLE 2-continued

| compound | FD-MS | compound | FD-MS |
|---|---|---|---|
| Sub 2-41 | m/z = 461.19($C_{33}H_{23}N_3$ = 461.56) | Sub 2-42 | m/z = 626.27($C_{47}H_{34}N_2$ = 626.79) |
| Sub 2-43 | m/z = 565.23($C_{39}H_{22}N_5$ = 565.67) | Sub 2-44 | m/z = 415.21($C_{30}H_{17}D_5N_2$ = 415.54) |
| Sub 2-45 | m/z = 486.21($C_{36}H_{26}N_2$ = 486.61) | Sub 2-46 | m/z = 415.21($C_{30}H_{17}D_5N_2$ = 415.54) |

Synthesis Examples of Final Products 1

Synthesis Examples of 1-37

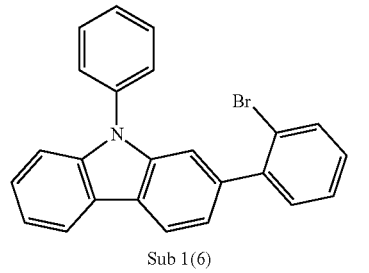

Sub 1(6)

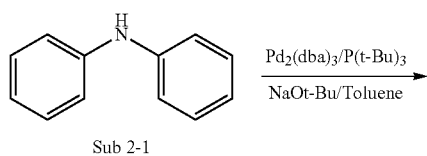

Sub 2-1

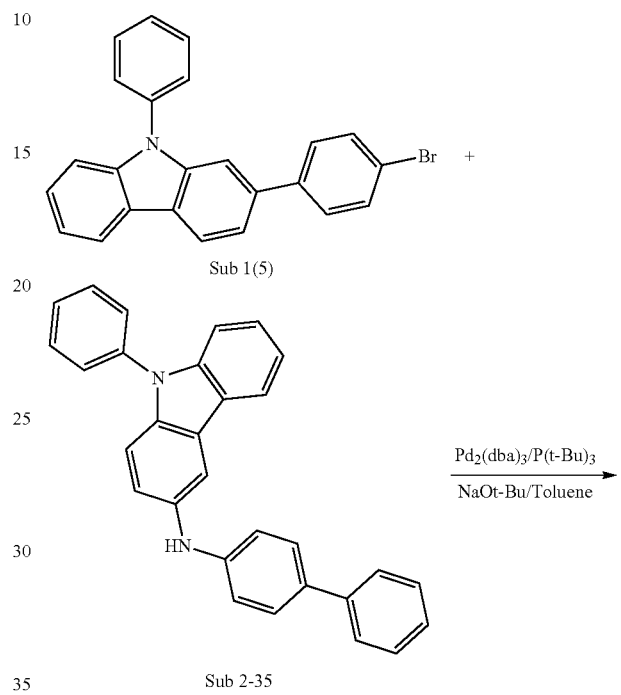

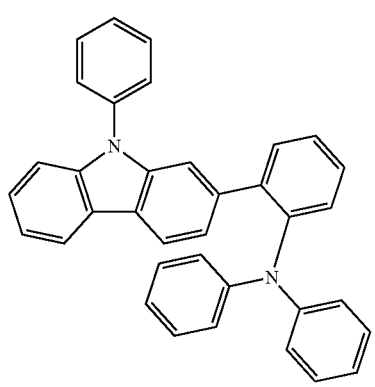

1-37

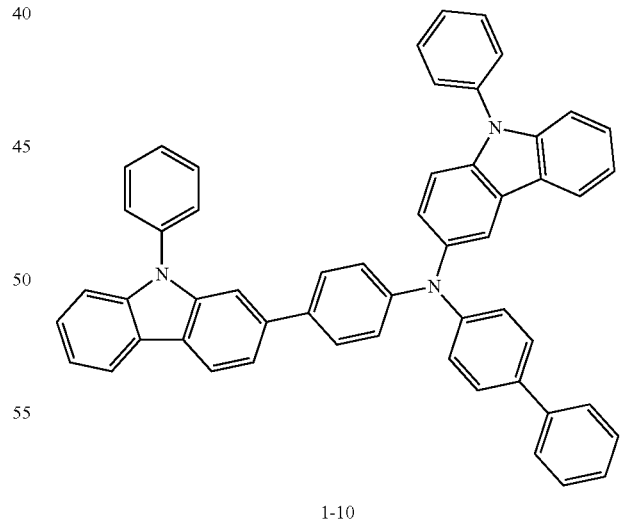

1-10

Sub 2-1 (8.0 g, 47.3 mmol) was added in a round bottom flask and dissolved in toluene (500 mL), Sub 1(6) (20.7 g, 52.0 mmol), Pd$_2$(dba)$_3$ (2.4 g, 2.6 mmol), P(t-Bu)$_3$ (1.05 g, 5.2 mmol), NaOt-Bu (13.6 g, 141.8 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 16.1 g of the product. (yield: 70%) Synthesis Examples of 1-10

Sub 2-35 (19.4 g, 47.3 mmol), toluene (500 mL), Sub 1(5) (20.7 g, 52.0 mmol), Pd$_2$(dba)$_3$ (2.4 g, 2.6 mmol), P(t-Bu)$_3$ (1.05 g, 5.2 mmol), NaOt-Bu (13.6 g, 141.8 mmol) were added, the same procedure as described in the synthesis method of the 1-37 was carried out to obtain 24.8 g of the product 1-10. (yield: 72%).

Synthesis Examples of 1-54

Synthesis of Inter_A-1

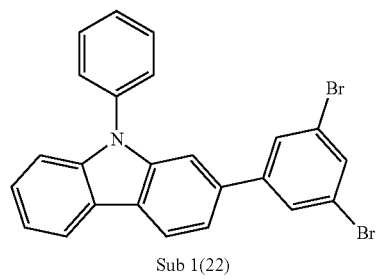

Sub 1(22)

+

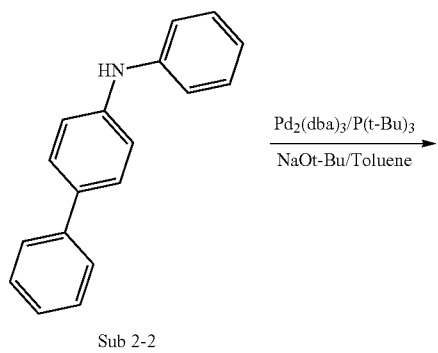

Sub 2-2

Pd₂(dba)₃/P(t-Bu)₃
―――――――――――→
NaOt-Bu/Toluene

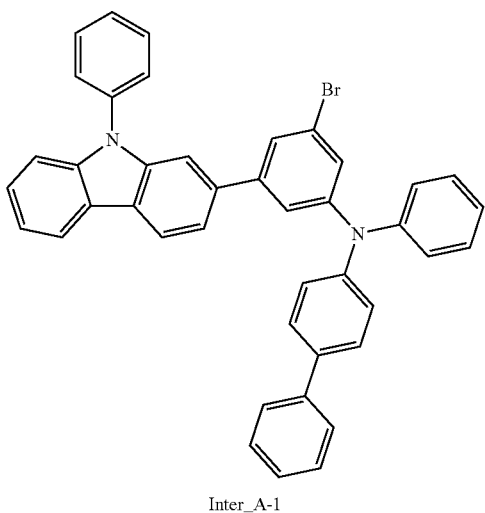

Inter_A-1

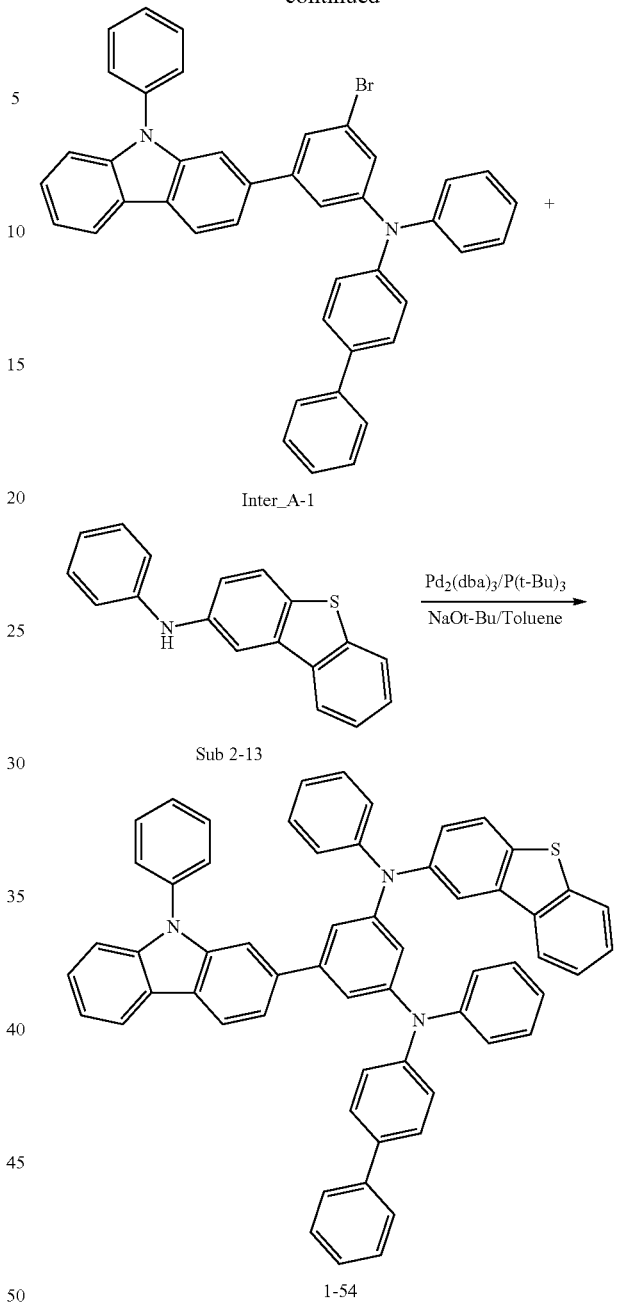

Synthesis Method of Inter A-1

Sub 2-2 (11.6 g, 47.3 mmol), toluene (500 mL), Sub 1(22) (24.8 g, 52.0 mmol), Pd₂(dba)₃ (2.4 g, 2.6 mmol), P(t-Bu)₃ (1.05 g, 5.2 mmol), NaOt-Bu (13.6 g, 141.8 mmol) were added, the same procedure as described in the synthesis method of the 1-37 was carried out to obtain 22.8 g of the product Inter_A-1. (yield: 75%).

Synthesis Method of 1-54

Sub 2-13 (8 g, 29.05 mmol), Inter_A-1 (20.5 g, 32 mmol), toluene (305 mL), Pd₂(dba)₃ (1.5 g, 1.6 mmol), P(t-Bu)₃ (0.65 g, 3.2 mmol), NaOt-Bu (8.4 g, 87.2 mmol) were added, the same procedure as described in the synthesis method of the 1-37 was carried out to obtain 18 g of the product 1-54. (yield: 74%).

Synthesis Examples of 2-5

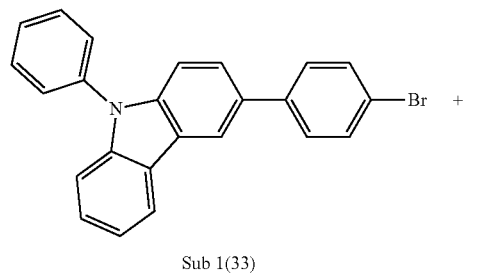

Sub 1(33)

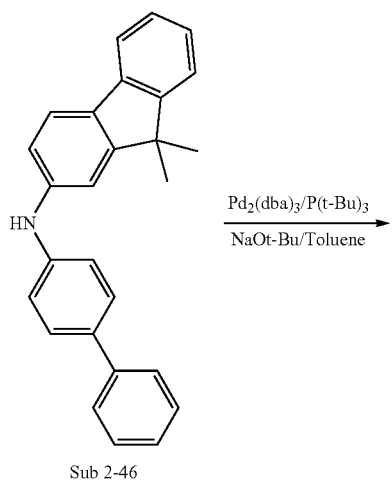

Sub 2-46

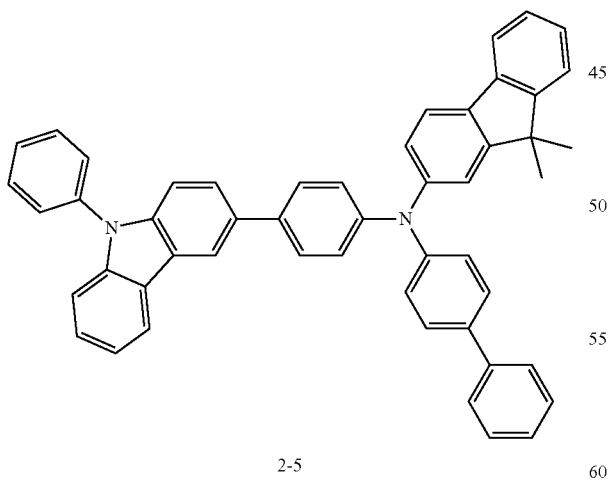

2-5

Sub 2-46 (7.2 g, 20 mmol), Sub 1(33) (8.73 g, 22 mmol), Pd$_2$(dba)$_3$ (1 g, 1.1 mmol), P(t-Bu)$_3$ (0.4 g, 2.2 mmol), NaOt-Bu (5.74 g, 60 mmol), toluene (210 mL) were added, the same procedure as described in the synthesis method of the 1-37 was carried out to obtain 11.5 g of the product 2-5. (yield: 85%).

Synthesis Examples of 2-18

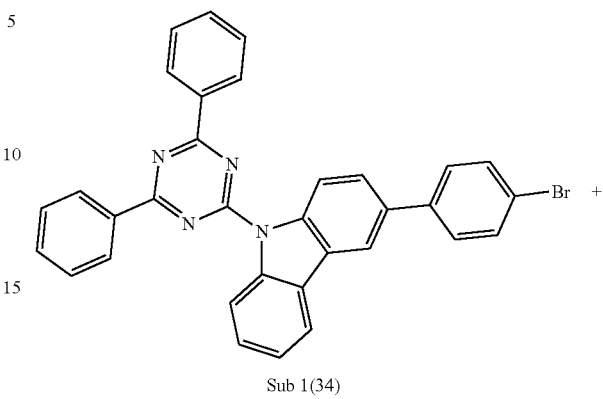

Sub 1(34)

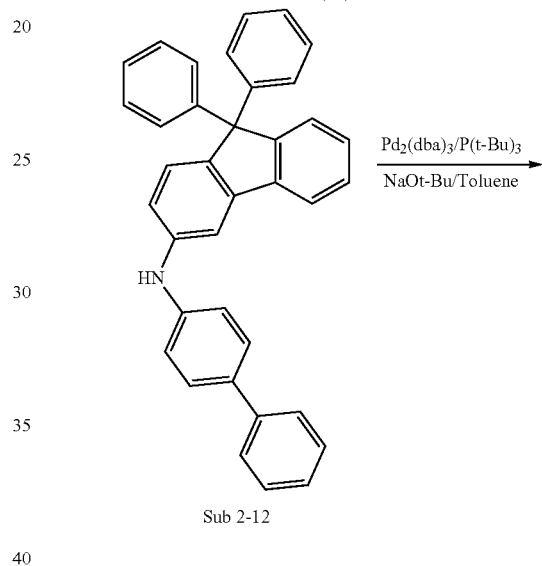

Sub 2-12

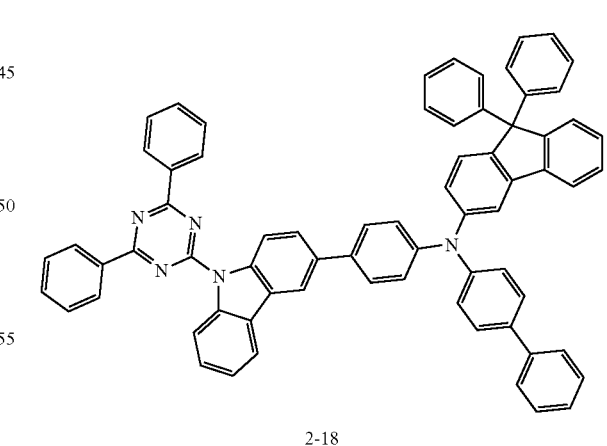

2-18

Sub 2-12 (9.7 g, 20 mmol), Sub 1(34) (12.2 g, 22 mmol), Pd$_2$(dba)$_3$ (1.0 g, 1.1 mmol), P(t-Bu)$_3$ (0.4 g, 2.2 mmol), NaOt-Bu (5.8 g, 60 mmol), toluene (210 mL) were added, the same procedure as described in the synthesis method of the 1-37 was carried out to obtain 15.5 g of the product 2-18. (yield: 81%).

Synthesis Examples of 2-60

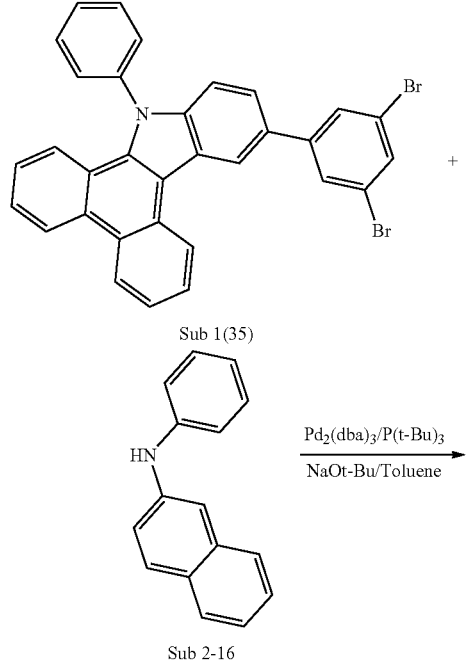

Sub 1(35)

Sub 2-16

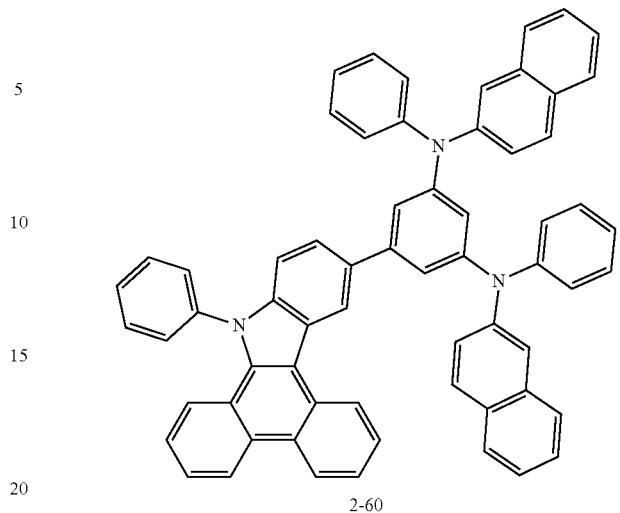

2-60

Sub 1(35) (13.9 g, 24.1 mmol), Sub 2-16 (11.0 g, 50 mmol), $Pd_2(dba)_3$ (2.2 g, 2.4 mmol), $P(t\text{-}Bu)_3$ (1 g, 4.8 mmol), NaOt-Bu (8.3 g, 86.7 mmol), toluene (260 mL) were added, the same procedure as described in the synthesis method of the 1-37 was carried out to obtain 16.5 g of the product 2-60. (yield: 80%).

TABLE 3

| compound | FD-MS | compound | FD-MS |
|---|---|---|---|
| 1-1 | m/z = 562.24($C_{42}H_{30}N_2$ = 562.72) | 1-2 | m/z = 602.27($C_{45}H_{34}N_2$ = 602.78) |
| 1-3 | m/z = 563.24($C_{41}H_{29}N_3$ = 563.70) | 1-4 | m/z = 714.30($C_{54}H_{38}N_2$ = 714.91) |
| 1-5 | m/z = 678.30($C_{51}H_{38}N_2$ = 678.88) | 1-6 | m/z = 802.33($C_{61}H_{42}N_2$ = 803.02) |
| 1-7 | m/z = 800.32($C_{61}H_{40}N_2$ = 801.01) | 1-8 | m/z = 563.24($C_{41}H_{29}N_3$ = 563.70) |
| 1-9 | m/z = 668.23($C_{48}H_{32}N_2S$ = 668.86) | 1-10 | m/z = 727.30($C_{54}H_{37}N_3$ = 727.91) |
| 1-11 | m/z = 652.25($C_{48}H_{32}N_2O$ = 652.80) | 1-12 | m/z = 662.27($C_{50}H_{34}N_2$ = 662.84) |
| 1-13 | m/z = 536.23($C_{40}H_{28}N_2$ = 536.68) | 1-14 | m/z = 586.24($C_{44}H_{30}N_2$ = 586.74) |
| 1-15 | m/z = 712.29($C_{54}H_{36}N_2$ = 712.90) | 1-16 | m/z = 714.30($C_{54}H_{38}N_2$ = 714.91) |
| 1-17 | m/z = 754.33($C_{57}H_{42}N_2$ = 754.98) | 1-18 | m/z = 957.38($C_{70}H_{47}N_5$ = 958.18) |
| 1-19 | m/z = 965.38($C_{73}H_{47}N_3$ = 966.20) | 1-20 | m/z = 719.24($C_{51}H_{33}N_3S$ = 719.91) |
| 1-21 | m/z = 758.24($C_{54}H_{34}N_2OS$ = 758.94) | 1-22 | m/z = 893.38($C_{67}H_{47}N_3$ = 894.13) |
| 1-23 | m/z = 652.25($C_{48}H_{32}N_2O$ = 652.80) | 1-24 | m/z = 662.27($C_{50}H_{34}N_2$ = 662.84) |
| 1-25 | m/z = 562.24($C_{42}H_{30}N_2$ = 562.72) | 1-26 | m/z = 612.26($C_{46}H_{32}N_2$ = 612.78) |
| 1-27 | m/z = 688.29($C_{52}H_{36}N_2$ = 688.87) | 1-28 | m/z = 714.30($C_{54}H_{38}N_2$ = 714.91) |
| 1-29 | m/z = 754.33($C_{57}H_{42}N_2$ = 754.98) | 1-30 | m/z = 878.37($C_{67}H_{46}N_2$ = 879.12) |
| 1-31 | m/z = 876.35($C_{67}H_{44}N_2$ = 877.10) | 1-32 | m/z = 639.27($C_{47}H_{33}N_3$ = 369.80) |
| 1-33 | m/z = 768.26($C_{56}H_{36}N_2S$ = 768.98) | 1-34 | m/z = 833.29($C_{60}H_{39}N_3S$ = 834.05) |
| 1-35 | m/z = 742.26($C_{54}H_{34}N_2O_S$ = 742.88) | 1-36 | m/z = 778.333($C_{59}H_{42}N_2$ = 779.00) |
| 1-37 | m/z = 486.21($C_{36}H_{26}N_2$ = 486.62) | 1-38 | m/z = 536.23($C_{40}H_{28}N_2$ = 536.68) |
| 1-39 | m/z = 612.26($C_{46}H_{32}N_2$ = 612.78) | 1-40 | m/z = 638.27($C_{48}H_{34}N_2$ = 638.81) |
| 1-41 | m/z = 491.24($C_{36}H_{21}D_5N_2$ = 491.65) | 1-42 | m/z = 612.26($C_{46}H_{32}N_2$ = 612.78) |
| 1-43 | m/z = 794.28($C_{58}H_{38}N_2S$ = 795.02) | 1-44 | m/z = 656.26($C_{48}H_{33}FN_2$ = 656.80) |
| 1-45 | m/z = 717.29($C_{51}H_{35}N_5$ = 717.88) | 1-46 | m/z = 728.32($C_{55}H_{40}N_2$ = 728.94) |
| 1-47 | m/z = 842.34($C_{62}H_{42}N_4$ = 843.05) | 1-48 | m/z = 714.30($C_{54}H_{38}N_2$ = 714.91) |
| 1-49 | m/z = 653.28($C_{48}H_{35}N_3$ = 653.81) | 1-50 | m/z = 703.30($C_{52}H_{37}N_3$ = 703.87) |
| 1-51 | m/z = 805.35($C_{60}H_{43}N_3$ = 806.00) | 1-52 | m/z = 753.31($C_{56}H_{39}N_3$ = 753.93) |
| 1-53 | m/z = 818.34($C_{60}H_{42}N_4$ = 819.00) | 1-54 | m/z = 835.30($C_{60}H_{41}N_3S$ = 836.05) |
| 1-55 | m/z = 655.27($C_{46}H_{33}N_5$ = 655.79) | 1-56 | m/z = 885.32($C_{64}H_{43}N_3S$ = 886.11) |
| 1-57 | m/z = 759.27($C_{54}H_{37}N_3S$ = 759.96) | 1-58 | m/z = 706.28($C_{49}H_{34}N_6$ = 706.83) |
| 1-59 | m/z = 960.39($C_{69}H_{48}N_6$ = 961.16) | 1-60 | m/z = 853.35($C_{64}H_{43}N_3$ = 854.05) |
| 1-61 | m/z = 894.37($C_{66}H_{46}N_4$ = 895.10) | 1-62 | m/z = 834.38($C_{62}H_{38}D_5N_3$ = 835.06) |
| 1-63 | m/z = 855.36($C_{64}H_{45}N_3$ = 856.06) | 1-64 | m/z = 853.35($C_{64}H_{43}N_3$ = 854.05) |
| 1-65 | m/z = 794.37($C_{60}H_{46}N_2$ = 795.04) | 1-66 | m/z = 987.39($C_{71}H_{49}N_5O$ = 988.21) |
| 1-67 | m/z = 1021.44($C_{77}H_{55}N_3$ = 1022.31) | 1-68 | m/z = 737.23($C_{51}H_{32}FN_3S$ = 737.90) |
| 2-1 | m/z = 562.24($C_{42}H_{30}N_2$ = 562.72) | 2-2 | m/z = 602.27($C_{45}H_{34}N_2$ = 602.78) |
| 2-3 | m/z = 563.24($C_{41}H_{29}N_3$ = 563.70) | 2-4 | m/z = 714.30($C_{54}H_{38}N_2$ = 714.91) |
| 2-5 | m/z = 678.30($C_{51}H_{38}N_2$ = 678.88) | 2-6 | m/z = 802.33($C_{61}H_{42}N_2$ = 803.02) |
| 2-7 | m/z = 800.32($C_{61}H_{40}N_2$ = 801.01) | 2-8 | m/z = 563.24($C_{41}H_{29}N_3$ = 563.70) |
| 2-9 | m/z = 668.23($C_{48}H_{32}N_2S$ = 668.86) | 2-10 | m/z = 727.30($C_{54}H_{37}N_3$ = 727.91) |

TABLE 3-continued

| compound | FD-MS | compound | FD-MS |
|---|---|---|---|
| 2-11 | m/z = 652.25($C_{48}H_{32}N_2O$ = 652.80) | 2-12 | m/z = 662.27($C_{50}H_{34}N_2$ = 662.84) |
| 2-13 | m/z = 536.23($C_{40}H_{28}N_2$ = 536.68) | 2-14 | m/z = 586.24($C_{44}H_{30}N_2$ = 586.74) |
| 2-15 | m/z = 712.29($C_{54}H_{36}N_2$ = 712.90) | 2-16 | m/z = 714.30($C_{54}H_{38}N_2$ = 714.91) |
| 2-17 | m/z = 754.33($C_{57}H_{42}N_2$ = 754.98) | 2-18 | m/z = 957.38($C_{70}H_{47}N_5$ = 958.18) |
| 2-19 | m/z = 965.38($C_{73}H_{47}N_3$ = 966.20) | 2-20 | m/z = 719.24($C_{51}H_{33}N_3S$ = 719.91) |
| 2-21 | m/z = 758.24($C_{54}H_{34}N_2OS$ = 758.94) | 2-22 | m/z = 893.38($C_{67}H_{47}N_3$ = 894.13) |
| 2-23 | m/z = 652.25($C_{48}H_{32}N_2O$ = 652.80) | 2-24 | m/z = 662.27($C_{50}H_{34}N_2$ = 662.84) |
| 2-25 | m/z = 562.24($C_{42}H_{30}N_2$ = 562.72) | 2-26 | m/z = 612.26($C_{46}H_{32}N_2$ = 612.78) |
| 2-27 | m/z = 688.29($C_{52}H_{36}N_2$ = 688.87) | 2-28 | m/z = 714.30($C_{54}H_{38}N_2$ = 714.91) |
| 2-29 | m/z = 754.33($C_{57}H_{42}N_2$ = 754.98) | 2-30 | m/z = 878.37($C_{67}H_{46}N_2$ = 879.12) |
| 2-31 | m/z = 876.35($C_{67}H_{44}N_2$ = 877.10) | 2-32 | m/z = 639.27($C_{47}H_{33}N_3$ = 369.80) |
| 2-33 | m/z = 768.26($C_{56}H_{36}N_2S$ = 768.98) | 2-34 | m/z = 833.29($C_{60}H_{39}N_3S$ = 834.05) |
| 2-35 | m/z = 742.26($C_{54}H_{34}N_2O_5$ = 742.88) | 2-36 | m/z = 778.333($C_{59}H_{42}N_2$ = 779.00) |
| 2-37 | m/z = 486.21($C_{36}H_{26}N_2$ = 486.62) | 2-38 | m/z = 536.23($C_{40}H_{28}N_2$ = 536.68) |
| 2-39 | m/z = 612.26($C_{46}H_{32}N_2$ = 612.78) | 2-40 | m/z = 638.27($C_{48}H_{34}N_2$ = 638.81) |
| 2-41 | m/z = 491.24($C_{36}H_{21}D_5N_2$ = 491.65) | 2-42 | m/z = 612.26($C_{46}H_{32}N_2$ = 612.78) |
| 2-43 | m/z = 794.28($C_{58}H_{38}N_2S$ = 795.02) | 2-44 | m/z = 656.26($C_{48}H_{33}FN_2$ = 656.80) |
| 2-45 | m/z = 717.29($C_{51}H_{35}N_5$ = 717.88) | 2-46 | m/z = 728.32($C_{55}H_{40}N_2$ = 728.94) |
| 2-47 | m/z = 842.34($C_{62}H_{42}N_4$ = 843.05) | 2-48 | m/z = 714.30($C_{54}H_{38}N_2$ = 714.91) |
| 2-49 | m/z = 653.28($C_{48}H_{35}N_3$ = 653.81) | 2-50 | m/z = 703.30($C_{52}H_{37}N_3$ = 703.87) |
| 2-51 | m/z = 805.35($C_{60}H_{43}N_3$ = 806.00) | 2-52 | m/z = 753.31($C_{56}H_{39}N_3$ = 753.93) |
| 2-53 | m/z = 818.34($C_{60}H_{42}N_4$ = 819.00) | 2-54 | m/z = 835.30($C_{60}H_{41}N_3S$ = 836.05) |
| 2-55 | m/z = 655.27($C_{46}H_{33}N_5$ = 655.79) | 2-56 | m/z = 885.32($C_{64}H_{43}N_3S$ = 886.11) |
| 2-57 | m/z = 759.27($C_{54}H_{37}N_3S$ = 759.96) | 2-58 | m/z = 706.28($C_{49}H_{34}N_6$ = 706.83) |
| 2-59 | m/z = 960.39($C_{69}H_{48}N_6$ = 961.16) | 2-60 | m/z = 853.35($C_{64}H_{43}N_3$ = 854.05) |
| 2-61 | m/z = 894.37($C_{66}H_{46}N_4$ = 895.10) | 2-62 | m/z = 834.38($C_{62}H_{38}D_5N_3$ = 835.06) |
| 2-63 | m/z = 855.36($C_{64}H_{45}N_3$ = 856.06) | 2-64 | m/z = 853.35($C_{64}H_{43}N_3$ = 854.05) |
| 2-65 | m/z = 794.37($C_{60}H_{46}N_2$ = 795.04) | 2-66 | m/z = 987.39($C_{71}H_{49}N_5O$ = 988.21) |
| 2-67 | m/z = 1021.44($C_7H_{55}N_3$ = 1022.31) | 2-68 | m/z = 737.23($C_{51}H_{32}FN_3S$ = 737.90) |

Synthesis Examples 2

The final product 2 represented by Formula 2 of the present invention is prepared by reacting Sub 3 and Sub 4 as shown in the following Reaction Scheme 4.

Synthesis Example of Sub 3

Sub 3 of Reaction Scheme 4 can be synthesized by the reaction path of the following Reaction Scheme 5, but is not limited thereto.

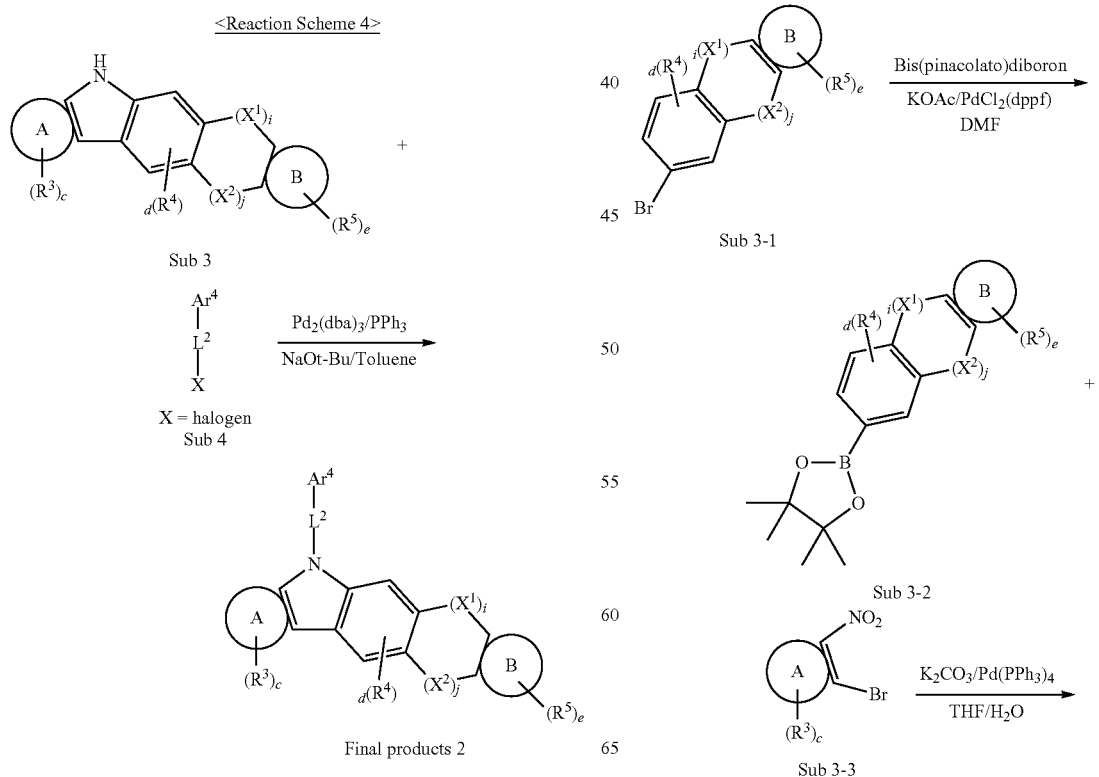

-continued

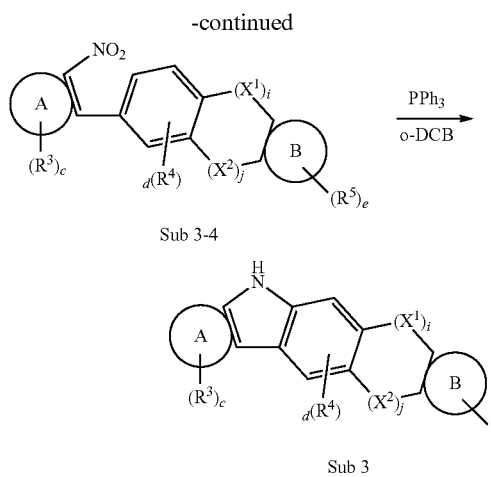

Sub 3-4

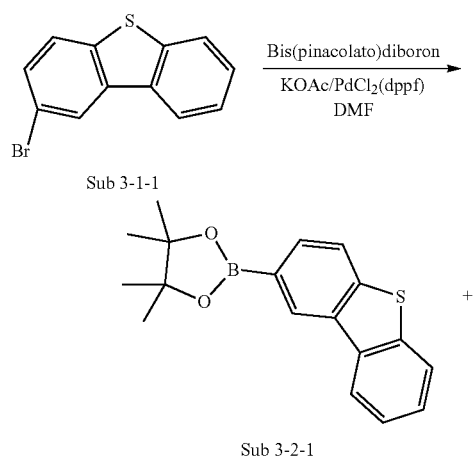

Sub 3

Synthesis Examples of Sub 3(1)

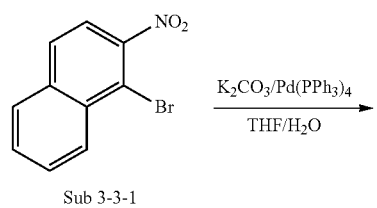

Sub 3-1-1

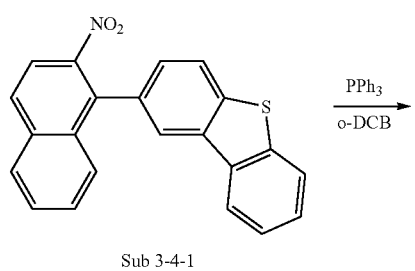

Sub 3-4-1

-continued

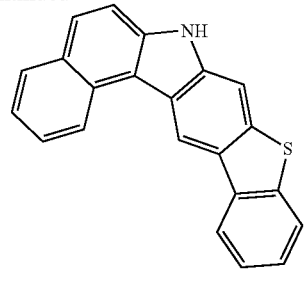

Sub 3(1)

Synthesis Method of Sub 3-2-1

After 3-1-1 (40.8 g, 155 mmol), bis(pinacolato)diboron (43.4 g, 171 mmol), KOAc (46 g, 466 mmol), PdCl$_2$(dppf) (3.8 g, 4.7 mmol) were dissolved in DMF (980 mL), and refluxed at 120° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was recrystallized by CH$_2$Cl$_2$ and methanol solvent to obtain Sub 3-2-1. (38.5 g, 80%)

Synthesis Method of Sub 3-4-1

Sub 3-2-1 (34.4 g, 111 mmol), Sub 3-3-1 (33.5 g, 133 mmol), K$_2$CO$_3$ (46.03 g, 333 mmol), Pd(PPh$_3$)$_4$ (7.7 g, 6.66 mmol) were added in a round bottom flask and THF (490 mL) and water (245 mL) were added to dissolve and refluxed at 80° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was separated by silica-gel column chromatography to obtain Sub 3-4-1. (31.2 g, 79%)

Synthesis Method of Sub 3(1)

Sub 3-4-1 (20 g, 56.3 mmol) and triphenylphosphine (37 g, 141 mmol) were dissolved in o-dichlorobenzene (235 mL) and refluxed for 24 hours. When the reaction was completed, the solvent was removed using reduced pressure distillation. The resulting compound was separated by silicagel column chromatography and recrystallized to obtain Sub 3(1). (14.7 g, 81%)

Synthesis Example of Sub 3(2)

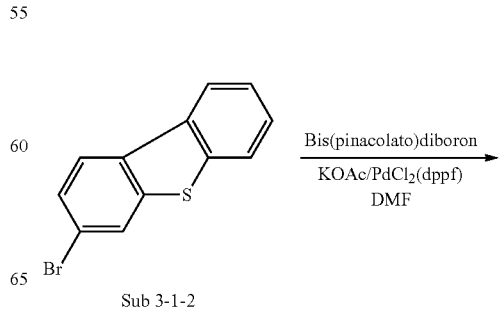

Sub 3-1-2

Synthesis Example of Sub 3(7)

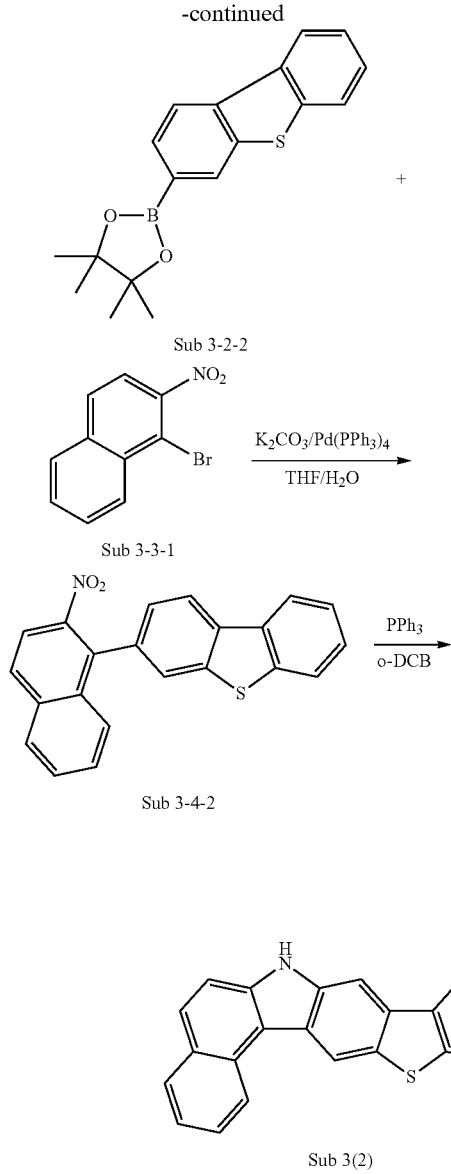

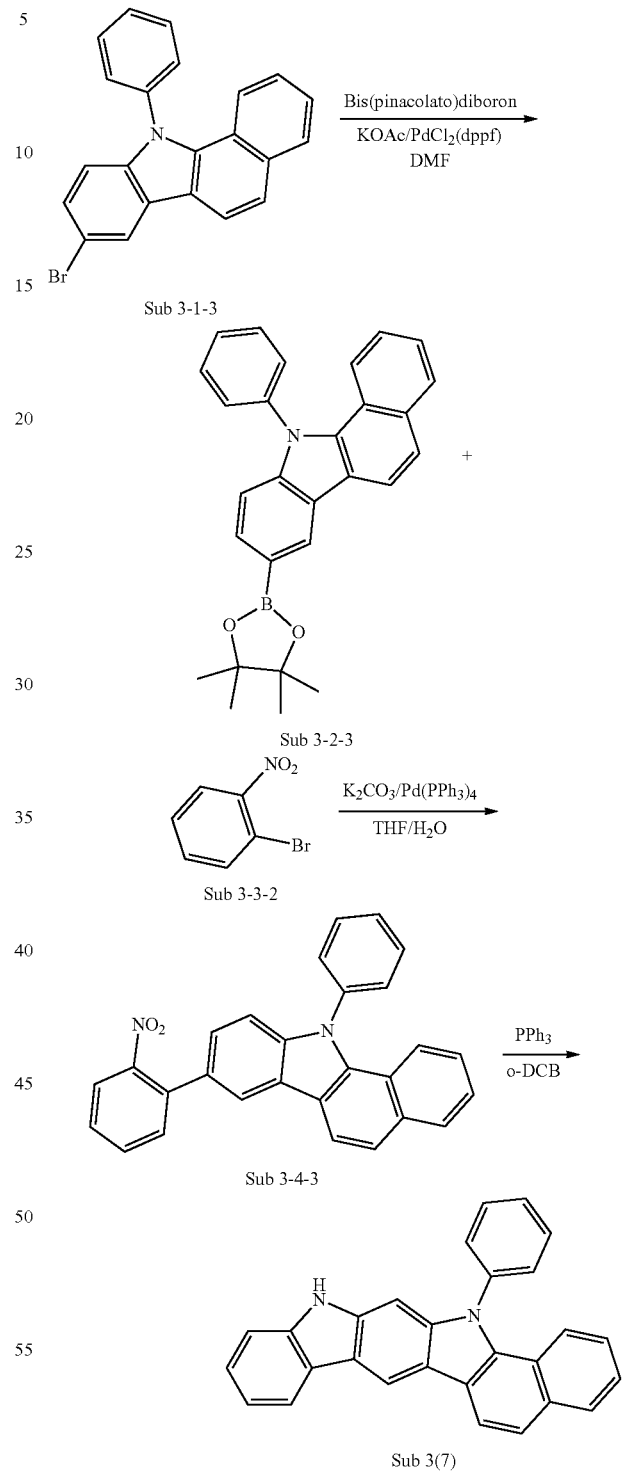

Synthesis Method of Sub 3-2-2

Sub 3-1-2 (40.8 g, 155 mmol) was carried out in the same manner as in Sub 3-2-1 to give the product Sub 3-2-2 (37.5 g, 78%).

Synthesis Method of Sub 3-4-2

Sub 3-2-2 (34.4 g, 111 mmol) and Sub 3-3-1 (33.5 g, 133 mmol) were carried out in the same manner as in Sub 3-4-1 to give the product Sub 3-4-2 (30.4 g, 77%).

Synthesis Method of Sub 3(2)

Sub 3-4-2 (20 g, 56.3 mmol) was carried out in the same manner as in Sub 3(1) to give the product Sub 3(2) (14.4 g, 79%).

Synthesis Method of Sub 3-2-3

Sub 3-1-3 (57.7 g, 155 mmol) was carried out in the same manner as in Sub 3-2-1 to give the product Sub 3-2-3 (57.7 g, 78%).

Synthesis Method of Sub 3-4-3

Sub 3-2-3 (46.5 g, 111 mmol) and Sub 3-3-2 (26.9 g, 133 mmol) were carried out in the same manner as in Sub 3-4-1 to give the product Sub 3-4-3 (37.3 g, 81%).

Synthesis Method of Sub 3(7)

Sub 3-4-3 (23.3 g, 56.3 mmol) was carried out in the same manner as in Sub 3(1) to give the product Sub 3 (7) (17.9 g, 83%).

Synthesis Example of Sub 3(13)

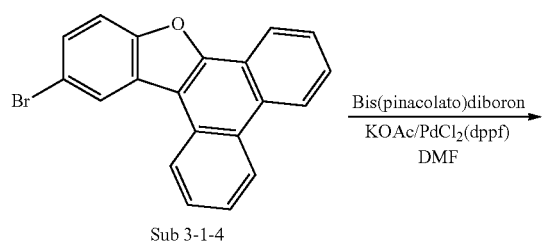

Sub 3-1-4

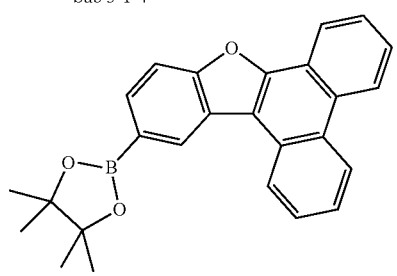

Sub 3-2-4

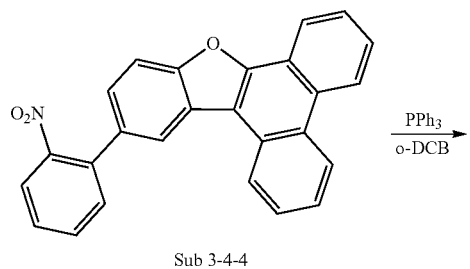

Sub 3-4-4

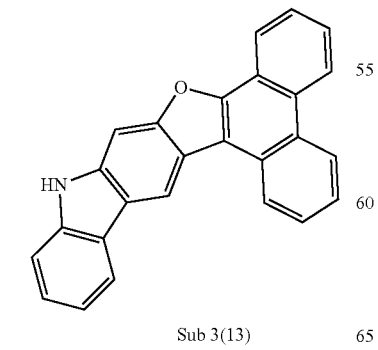

Sub 3(13)

Synthesis Method of Sub 3-2-4

Sub 3-1-4 (53.8 g, 155 mmol) was carried out in the same manner as in Sub 3-2-1 to give the product Sub 3-2-4 (46.4 g, 76%).

Synthesis Method of Sub 3-4-4

Sub 3-2-4 (43.8 g, 111 mmol) and Sub 3-3-2 (26.9 g, 133 mmol) were carried out in the same manner as in Sub 3-4-1 to give the product Sub 3-4-4 (34.6 g, 80%).

Synthesis Method of Sub 3(13)

Sub 3-4-4 (21.9 g, 56.3 mmol) was carried out in the same manner as in Sub 3(1) to give the product Sub 3(13) (16.1 g, 81%).

Synthesis Example of Sub 3(26)

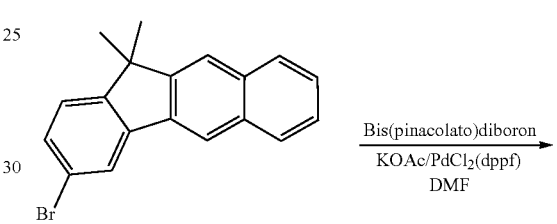

Sub 3-1-5

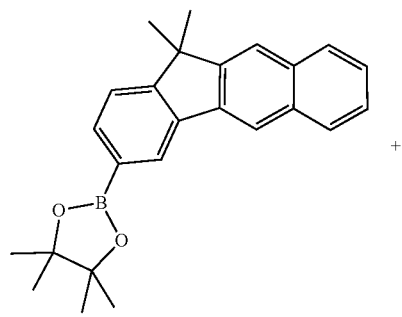

Sub 3-2-5

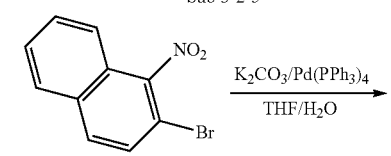

Sub 3-3-3

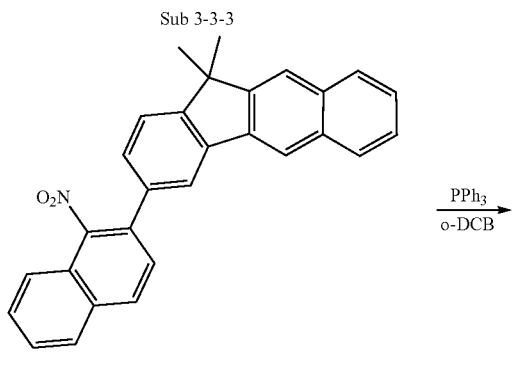

Sub 3-4-5

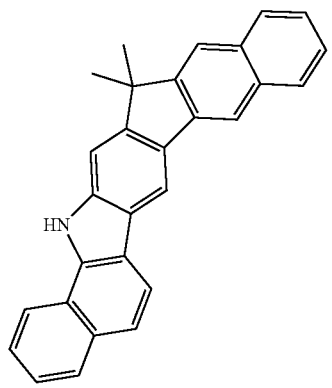

Sub 3(26)

Synthesis Method of Sub 3-2-5

Sub 3-1-5(50.1 g, 155 mmol) was carried out in the same manner as in Sub 3-2-1 to give the product Sub 3-2-5 (44.2 g, 76%).

Synthesis Method of Sub 3-4-5

Sub 3-2-5 (41.1 g, 111 mmol) and Sub 3-3-3(33.5 g, 133 mmol) were carried out in the same manner as in Sub 3-4-1 to give the product Sub 3-4-5 (37.4 g, 81%).

Synthesis Method of Sub 3(26)

Sub 3-4-5(23.4 g, 56.3 mmol) was carried out in the same manner as in Sub 3(1) to give the product Sub 3(26) (17.9 g, 83%).

Synthesis Example of Sub 3(39)

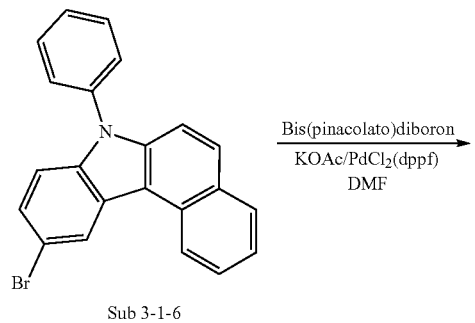

Sub 3-1-6

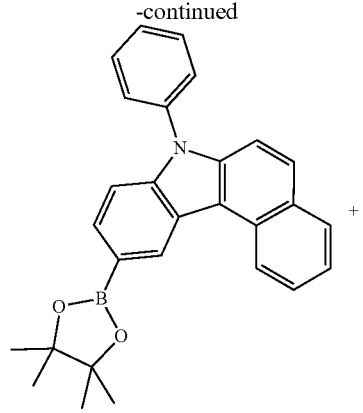

Sub 3-2-6

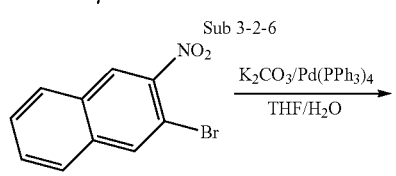

Sub 3-3-4

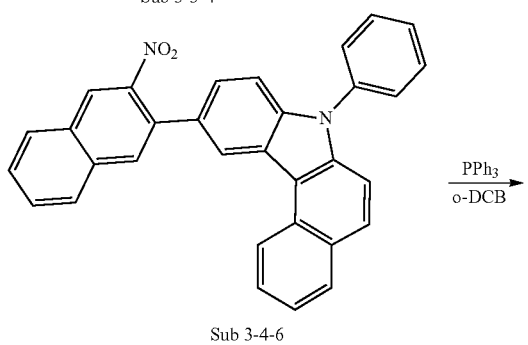

Sub 3-4-6

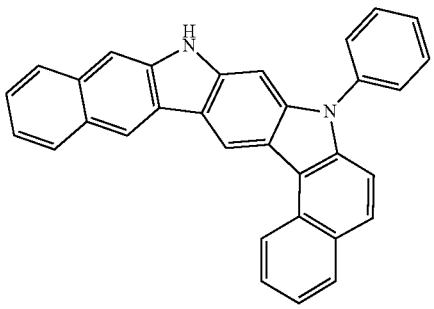

Sub 3(39)

Synthesis Method of Sub 3-2-6

Sub 3-1-6(57.7 g, 155 mmol) was carried out in the same manner as in Sub 3-2-1 to give the product Sub 3-2-6 (51.3 g, 79%).

Synthesis Method of Sub 3-4-6

Sub 3-2-6 (46.5 g, 111 mmol) and Sub 3-3-4(33.5 g, 133 mmol) were carried out in the same manner as in Sub 3-4-1 to give the product Sub 3-4-6 (41.2 g, 80%).

Synthesis Method of Sub 3(39)

Sub 3-4-6(26.2 g, 56.3 mmol) was carried out in the same manner as in Sub 3(1) to give the product Sub 3(39) (19.7 g, 81%).

Synthesis Example of Sub 3(45)

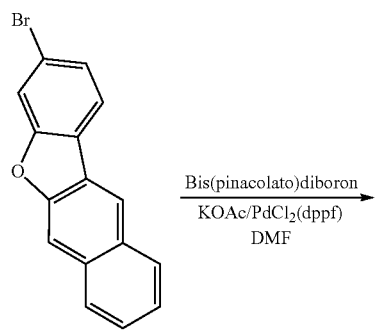

Sub 3-1-7

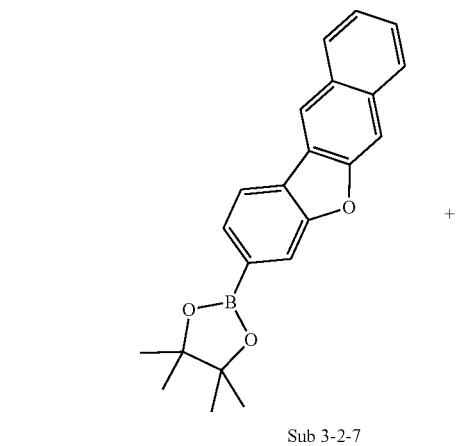

Sub 3-2-7

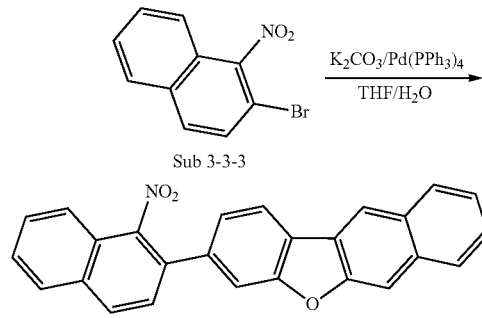

Sub 3-4-7

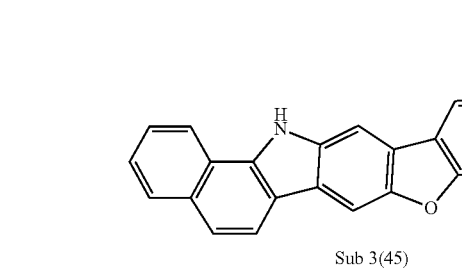

Sub 3(45)

Synthesis Method of Sub 3-2-7

Sub 3-1-7 (46.1 g, 155 mmol) was carried out in the same manner as in Sub 3-2-1 to give the product Sub 3-2-7 (43.2 g, 81%).

Synthesis Method of Sub 3-4-7

Sub 3-2-7 (38.2 g, 111 mmol) and Sub 3-3-3 (33.5 g, 133 mmol) were carried out in the same manner as in Sub 3-4-1 to give the product Sub 3-4-7 (36.7 g, 85%).

Synthesis Method of Sub 3(45)

Sub 3-4-7 (21.9 g, 56.3 mmol) was carried out in the same manner as in Sub 3(1) to give the product Sub 3(45) (16.3 g, 81%).

Examples of Sub 3 include, but are not limited to, the followings.

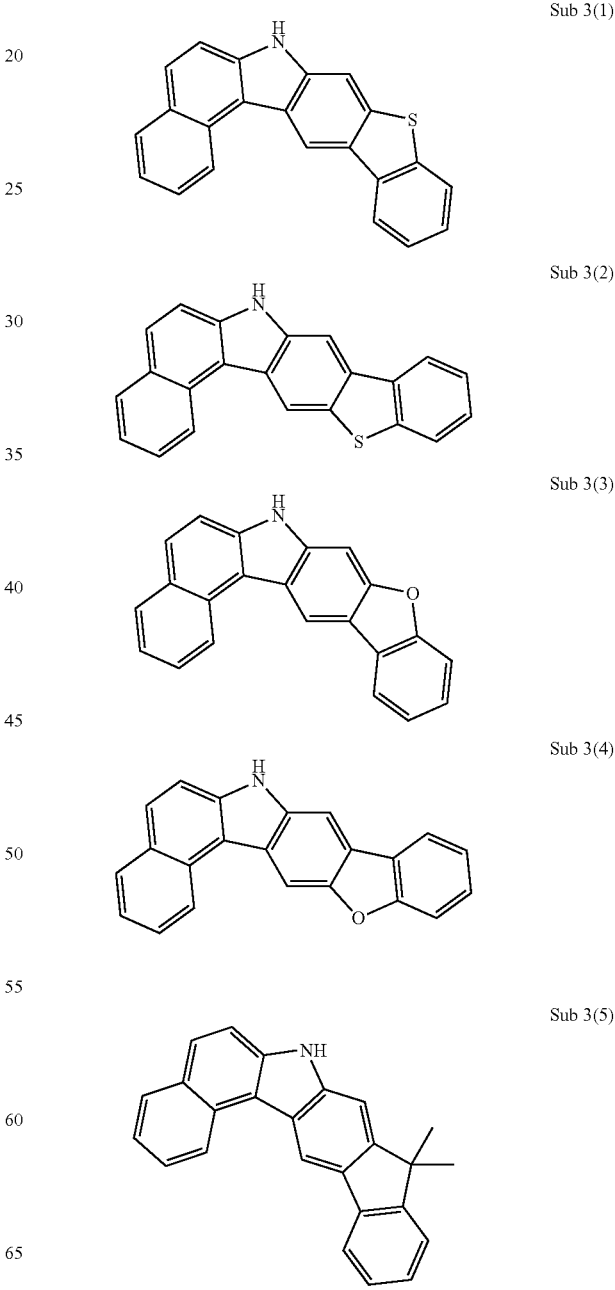

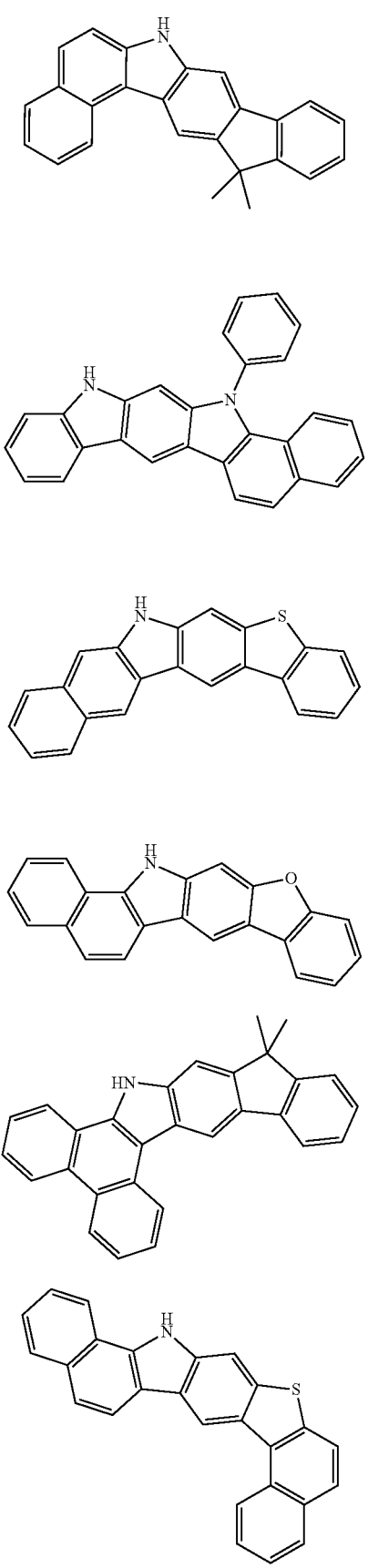
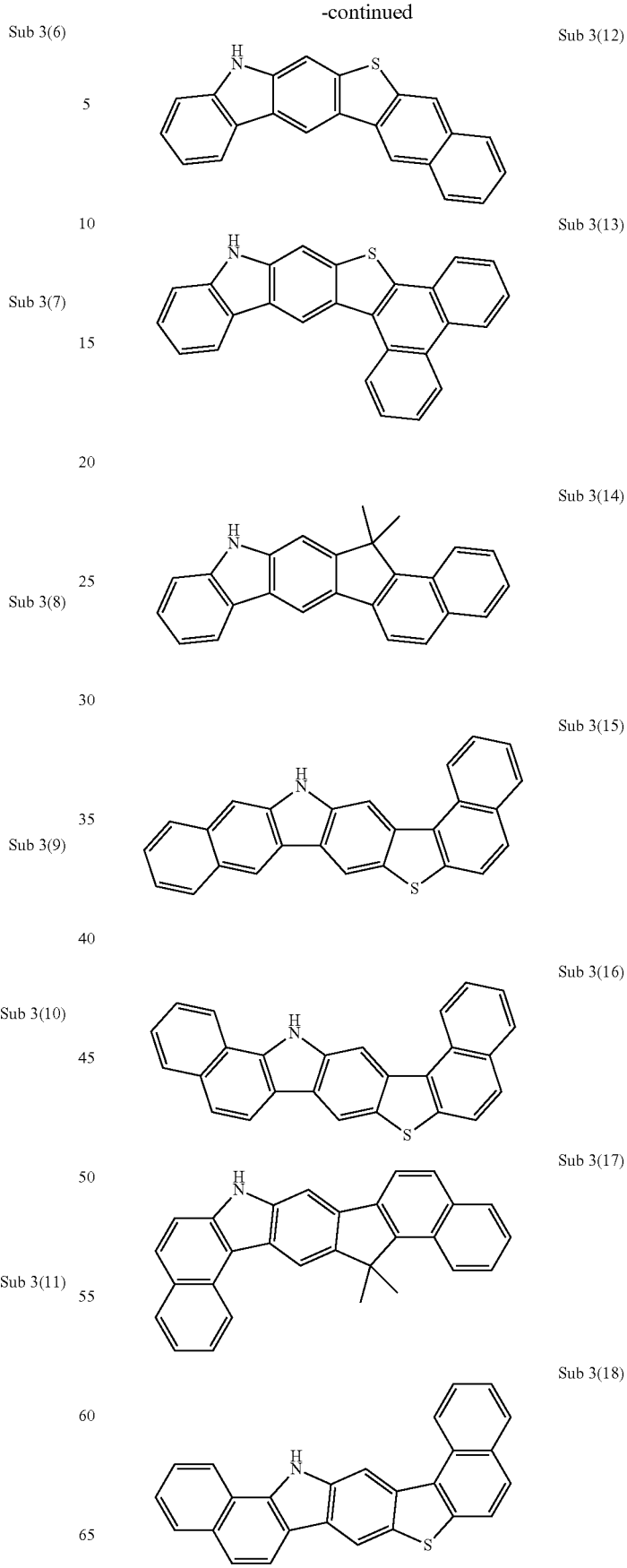

Sub 3(19)
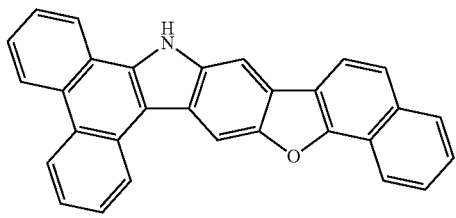
Sub 3(24)
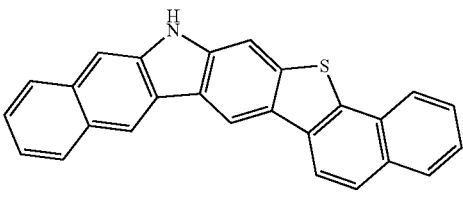
Sub 3(20)
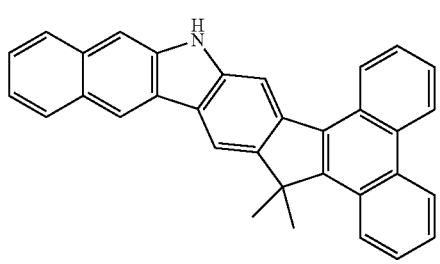
Sub 3(25)
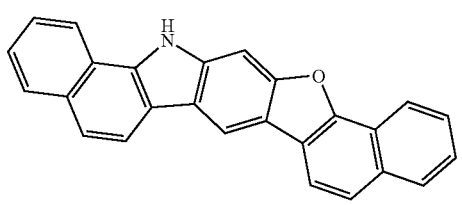
Sub 3(21)
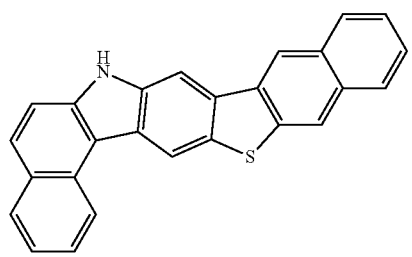
Sub 3(26)
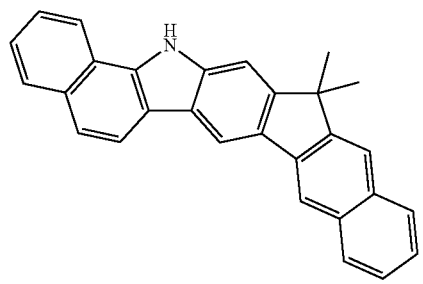
Sub 3(22)
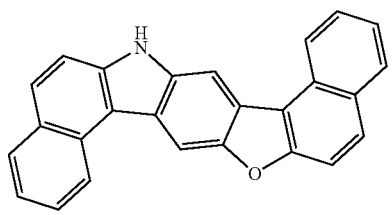
Sub 3(27)
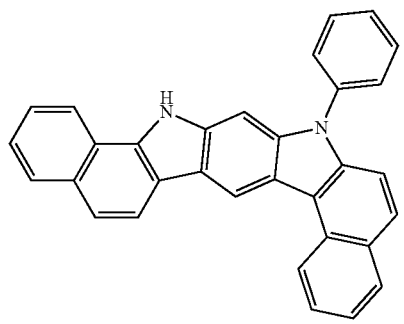
Sub 3(23)
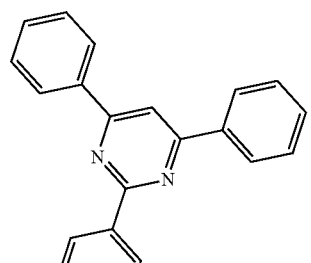
Sub 3(28)
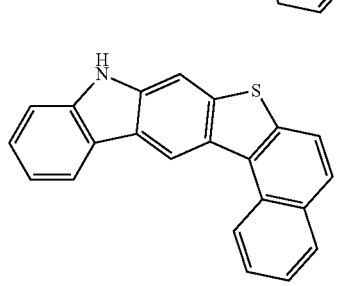
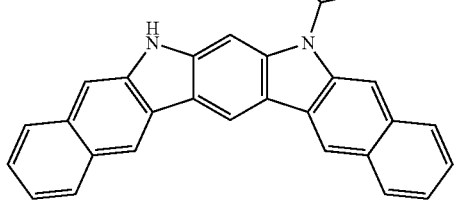
Sub 3(29)
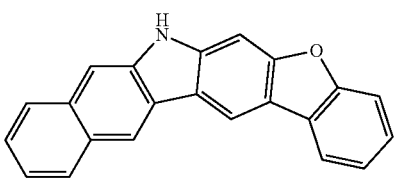

-continued
Sub 3(30)
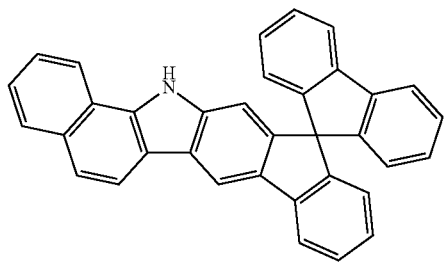
Sub 3(35)
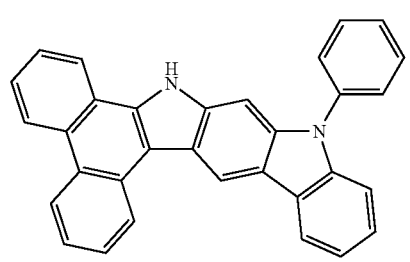
Sub 3(36)
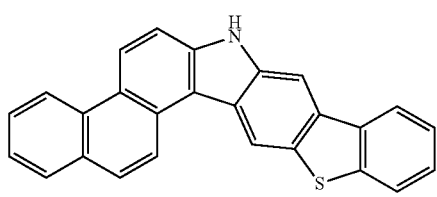
Sub 3(37)
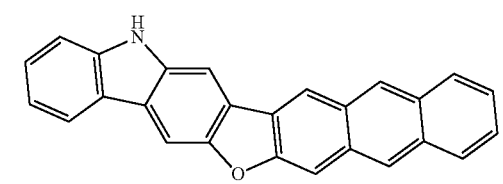
Sub 3(38)
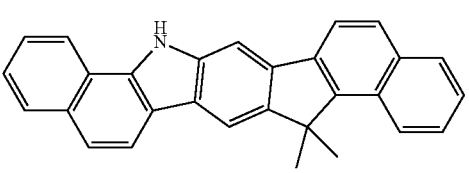
Sub 3(39)
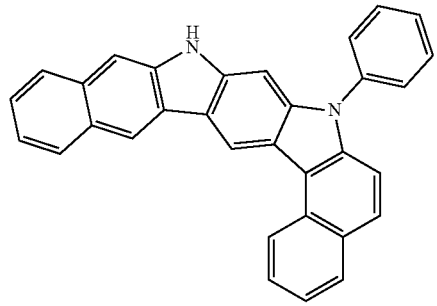
-continued
Sub 3(40)
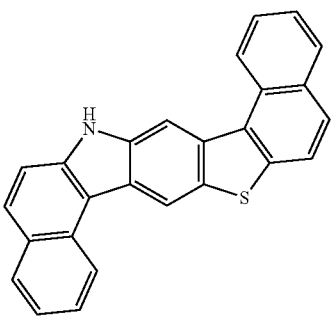
Sub 3(41)
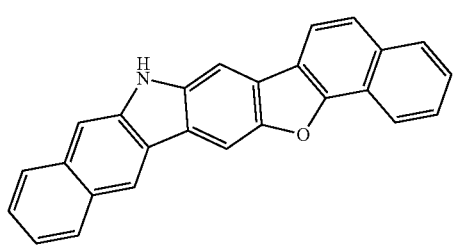
Sub 3(42)
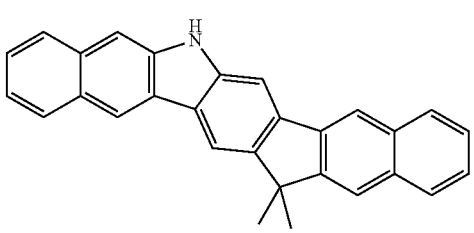
Sub 3(43)
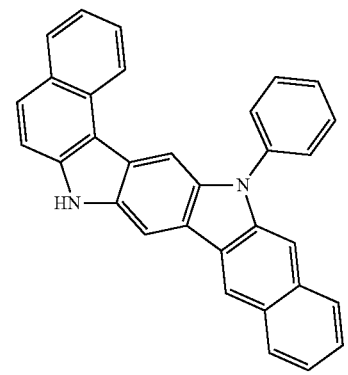
Sub 3(44)
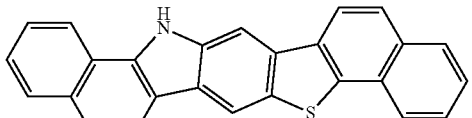
Sub 3(45)
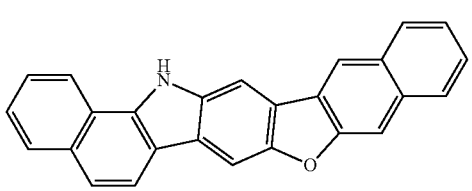

Sub 3(46)
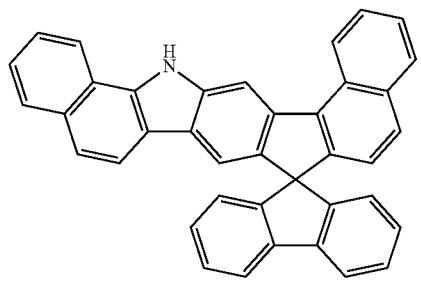
Sub 3(47)
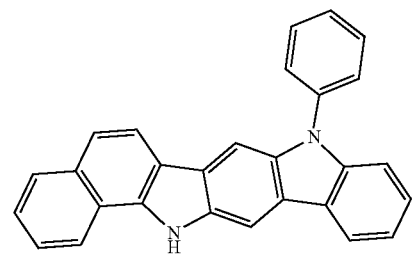
Sub 3(48)
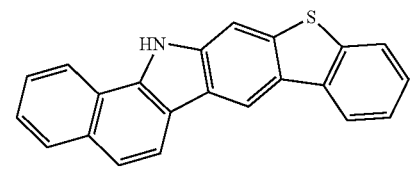
Sub 3(49)
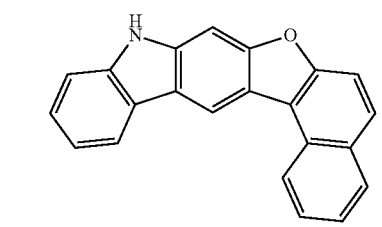
Sub 3(50)
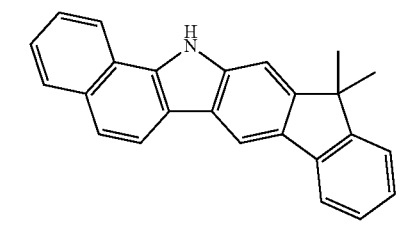
Sub 3(51)
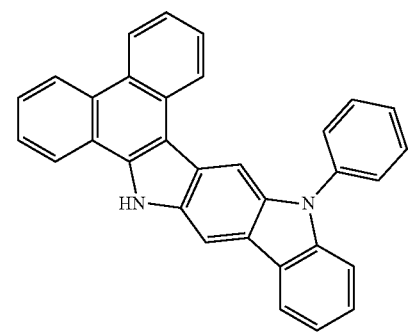
Sub 3(52)
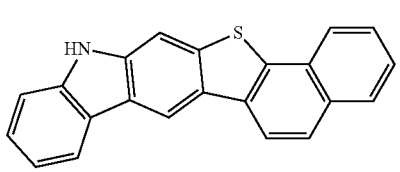
Sub 3(53)
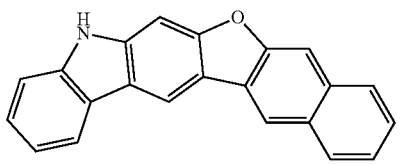
Sub 3(54)
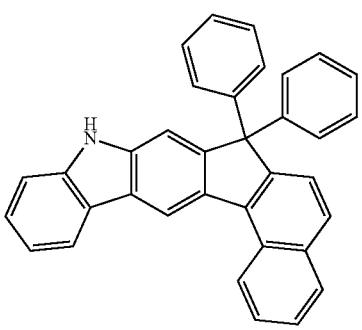
Sub 3(55)
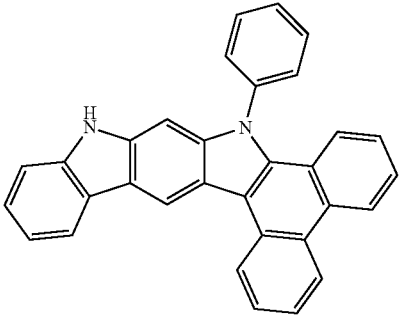
Sub 3(56)
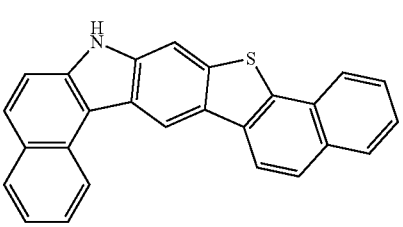
Sub 3(57)
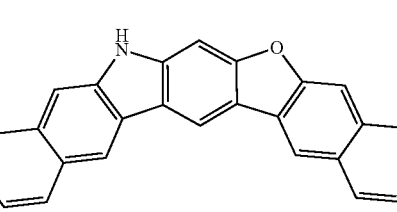

Sub 3(58)

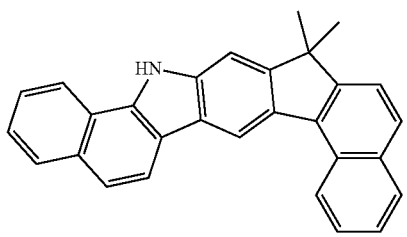

TABLE 4

| compound | FD-MS | compound | FD-MS |
|---|---|---|---|
| Sub 3(1) | m/z = 323.08($C_{22}H_{13}NS$ = 323.41) | Sub 3(2) | m/z = 323.08($C_{22}H_{13}NS$ = 323.41) |
| Sub 3(3) | m/z = 307.10($C_{22}H_{13}NO$ = 307.34) | Sub 3(4) | m/z = 307.10($C_{22}H_{13}NO$ = 307.34) |
| Sub 3(5) | m/z = 333.15($C_{25}H_{19}N$ = 333.43) | Sub 3(6) | m/z = 382.15($C_{28}H_{18}N_2$ = 382.46) |
| Sub 3(7) | m/z = 382.15($C_{28}H_{18}N_2$ = 382.47) | Sub 3(8) | m/z = 323.08($C_{22}H_{13}NS$ = 323.41) |
| Sub 3(9) | m/z = 307.10($C_{22}H_{13}NO$ = 307.35) | Sub 3(10) | m/z = 383.17($C_{29}H_{21}N$ = 383.49) |
| Sub 3(11) | m/z = 373.09($C_{26}H_{15}NS$ = 373.47) | Sub 3(12) | m/z = 323.08($C_{22}H_{13}NS$ = 323.41) |
| Sub 3(13) | m/z = 357.12($C_{26}H_{15}NO$ = 357.41) | Sub 3(14) | m/z = 333.15($C_{25}H_{19}N$ = 333.43) |
| Sub 3(15) | m/z = 373.09($C_{26}H_{15}NS$ = 373.47) | Sub 3(16) | m/z = 357.12($C_{26}H_{15}NO$ = 357.41) |
| Sub 3(17) | m/z = 383.17($C_{29}H_{21}N$ = 383.49) | Sub 3(18) | m/z = 373.09($C_{26}H_{15}NS$ = 373.47) |
| Sub 3(19) | m/z = 407.13($C_{30}H_{17}NO$ = 407.47) | Sub 3(20) | m/z = 433.18($C_{33}H_{23}N$ = 433.55) |
| Sub 3(21) | m/z = 373.09($C_{26}H_{15}NS$ = 373.47) | Sub 3(22) | m/z = 357.12($C_{26}H_{15}NO$ = 357.41) |
| Sub 3(23) | m/z = 662.25($C_{48}H_{30}N_4$ = 662.80) | Sub 3(24) | m/z = 373.09($C_{26}H_{15}NS$ = 373.47) |
| Sub 3(25) | m/z = 357.12($C_{26}H_{15}NO$ = 357.41) | Sub 3(26) | m/z = 383.17($C_{29}H_{21}N$ = 383.49) |
| Sub 3(27) | m/z = 432.16($C_{32}H_{20}N_2$ = 432.53) | Sub 3(28) | m/z = 323.08($C_{22}H_{13}NS$ = 323.41) |
| Sub 3(29) | m/z = 307.10($C_{22}H_{13}NO$ = 307.35) | Sub 3(30) | m/z = 455.17($C_{35}H_{21}N$ = 455.56) |
| Sub 3(31) | m/z = 432.16($C_{32}H_{20}N_2$ = 432.53) | Sub 3(32) | m/z = 323.08($C_{22}H_{13}NS$ = 323.41) |
| Sub 3(33) | m/z = 307.10($C_{22}H_{13}NO$ = 307.35) | Sub 3(34) | m/z = 383.17($C_{29}H_{21}N$ = 383.49) |
| Sub 3(35) | m/z = 432.16($C_{32}H_{20}N_2$ = 439.53) | Sub 3(36) | m/z = 373.09($C_{26}H_{15}NS$ = 373.47) |
| Sub 3(37) | m/z = 357.12($C_{26}H_{15}NO$ = 357.41) | Sub 3(38) | m/z = 383.17($C_{29}H_{21}N$ = 383.49) |
| Sub 3(39) | m/z = 432.16($C_{32}H_{20}N_2$ = 432.53) | Sub 3(40) | m/z = 373.09($C_{26}H_{15}NS$ = 373.47) |
| Sub 3(41) | m/z = 357.12($C_{26}H_{15}NO$ = 357.41) | Sub 3(42) | m/z = 383.17($C_{29}H_{21}N$ = 383.49) |
| Sub 3(43) | m/z = 432.16($C_{32}H_{20}N_2$ = 432.53) | Sub 3(44) | m/z = 373.09($C_{26}H_{15}NS$ = 373.47) |
| Sub 3(45) | m/z = 357.12($C_{26}H_{15}NO$ = 357.41) | Sub 3(46) | m/z = 505.18($C_{39}H_{23}N$ = 505.62) |
| Sub 3(47) | m/z = 382.15($C_{28}H_{18}N_2$ = 382.47) | Sub 3(48) | m/z = 323.08($C_{22}H_{13}NS$ = 323.41) |
| Sub 3(49) | m/z = 307.10($C_{22}H_{13}NO$ = 307.35) | Sub 3(50) | m/z = 333.15($C_{25}H_{19}N$ = 333.43) |
| Sub 3(51) | m/z = 432.16($C_{32}H_{20}N_2$ = 432.53) | Sub 3(52) | m/z = 323.08($C_{22}H_{13}NS$ = 323.41) |
| Sub 3(53) | m/z = 307.10($C_{22}H_{13}NO$ = 307.35) | Sub 3(54) | m/z = 457.18($C_{35}H_{23}N$ = 457.58) |
| Sub 3(55) | m/z = 432.16($C_{32}H_{20}N_2$ = 432.53) | Sub 3(56) | m/z = 373.09($C_{26}H_{15}NS$ = 373.47) |
| Sub 3(57) | m/z = 357.12($C_{26}H_{15}NO$ = 357.41) | Sub 3(58) | m/z = 383.17($C_{29}H_{21}N$ = 383.49) |
| Sub 3(59) | m/z = 616.17($C_{42}H_{24}N_4S$ = 616.74) | Sub 3(60) | m/z = 323.08($C_{22}H_{13}NS$ = 323.41) |
| Sub 3(61) | m/z = 307.10($C_{22}H_{13}NO$ = 307.35) | Sub 3(62) | m/z = 373.09($C_{26}H_{15}NS$ = 373.47) |
| Sub 3(63) | m/z = 432.16($C_{32}H_{20}N_2$ = 432.53) | Sub 3(64) | m/z = 373.09($C_{26}H_{15}NS$ = 373.47) |
| Sub 3(65) | m/z = 357.12($C_{26}H_{15}NO$ = 357.41) | Sub 3(66) | m/z = 383.17($C_{29}H_{21}N$ = 383.49) |

Examples of Sub 4

Examples of Sub 4 include, but are not limited to, the followings.

Sub 4-1

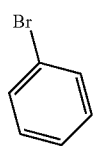

Sub 4-2

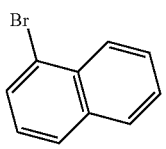

Sub 4-3

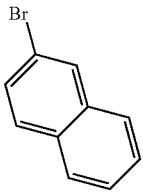

Sub 4-4

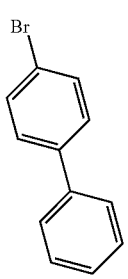

-continued
Sub 4-5
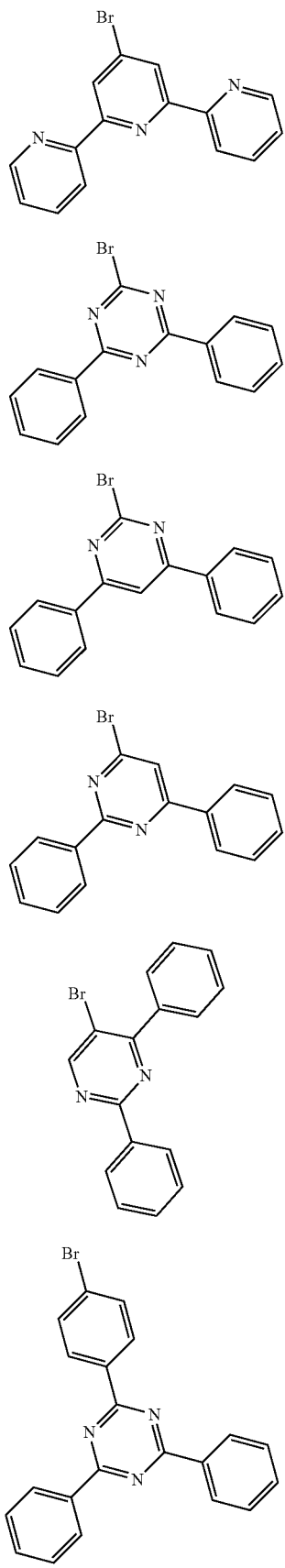
Sub 4-6
Sub 4-7
Sub 4-8
Sub 4-9
Sub 4-10
-continued
Sub 4-11
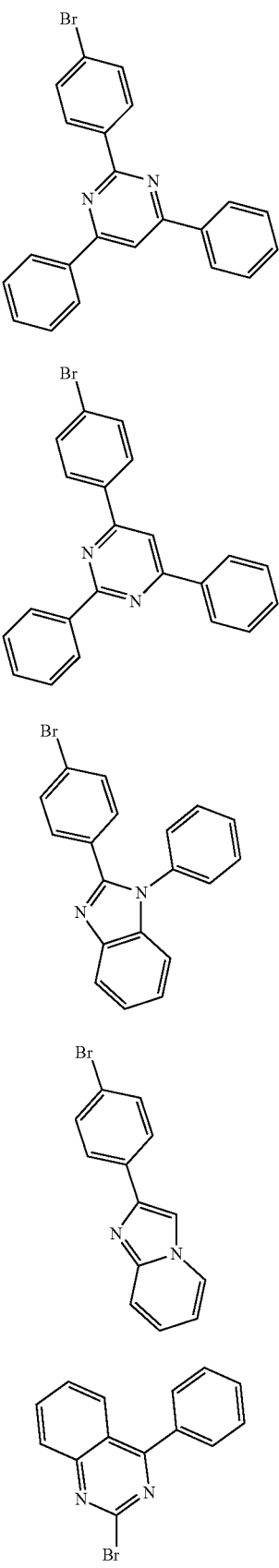
Sub 4-12
Sub 4-13
Sub 4-14
Sub 4-15

-continued

Sub 4-16

Sub 4-17

Sub 4-18

Sub 4-19

Sub 4-20

-continued

Sub 4-21

Sub 4-22

Sub 4-23

Sub 4-24

Sub 4-25

Sub 4-26

Sub 4-27
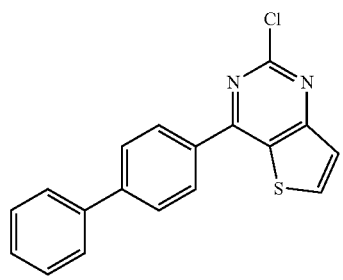
Sub 4-28
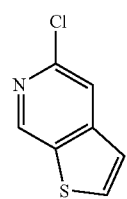
Sub 4-29
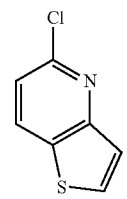
Sub 4-30
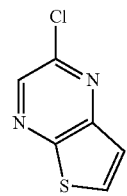
Sub 4-31
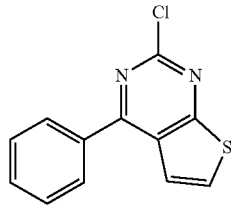
Sub 4-32
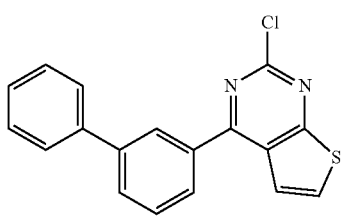
Sub 4-33
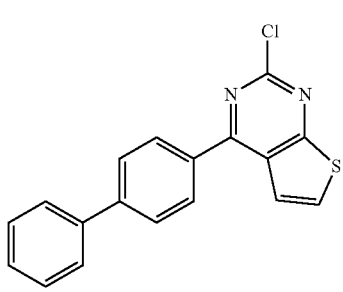
Sub 4-34
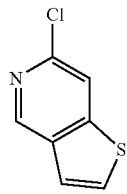
Sub 4-35
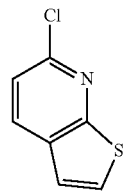
Sub 4-36
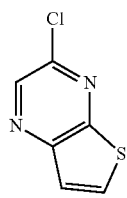
Sub 4-37
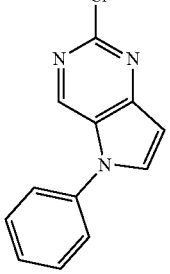
Sub 4-38
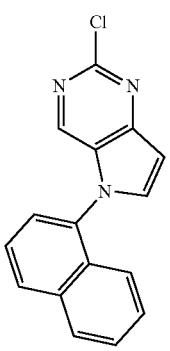
Sub 4-39
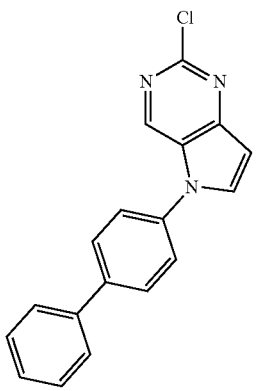

-continued
Sub 4-40
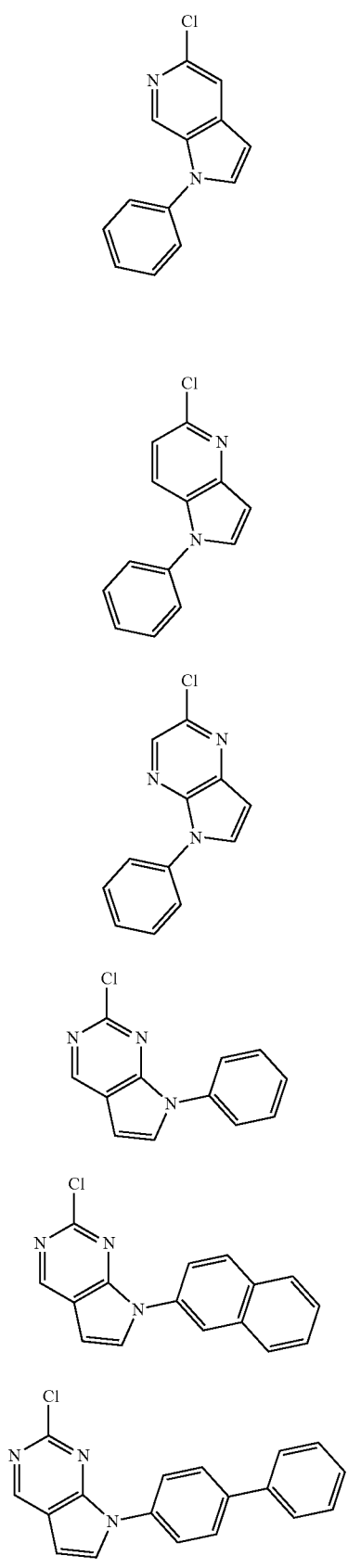
Sub 4-41
Sub 4-42
Sub 4-43
Sub 4-44
Sub 4-45
-continued
Sub 4-46
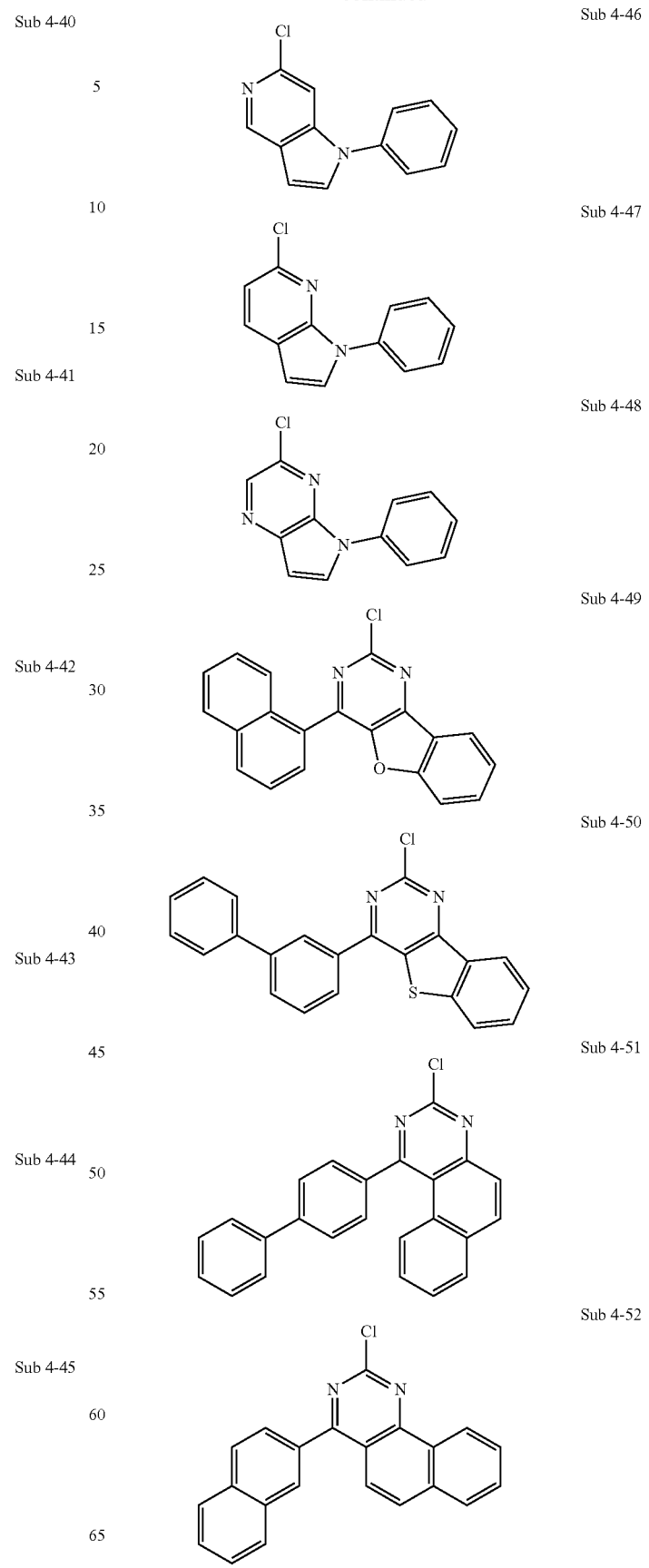
Sub 4-47
Sub 4-48
Sub 4-49
Sub 4-50
Sub 4-51
Sub 4-52

-continued

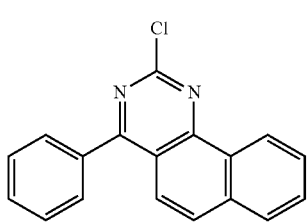

Sub 4-53

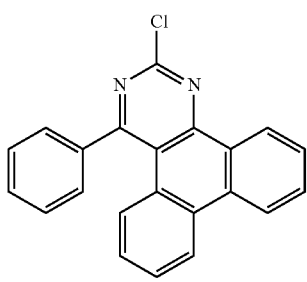

Sub 4-54

TABLE 5

| compound | FD-MS | compound | FD-MS |
| --- | --- | --- | --- |
| Sub 4-1 | m/z = 155.96($C_6H_5Br$ = 157.01) | Sub 4-2 | m/z = 205.97($C_{10}H_7Br$ = 207.07) |
| Sub 4-3 | m/z = 205.97($C_{10}H_7Br$ = 207.07) | Sub 4-4 | m/z = 231.99($C_{12}H_9Br$ = 233.10) |
| Sub 4-5 | m/z = 309.02($C_{17}H_{12}BrN$ = 310.19) | Sub 4-6 | m/z = 311.01($C_{15}H_{10}BrN_3$ = 312.16) |
| Sub 4-7 | m/z = 310.01($C_{16}H_{11}BrN_2$ = 311.18) | Sub 4-8 | m/z = 310.01($C_{16}H_{11}BrN_2$ = 311.18) |
| Sub 4-9 | m/z = 310.01($C_{16}H_{11}BrN_2$ = 311.18) | Sub 4-10 | m/z = 387.04($C_{21}H_{14}BrN_3$ = 388.26) |
| Sub 4-11 | m/z = 386.04($C_{22}H_{15}BrN_2$ = 387.27) | Sub 4-12 | m/z = 386.04($C_{22}H_{15}BrN_2$ = 387.27) |
| Sub 4-13 | m/z = 348.03($C_{19}H_{13}BrN_2$ = 349.22) | Sub 4-14 | m/z = 271.99($C_{13}H_9BrN_2$ = 273.13) |
| Sub 4-15 | m/z = 283.99($C_{14}H_9BrN_2$ = 285.14) | Sub 4-16 | m/z = 374.01($C_{20}H_{11}BrN_2O$ = 375.22) |
| Sub 4-17 | m/z = 400.06($C_{23}H_{17}BrN_2$ = 401.30) | Sub 4-18 | m/z = 360.03($C_{20}H_{13}BrN_2$ = 361.23) |
| Sub 4-19 | m/z = 476.09($C_{29}H_{21}BrN_2$ = 477.39) | Sub 4-20 | m/z = 284.99($C_{13}H_8BrN_3$ = 286.13) |
| Sub 4-21 | m/z = 289.03($C_{14}H_4D_5BrN_2$ = 290.2) | Sub 4-22 | m/z = 284.99($C_{13}H_8BrN_3$ = 286.13) |
| Sub 4-23 | m/z = 375.00($C_{19}H_{10}BrN_3O$ = 376.2) | Sub 4-24 | m/z = 401.05($C_{22}H_{16}BrN_3$ = 402.29) |
| Sub 4-25 | m/z = 296.02($C_{16}H_9ClN_2S$ = 296.77) | Sub 4-26 | m/z = 322.03($C_{18}H_{11}ClN_2S$ = 322.81) |
| Sub 4-27 | m/z = 322.03($C_{18}H_{11}ClN_2S$ = 322.81) | Sub 4-28 | m/z = 168.98($C_7H_4ClNS$ = 169.63) |
| Sub 4-29 | m/z = 168.98($C_7H_4ClNS$ = 169.63) | Sub 4-30 | m/z = 169.97($C_6H_3ClN_2S$ = 170.62) |
| Sub 4-31 | m/z = 246.00($C_{12}H_7ClN_2S$ = 246.72) | Sub 4-32 | m/z = 322.03($C_{18}H_{11}ClN_2S$ = 322.81) |
| Sub 4-33 | m/z = 322.03($C_{18}H_{11}ClN_2S$ = 322.81) | Sub 4-34 | m/z = 168.98($C_7H_4ClNS$ = 169.63) |
| Sub 4-35 | m/z = 168.98($C_7H_4ClNS$ = 169.63) | Sub 4-36 | m/z = 169.97($C_6H_3ClN_2S$ = 170.62) |
| Sub 4-37 | m/z = 229.04($C_{12}H_8ClN_3$ = 229.67) | Sub 4-38 | m/z = 279.06($C_{16}H_{10}ClN_3$ = 279.72) |
| Sub 4-39 | m/z = 305.07($C_{18}H_{12}ClN_3$ = 305.76) | Sub 4-40 | m/z = 228.05($C_{13}H_9ClN_2$ = 228.68) |
| Sub 4-41 | m/z = 228.05($C_{13}H_9ClN_2$ = 228.68) | Sub 4-42 | m/z = 229.04($C_{12}H_8ClN_3$ = 229.67) |
| Sub 4-43 | m/z = 229.04($C_{12}H_8ClN_3$ = 229.67) | Sub 4-44 | m/z = 279.06($C_{16}H_{10}ClN_3$ = 279.72) |
| Sub 4-45 | m/z = 305.07($C_{18}H_{12}ClN_3$ = 305.76) | Sub 4-46 | m/z = 228.05($C_{13}H_9ClN_2$ = 228.68) |
| Sub 4-47 | m/z = 228.05($C_{13}H_9ClN_2$ = 228.68) | Sub 4-48 | m/z = 229.04($C_{12}H_8ClN_3$ = 229.67) |
| Sub 4-49 | m/z = 330.1($C_{20}H_{11}ClN_2O$ = 330.77) | Sub 4-50 | m/z = 372.05($C_{22}H_{13}ClN_2S$ = 372.87) |
| Sub 4-51 | m/z = 366.09($C_{24}H_{15}ClN_2$ = 366.85) | Sub 4-52 | m/z = 340.08($C_{22}H_{13}ClN_2$ = 340.81) |
| Sub 4-53 | m/z = 290.06($C_{18}H_{11}ClN_2$ = 290.75) | Sub 4-54 | m/z = 340.08($C_{22}H_{13}ClN_2$ = 340.81) |

Synthesis Examples of Final Products 2

Synthesis Example of 3-6

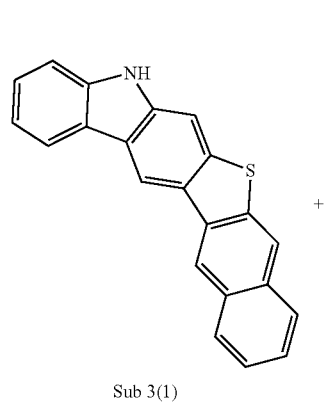

Sub 3(1)

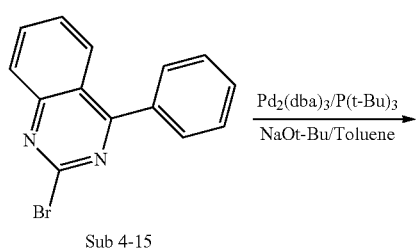

Sub 4-15

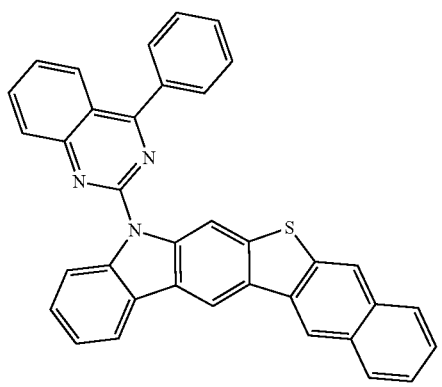

3-6

After Sub 3(1) (15.3 g, 47.3 mmol) was added in a round bottom flask and dissolved in toluene (500 mL), Sub 4-15 (14.8 g, 52.0 mmol), Pd$_2$(dba)$_3$ (2.4 g, 2.6 mmol), P(t-Bu)$_3$ (1.1 g, 5.2 mmol), NaOt-Bu (15 g, 156.1 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 19.0 g of the product. (yield: 76%)

Synthesis Example of 3-1

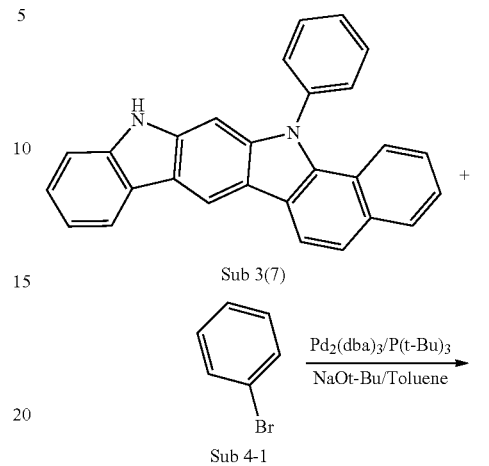

Sub 3(7)

Sub 4-1

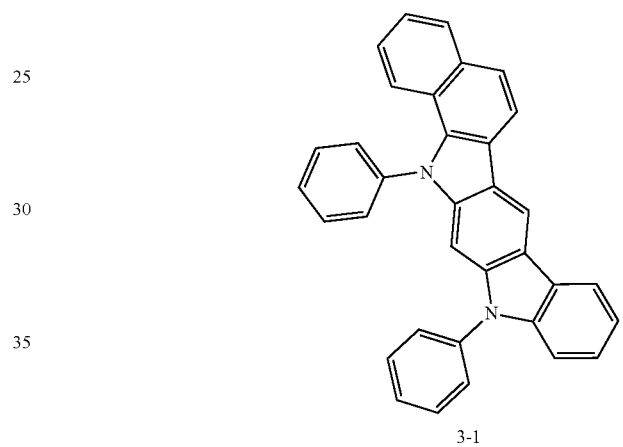

3-1

Sub 3(7) (18.1 g, 47.3 mmol), toluene (500 mL), Sub 4-1 (8.2 g, 52.0 mmol), Pd$_2$(dba)$_3$ (2.0 g, 2.2 mmol), P(t-Bu)$_3$ (0.9 g, 4.4 mmol), NaOt-Bu (12.7 g, 132 mmol) were added, the same procedure as described in the synthesis method of the 3-6 was carried out to obtain 16.7 g of the final product. (yield: 77%).

Synthesis Example of 3-7

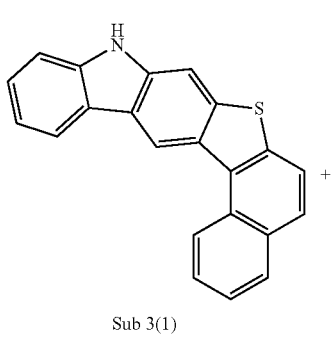

Sub 3(1)

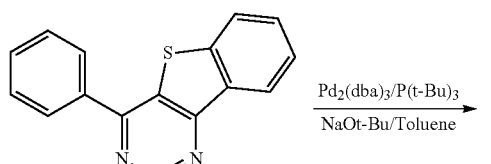

Sub 4-25

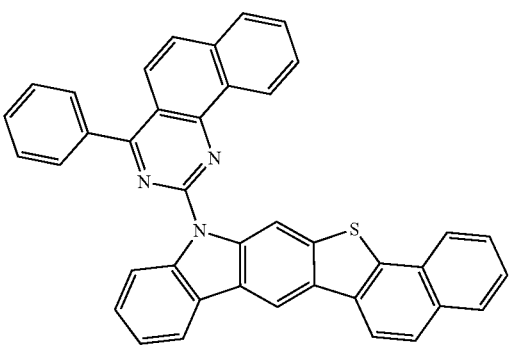

3-8

Sub 3(1)(15.3 g, 47.3 mmol) and Sub 4-53(15.1 g, 52.0 mmol) were carried out in the same manner as in the 3-6 to give 19.9 g of the final product. (yield: 73%).

Synthesis Example of 3-11

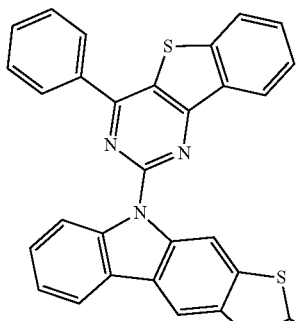

3-7

Sub 3(1)(15.3 g, 47.3 mmol) and Sub 4-25(15.4 g, 52.0 mmol) were carried out in the same manner as in the 3-6 to give 19.6 g of the final product. (yield: 71%).

Synthesis Example of 3-8

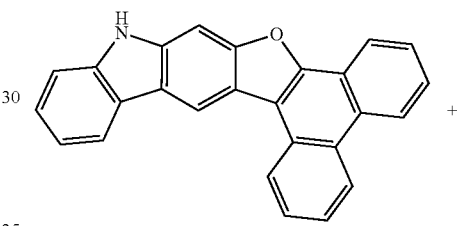

Sub 3-(13)

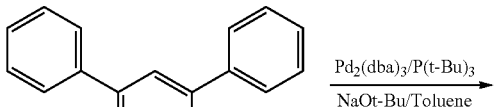

Sub 4-55

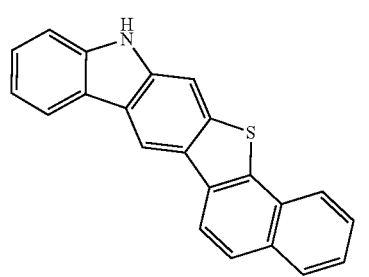

Sub 3(1)

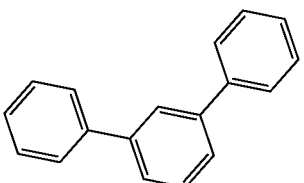

Sub 4-53

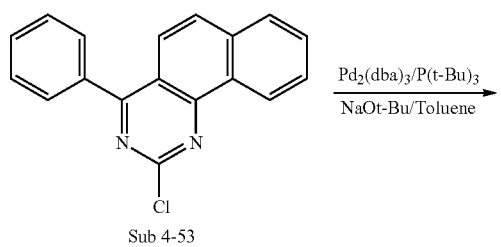

3-11

Sub 3(13)(16.9 g, 47.3 mmol) and Sub 4-55(16.1 g, 52.0 mmol) were carried out in the same manner as in the 3-6 to give 19.4 g of the final product. (yield: 70%).

Synthesis Example of 3-16
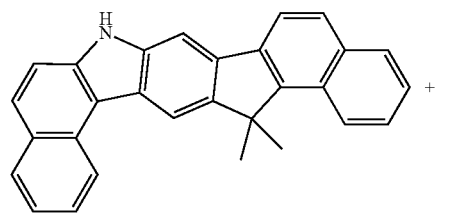
Sub 3(17)
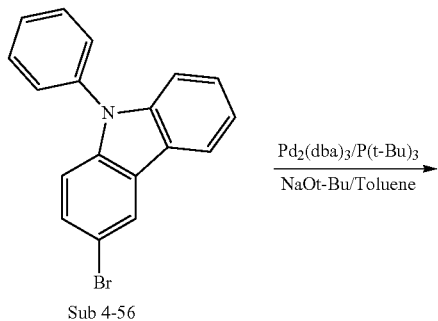
Sub 4-56
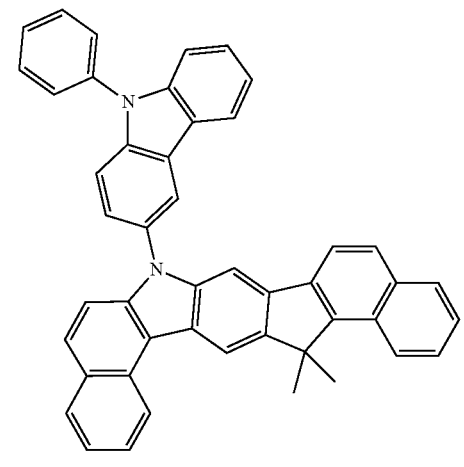
3-16
Sub 3(17)(18.1 g, 47.2 mmol) and Sub 4-56(16.7 g, 52.0 mmol) were carried out in the same manner as in the 3-6 to give 21.0 g of the final product. (yield: 71%).
Synthesis Example of 3-17
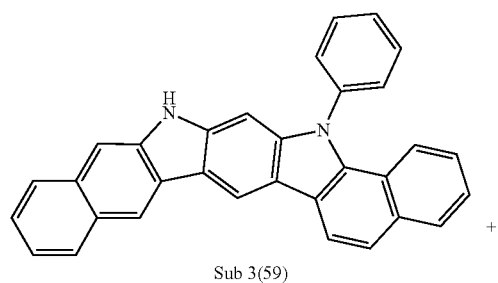
Sub 3(59)
-continued
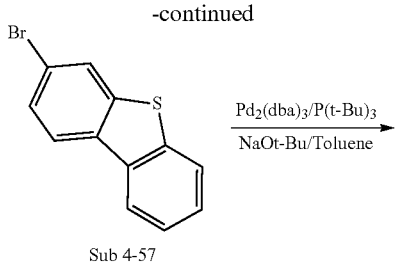
Sub 4-57
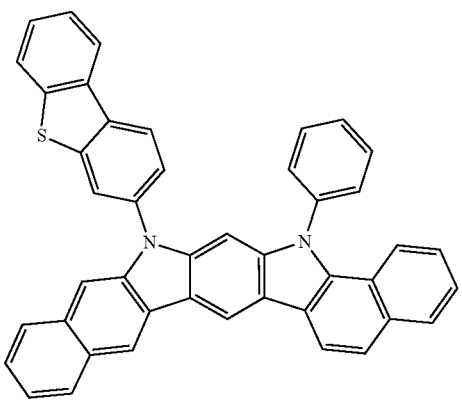
3-17
Sub 3(59)(20.5 g, 47.4 mmol) and Sub 4-57(13.7 g, 52.0 mmol) were carried out in the same manner as in the 3-6 to give 20.1 g of the final product. (yield: 69%).
Synthesis Example of 3-47
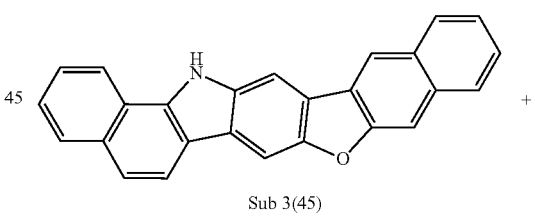
Sub 3(45)
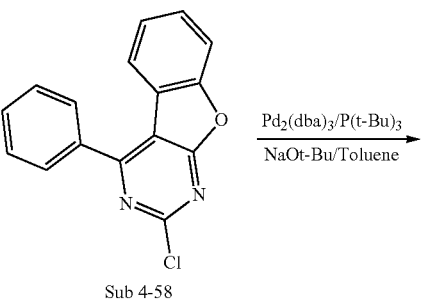
Sub 4-58

-continued
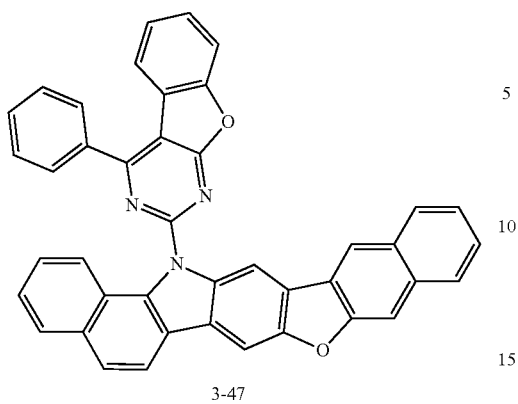
3-47
Sub 3(45)(16.9 g, 47.3 mmol) and Sub 4-58(14.6 g, 52.0 mmol) were carried out in the same manner as in the 3-6 to give 10.6 g of the final product. (yield: 74%).
Synthesis Example of 3-52
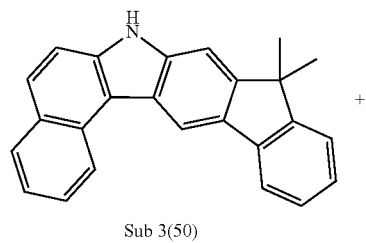
Sub 3(50)
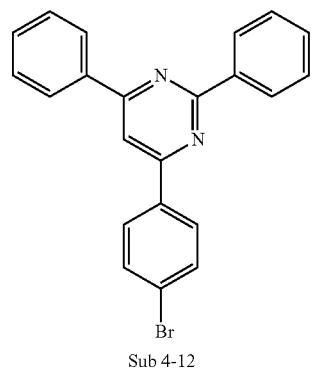
Sub 4-12
-continued
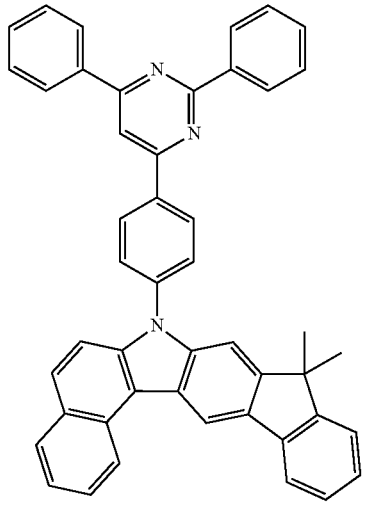
3-52
Sub 3(50)(15.8 g, 47.4 mmol) and Sub 4-12(20.2 g, 52.0 mmol) were carried out in the same manner as in the 3-6 to give 20.6 g of the final product. (yield: 70%).
Synthesis Example of 3-70
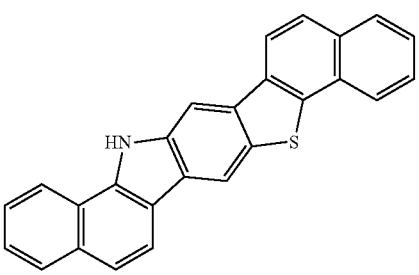
Sub 3(60)
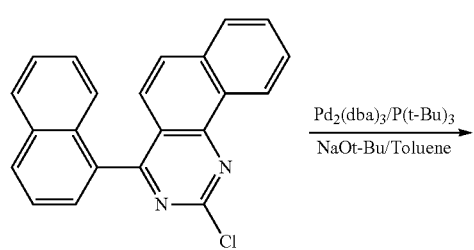
Sub 4-59

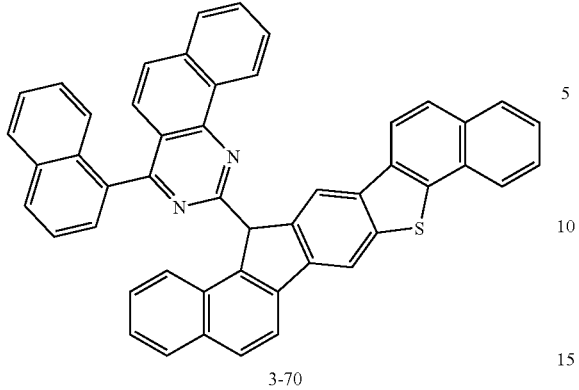

3-70

Sub 3(60)(17.7 g, 47.4 mmol) and Sub 4-59(17.8 g, 52.0 mmol) were carried out in the same manner as in the 3-6 to give 22.8 g of the final product. (yield: 73%).

TABLE 6

| compound | FD-MS | compound | FD-MS |
|---|---|---|---|
| 3-1 | m/z = 458.18($C_{34}H_{22}N_2$ = 458.56) | 3-2 | m/z = 449.12($C_{32}H_{19}NS$ = 449.57) |
| 3-3 | m/z = 433.15($C_{32}H_{19}NO$ = 433.51) | 3-4 | m/z = 535.23($C_{41}H_{29}N$ = 535.69) |
| 3-5 | m/z = 399.11($C_{28}H_{17}NS$ = 399.51) | 3-6 | m/z = 527.15($C_{36}H_{21}N_3S$ = 527.65) |
| 3-7 | m/z = 583.12($C_{38}H_{21}N_3S_2$ = 583.73) | 3-8 | m/z = 577.16($C_{40}H_{23}N_3S$ = 577.71) |
| 3-9 | m/z = 627.18($C_{44}H_{25}N_3S$ = 627.77) | 3-10 | m/z = 475.14($C_{34}H_{21}NS$ = 475.61) |
| 3-11 | m/z = 585.21($C_{44}H_{27}NO$ = 585.71) | 3-12 | m/z = 509.21($C_{39}H_{27}N$ = 509.65) |
| 3-13 | m/z = 509.19($C_{37}H_{23}N_3$ = 509.61) | 3-14 | m/z = 451 . . . 11($C_{30}H_{17}N_3S$ = 451.55) |
| 3-15 | m/z = 588.20($C_{41}H_{24}N_4O$ = 588.67) | 3-16 | m/z = 624.26($C_{47}H_{32}N_2$ = 624.79) |
| 3-17 | m/z = 614.18($C_{44}H_{26}N_2S$ = 614.77) | 3-18 | m/z = 449.12($C_{32}H_{19}NS$ = 449.57) |
| 3-19 | m/z = 573.17($C_{42}H_{23}NO_2$ = 573.65) | 3-20 | m/z = 664.26($C_{48}H_{32}N_4$ = 664.81) |
| 3-21 | m/z = 624.26($C_{47}H_{32}N_2$ = 624.79) | 3-22 | m/z = 603.18($C_{42}H_{25}N_3S$ = 603.74) |
| 3-23 | m/z = 664.23($C_{47}H_{28}N_4O$ = 664.77) | 3-24 | m/z = 737.28($C_{55}H_{35}N_3$ = 737.91) |
| 3-25 | m/z = 738.28($C_{54}H_{34}N_4$ = 738.89) | 3-26 | m/z = 679.21($C_{48}H_{29}N_3S$ = 679.84) |
| 3-27 | m/z = 625.22($C_{45}H_{27}N_3O$ = 625.73) | 3-28 | m/z = 575.24($C_{42}H_{29}N_3$ = 575.72) |
| 3-29 | m/z = 508.19($C_{38}H_{24}N_2$ = 508.62) | 3-30 | m/z = 449.12($C_{32}H_{19}NS$ = 449.57) |
| 3-31 | m/z = 433.15($C_{32}H_{19}NO$ = 433.51) | 3-32 | m/z = 531.20($C_{41}H_{25}N$ = 531.66) |
| 3-33 | m/z = 608.23($C_{46}H_{28}N_2$ = 608.74) | 3-34 | m/z = 475.14($C_{34}H_{21}NS$ = 475.61) |
| 3-35 | m/z = 384.13($C_{27}H_{16}N_2O$ = 384.44) | 3-36 | m/z = 614.25($C_{44}H_{30}N_4$ = 614.75) |
| 3-37 | m/z = 508.19($C_{38}H_{24}N_2$ = 508.62) | 3-38 | m/z = 449.12($C_{32}H_{19}NS$ = 449.57) |
| 3-39 | m/z = 433.15($C_{32}H_{19}NO$ = 433.51) | 3-40 | m/z = 459.20($C_{35}H_{25}N$ = 459.59) |
| 3-41 | m/z = 663.24($C_{47}H_{29}N_5$ = 663.78) | 3-42 | m/z = 603.18($C_{42}H_{25}N_3S$ = 603.74) |
| 3-43 | m/z = 587.20($C_{42}H_{25}N_3O$ = 587.68) | 3-44 | m/z = 613.25($C_{45}H_{31}N_3$ = 613.76) |
| 3-45 | m/z = 662.25($C_{48}H_{30}N_4$ = 662.80) | 3-46 | m/z = 577.16($C_{40}H_{23}N_3S$ = 577.71) |
| 3-47 | m/z = 601.18($C_{42}H_{23}N_3O_2$ = 601.67) | 3-48 | m/z = 759.27($C_{57}H_{33}N_3$ = 759.91) |
| 3-49 | m/z = 589.22($C_{42}H_{26}N_4$ = 586.70) | 3-50 | m/z = 630.19($C_{43}H_{26}N_4S$ = 630.77) |
| 3-51 | m/z = 613.22($C_{44}H_{27}N_3O$ = 613.72) | 3-52 | m/z = 639.27($C_{47}H_{33}N_3$ = 639.80) |
| 3-53 | m/z = 508.19($C_{38}H_{24}N_2$ = 508.62) | 3-54 | m/z = 449.12($C_{32}H_{19}NS$ = 449.57) |
| 3-55 | m/z = 433.15($C_{32}H_{19}NO$ = 433.51) | 3-56 | m/z = 609.25($C_{47}H_{31}N$ = 609.77) |
| 3-57 | m/z = 663.24($C_{47}H_{29}N_5$ = 663.78) | 3-58 | m/z = 604.17($C_{41}H_{24}N_4S$ = 604.73) |
| 3-59 | m/z = 587.20($C_{42}H_{25}N_3O$ = 587.68) | 3-60 | m/z613.25($C_{45}H_{31}N_3$ = 613.76) |
| 3-61 | m/z = 527.15($C_{36}H_{21}N_3S$ = 527.65) | 3-62 | m/z = 603.18($C_{42}H_{25}N_3S$ = 603.74) |
| 3-63 | m/z = 511.17($C_{36}H_{21}N_3O$ = 511.58) | 3-64 | m/z = 587.24($C_{43}H_{29}N_3$ = 587.73) |
| 3-65 | m/z = 692.20($C_{48}H_{28}N_4S$ = 692.84) | 3-66 | m/z = 577.16($C_{40}H_{23}N_3S$ = 577.71) |
| 3-67 | m/z = 561.18($C_{40}H_{23}N_3O$ = 561.64) | 3-68 | m/z = 653.19($C_{46}H_{27}N_3S$ = 653.80) |
| 3-69 | m/z = 736.26($C_{54}H_{32}N_4$ = 736.88) | 3-70 | m/z = 677.19($C_{48}H_{27}N_3S$ = 677.83) |
| 3-71 | m/z = 687.23($C_{50}H_{29}N_3O$ = 687.80) | 3-72 | m/z = 743.24($C_{53}H_{33}N_3S$ = 743.93) |
| 3-73 | m/z = 703.21($C_{50}H_{29}N_3S$ = 703.86) | 3-74 | m/z = 603.18($C_{42}H_{25}N_3S$ = 603.74) |
| 3-75 | m/z = 735.18($C_{50}H_{29}N_3S_2$ = 735.92) | 3-76 | m/z = 759.18($C_{52}H_{29}N_3S_2$ = 759.95) |
| 3-77 | m/z = 475.14($C_{34}H_{21}NS$ = 475.61) | 3-78 | m/z = 616.20($C_{44}H_{28}N_2S$ = 616.78) |
| 3-79 | m/z = 710.16($C_{47}H_{26}N_4S_2$ = 710.87) | 3-80 | m/z = 818.25($C_{58}H_{34}N_4S$ = 819.00) |
| 3-81 | m/z = 603.18($C_{42}H_{25}N_3S$ = 603.74) | 3-82 | m/z = 809.20($C_{56}H_{31}N_3S_2$ = 810.01) |
| 3-83 | m/z = 659.15($C_{44}H_{25}N_3S_2$ = 659.83) | 3-84 | m/z = 583.21($C_{40}H_{29}N_3S$ = 583.75) |
| 3-85 | m/z = 844.27($C_{60}H_{36}N_4S$ = 845.04) | 3-86 | m/z = 667.17($C_{46}H_{25}N_3OS$ = 667.79) |
| 3-87 | m/z = 703.23($C_{50}H_{29}N_3O_2$ = 703.80) | 3-88 | m/z = 629.21($C_{44}H_{27}N_3O_2$ = 629.72) |
| 3-89 | m/z = 473.18($C_{35}H_{23}NO$ = 473.58) | 3-90 | m/z = 600.22($C_{44}H_{28}N_2O$ = 600.72) |
| 3-91 | m/z = 858.25($C_{60}H_{34}N_4OS$ = 859.02) | 3-92 | m/z = 792.26($C_{55}H_{32}N_6O$ = 792.90) |
| 3-93 | m/z = 514.24($C_{38}H_{30}N_2$ = 514.67) | 3-94 | m/z = 701.28($C_{52}H_{35}N_3$ = 701.87) |
| 3-95 | m/z = 700.26($C_{51}H_{32}N_4$ = 700.85) | 3-96 | m/z = 764.29($C_{56}H_{36}N_4$ = 764.93) |
| 3-97 | m/z = 700.29($C_{53}H_{36}N_2$ = 700.89) | 3-98 | m/z = 576.26($C_{43}H_{32}N_2$ = 576.74) |
| 3-99 | m/z = 701.28($C_{52}H_{35}N_3$ = 701.87) | 3-100 | m/z = 761.28($C_{57}H_{35}N_3$ = 761.93) |

Otherwise, the synthesis examples of the present invention represented by Formulas 1 and 2 have been described, but these are all based on the Buchwald-Hartwig cross coupling reaction, Suzuki cross-coupling reaction, Intramolecular acid-induced cyclization reaction (J. mater. Chem. 1999, 9, 2095.), Pd(II)-catalyzed oxidative cyclization reaction (Org. Lett. 2011, 13, 5504), Grignard reaction, Cyclic Dehydration reaction and PPh3-mediated reductive cyclization reaction (J. Org. Chem. 2005, 70, 5014.), and those skilled in the art will readily understand that the above reaction proceeds even when, besides the substituent specified in the specific synthesis example, other substituents ($R^1$ to $R^5$, $Ar^1$ to $Ar^4$, $L^1$ to $L^2$, $X^1$ to $X^2$) defined in Formulas 1 and 2 are bonded.

For example, Sub 1+Sub 2→Final Products 1 reaction in Reaction Scheme 1, the synthetic reaction of Sub 2 in Reaction Scheme 3, Sub 3+Sub 4→Final Products 2 reaction in Reaction Scheme 4 are all based on the Buchwald-Hartwig cross coupling reaction, and Sub 1-3+Sub 1-4→Sub 1 reaction in Reaction Scheme 2 and Sub 3-2+Sub 3-3→Sub 3-4 in Reaction Scheme 5 are all based on the Suzuki cross-coupling reaction, and Sub 3-4→Sub 3 in Reaction Scheme 5 is based on the PPh3-mediated reductive cyclization reaction (J. Org. Chem. 2005, 70, 5014.) The above reactions will proceed even if a substituent not specifically mentioned is bonded.

Evaluation of Manufacture of Organic Electric Element

Example 1) Manufacture and Evaluation of Red Organic Light Emitting Diode

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. On the hole transport layer, a mixture of the compounds represented by Formulas 1 and 2 as a host in a ratio of 50:50 was used as a host, and as a dopant, an emitting layer with a thickness of 30 nm was deposited on the hole transport layer by doping (piq)$_2$Ir(acac) [bis-(1-phenylisoquinolyl)iridium(III)acetylacetonate] with a weight of 95:5. (1,1'-bisphenyl)-4-olato)bis(2-methyl-8-quinolinolato)aluminum (hereinafter abbreviated as BAlq) was vacuum deposited as a hole blocking layer to a thickness of 10 nm, and tris(8-quinolinol)aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m$^2$. In the following table, the manufacture of a device and the results of evaluation are shown.

Comparative Examples 1 to 3

An organic electroluminescent device was manufactured in the same manner as in Example 1, except that the compound represented by Formula 2 was used as a host alone.

Comparative Example 4

An organic electroluminescent device was manufactured in the same manner as in Example 1, except that the comparative compound 1 was used as a host alone.

Comparative Example 5

An organic electroluminescent device was manufactured in the same manner as in Example 1, except that the comparative compound 2 was used as a host alone.

Comparative Example 6

An organic electroluminescent device was manufactured in the same manner as in Example 1, except that the comparative compound 3 was used as a host alone.

Comparative Example 7

An organic electroluminescent device was manufactured in the same manner as in Example 1, except that the comparative compound 4 was used as a host alone.

Comparative Example 8

An organic electroluminescent device was manufactured in the same manner as in Example 1, except that comparative compound 1 and 2 were mixed and used as a host.

Comparative Example 9

An organic electroluminescent device was manufactured in the same manner as in Example 1, except that comparative compound 3 and 4 were mixed and used as a host.

Comparative Example 10

An organic electroluminescent device was manufactured in the same manner as in Example 1, except that the compound represented by Formula 1 and the comparative compound 4 were mixed and used as a host.

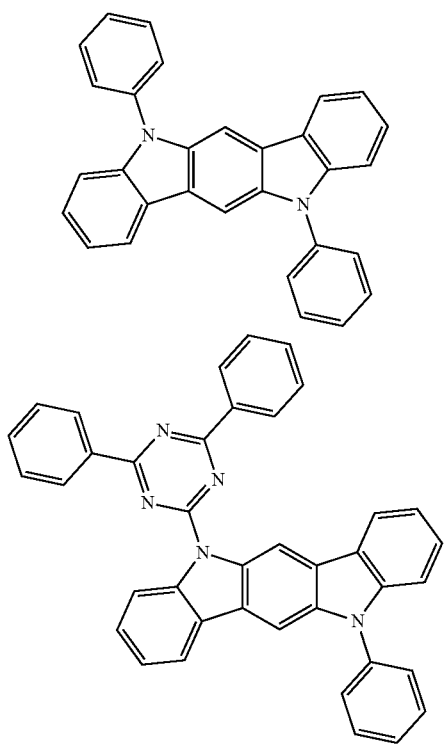

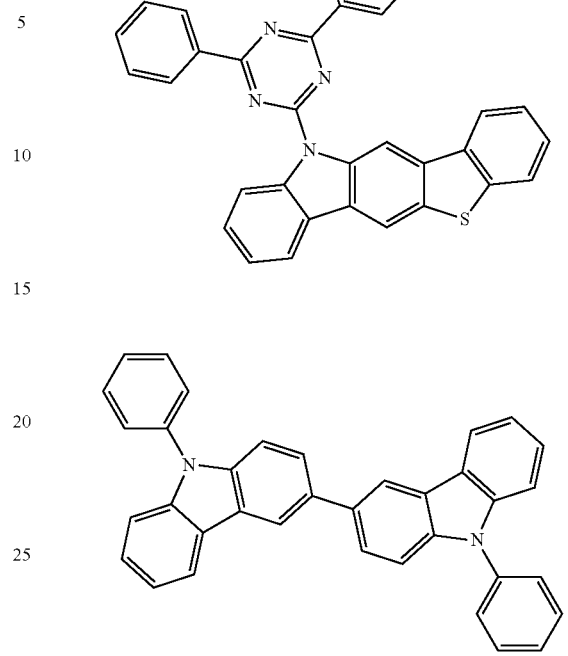

TABLE 7

| | First host | Second host | Voltage | Current Density | Brightness (cd/m$^2$) | Efficiency | Lifetime T(95) |
|---|---|---|---|---|---|---|---|
| comparative example(1) | — | compound (3-6) | 6.6 | 19.1 | 2500.0 | 13.1 | 100.3 |
| comparative example(2) | — | compound (3-61) | 6.8 | 19.5 | 2500.0 | 12.8 | 98.8 |
| comparative example(3) | — | compound (3-74) | 6.9 | 20.2 | 2500.0 | 12.4 | 101.2 |
| comparative example(4) | — | comparative compound 1 | 7.3 | 22.5 | 2500.0 | 11.1 | 76.3 |
| comparative example(5) | — | comparative compound 2 | 7.2 | 21.7 | 2500.0 | 11.5 | 78.9 |
| comparative example(6) | — | comparative compound 3 | 7.1 | 21.0 | 2500.0 | 11.9 | 82.4 |
| comparative example(7) | — | comparative compound 4 | 7.4 | 22.3 | 2500.0 | 11.2 | 74.5 |
| comparative example(8) | comparative compound 1 | comparative compound 2 | 6.5 | 14.8 | 2500.0 | 16.9 | 105.9 |
| comparative example(9) | comparative compound 3 | comparative compound 4 | 6.4 | 13.7 | 2500.0 | 18.3 | 106.1 |
| comparative example(10) | compound (2-5) | comparative compound 3 | 6.2 | 11.6 | 2500.0 | 21.5 | 108.8 |
| example(1) | compound (1-1) | compound (3-6) | 5.9 | 8.2 | 2500.0 | 30.4 | 128.3 |
| example(2) | compound (1-6) | compound (3-6) | 5.8 | 8.3 | 2500.0 | 30.1 | 128.3 |
| example(3) | compound (1-9) | compound (3-6) | 5.5 | 7.6 | 2500.0 | 32.8 | 125.1 |
| example(4) | compound (1-28) | compound (3-6) | 5.9 | 8.3 | 2500.0 | 30.1 | 126.5 |
| example(5) | compound (1-54) | compound (3-6) | 4.8 | 8.0 | 2500.0 | 31.4 | 129.2 |
| example(6) | compound (2-5) | compound (3-6) | 5.8 | 8.0 | 2500.0 | 31.2 | 125.5 |
| example(7) | compound (2-17) | compound (3-6) | 5.3 | 8.1 | 2500.0 | 30.7 | 128.3 |
| example(8) | compound (2-40) | compound (3-6) | 5.1 | 7.8 | 2500.0 | 32.0 | 127.8 |
| example(9) | compound (2-41) | compound (3-6) | 5.1 | 7.9 | 2500.0 | 31.5 | 125.3 |

TABLE 7-continued

|  | First host | Second host | Voltage | Current Density | Brightness (cd/m$^2$) | Efficiency | Lifetime T(95) |
|---|---|---|---|---|---|---|---|
| example(10) | compound (2-49) | compound (3-6) | 5.8 | 7.9 | 2500.0 | 31.6 | 126.8 |
| example(11) | compound (1-1) | compound (3-7) | 5.0 | 9.3 | 2500.0 | 27.0 | 122.0 |
| example(12) | compound (1-6) | compound (3-7) | 5.0 | 9.4 | 2500.0 | 26.5 | 122.3 |
| example(13) | compound (1-9) | compound (3-7) | 5.9 | 9.9 | 2500.0 | 25.3 | 120.4 |
| example(14) | compound (1-28) | compound (3-7) | 5.4 | 9.5 | 2500.0 | 26.2 | 121.5 |
| example(15) | compound (1-54) | compound (3-7) | 4.8 | 9.8 | 2500.0 | 25.6 | 121.7 |
| example(16) | compound (2-5) | compound (3-7) | 5.9 | 9.3 | 2500.0 | 26.9 | 124.2 |
| example(17) | compound (2-17) | compound (3-7) | 5.5 | 9.7 | 2500.0 | 25.9 | 122.0 |
| example(18) | compound (2-40) | compound (3-7) | 5.1 | 10.0 | 2500.0 | 25.0 | 122.8 |
| example(19) | compound (2-41) | compound (3-7) | 5.5 | 9.8 | 2500.0 | 25.6 | 123.4 |
| example(20) | compound (2-49) | compound (3-7) | 5.6 | 9.8 | 2500.0 | 25.4 | 124.1 |
| example(21) | compound (1-1) | compound (3-8) | 5.1 | 9.9 | 2500.0 | 25.2 | 121.1 |
| example(22) | compound (1-6) | compound (3-8) | 5.6 | 9.8 | 2500.0 | 25.4 | 121.6 |
| example(23) | compound (1-9) | compound (3-8) | 5.1 | 9.6 | 2500.0 | 26.2 | 120.4 |
| example(24) | compound (1-28) | compound (3-8) | 5.3 | 9.9 | 2500.0 | 25.3 | 122.8 |
| example(25) | compound (1-54) | compound (3-8) | 4.9 | 9.7 | 2500.0 | 25.8 | 122.5 |
| example(26) | compound (2-5) | compound (3-8) | 5.7 | 9.5 | 2500.0 | 26.2 | 124.6 |
| example(27) | compound (2-17) | compound (3-8) | 5.3 | 10.0 | 2500.0 | 25.1 | 120.3 |
| example(28) | compound (2-40) | compound (3-8) | 5.5 | 9.7 | 2500.0 | 25.7 | 121.9 |
| example(29) | compound (2-41) | compound (3-8) | 5.4 | 9.5 | 2500.0 | 26.4 | 122.5 |
| example(30) | compound (2-49) | compound (3-8) | 5.5 | 9.6 | 2500.0 | 26.2 | 120.2 |
| example(31) | compound (1-1) | compound (3-9) | 5.3 | 9.4 | 2500.0 | 26.7 | 122.2 |
| example(32) | compound (1-6) | compound (3-9) | 5.5 | 9.9 | 2500.0 | 25.3 | 123.4 |
| example(33) | compound (1-9) | compound (3-9) | 5.5 | 9.8 | 2500.0 | 25.5 | 124.3 |
| example(34) | compound (1-28) | compound (3-9) | 5.3 | 9.8 | 2500.0 | 25.6 | 120.4 |
| example(35) | compound (1-54) | compound (3-9) | 5.0 | 9.6 | 2500.0 | 26.2 | 120.3 |
| example(36) | compound (2-5) | compound (3-9) | 5.7 | 9.4 | 2500.0 | 26.7 | 123.3 |
| example(37) | compound (2-17) | compound (3-9) | 5.3 | 9.7 | 2500.0 | 25.7 | 121.0 |
| example(38) | compound (2-40) | compound (3-9) | 5.3 | 9.9 | 2500.0 | 25.4 | 121.3 |
| example(39) | compound (2-41) | compound (3-9) | 5.7 | 9.9 | 2500.0 | 25.2 | 121.3 |
| example(40) | compound (2-49) | compound (3-9) | 5.3 | 9.3 | 2500.0 | 27.0 | 123.0 |
| example(41) | compound (1-1) | compound (3-15) | 5.7 | 9.8 | 2500.0 | 25.4 | 120.6 |
| example(42) | compound (1-6) | compound (3-15) | 5.3 | 9.4 | 2500.0 | 26.6 | 124.7 |
| example(43) | compound (1-9) | compound (3-15) | 5.3 | 9.7 | 2500.0 | 25.8 | 124.0 |
| example(44) | compound (1-28) | compound (3-15) | 5.0 | 9.9 | 2500.0 | 25.2 | 120.8 |
| example(45) | compound (1-54) | compound (3-15) | 4.8 | 9.8 | 2500.0 | 25.6 | 124.1 |
| example(46) | compound (2-5) | compound (3-15) | 5.6 | 9.8 | 2500.0 | 25.5 | 121.0 |
| example(47) | compound (2-17) | compound (3-15) | 5.6 | 9.9 | 2500.0 | 25.2 | 121.9 |

TABLE 7-continued

| | First host | Second host | Voltage | Current Density | Brightness (cd/m$^2$) | Efficiency | Lifetime T(95) |
|---|---|---|---|---|---|---|---|
| example(48) | compound (2-40) | compound (3-15) | 5.1 | 9.9 | 2500.0 | 25.1 | 124.3 |
| example(49) | compound (2-41) | compound (3-15) | 5.4 | 9.8 | 2500.0 | 25.6 | 122.6 |
| example(50) | compound (2-49) | compound (3-15) | 5.0 | 9.4 | 2500.0 | 26.6 | 121.7 |
| example(51) | compound (1-1) | compound (3-37) | 5.5 | 9.3 | 2500.0 | 26.8 | 124.7 |
| example(52) | compound (1-6) | compound (3-37) | 5.2 | 9.3 | 2500.0 | 26.8 | 122.9 |
| example(53) | compound (1-9) | compound (3-37) | 5.1 | 9.6 | 2500.0 | 26.2 | 123.1 |
| example(54) | compound (1-28) | compound (3-37) | 5.7 | 9.8 | 2500.0 | 25.5 | 125.0 |
| example(55) | compound (1-54) | compound (3-37) | 4.8 | 10.0 | 2500.0 | 25.0 | 124.1 |
| example(56) | compound (2-5) | compound (3-37) | 5.2 | 9.4 | 2500.0 | 26.7 | 122.1 |
| example(57) | compound (2-17) | compound (3-37) | 5.6 | 9.6 | 2500.0 | 26.1 | 123.5 |
| example(58) | compound (2-40) | compound (3-37) | 5.8 | 9.6 | 2500.0 | 26.0 | 123.1 |
| example(59) | compound (2-41) | compound (3-37) | 5.2 | 9.8 | 2500.0 | 25.4 | 124.9 |
| example(60) | compound (2-49) | compound (3-37) | 5.6 | 9.7 | 2500.0 | 25.9 | 124.0 |
| example(61) | compound (1-1) | compound (3-46) | 5.9 | 9.5 | 2500.0 | 26.4 | 124.3 |
| example(62) | compound (1-6) | compound (3-46) | 5.2 | 9.7 | 2500.0 | 25.8 | 120.6 |
| example(63) | compound (1-9) | compound (3-46) | 5.6 | 9.5 | 2500.0 | 26.4 | 123.6 |
| example(64) | compound (1-28) | compound (3-46) | 5.5 | 9.6 | 2500.0 | 26.0 | 121.4 |
| example(65) | compound (1-54) | compound (3-46) | 5.0 | 9.5 | 2500.0 | 26.4 | 124.2 |
| example(66) | compound (2-5) | compound (3-46) | 5.6 | 9.4 | 2500.0 | 26.5 | 120.0 |
| example(67) | compound (2-17) | compound (3-46) | 5.7 | 9.7 | 2500.0 | 25.8 | 122.0 |
| example(68) | compound (2-40) | compound (3-46) | 5.4 | 9.5 | 2500.0 | 26.4 | 122.6 |
| example(69) | compound (2-41) | compound (3-46) | 5.8 | 9.4 | 2500.0 | 26.5 | 122.4 |
| example(70) | compound (2-49) | compound (3-46) | 5.3 | 9.5 | 2500.0 | 26.4 | 120.7 |
| example(71) | compound (1-1) | compound (3-50) | 5.1 | 9.7 | 2500.0 | 25.9 | 123.5 |
| example(72) | compound (1-6) | compound (3-50) | 5.9 | 9.6 | 2500.0 | 26.1 | 122.5 |
| example(73) | compound (1-9) | compound (3-50) | 5.5 | 9.5 | 2500.0 | 26.2 | 124.7 |
| example(74) | compound (1-28) | compound (3-50) | 5.6 | 9.8 | 2500.0 | 25.5 | 122.2 |
| example(75) | compound (1-54) | compound (3-50) | 4.9 | 9.6 | 2500.0 | 26.1 | 121.2 |
| example(76) | compound (2-5) | compound (3-50) | 5.7 | 9.4 | 2500.0 | 26.6 | 122.7 |
| example(77) | compound (2-17) | compound (3-50) | 5.7 | 9.4 | 2500.0 | 26.7 | 122.9 |
| example(78) | compound (2-40) | compound (3-50) | 5.2 | 9.6 | 2500.0 | 26.1 | 124.5 |
| example(79) | compound (2-41) | compound (3-50) | 5.6 | 10.0 | 2500.0 | 25.1 | 120.3 |
| example(80) | compound (2-49) | compound (3-50) | 5.5 | 9.4 | 2500.0 | 26.5 | 124.8 |
| example(81) | compound (1-1) | compound (3-61) | 5.8 | 9.1 | 2500.0 | 27.4 | 133.3 |
| example(82) | compound (1-6) | compound (3-61) | 5.4 | 8.9 | 2500.0 | 28.1 | 135.0 |
| example(83) | compound (1-9) | compound (3-61) | 5.4 | 8.7 | 2500.0 | 28.8 | 131.3 |
| example(84) | compound (1-28) | compound (3-61) | 5.6 | 8.7 | 2500.0 | 28.6 | 133.6 |
| example(85) | compound (1-54) | compound (3-61) | 5.0 | 9.0 | 2500.0 | 27.7 | 130.7 |

TABLE 7-continued

|  | First host | Second host | Voltage | Current Density | Brightness (cd/m$^2$) | Efficiency | Lifetime T(95) |
|---|---|---|---|---|---|---|---|
| example(86) | compound (2-5) | compound (3-61) | 5.7 | 8.6 | 2500.0 | 29.2 | 133.2 |
| example(87) | compound (2-17) | compound (3-61) | 5.9 | 8.9 | 2500.0 | 28.2 | 132.1 |
| example(88) | compound (2-40) | compound (3-61) | 5.0 | 8.8 | 2500.0 | 28.4 | 131.2 |
| example(89) | compound (2-41) | compound (3-61) | 5.9 | 9.2 | 2500.0 | 27.3 | 133.5 |
| example(90) | compound (2-49) | compound (3-61) | 5.3 | 8.6 | 2500.0 | 29.1 | 130.3 |
| example(91) | compound (1-1) | compound (3-74) | 5.9 | 9.7 | 2500.0 | 25.8 | 123.4 |
| example(92) | compound (1-6) | compound (3-74) | 5.9 | 10.0 | 2500.0 | 25.1 | 121.9 |
| example(93) | compound (1-9) | compound (3-74) | 5.7 | 9.6 | 2500.0 | 26.1 | 120.7 |
| example(94) | compound (1-28) | compound (3-74) | 5.2 | 9.7 | 2500.0 | 25.7 | 122.6 |
| example(95) | compound (1-54) | compound (3-74) | 4.8 | 9.9 | 2500.0 | 25.4 | 120.1 |
| example(96) | compound (2-5) | compound (3-74) | 5.4 | 9.4 | 2500.0 | 26.7 | 123.1 |
| example(97) | compound (2-17) | compound (3-74) | 5.0 | 9.4 | 2500.0 | 26.6 | 124.0 |
| example(98) | compound (2-40) | compound (3-74) | 5.5 | 10.0 | 2500.0 | 25.1 | 124.4 |
| example(99) | compound (2-41) | compound (3-74) | 5.7 | 9.3 | 2500.0 | 26.8 | 121.1 |
| example(100) | compound (2-49) | compound (3-74) | 5.6 | 9.3 | 2500.0 | 26.8 | 123.2 |

As can be seen from the results of Table 7, when the organic electric element material of the present invention represented by Formulas 1 and 2 is mixed and used as a phosphorescent host (Examples 1 to 100), it was confirmed that the driving voltage, efficiency, and life span were significantly improved as compared with the element (comparative examples 1 to 7) using a single material.

More specifically, in Comparative Examples 1 to 7, wherein the compounds of the present invention represented by Formula 2 and comparative compounds 1 to 4 are used alone as a phosphorescent host, Comparative Examples 1 to 3 using the compounds (3-6, 3-61, and 3-74) of the present invention had higher efficiency and longer life span than Comparative Examples 4 to 7 using the comparative compound.

Also, Comparative Example 8 and 9 wherein Comparative Compound 1 and 2 or Comparative Compound 3 and 4 were mixed and used as a phosphorescent host were found to exhibit higher efficiency than Comparative Examples 1 to 7 using the single substance.

Comparing Comparative Example 8 with 9, Comparative Example 9 using a mixture containing a polycyclic compound having a different heteroatom (N, S) among the 5-membered compounds had higher efficiency than Comparative Example 8 mixed a 5-membered heterocyclic compound having the same nitrogen atom.

Among the compounds of the present invention, comparing Comparative Example 10 using a mixture of Compound 2-5 corresponding to Formula 1 and Comparative Compound 3, and Comparative Example 9 using a mixture of Comparative Compound 3 and 4, when the comparative compound 3 was commonly used and the biscarbazole substance (Comparative Example 9) and Compound 2-5 corresponding to the present invention Formula 1 were used as the host material, Comparative Example 10 using the compound 2-5 exhibited a higher efficiency and a relatively longer life span.

And it was confirmed that Example 1 to 100 using the mixture of the compound of Formula 1 and 2 as a host exhibited remarkably high efficiency and long life span than the Comparative Example 1 to 10.

On the basis of the above experimental results, the inventors of the present invention have found that, in the case of a mixture of the substance of Formula 1 and the substance of Formula 2, they have novel characteristics other than those for the respective materials, and have measured the PL lifetime using the substance of Formula 1, the substance of Formula 2, and the mixture of the present invention. As a result, it was confirmed that a new PL wavelength (556 nm) was formed when the compounds of Formulas 1 and 2 were mixed, and the decreasing and disappearing time of the newly formed PL wavelength increased from about 60 times to about 360 times compared to the reduction and disappearance times of substances Formula 1 and 2, respectively. It is considered when mixed with the compound of the present invention, not only electrons and holes are moved through the energy level of each substance, but also the efficiency and life span are increased by electron, hole transport or energy transfer by a new region (exciplex) having a new energy level formed due to mixing. As a result, when the mixture of the present invention is used, the mixed thin film is an important example showing exciplex energy transfer and light emitting process.

The reason why the combination of the present invention is superior to Comparative Examples 8 to 10 in which a comparative compound is used as a phosphorescent host is that the high Ti and high LUMO energy values improve the electron blocking ability and allow more holes to be moved to the emitting layer more quickly and easily when a compound represented by the general Formula 1 having a strong hole property is mixed with a polycyclic compound represented by Formula 2, which is characterized not only by electron but also by hole stability and high Ti. As a result, the charge balance in the emitting layer of holes and electrons is increased, so that light emission is well performed inside the emitting layer rather than at the interface of the hole transport layer, and therefore the deterioration in the HTL interface is also reduced, thereby maximizing the driving voltage, efficiency and life span of the device. That is, it is considered that the combination of Formula 1 and 2 is electrochemically synergistic to improve the performance of the entire device.

Example 2) Manufacture and Evaluation of Red Organic Light Emitting Diode by Mixing Ratio

TABLE 8

| | First host | Second host | Mixing ratio (first host:second host) | Voltage | Current Density | Brightness (cd/m2) | Efficiency | Lifetime T(95) |
|---|---|---|---|---|---|---|---|---|
| example(101) | compound (1-54) | compound (3-6) | 2:8 | 4.8 | 8.1 | 2500.0 | 30.8 | 130.5 |
| example(102) | compound (1-54) | compound (3-6) | 3:7 | 4.8 | 8.0 | 2500.0 | 31.4 | 129.2 |
| example(103) | compound (1-54) | compound (3-6) | 4:6 | 5.2 | 8.7 | 2500.0 | 28.7 | 120.6 |
| example(104) | compound (1-54) | compound (3-6) | 5:5 | 5.5 | 10.0 | 2500.0 | 25.1 | 115.4 |
| example(105) | compound (2-5) | compound (3-61) | 2:8 | 5.6 | 8.5 | 2500.0 | 29.4 | 134.7 |
| example(106) | compound (2-5) | compound (3-61) | 3:7 | 5.7 | 8.6 | 2500.0 | 29.2 | 133.2 |
| example(107) | compound (2-5) | compound (3-61) | 4:6 | 5.8 | 9.5 | 2500.0 | 26.4 | 125.6 |
| example(108) | compound (2-5) | compound (3-61) | 5:5 | 6.0 | 10.2 | 2500.0 | 24.5 | 116.8 |

As shown in Table 8, the mixture of the compound of the present invention was measured by fabricating the device in (2:8, 3:7, 4:6, 5:5). To explain the results in detail, in the result of the mixture of the compound 1-54 and 3-6, the results of the driving voltage, the efficiency and the life span were similarly excellent at 2:8 and 3:7, but as the ratio of the first host increases, such as 4:6 and 5:5, the results of the driving voltage, the efficiency and the life span are gradually decreased, this was also the same in the result of the mixture of the compound 2-5 and 3-61. This can be explained by the fact that the charge balance in the emitting layer is maximized when an appropriate amount of the compound represented by Formula 1 having strong hole properties such as 2:8 and 3:7 is mixed.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:

1. An organic electric element comprising: a first electrode, a second electrode, and an organic material layer formed between the first electrode and the second electrode, wherein the organic material layer comprises an emitting layer and the emitting layer comprises a first host compound represented by Formula 1 and a second host compound represented by Formula 2:

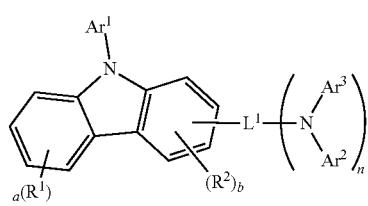

Formula 1

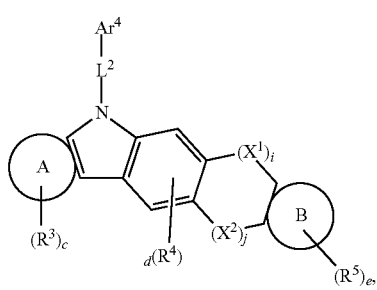

Formula 2 wherein:
1) $Ar^1$, $Ar^2$, $Ar^3$, and $Ar^4$ are each independently selected from the group consisting of a $C_6$-$C_{60}$ aryl group, a fluorenyl group, a $C_2$-$C_{60}$ heterocyclic group including at least one hetero atom of O, N, S, Si or P, a fused ring group of a $C_3$-$C_{60}$ aliphatic ring with a $C_6$-$C_{60}$ aromatic ring, and a $C_1$-$C_{50}$ alkyl group, wherein $Ar^2$ and $Ar^3$ may combine to each other to form a ring,
2) a is an integer of 0 to 4, and b is an integer of 0 to 3, and c and e are each independently an integer of 0 to 10, and d is an integer of 0 to 2,
3) $R^1$, $R^2$, $R^3$, $R^4$ and $R^5$ are the same or different from each other, and are each independently selected from the group consisting of deuterium, halogen, a $C_6$-$C_{60}$ aryl group, a fluorenyl group, a $C_2$-$C_{60}$ heterocyclic group including at least one heteroatom of O, N, S, Si or P, a fused ring group of a $C_3$-$C_{60}$ aliphatic ring with a $C_6$-$C_{60}$ aromatic ring, a $C_1$-$C_{60}$ alkyl group, a $C_2$-$C_{20}$ alkenyl group, and a $C_2$-$C_{20}$ alkynyl group; or in case a, b, c, and e are 2 or more, d is 2, $R^1$, $R^2$, $R^3$, $R^4$ and $R^5$ are each in plural being the same or different, and a plurality of $R^1$ or a plurality of $R^2$ or a plurality of $R^3$ or a plurality of $R^5$ may combine to each other to form a ring,
4) $L^1$ and $L^2$ are each independently selected from the group consisting of a single bond, a $C_6$-$C_{60}$ arylene group, a fluorenylene group, a fused ring group of a $C_3$-$C_{60}$ aliphatic ring with a $C_6$-$C_{60}$ aromatic ring, and a $C_2$-$C_{60}$ heterocyclic group,
5) A and B are each independently a $C_6$-$C_{60}$ aryl group or a $C_2$-$C_{20}$ heterocyclic group,
6) i and j are independently 0 or 1, with the proviso that i+j is 1 or more, and when i or j is 0, it means a direct bond,
7) $X^1$ and $X^2$ are independently NR', O, S, or CR'R", wherein R' and R" are independently hydrogen, a $C_6$-$C_{60}$ aryl group, a fluorenyl group, a $C_3$-$C_{60}$ heterocyclic group, or a $C_1$-$C_{50}$ alkyl group, wherein R' and R" may combine to each other to form a spiro, and
8) n is an integer of 1 or 2, and when n is 2, two $Ar^2$ are the same or different from each other, and two $Ar^3$ are each the same or different from each other,
wherein the aryl group, fluorenyl group, heterocyclic group, fused ring group, and alkyl group of $Ar^1$ to $Ar^4$ and $R^1$ to $R^5$, the alkenyl group of $R^1$ to $R^5$, the arylene group, fluorenylene group, heterocyclic group, and fused ring group of $L^1$ and $L^2$, the aryl group, fluorenyl group, heterocyclic group, and alkyl group of R' and R" may be substituted with one or more substituents selected from the group consisting of deuterium, halogen, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group, wherein the substituents may combine each other and form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination thereof.

2. The organic electric element according to claim 1, wherein the first host compound represented by Formula 1 is represented by Formula 3 or 4:

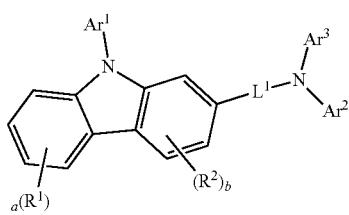

Formula 3

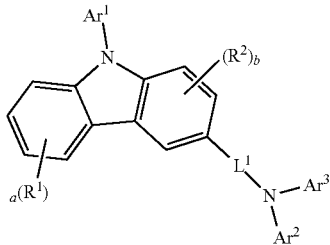

Formula 4 wherein $R^1$, $R^2$, $L^1$, $Ar^1$, $Ar^2$, $Ar^3$, a and b are the same as defined in claim 1.

3. The organic electric element according to claim 1, wherein $L^1$ and $L^2$ are selected from the group consisting of the following Formulas (A-1) to (A-12):

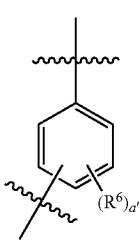

(A-1)

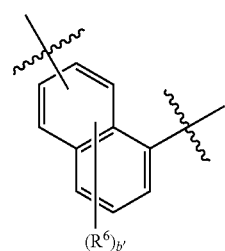

(A-2)

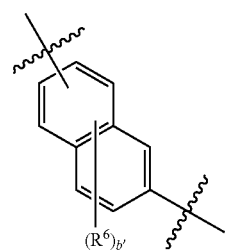

(A-3)

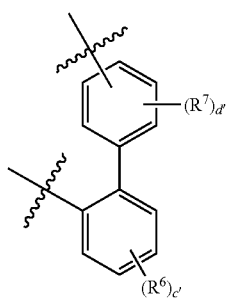

(A-4)

(A-5) 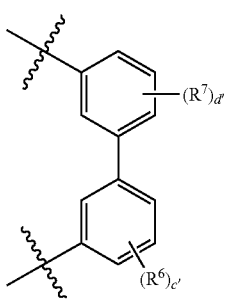

(A-6) 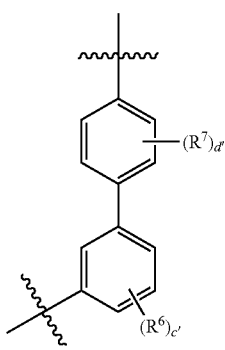

(A-7) 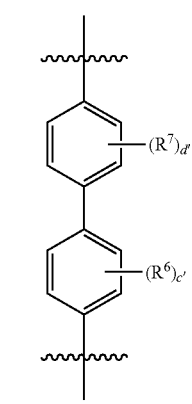

(A-8) 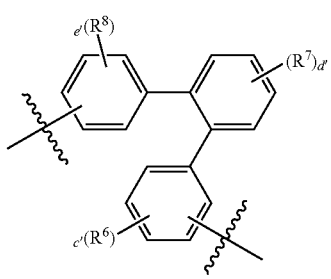

(A-9) 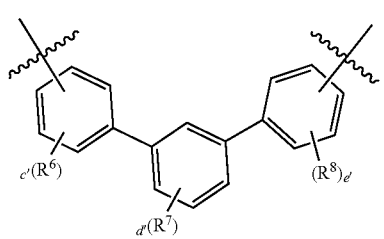

(A-10) 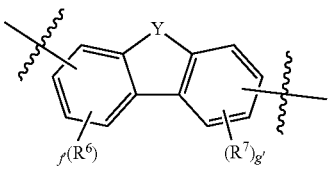

(A-11) 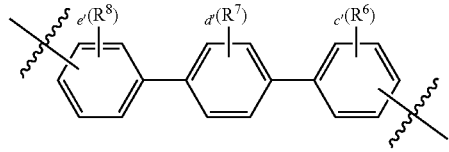

(A-12) 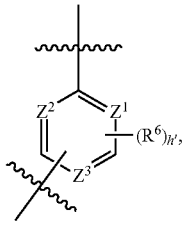

wherein:

1) a', c', d' and e' are an integer of 0 to 4, and b' is an integer of 0 to 5, and f' and g' are an integer of 0 to 3, and h' is an integer of 0 to 1, 2) $R^6$, $R^7$ and $R^8$ are the same or different from each other, and are each independently selected from the group consisting of deuterium, halogen, a $C_6$-$C_{60}$ aryl group, a fluorenyl group, a $C_2$-$C_{60}$ heterocyclic group including at least one heteroatom of O, N, S, Si or P, a fused ring group of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxy group, wherein when f' and g' are 2 or more, $R^6$, $R^7$ and $R^8$ are each in plural being the same or different, and a plurality of $R^6$ or a plurality of $R^7$ or plurality of $R^8$ may combine to each other to form an aromatic or a heteroaromatic ring, and wherein two adjacent $R^6$ and $R^7$, or $R^7$ and $R^8$ may combine to form an aromatic or heteroaromatic ring, 3) Y is NR', O, S or CR'R'', 4) R' and R'' are the same as defined in claim 1, 5) $Z^1$, $Z^2$ and $Z^3$ are independently of each other CR' or N and at least one is N.

4. The organic electric element according to claim 1, wherein the first host compound represented by Formula 1 is represented by any of the following Formulas 5 to 8:

Formula 5

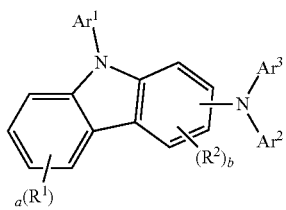

-continued

Formula 6

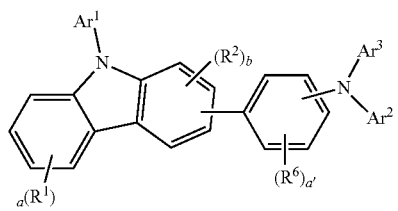

Formula 7

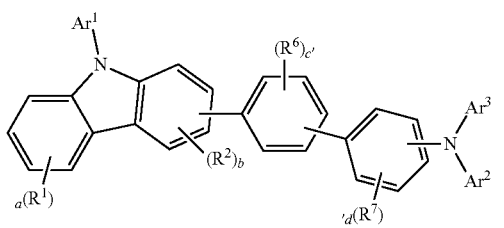

Formula 8

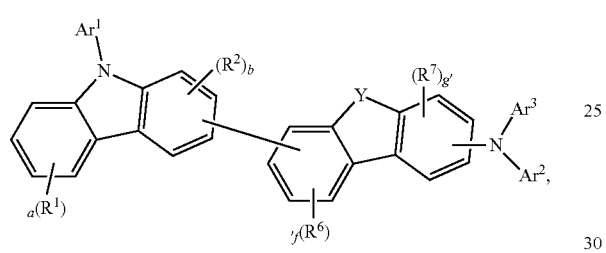

wherein:
1) $R^1$, $R^2$, $Ar^1$, $Ar^2$, $Ar^3$, a, b, R' and R" are the same as defined in claim 1,
2) $R^6$ and $R^7$ are the same or different from each other, and are each independently selected from the group consisting of deuterium, halogen, a $C_6$-$C_{60}$ aryl group, a fluorenyl group, a $C_2$-$C_{60}$ heterocyclic group including at least one heteroatom of O, N, S, Si or P, a fused ring group of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{ao}$ alkoxyl group, and a $C_6$-$C_{30}$ aryloxy group, or in case f' and g' are 2 or more, $R^6$ and $R^7$ are each in plural being the same or different, and a plurality of $R^6$ or a plurality of $R^7$ or a plurality of $R^8$ or adjacent $R^6$ and $R^7$, or adjacent $R^7$ and $R^8$ may combine to each other to form an aromatic or a heteroaromatic ring,
3) a', c' and d' are each an integer of 0 to 4, and f' and g' are each an integer of 0 to 3, and
4) Y is NR', O, S or CR'R".

5. The organic electric element according to claim 1, wherein the first host compound represented by Formula 1 is represented by any of the following Formulas 9 to 20:

Formula 9

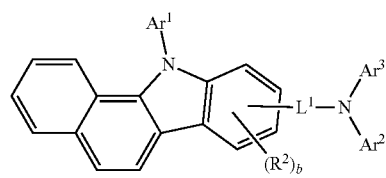

-continued

Formula 10

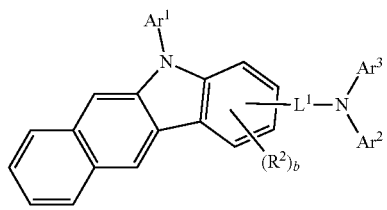

Formula 11

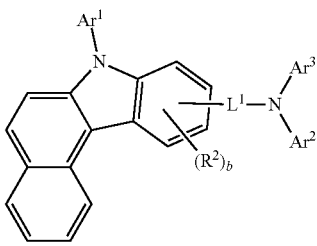

Formula 12

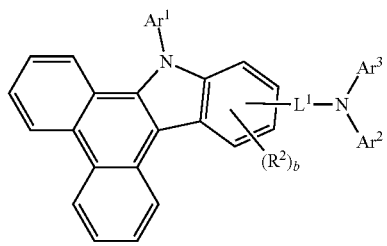

Formula 13

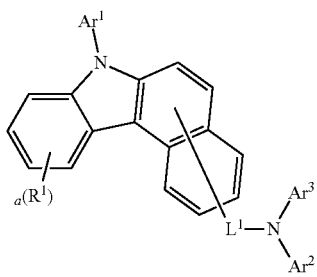

Formula 14

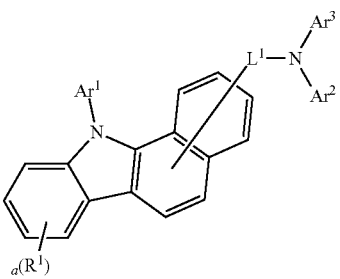

Formula 15

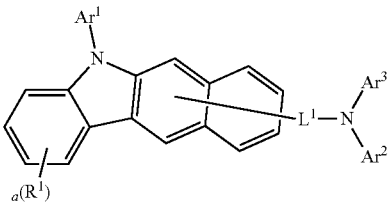

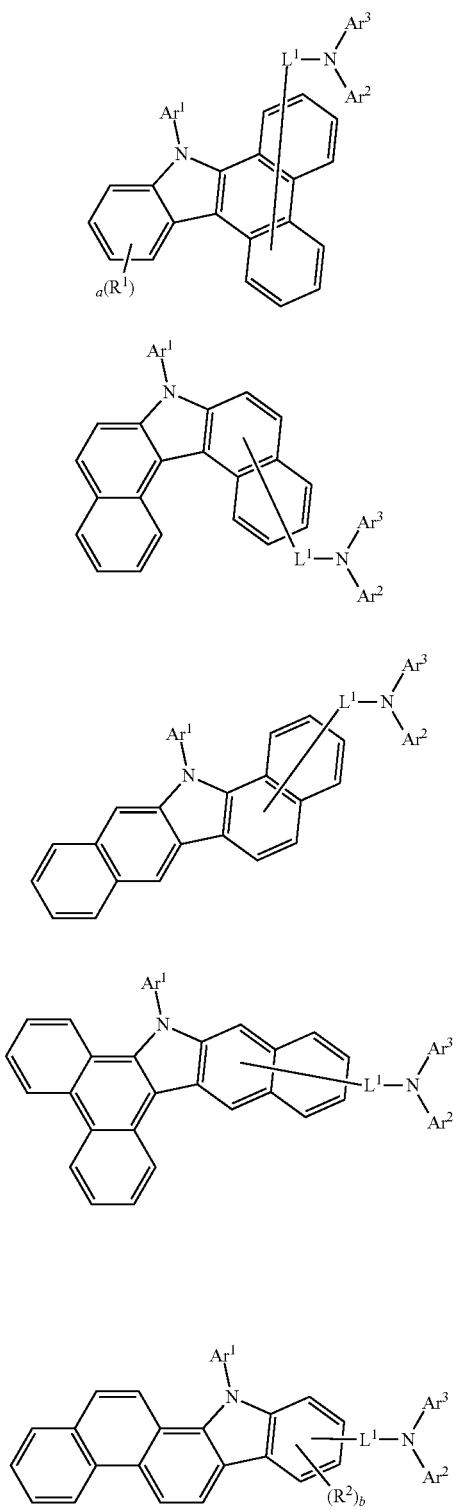

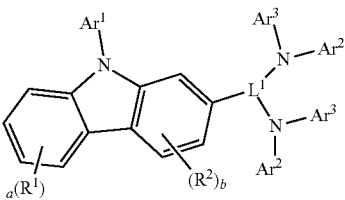
Formula 16

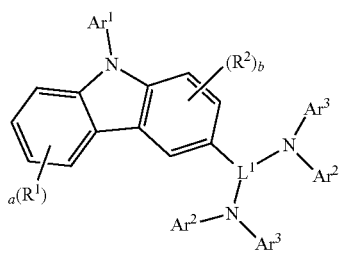
Formula 21, Formula 22 wherein $R^1$, $R^2$, $L^1$, $Ar^1$, $Ar^2$, $Ar^3$, a and b are the same as defined in claim 1.

7. The organic electric element according to claim 1, wherein n is 1 in Formula 1.

8. The organic electric element according to claim 1, wherein n is 2 in Formula 1.

9. The organic electric element claim 1, wherein the first host compound represented by Formula 1 comprises a compound represented by the following Formula 23:

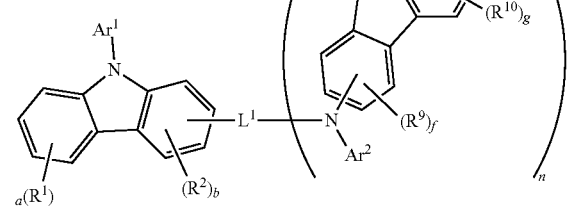
Formula 23 wherein:
1) $R^1$, $R^2$, $L^1$, $Ar^1$, $Ar^2$, a, b and n are the same as defined in claim 1,
2) f is an integer of 0 to 3, and g is an integer of 0 to 4,
3) $R^9$ and $R^{10}$ are the same or different from each other, and are each independently selected from the group consisting of deuterium, halogen, a $C_6$-$C_{60}$ aryl group, a fluorenyl group, a $C_2$-$C_{60}$ heterocyclic group including at least one heteroatom of O, N, S, Si or P, a fused ring group of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxy group; or in case f and g are 2 or more, $R^9$ and $R^{10}$ are each in plural being the same or different, and a plurality of $R^9$ or a plurality of $R^{10}$ or adjacent $R^9$ and $R^{10}$ may combine to each other to form an aromatic or a heteroaromatic ring,
4) Y is NR', O, S or CR'R", and
5) R' and R" are the same as defined in claim 1.

10. The organic electric element according to claim 1, wherein the second host compound represented by Formula 2 is represented by the following Formula 24 or 25, wherein, $R^1$, $R^2$, $L^1$, $Ar^1$, $Ar^2$, $Ar^3$, a and b are the same as defined in claim 1.

6. The organic electric element according to claim 1, wherein the first host compound represented by Formula 1 comprises a compound represented by any of the following Formulas 21 to 22:

Formula 24

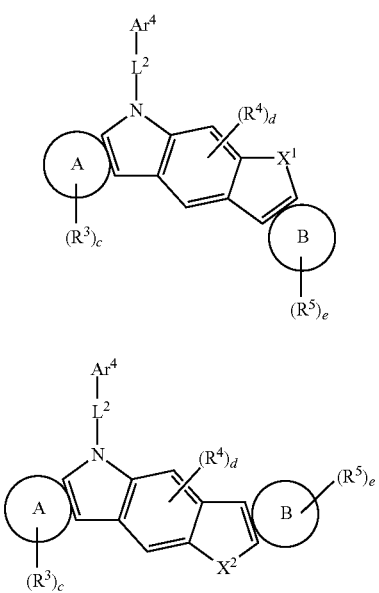

Formula 25 wherein R³, R⁴, R⁵, Ar⁴, L², c, d, e, A, B, X¹ and X² are the same as defined in claim 1.

11. The organic electric element according to claim 1, wherein A and B in Formula 2 are selected from the group consisting of the following Formulas (B-1) to (B-7):

(B-1)
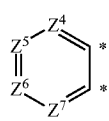

(B-2)
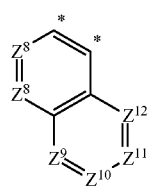

(B-3)
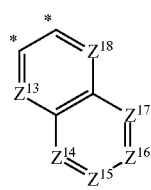

(B-4)
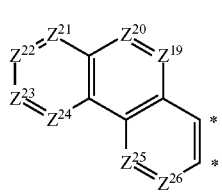

(B-5)
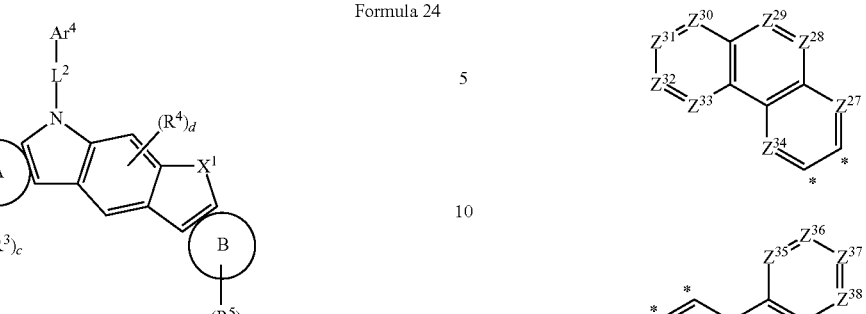

(B-6)

(B-7)
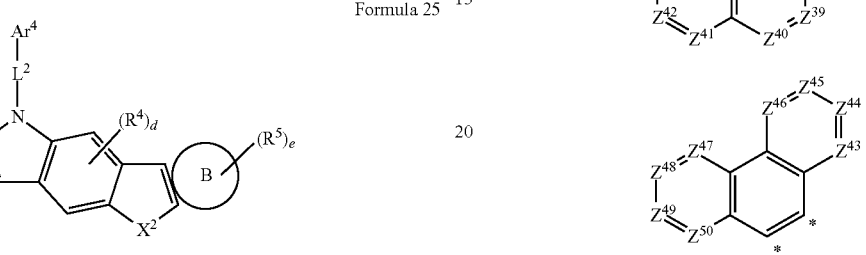

wherein,

1) $Z^4$ to $Z^{50}$ are CR' or N,

2) R' is the same as defined in claim 1,

3) * indicates the position to be condensed.

12. The organic electric element according to claim 1, wherein R⁴s in Formula 2 where d is 2, combine to each other to form an aromatic ring or a heteroaromatic ring.

13. The organic electric element according to claim 1, wherein the second host compound represented by Formula 2 comprises a compound represented by any of the following Formulas 26 to 45:

Formula 26
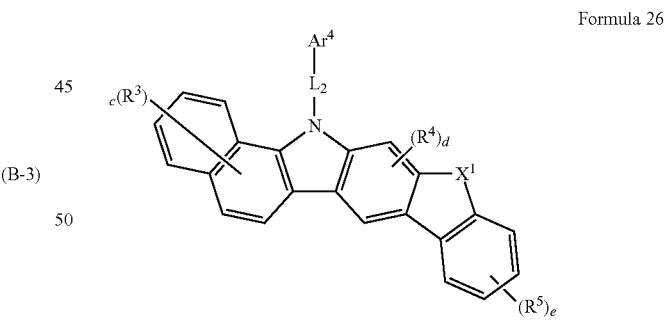

Formula 27
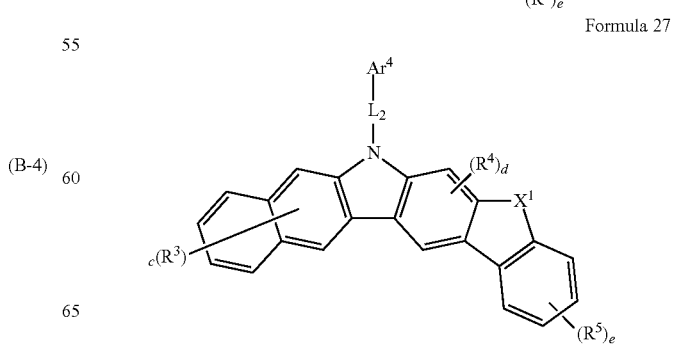

Formula 28
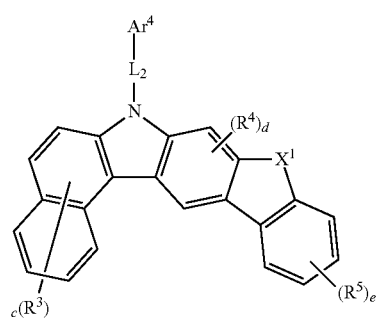
Formula 29
Formula 30
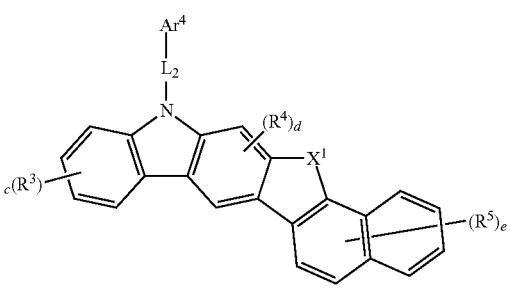
Formula 31
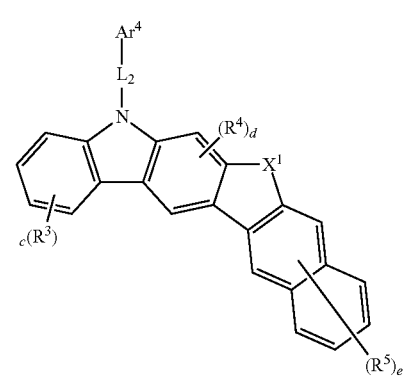
Formula 32
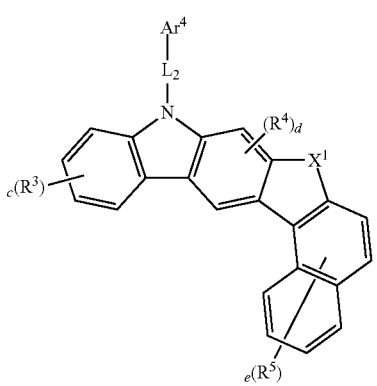
Formula 33
Formula 34
Formula 35

Formula 36
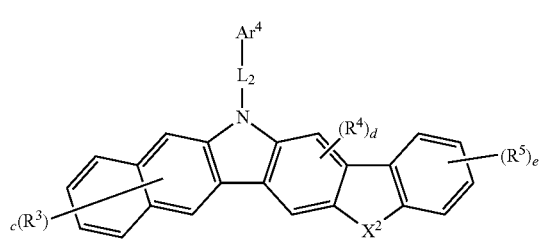
Formula 37
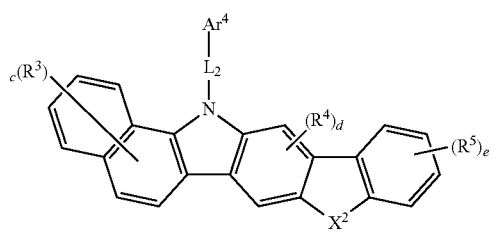
Formula 38
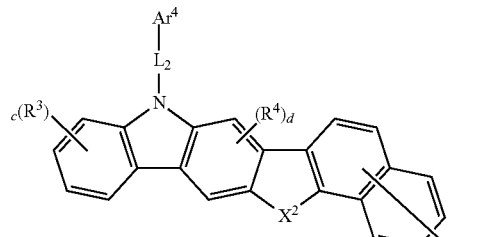
Formula 39
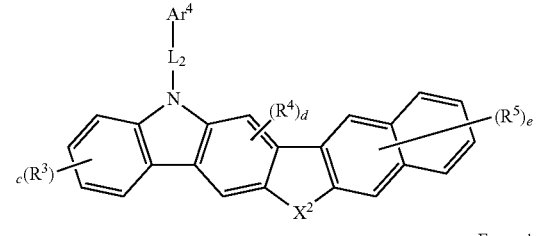
Formula 40
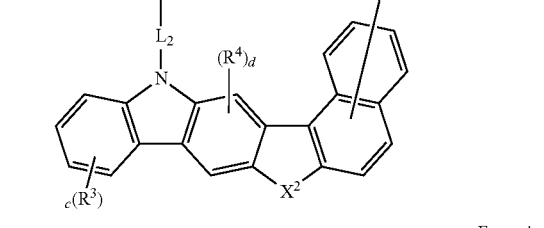
Formula 41
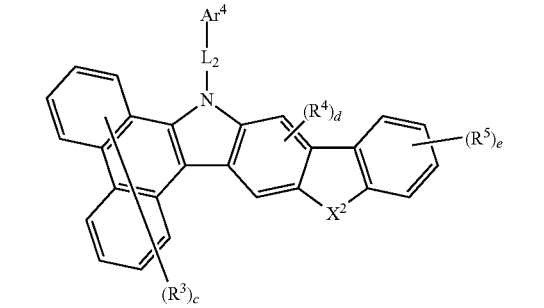
Formula 42
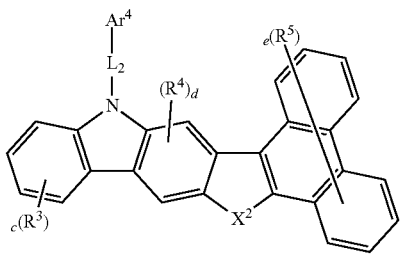
Formula 43
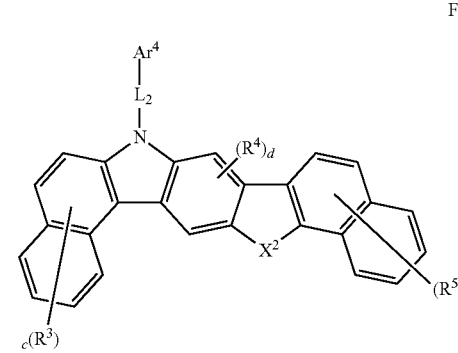
Formula 44
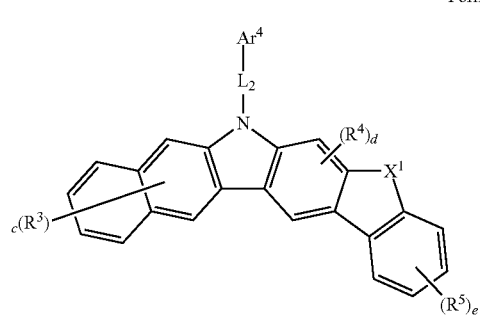
Formula 45
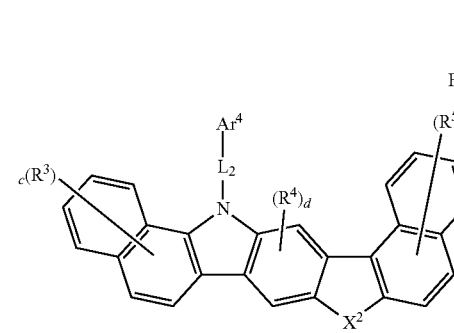
wherein,
$Ar^4$, $X^1$, $X^2$, $R^3$, $R^4$, $R^5$, $L^2$, c, d, and e are the same as defined in claim 1.
14. The organic electric element according to claim 1, wherein the second host compound represented by Formula 2 comprises any one of compounds represented by the following Formulas 46 to 53:

Formula 46
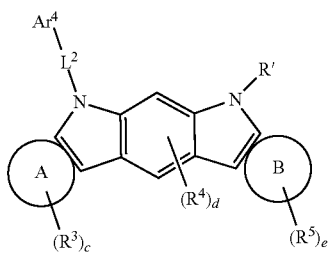
Formula 47
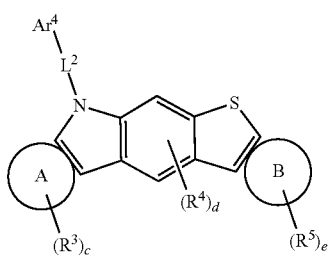
Formula 48
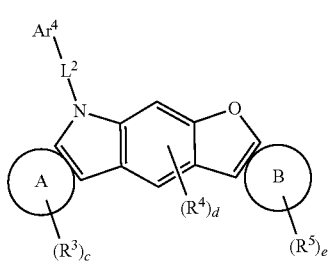
Formula 49
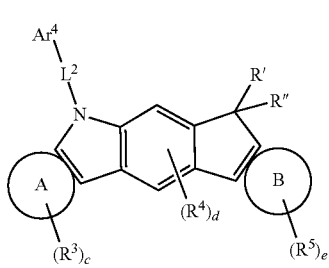
Formula 50
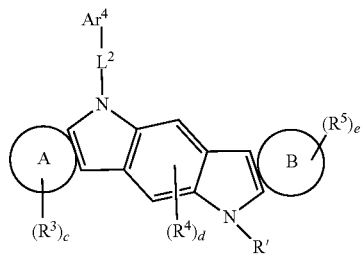
Formula 51
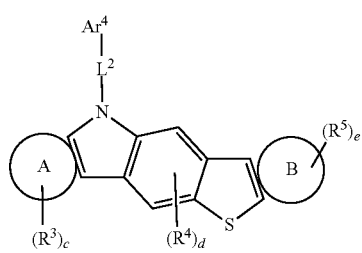
Formula 52
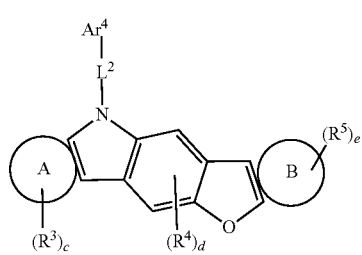
Formula 53
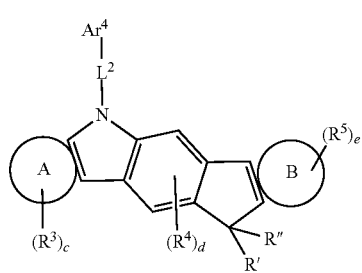
wherein,
$R^3$, $R^4$, $R^5$, $Ar^4$, $L^2$, c, d, e, A, B, R' and R" are the same as defined in claim 1.
15. The organic electric element according to claim 1, wherein the first host compound represented by Formula 1 is one of the following Compounds 1-1 to 1-68 and Compounds 2-1 to 2-68:

205         206
1-1
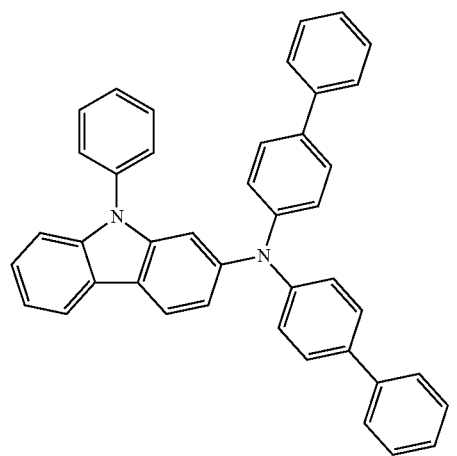
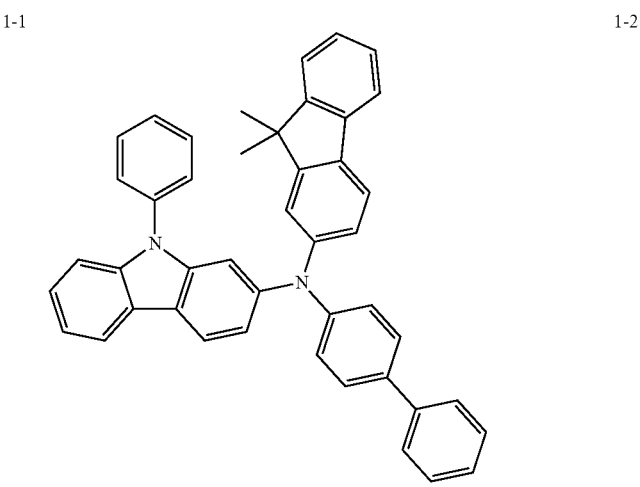
1-2
1-3
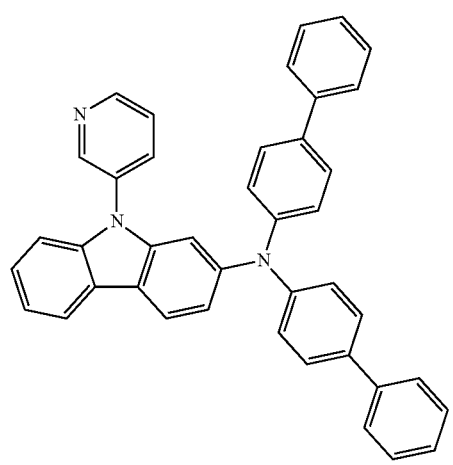
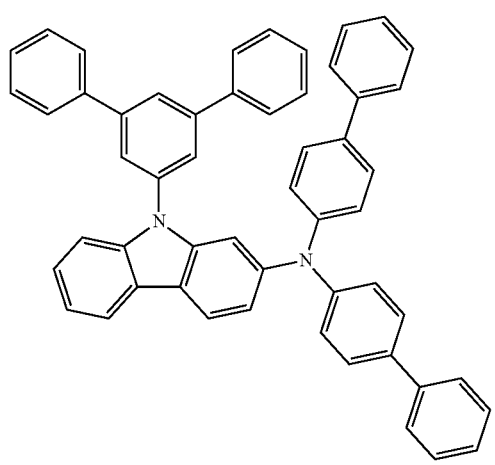
1-4
1-5
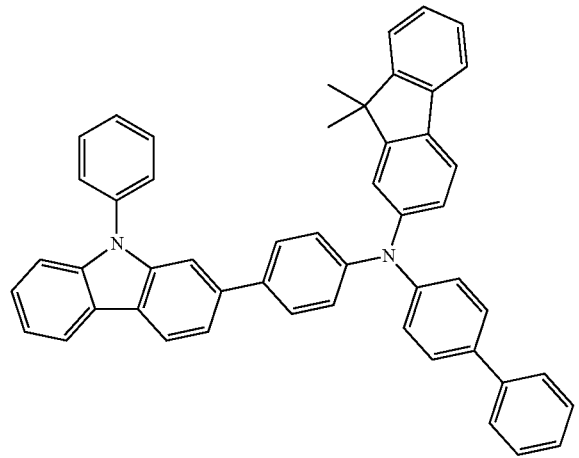
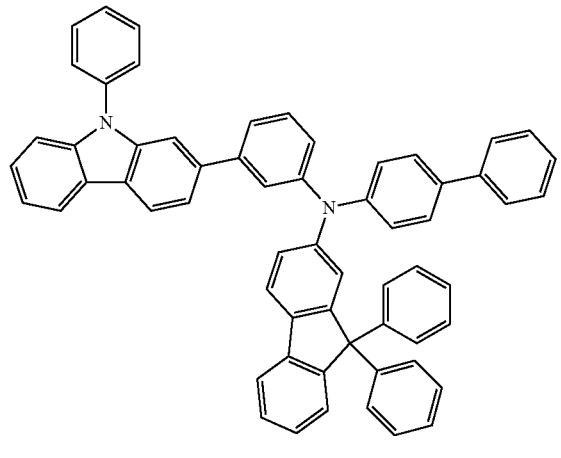
1-6

-continued
1-7
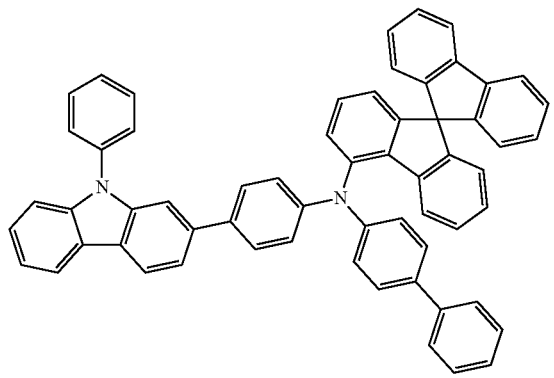
1-8
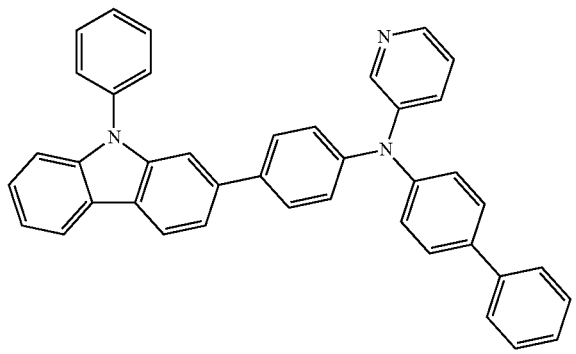
1-9
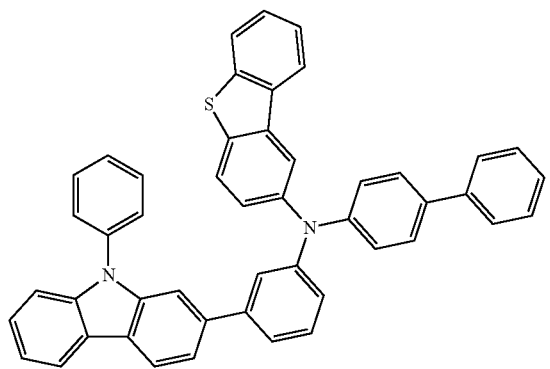
1-10
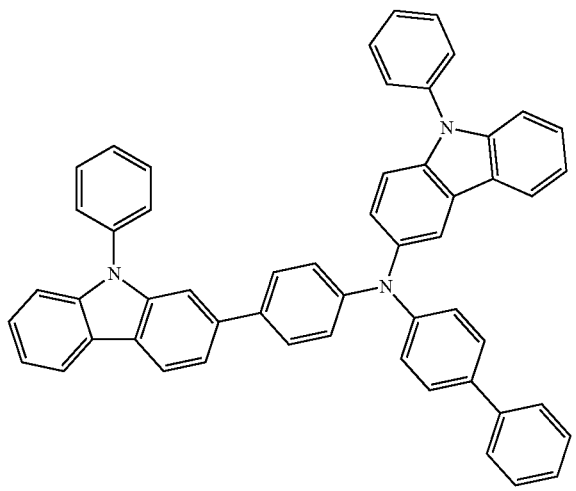
1-11
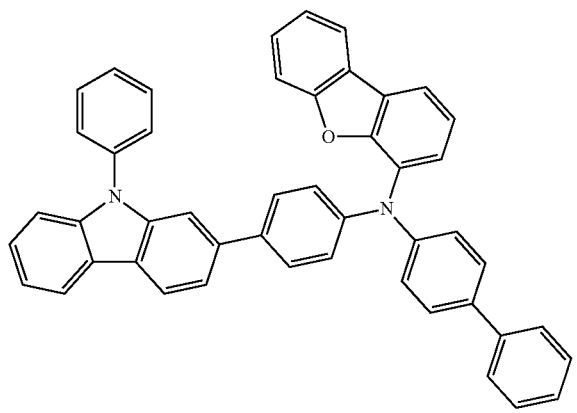
1-12
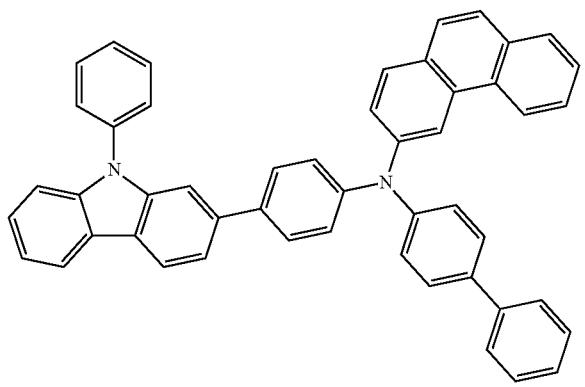

-continued
1-13
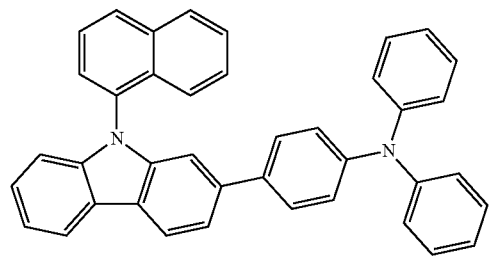
1-14
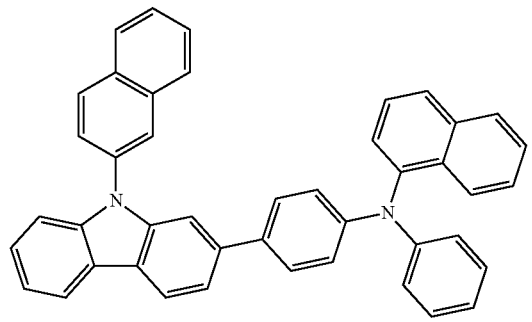
1-15
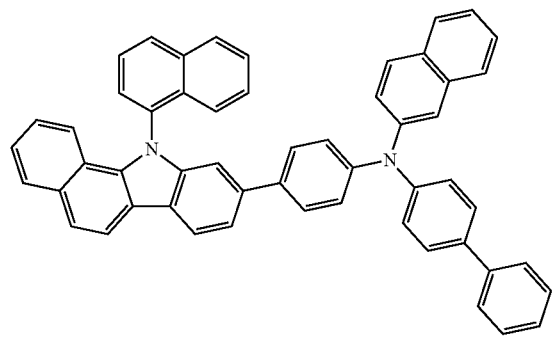
1-16
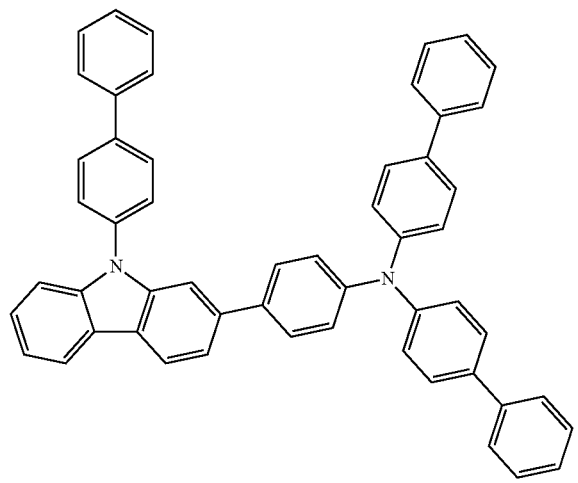
1-17
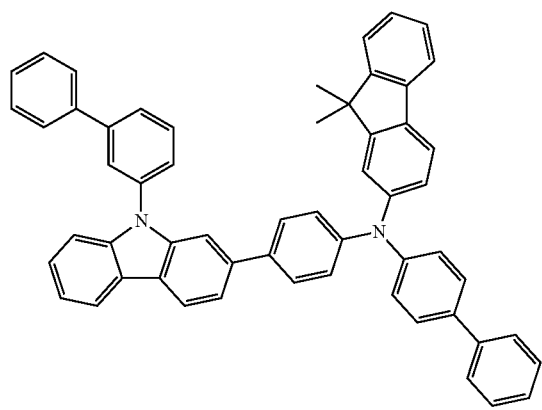
1-18
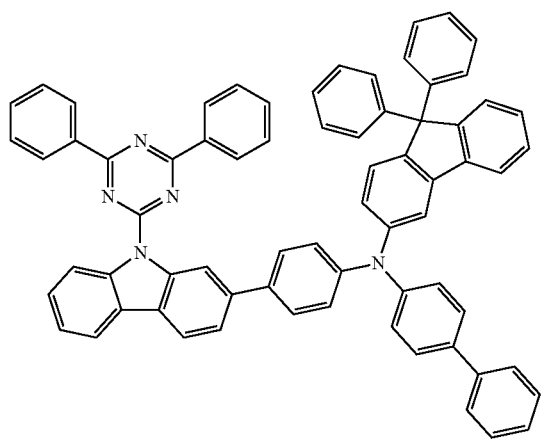

-continued
1-19
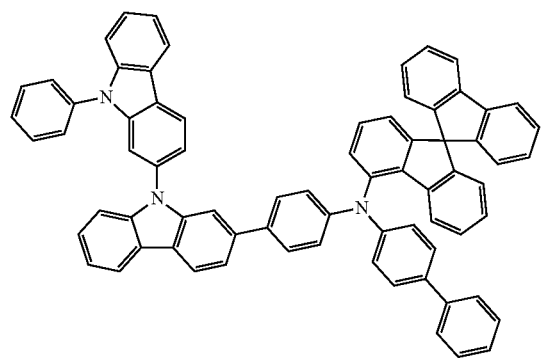
1-20
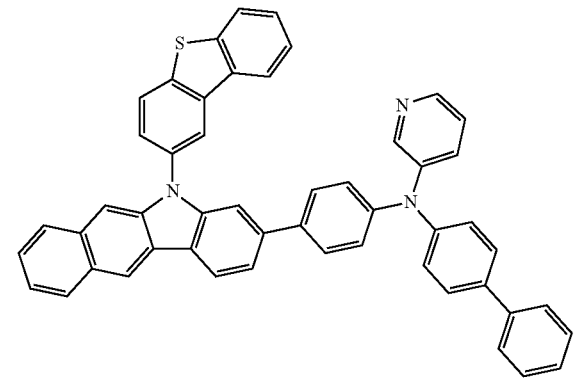
1-21
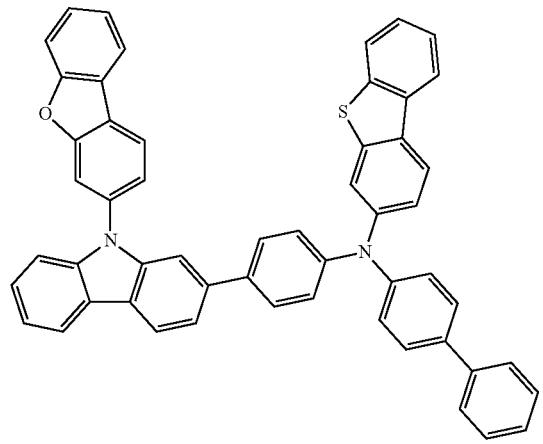
1-22
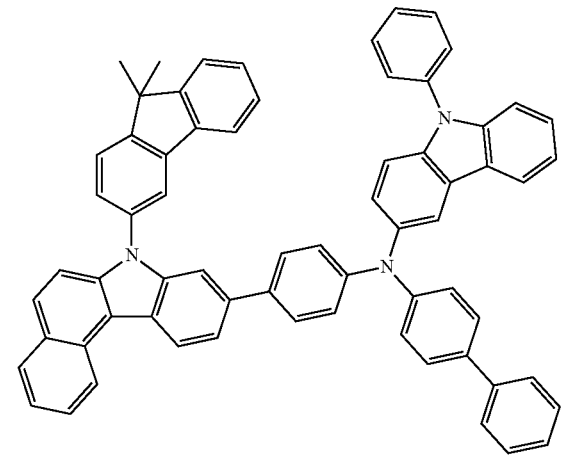
1-23
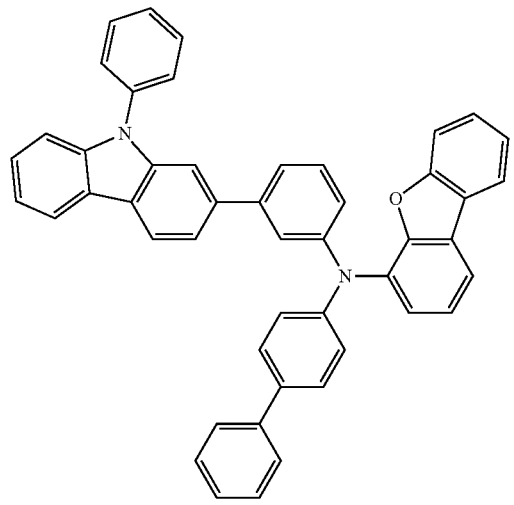
1-24
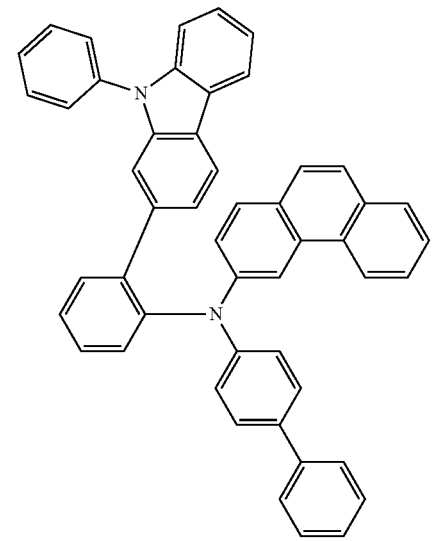

-continued
1-25
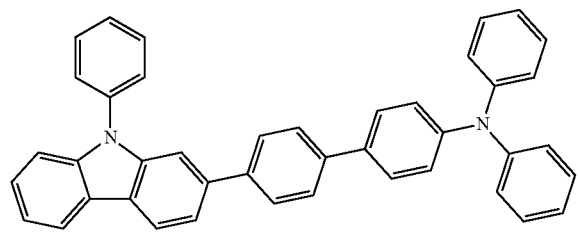
1-26
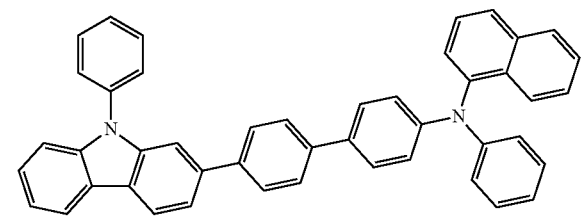
1-27
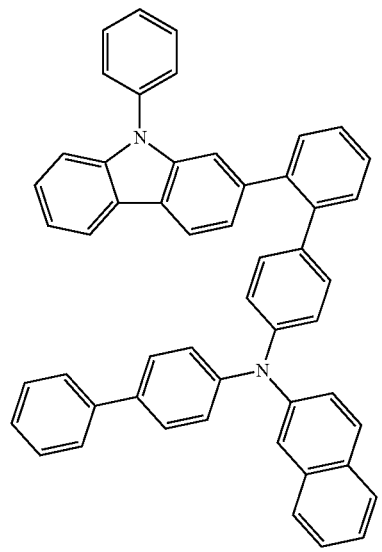
1-28
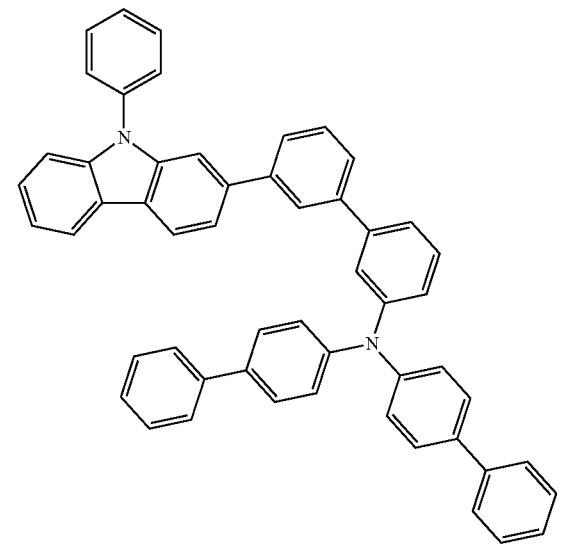
1-29
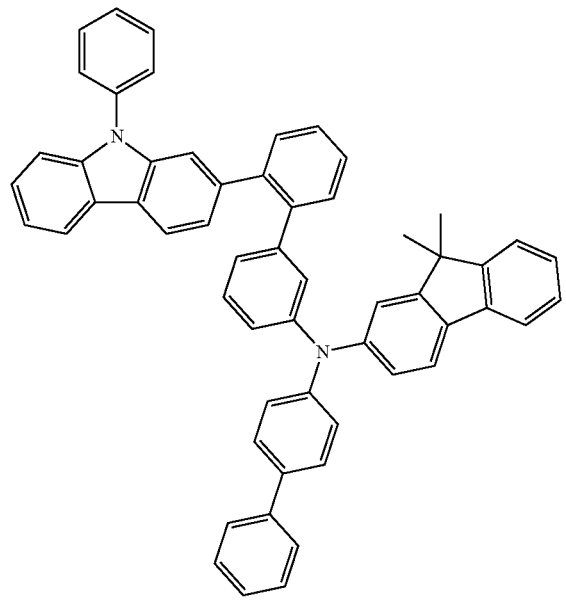
1-30
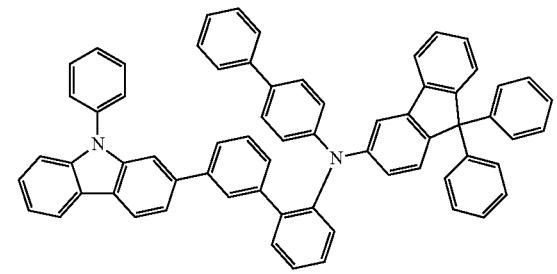

-continued
1-31
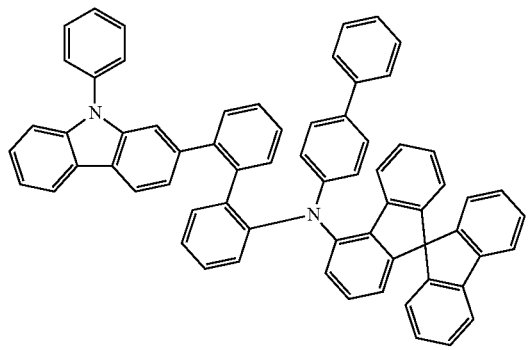
1-32
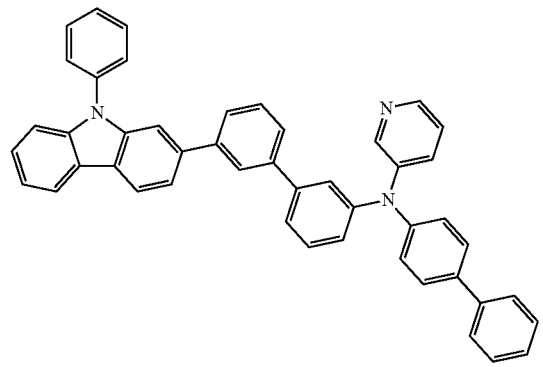
1-33
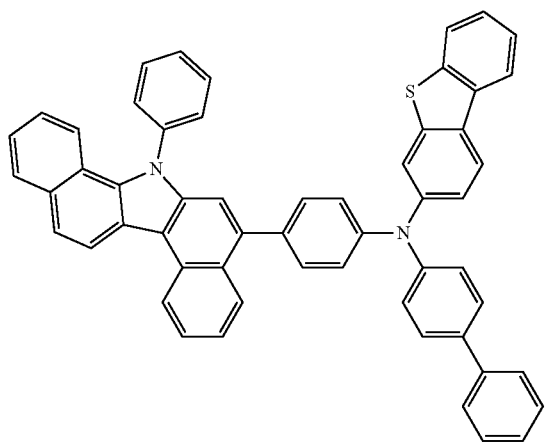
1-34
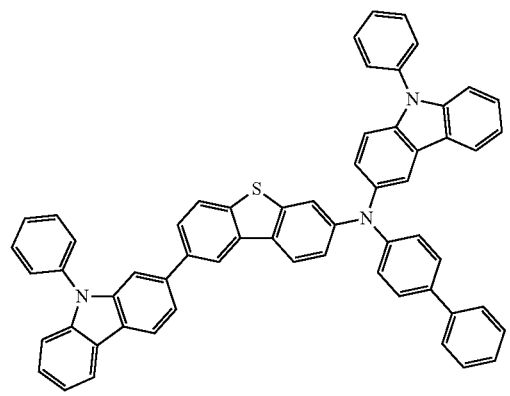
1-35
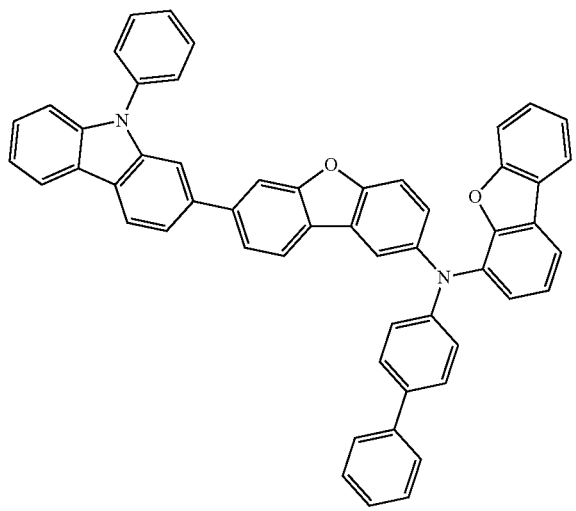
1-36
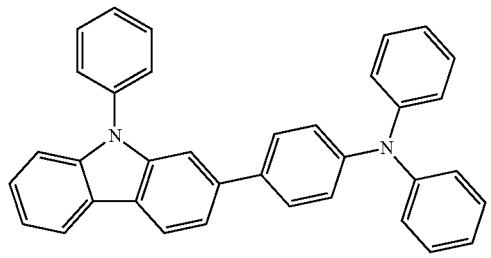
1-37
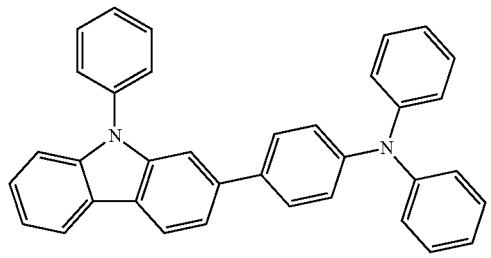
1-38
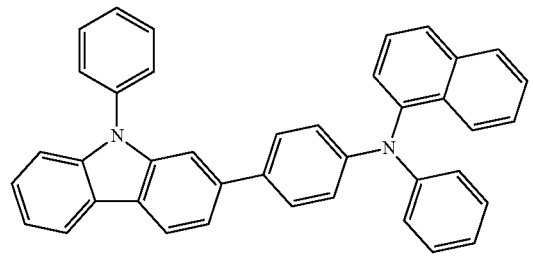

1-39
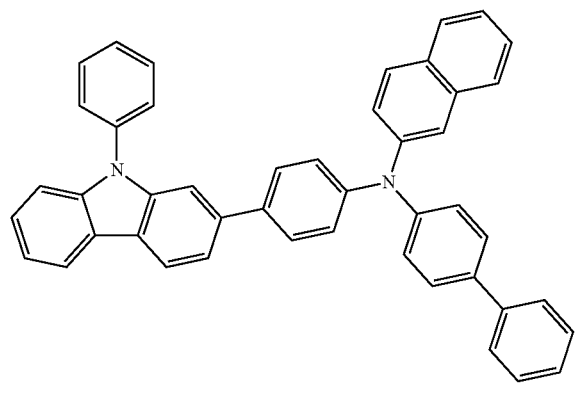
1-40
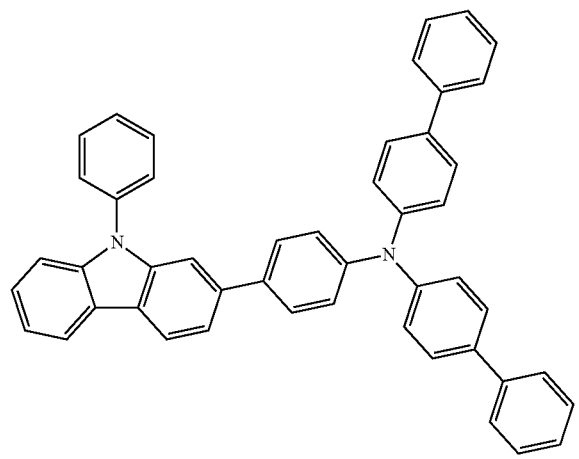
1-41
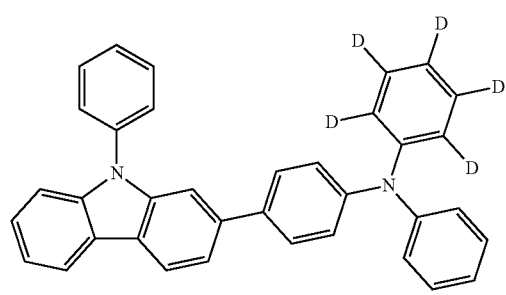
1-42
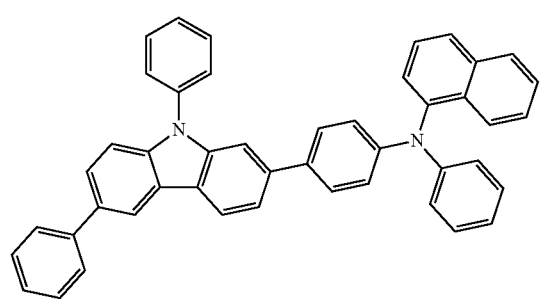
1-43
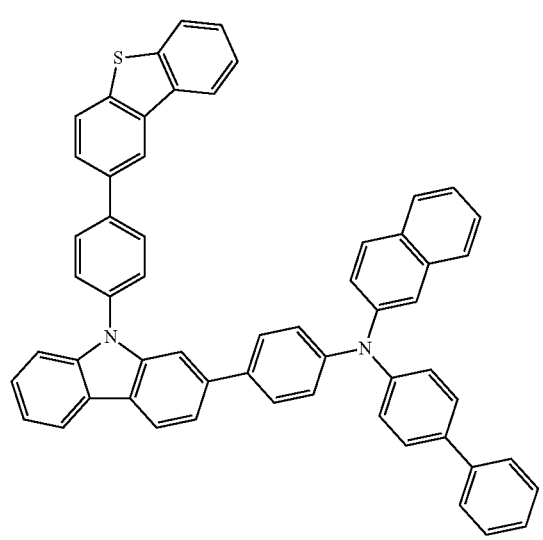
1-44
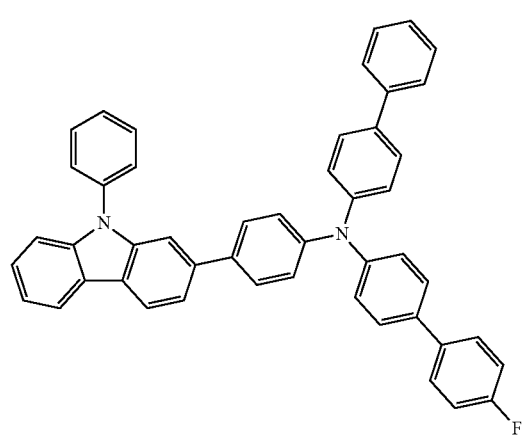

-continued
1-45
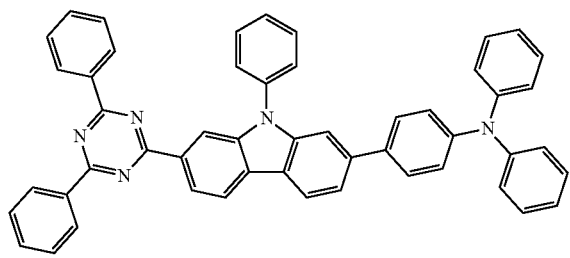
1-46
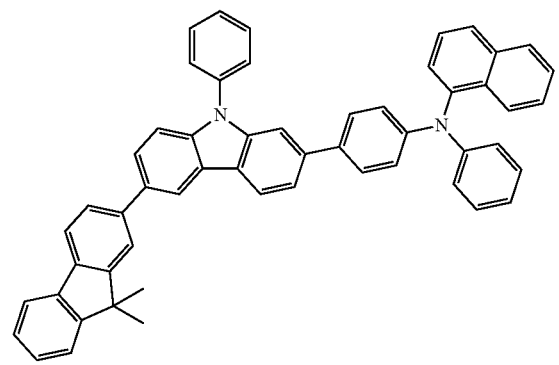
1-47
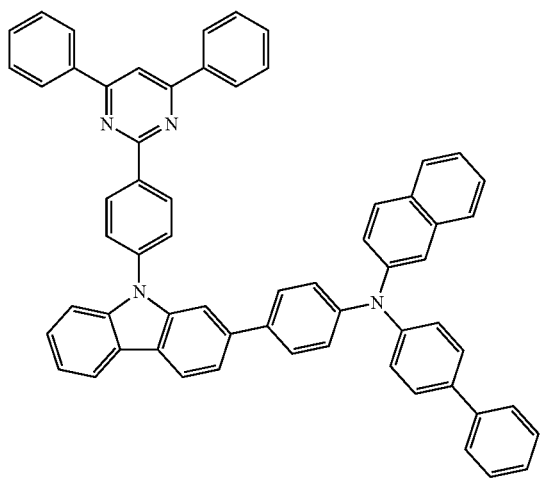
1-48
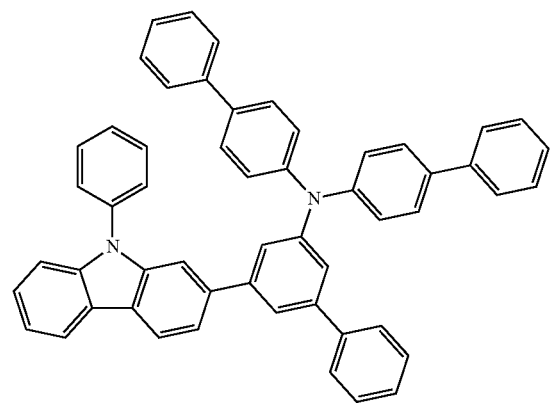
1-49
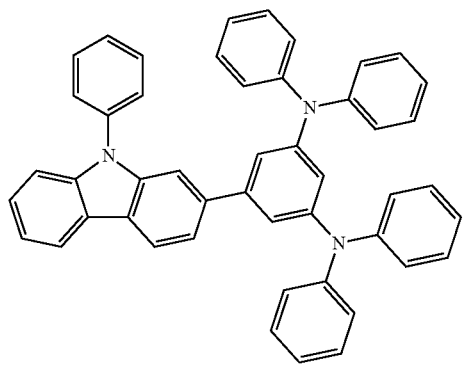
1-50
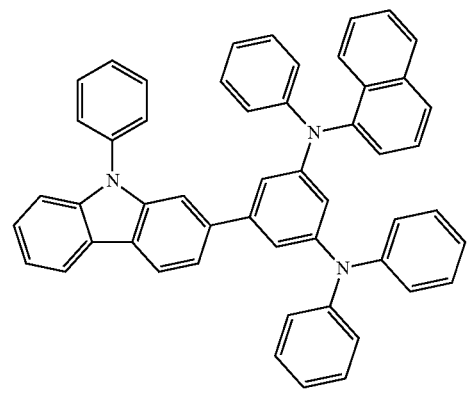

-continued
1-51
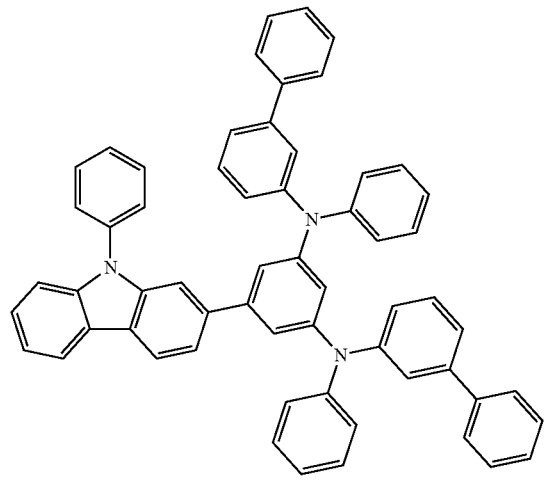
1-52
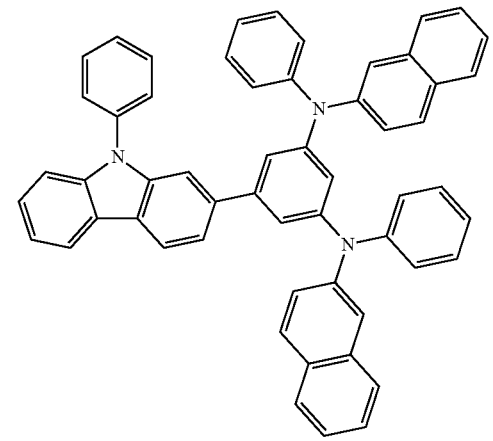
1-53
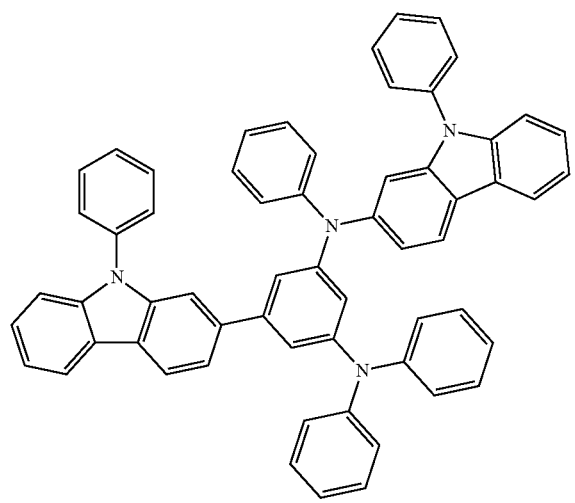
1-54
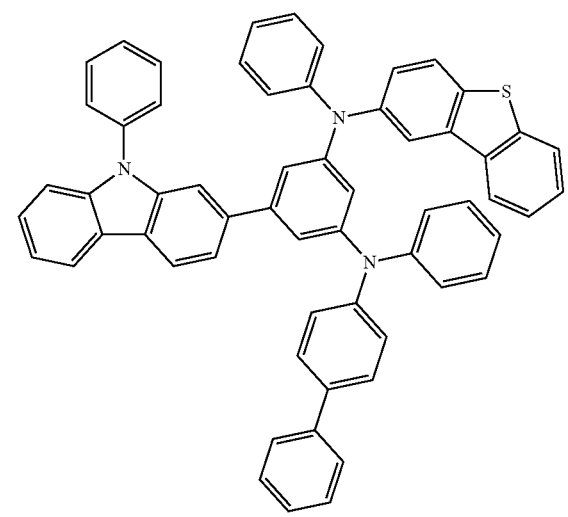
1-55
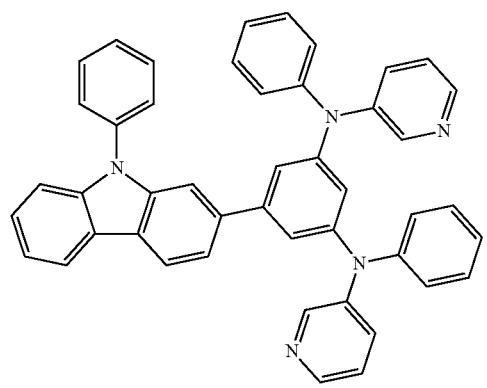
1-56
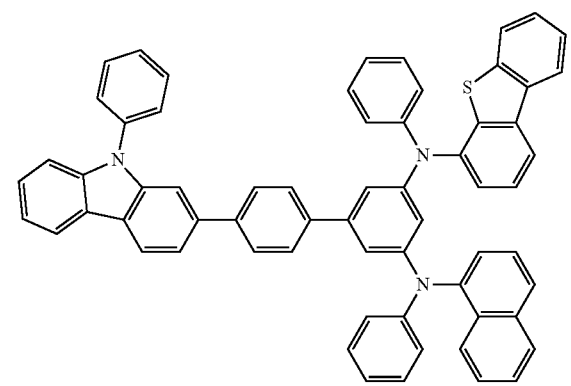

-continued
1-57
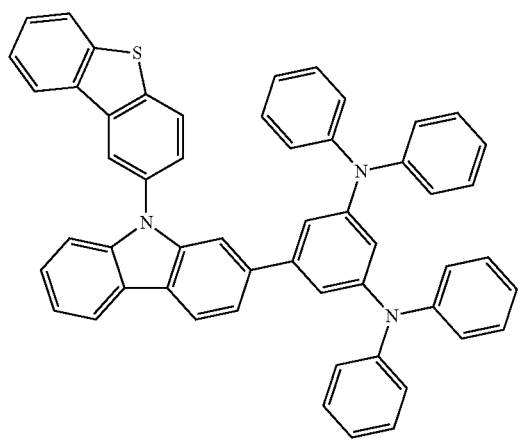
1-58
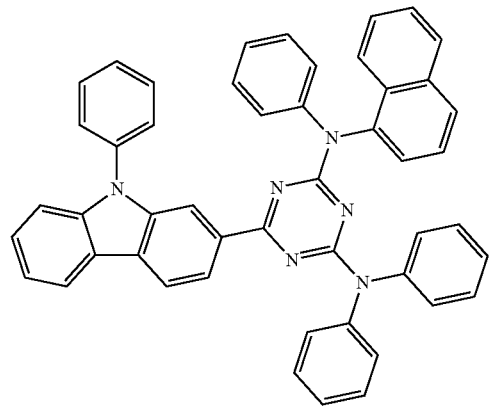
1-59
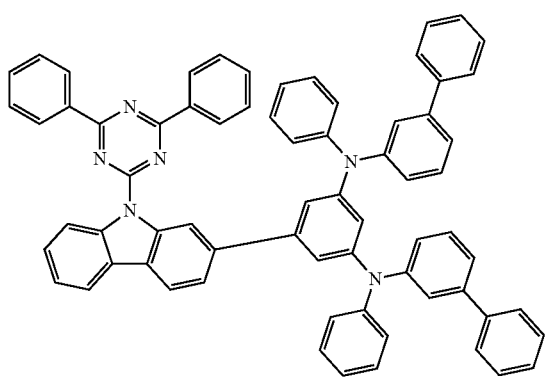
1-60
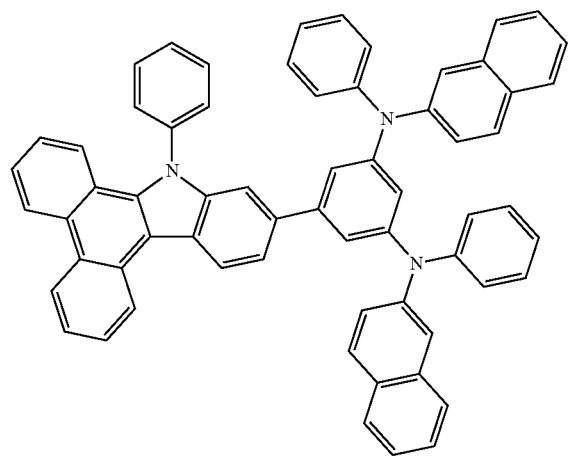
1-61
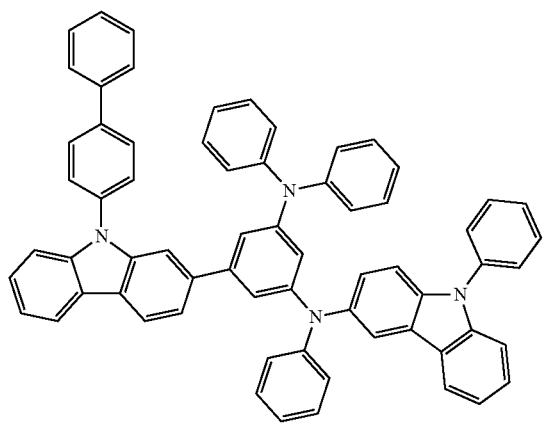
1-62
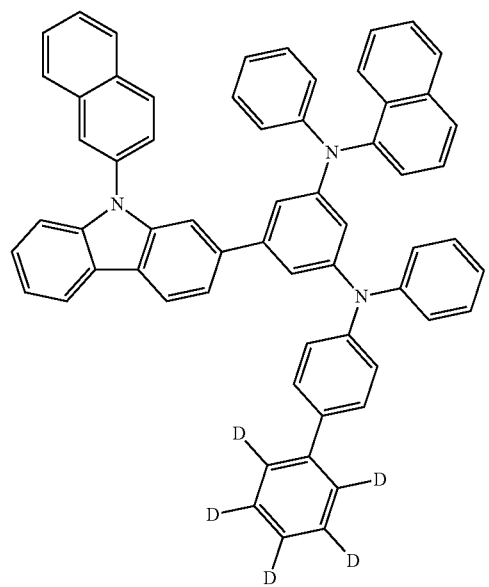

-continued
1-63
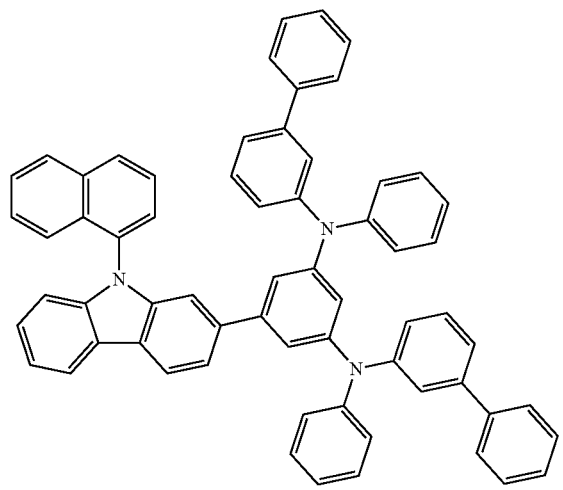
1-64
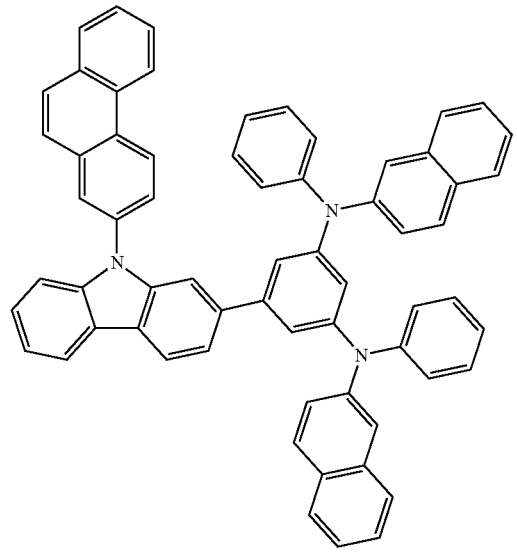
1-65
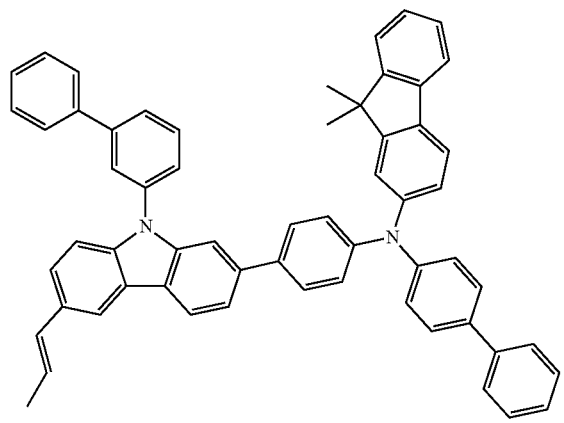
1-66
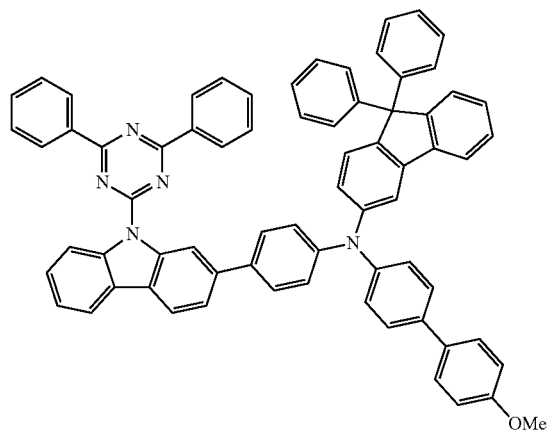
1-67
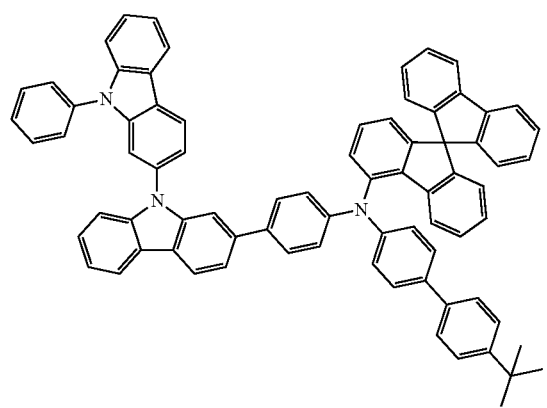
1-68
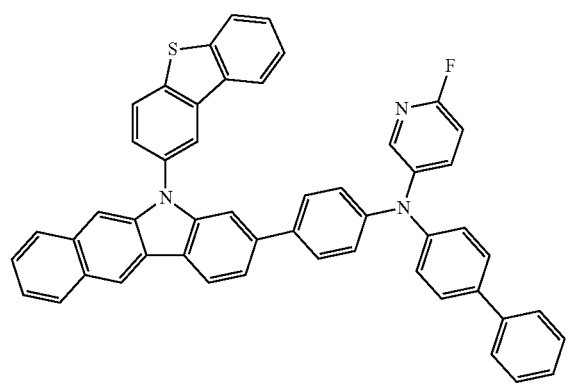

-continued
2-1
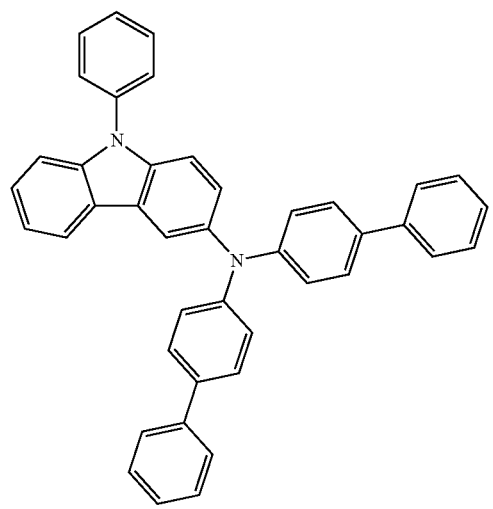
2-2
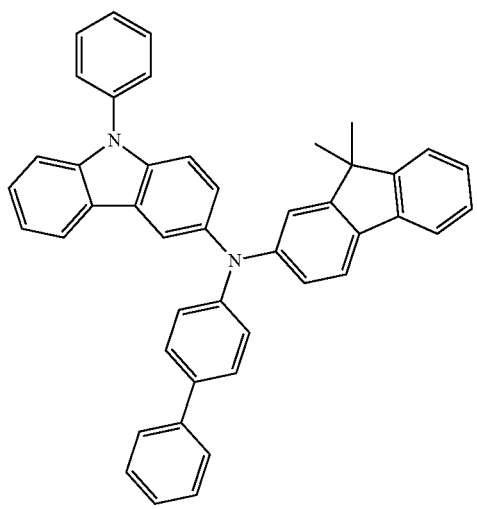
2-3
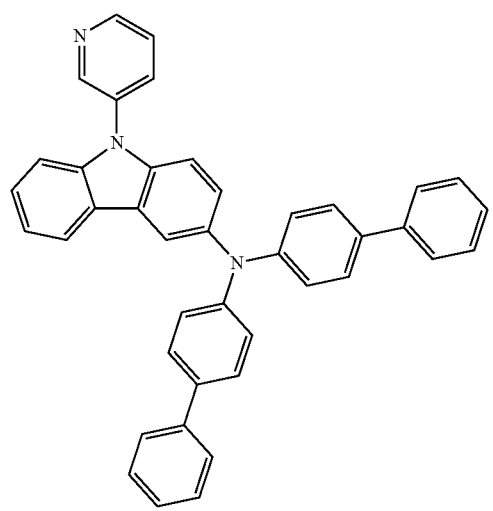
2-4
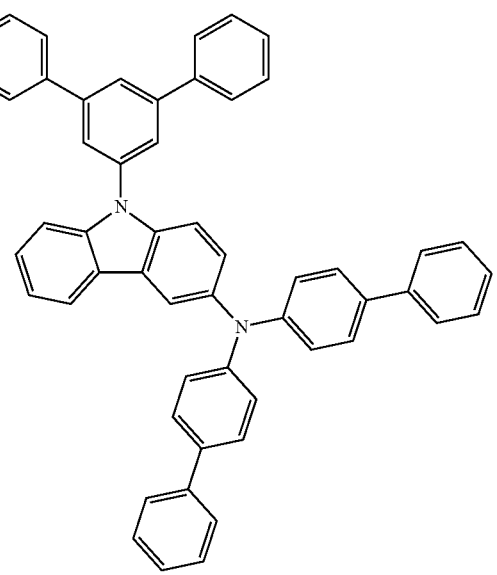

2-5
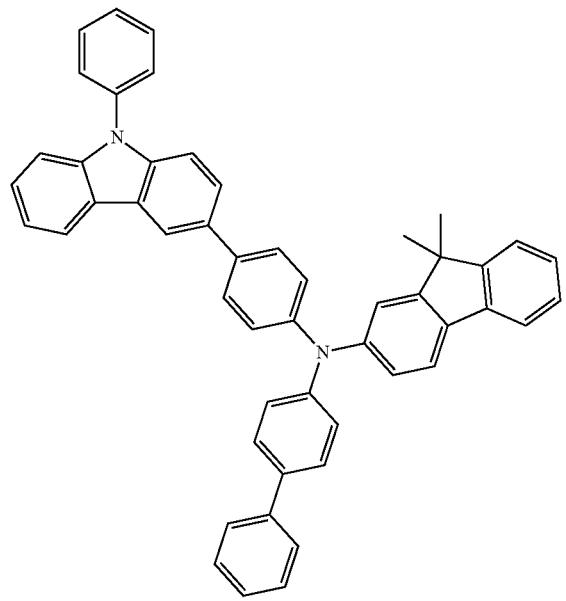
2-6
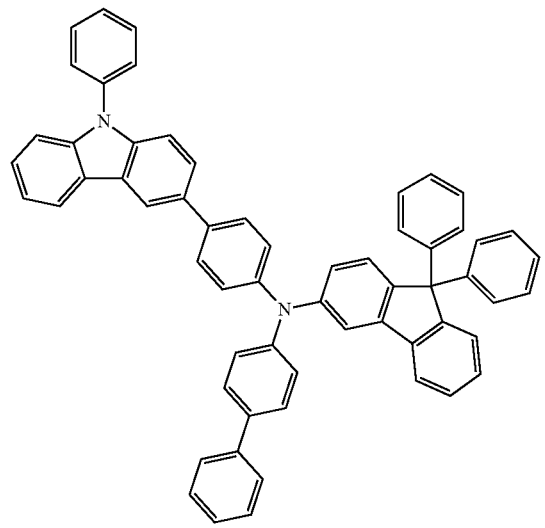
2-7
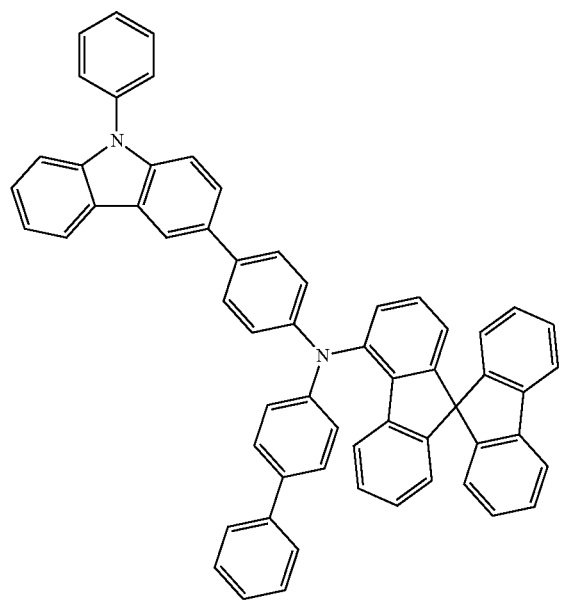
2-8
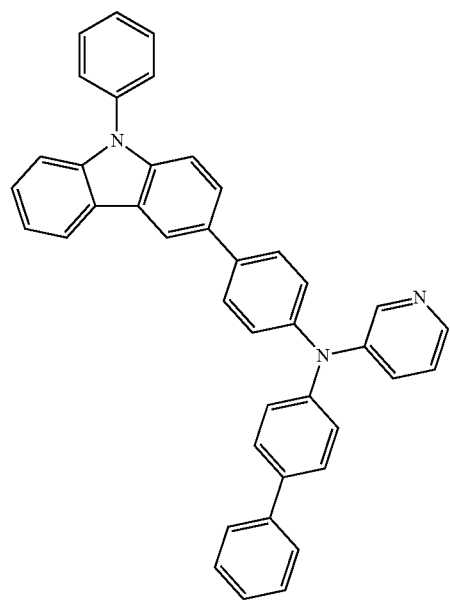

-continued
2-9
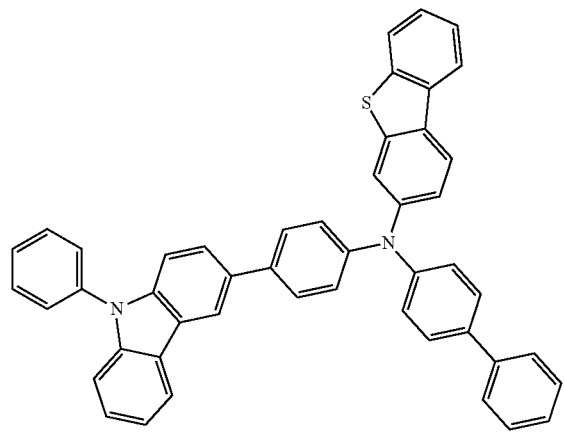
2-10
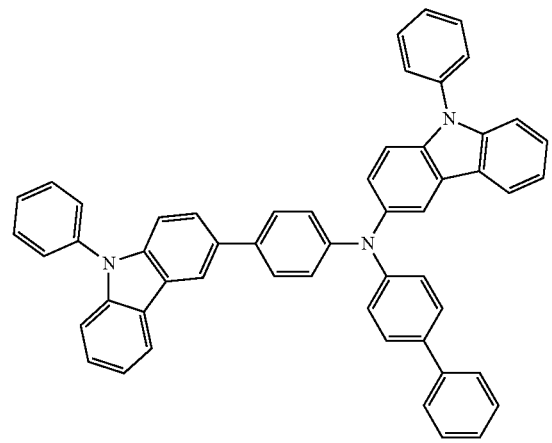
2-11
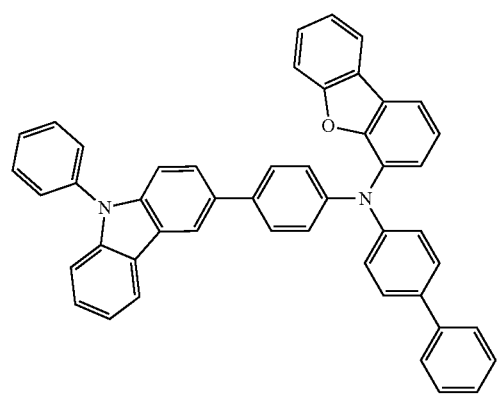
2-12
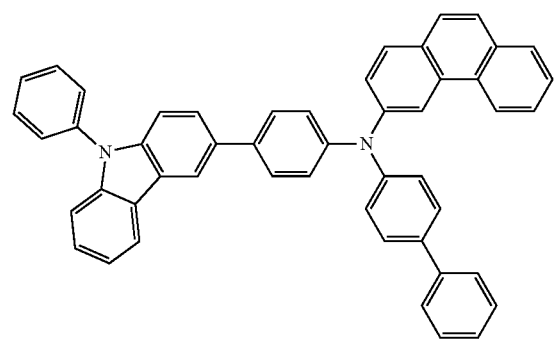
2-13
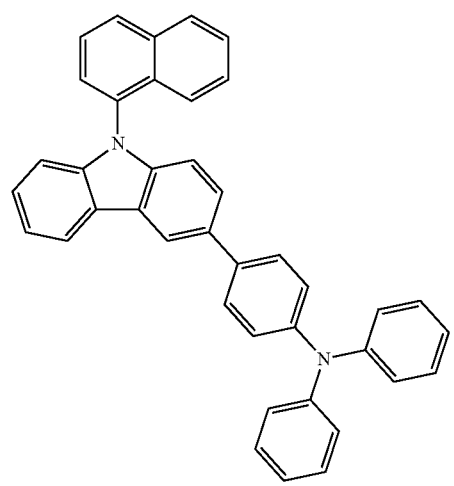
2-14
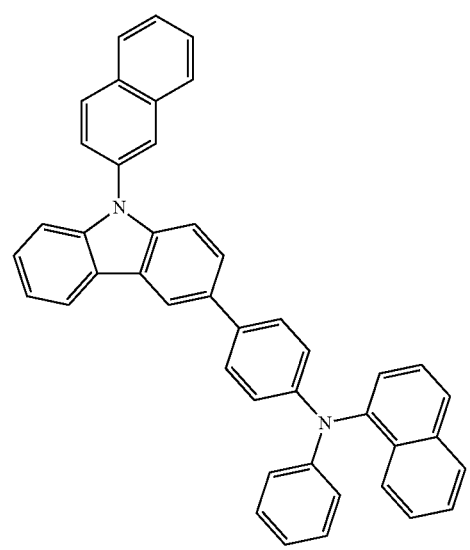

-continued
2-15
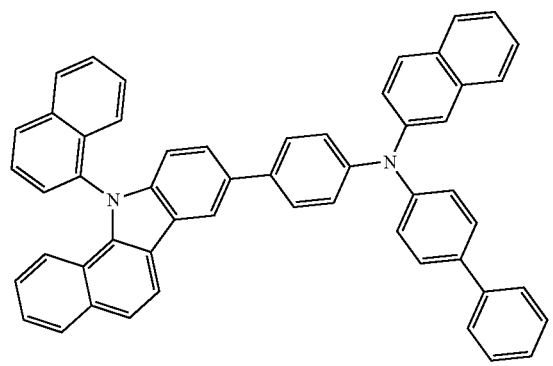
2-16
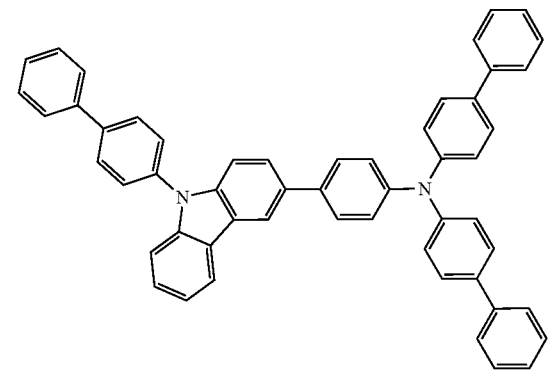
2-17
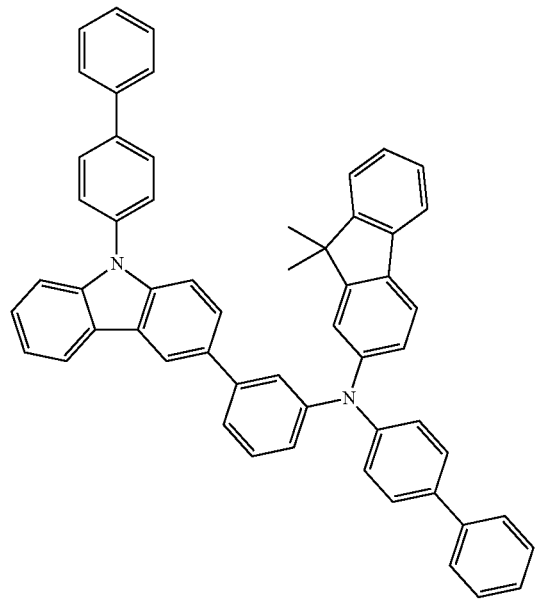
2-18
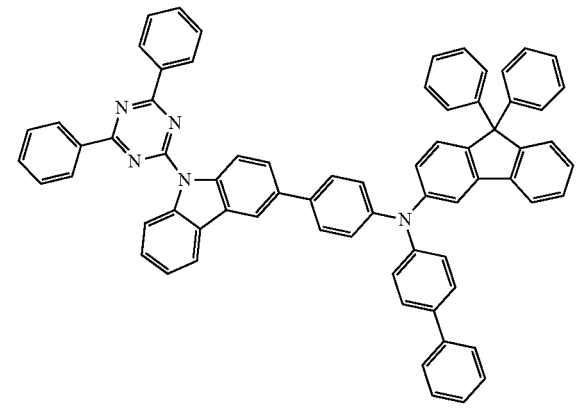
2-19
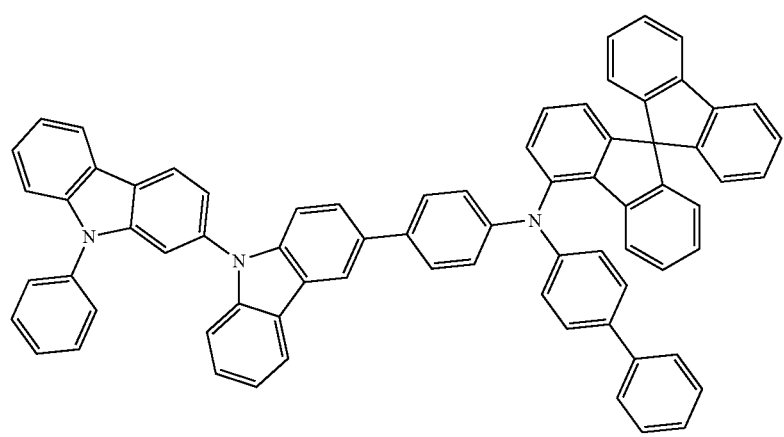

-continued
2-20
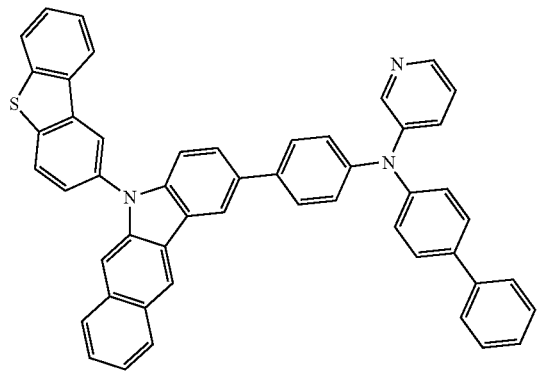
2-21
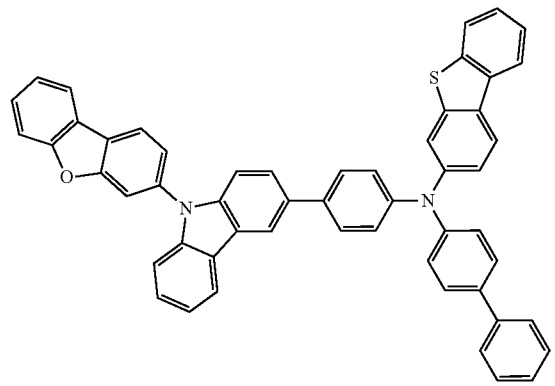
2-22
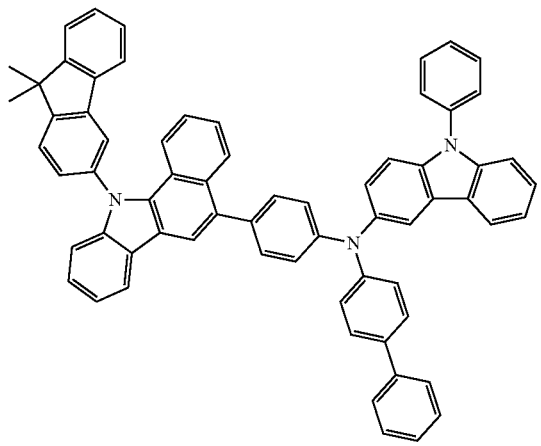
2-23
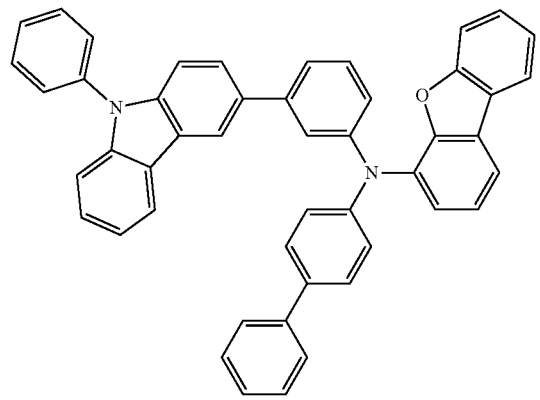
2-24
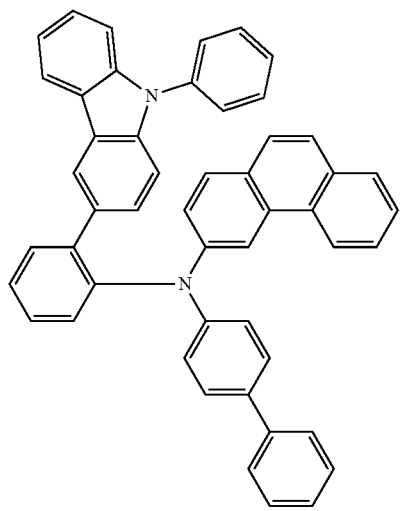
2-25
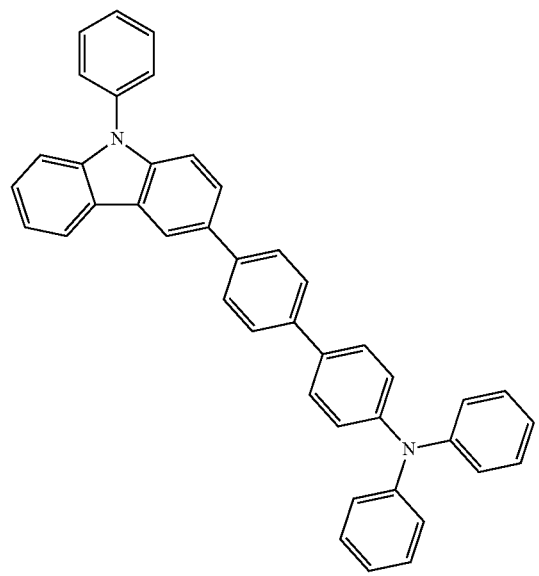

-continued
2-26
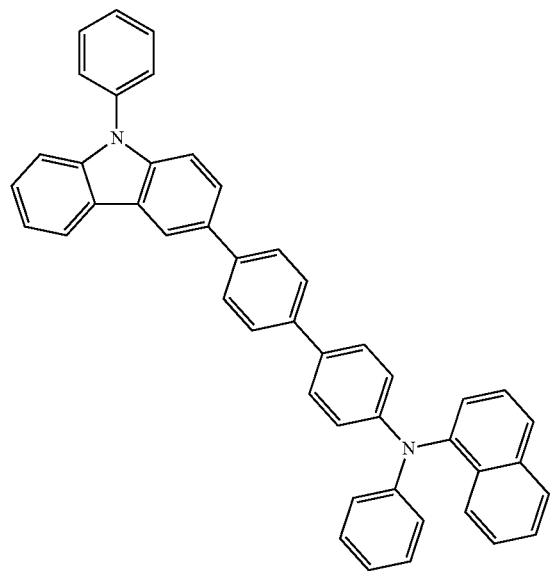
2-27
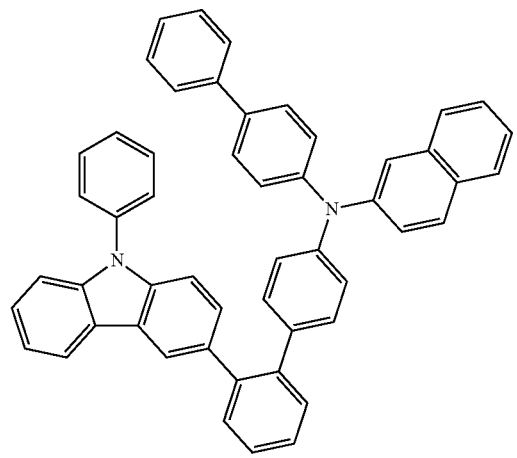
2-28
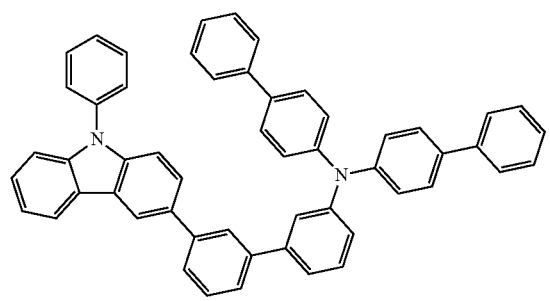
2-29
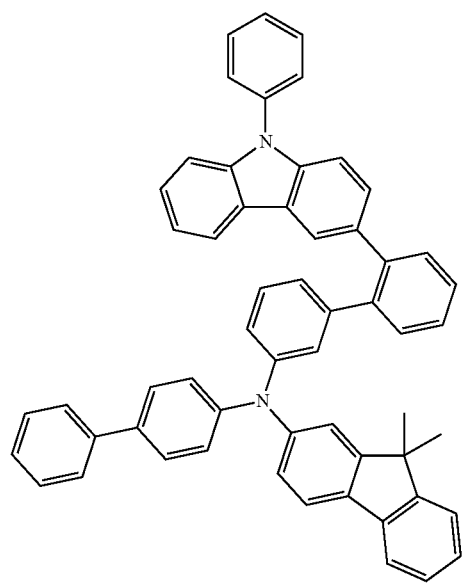

-continued
2-30
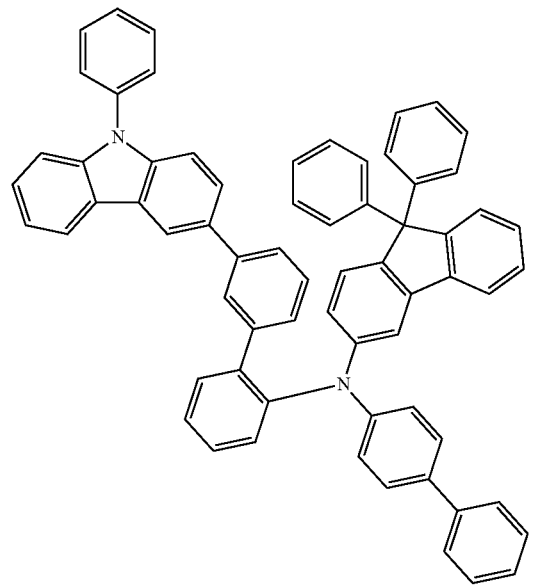
2-31
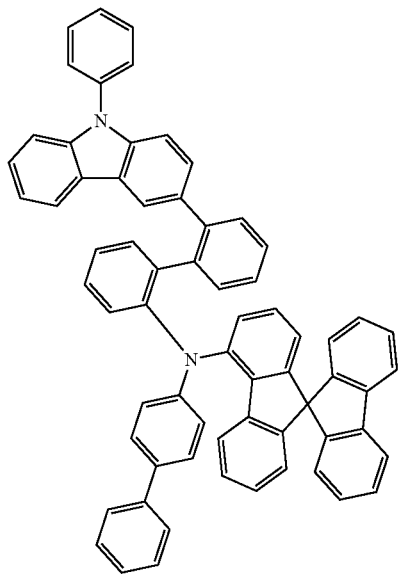
2-32
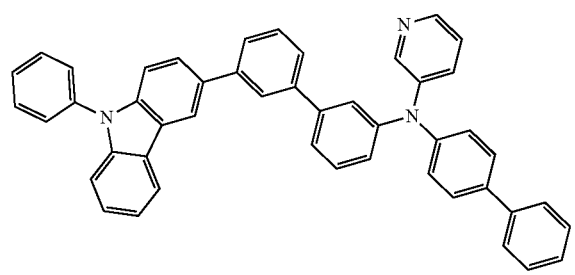
2-33
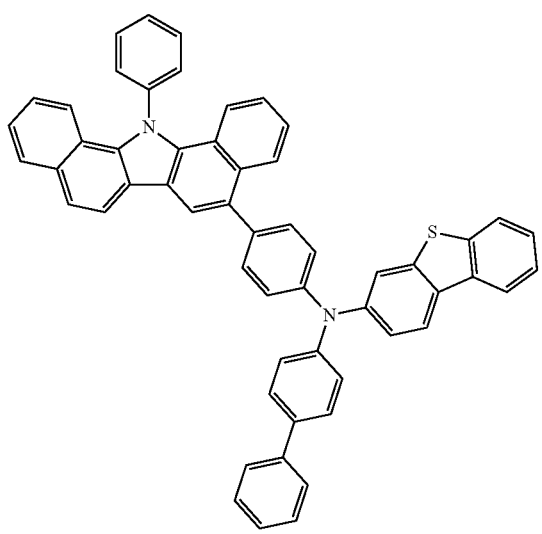
2-34
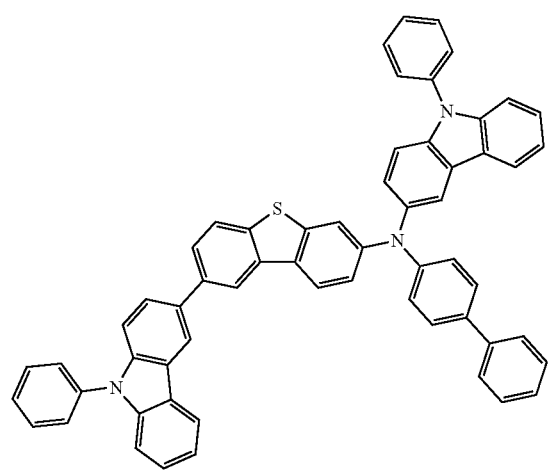
2-35
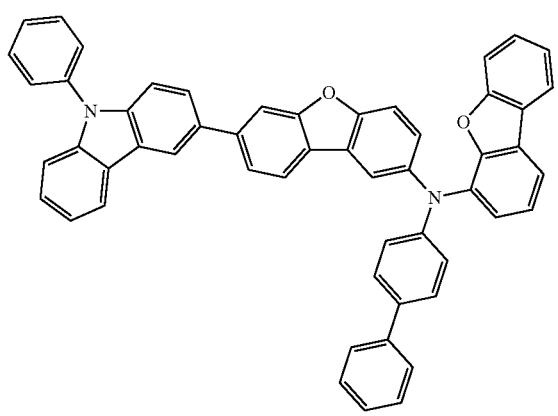

-continued
2-36
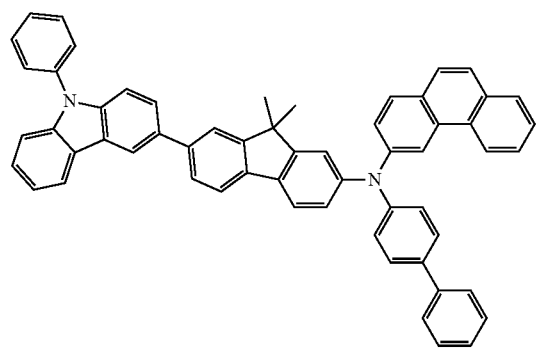
2-37
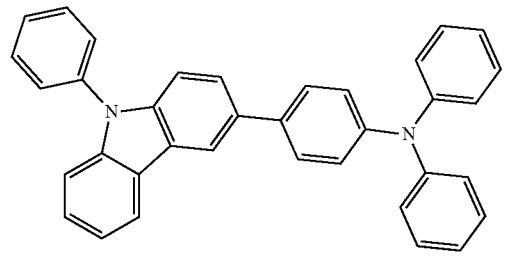
2-38
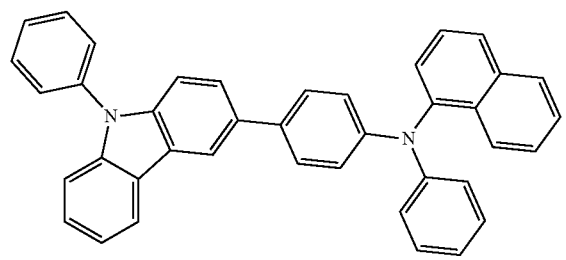
2-39
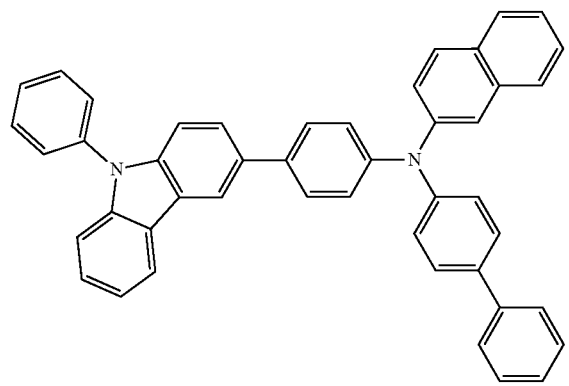
2-40
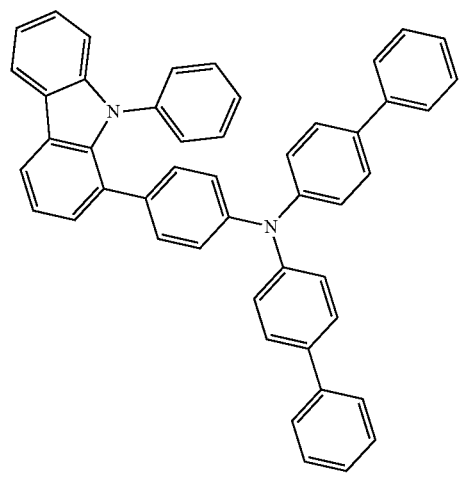
2-41
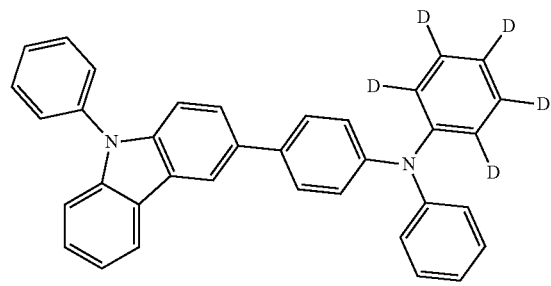
2-42
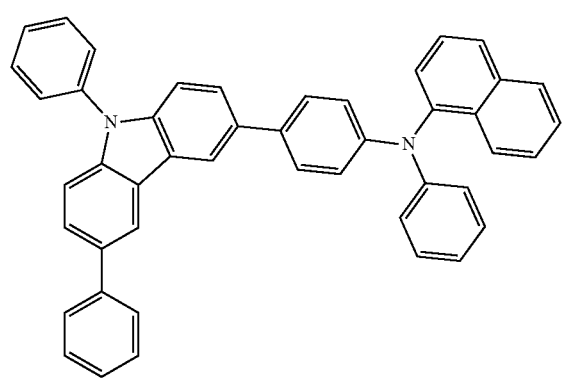
2-43
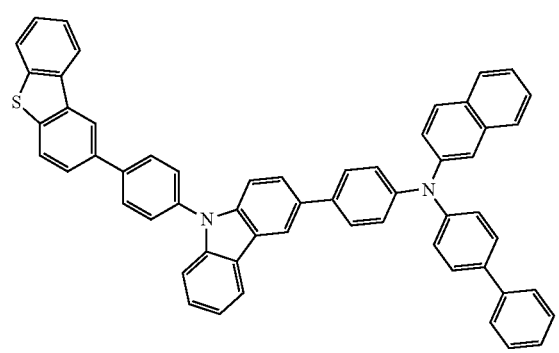

-continued
2-44
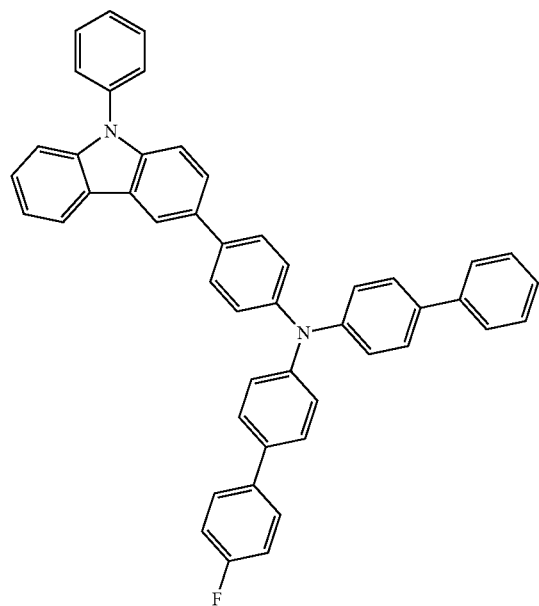
2-45
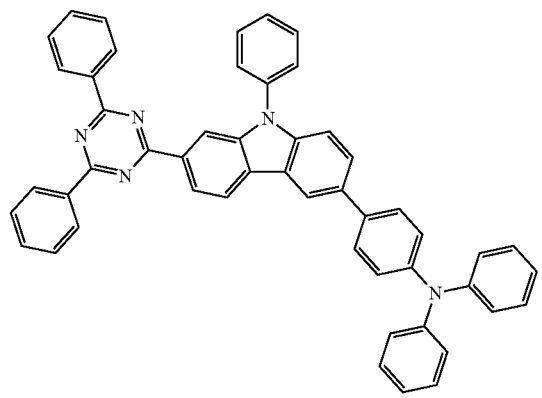
2-46
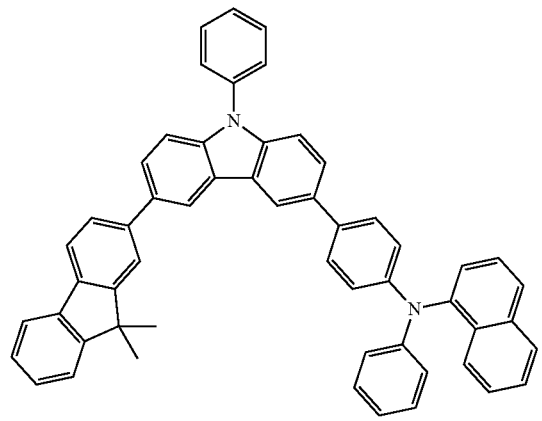
2-47
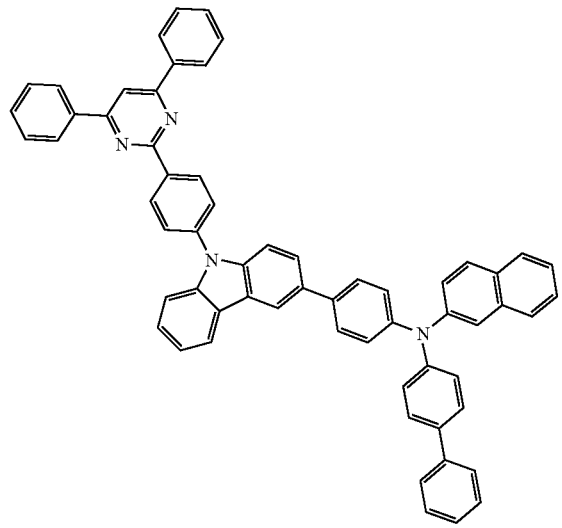
2-48
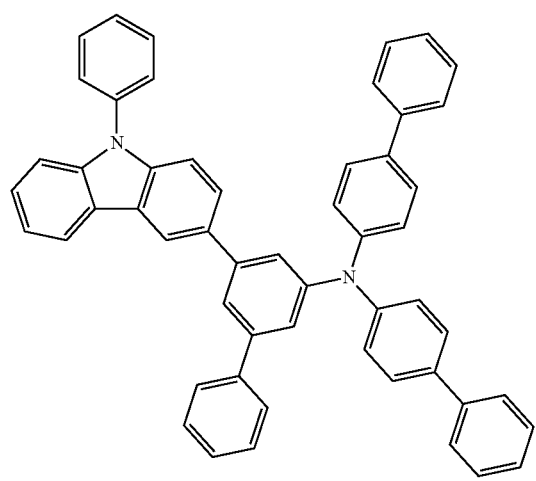
2-49
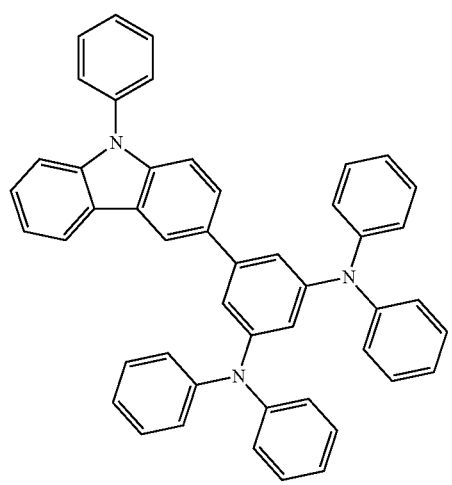

-continued
2-50
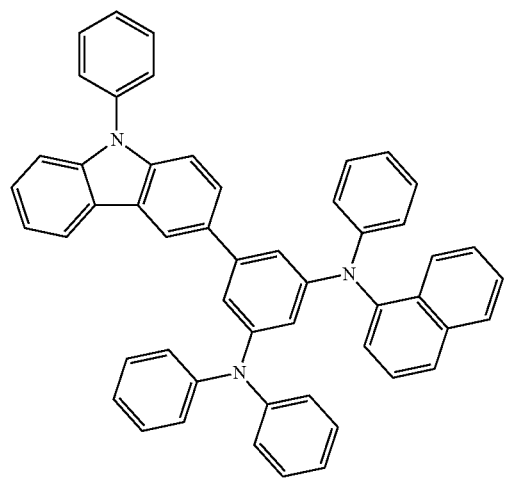
2-51
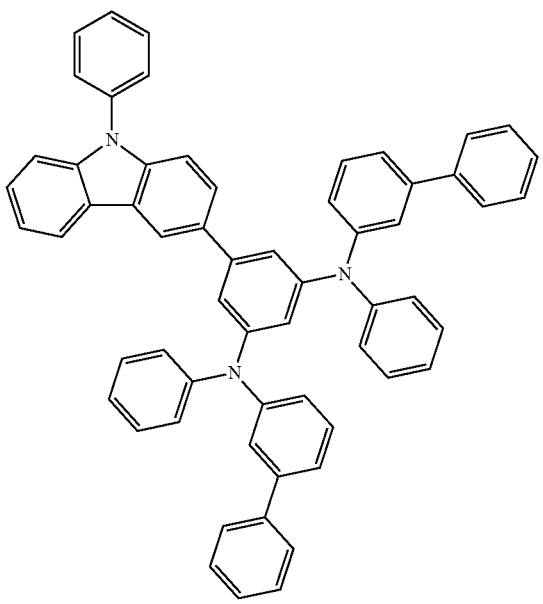
2-52
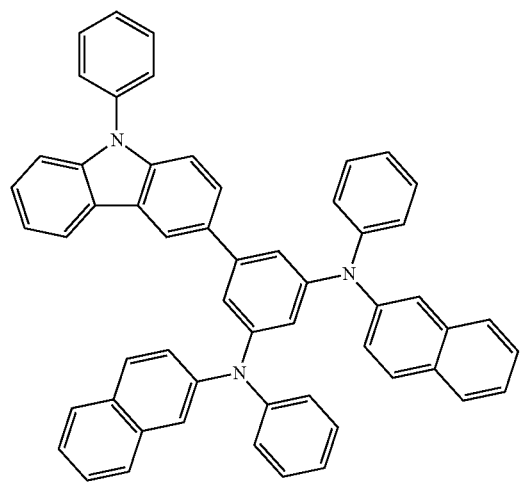
2-53
2-54
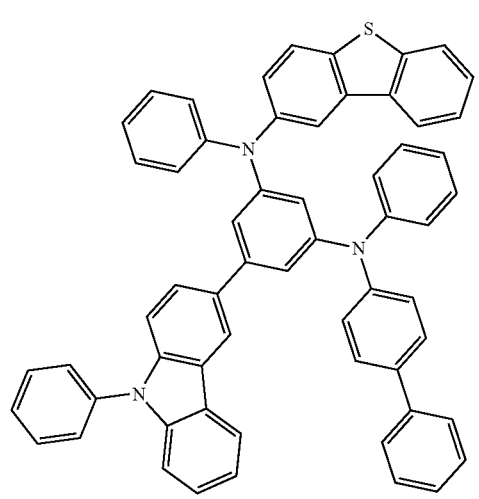
2-55
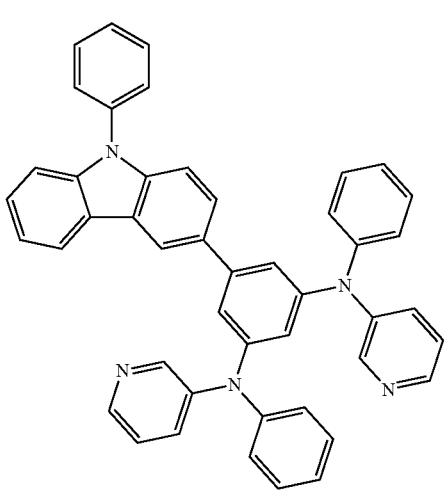

-continued
2-56
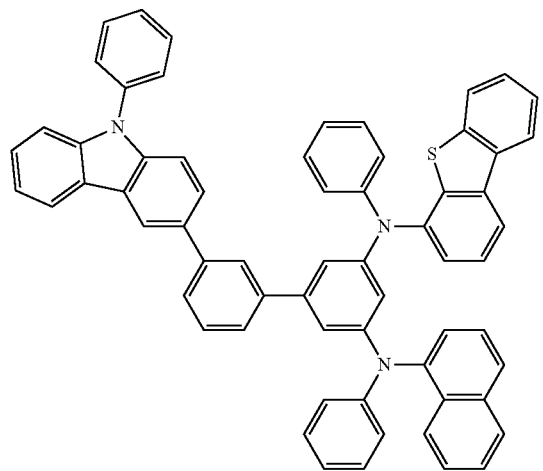
2-57
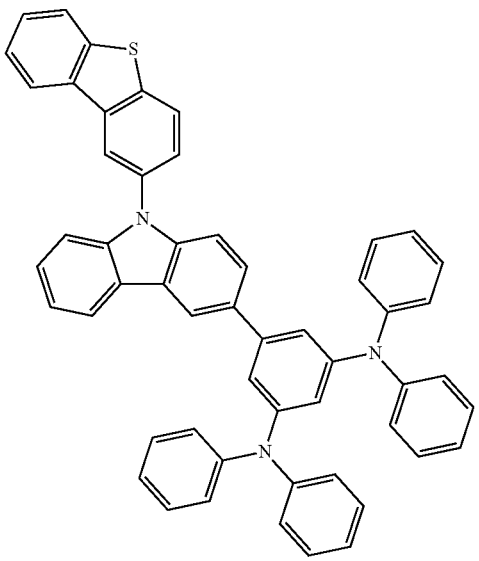
2-58
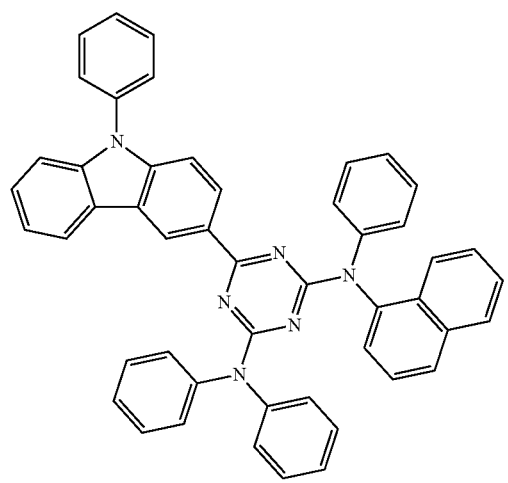
2-59
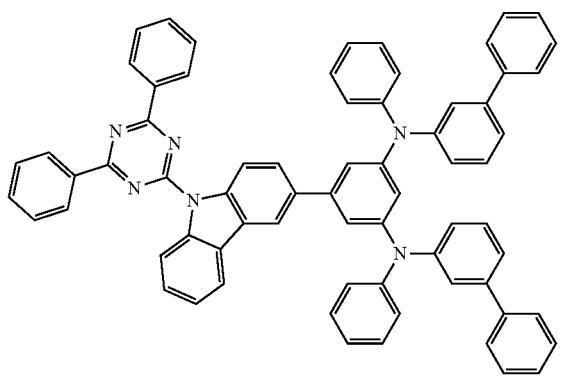
2-60
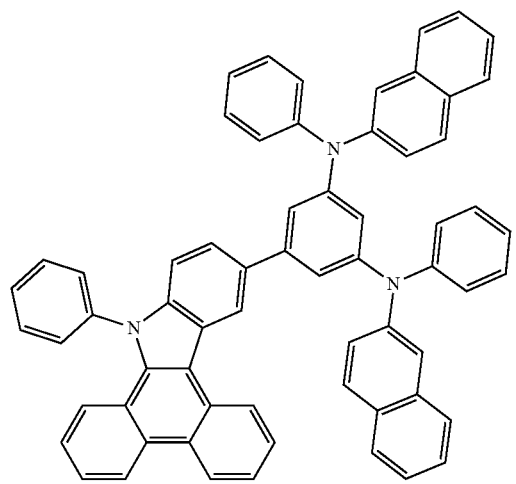
2-61
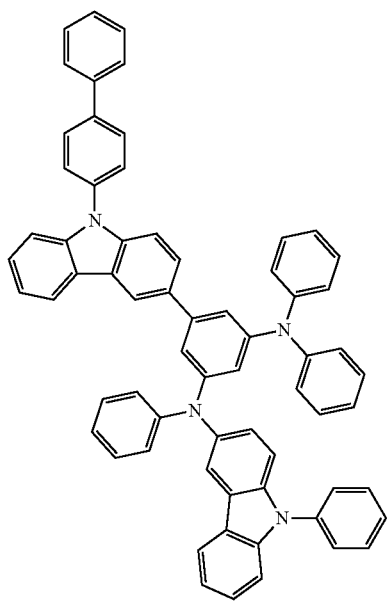

-continued
2-62
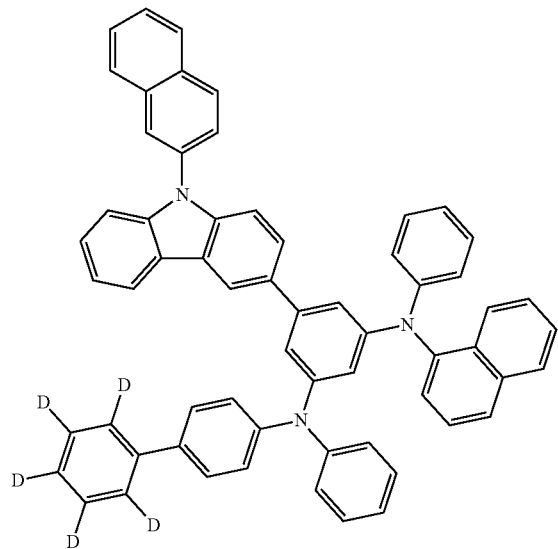
2-63
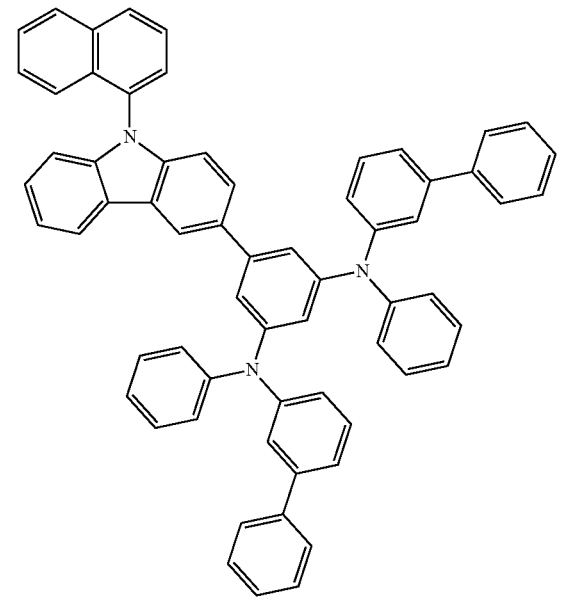
2-64
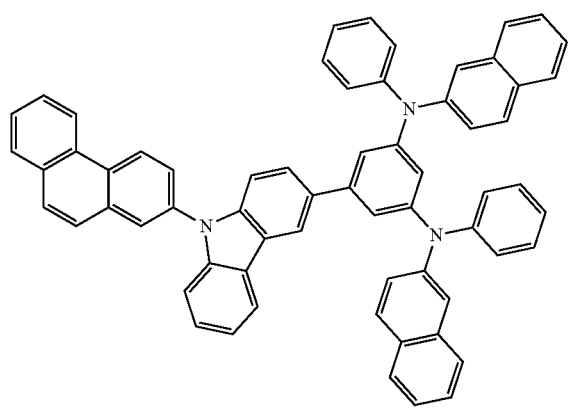
2-65
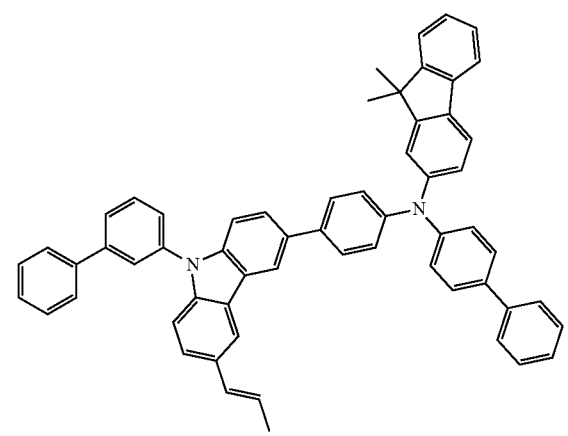
2-66
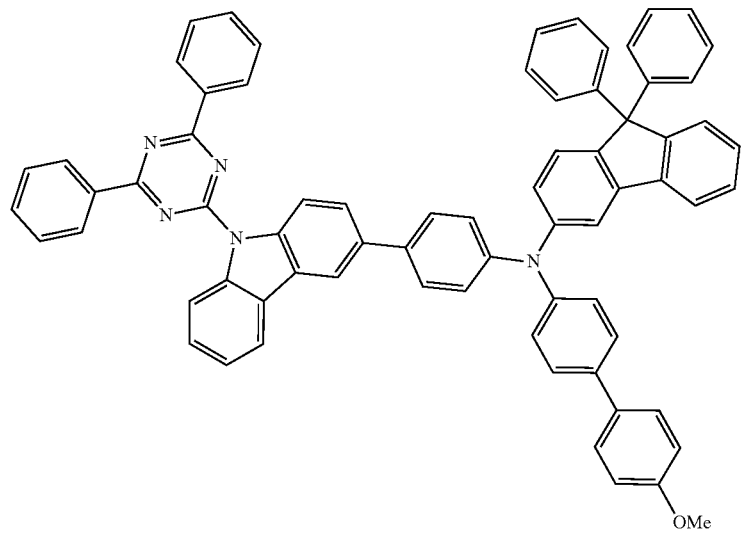

2-67
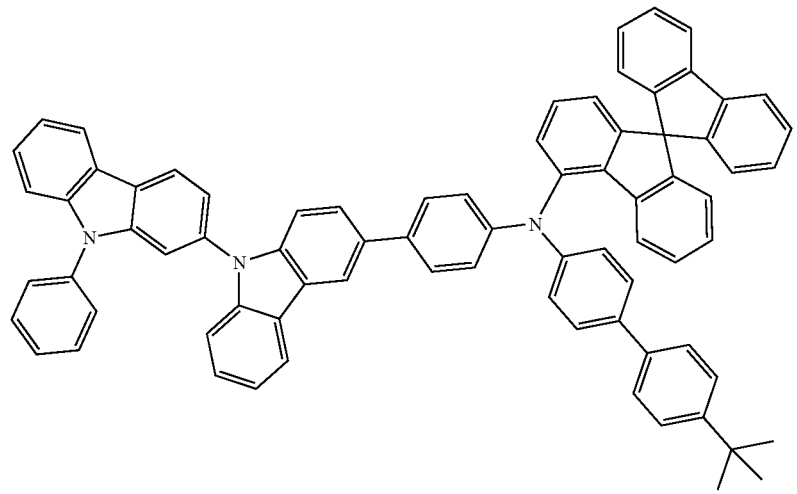
2-68
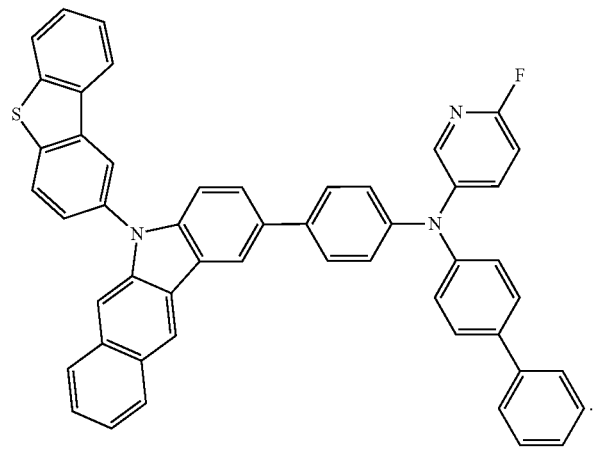
16. The organic electric element according to claim 1, wherein the second host compound represented by Formula 2 comprises one of the following Compounds 3-1 to 3-100:
3-1
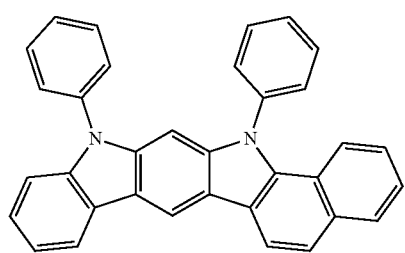
3-2
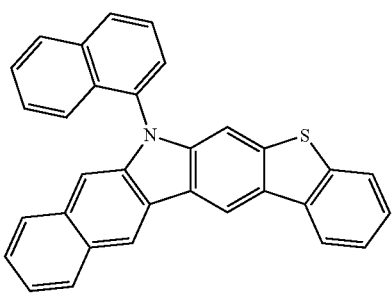

-continued
3-3
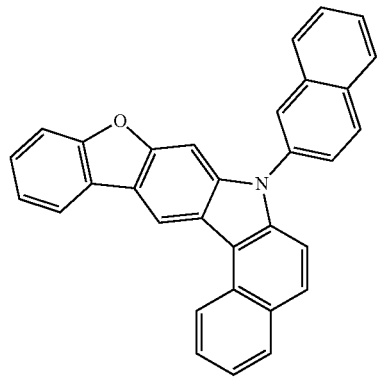
3-7
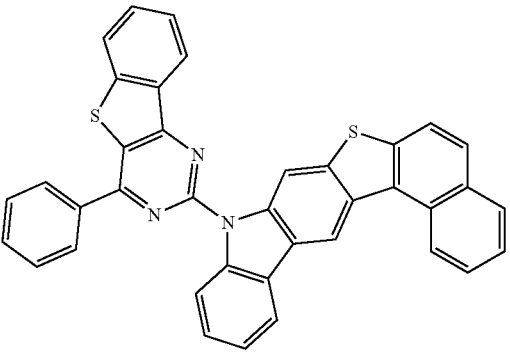
3-4
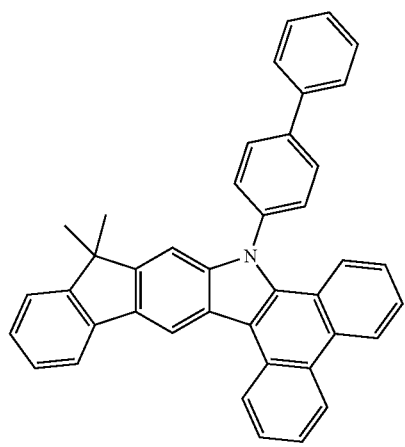
3-8
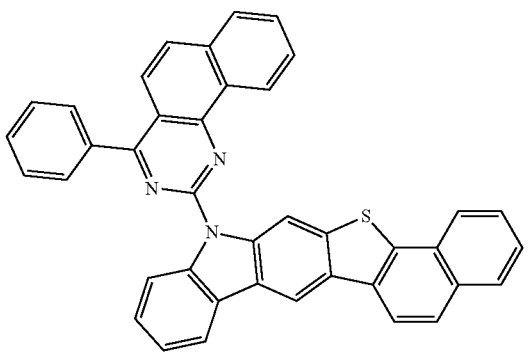
3-5
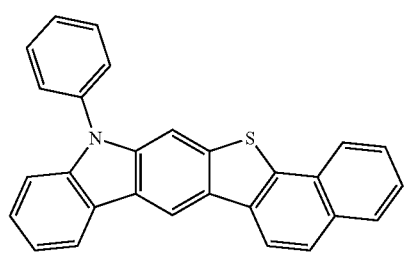
3-9
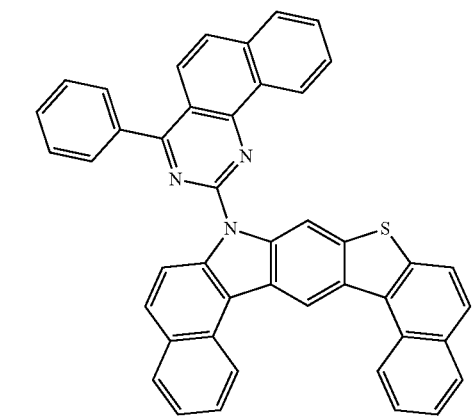
3-6
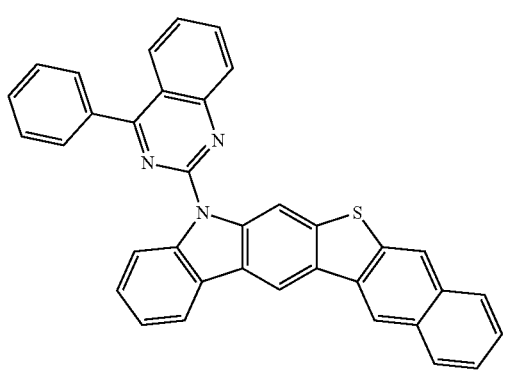
3-10
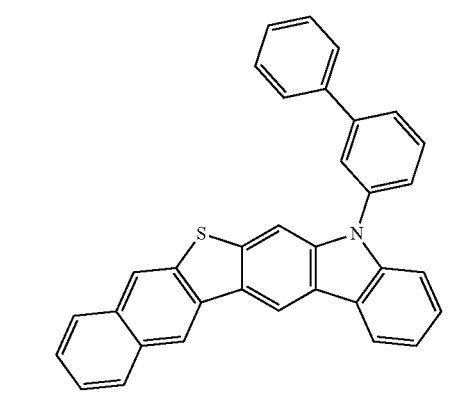

3-11
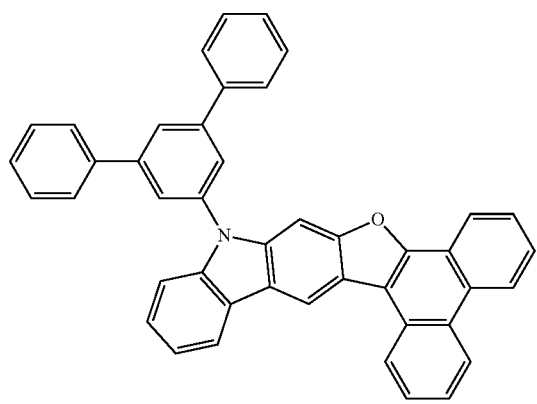
3-15
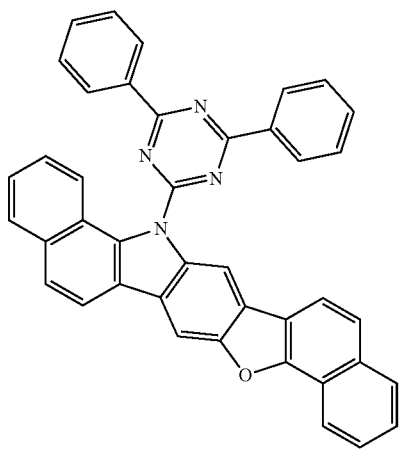
3-12
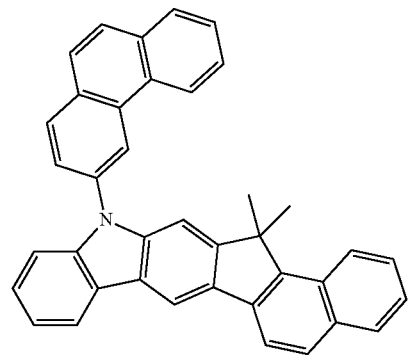
3-16
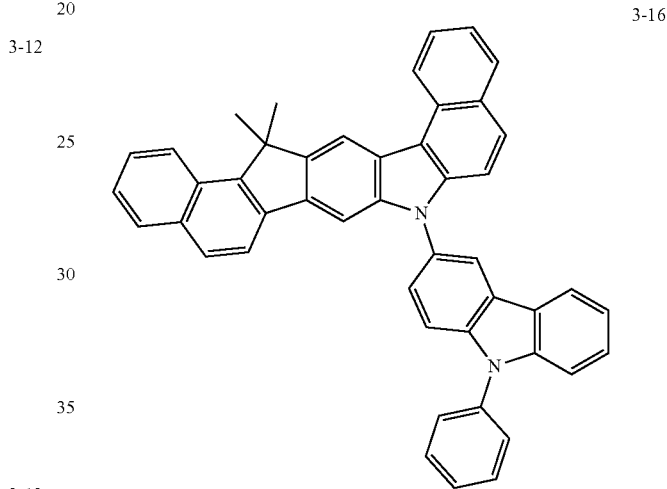
3-13
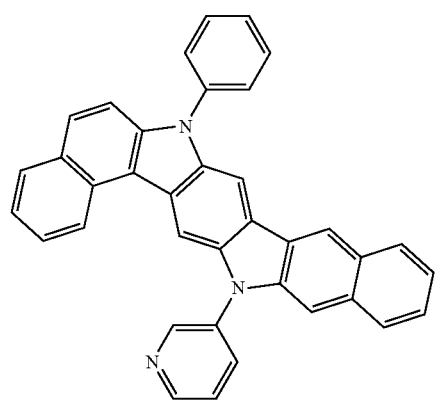
3-17
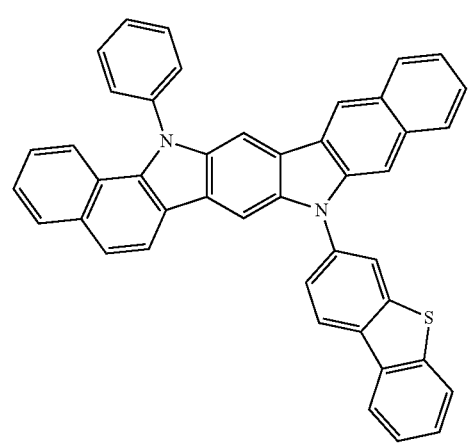
3-14
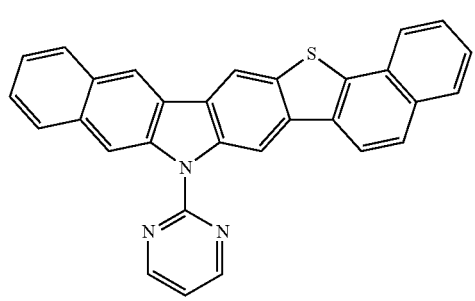
3-18
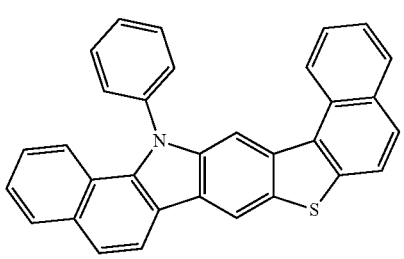

257
-continued
3-19
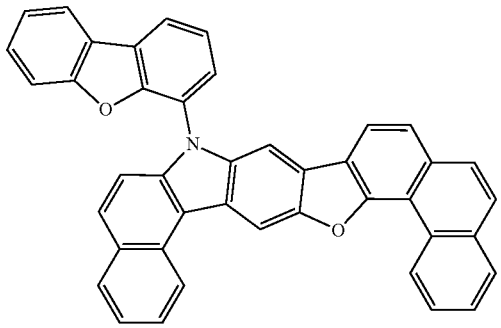
3-20
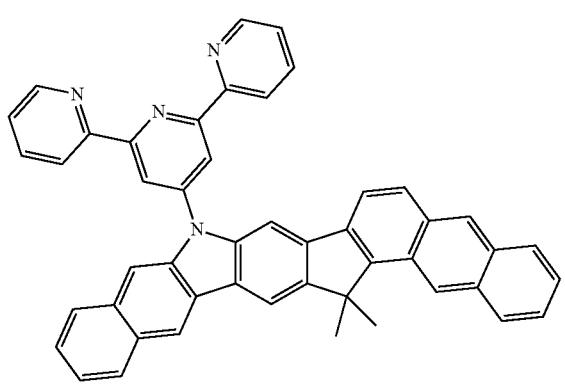
3-21
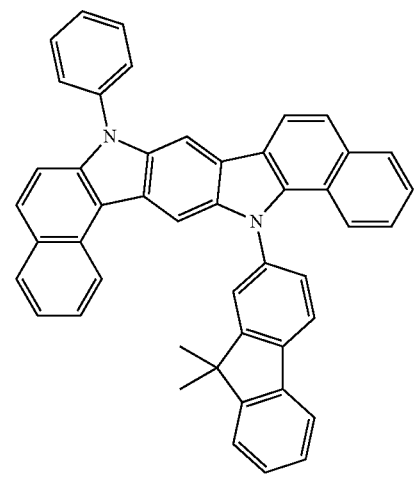
3-22
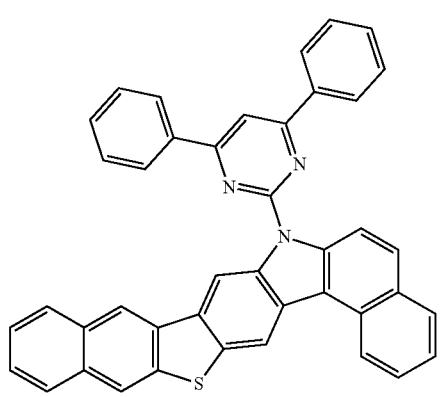
258
-continued
3-23
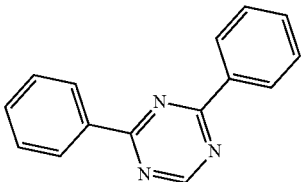
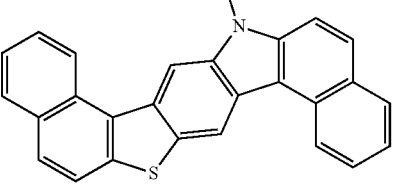
3-24
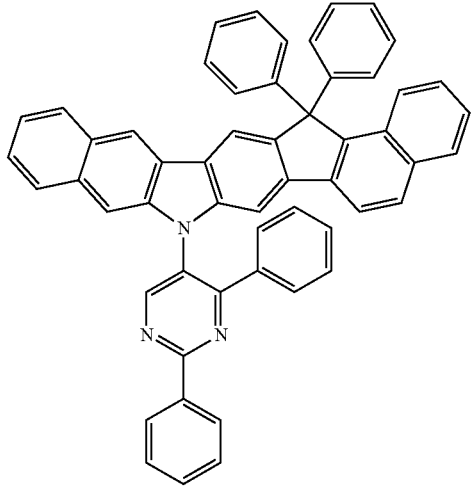
3-25
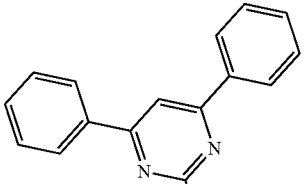
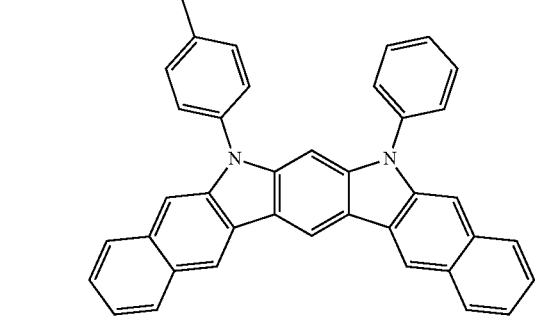

3-26
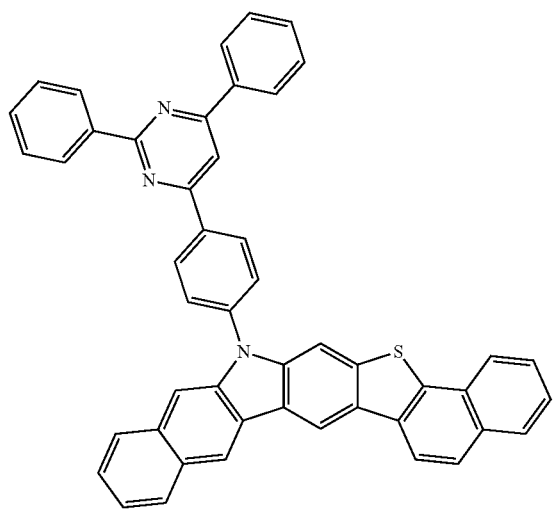
3-27
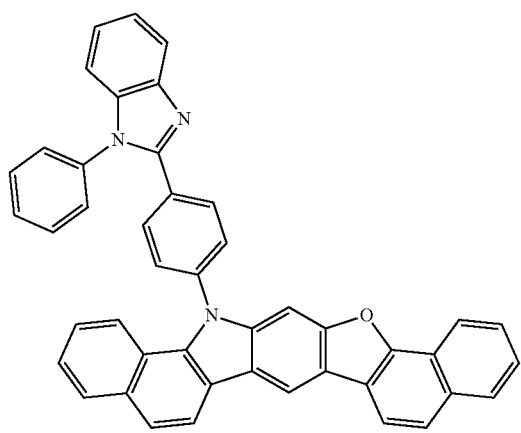
3-28
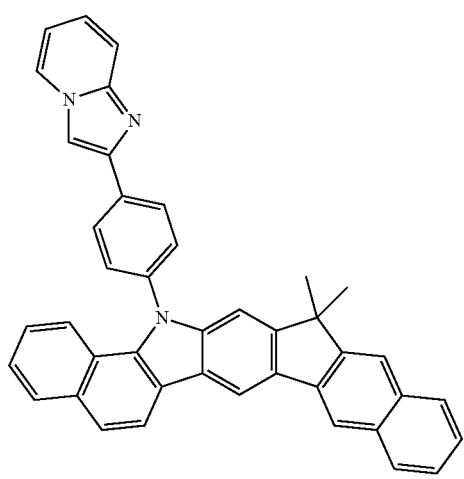
3-29
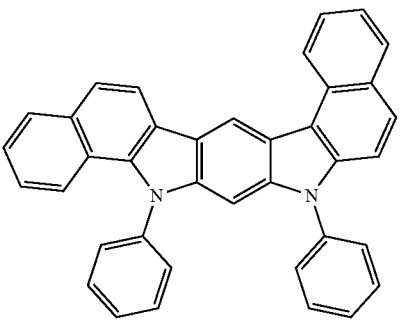
3-30
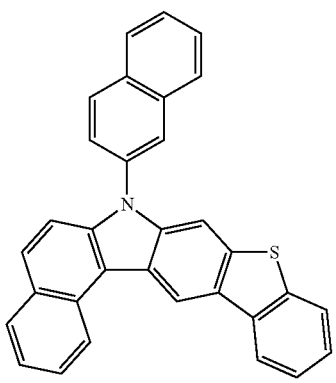
3-31
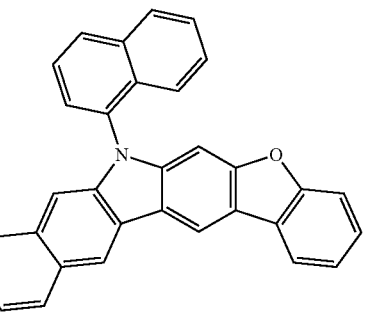
3-32
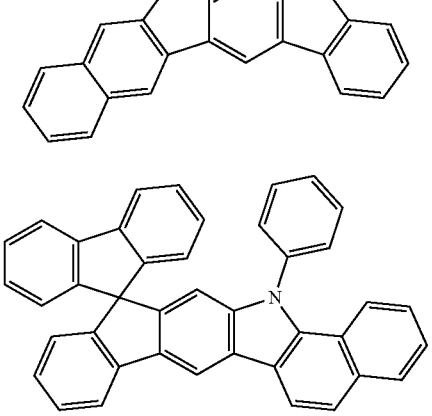
3-33
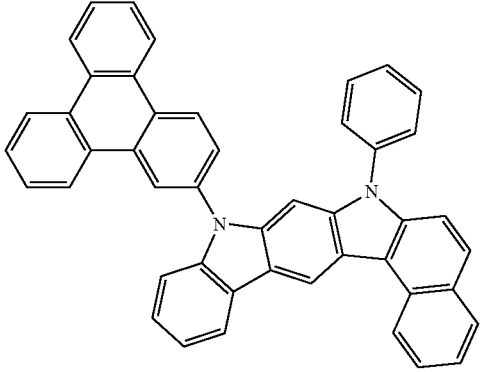

3-34
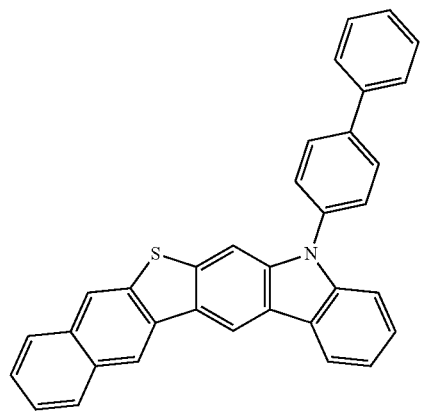
3-35
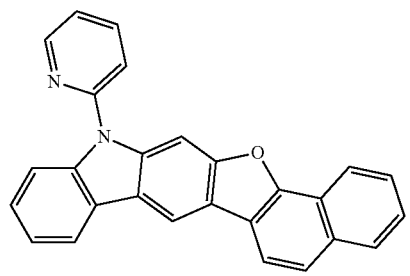
3-36
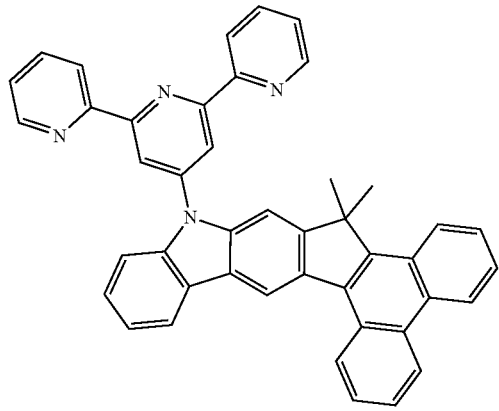
3-37
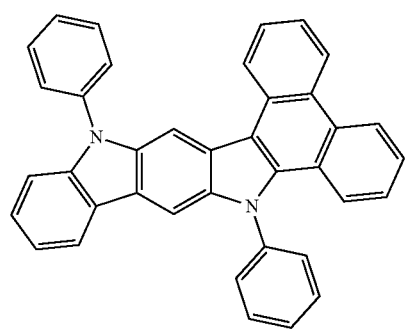
3-38
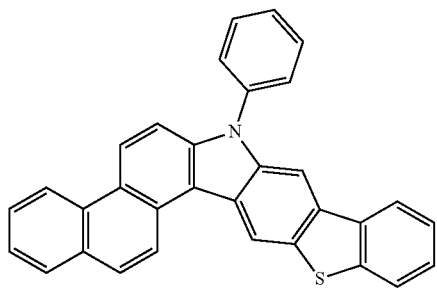
3-39
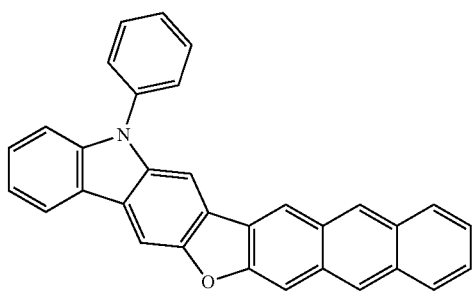
3-40
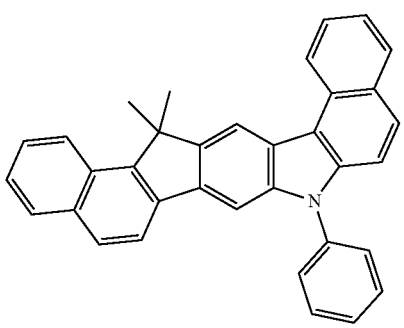
3-41
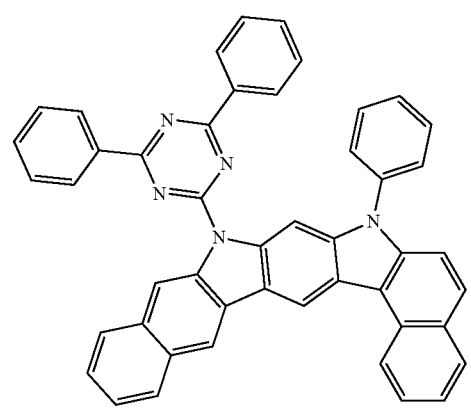

-continued
3-42
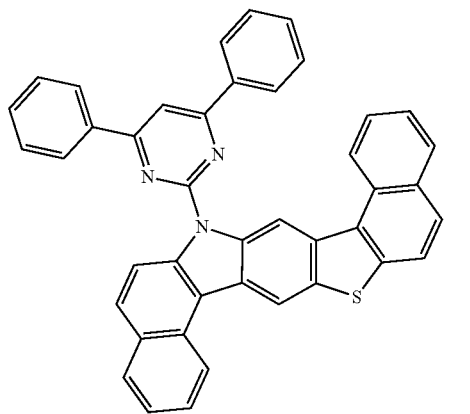
3-43
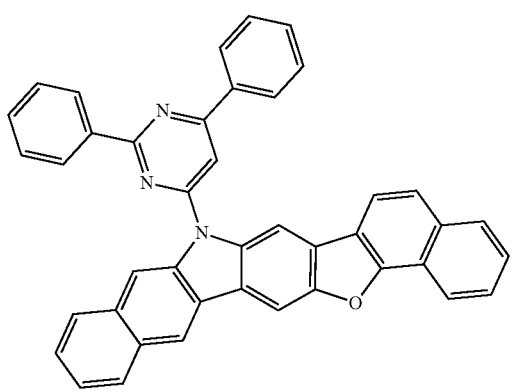
3-44
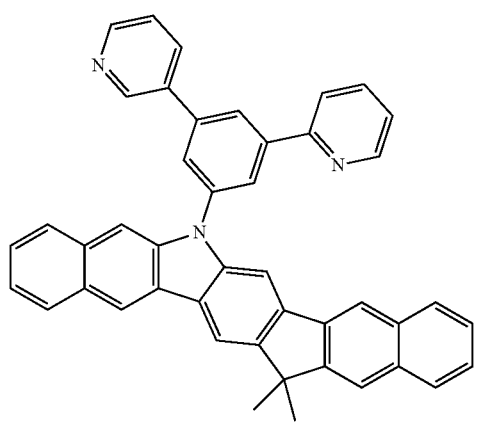
-continued
3-45
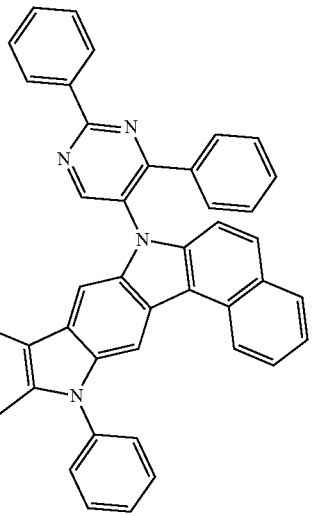
3-46
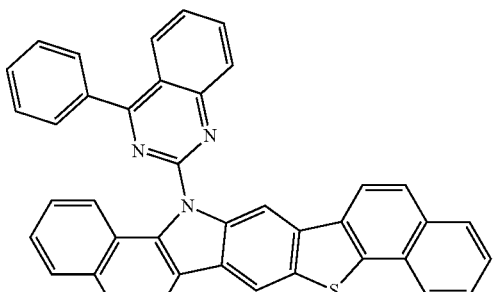
3-47
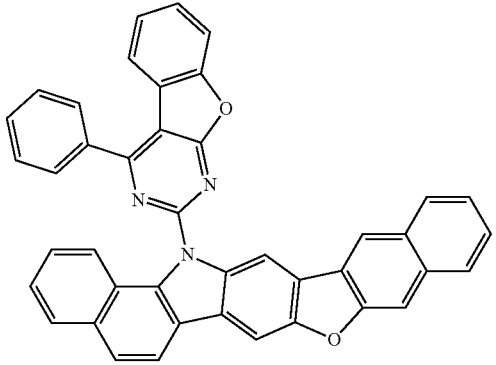
3-48
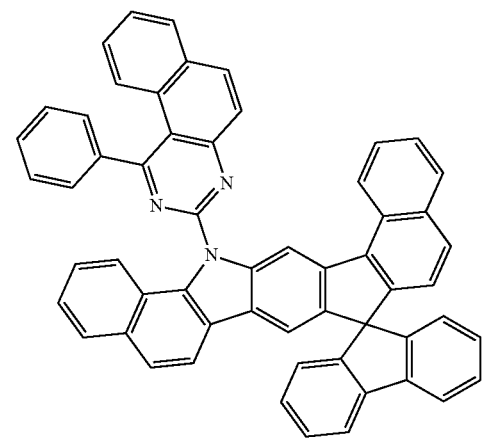

3-49
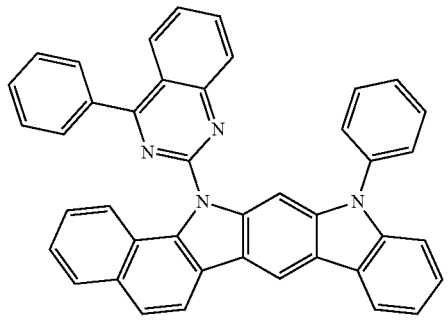
3-50
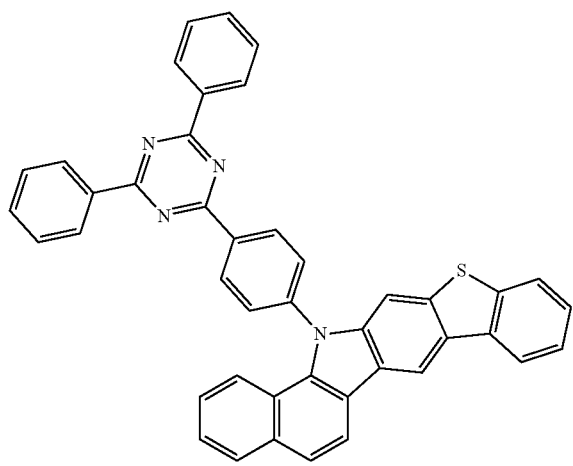
3-51
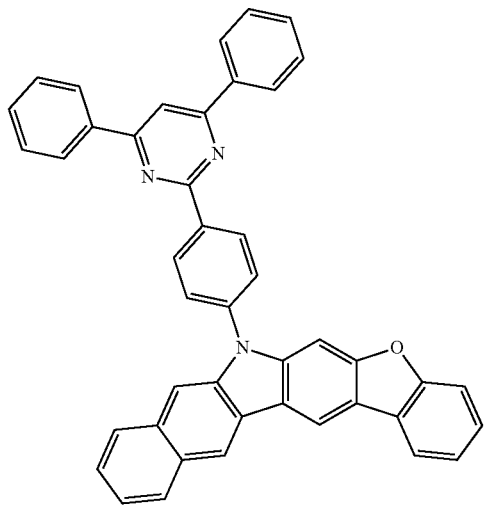
3-52
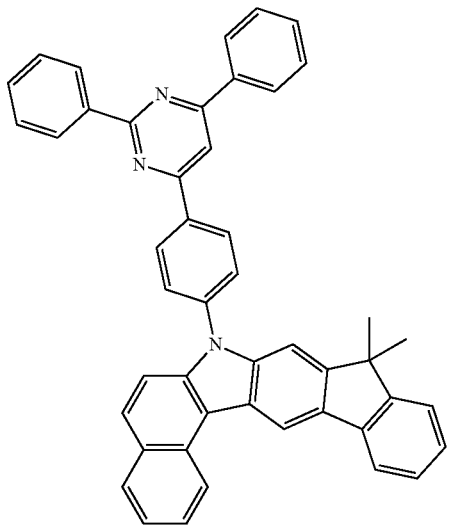
3-53
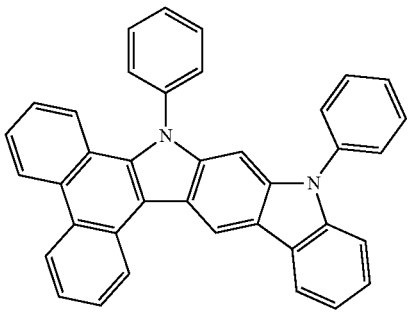
3-54
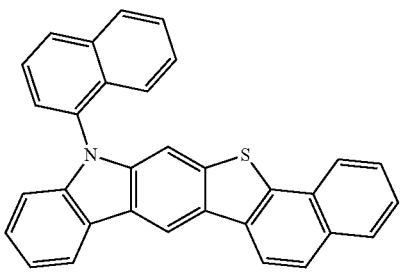
3-55
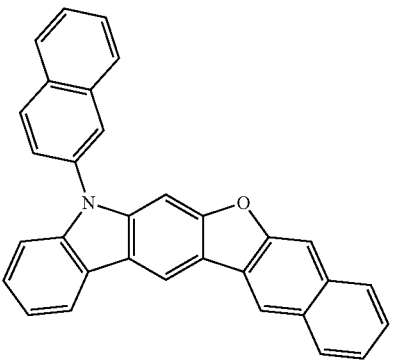

3-56
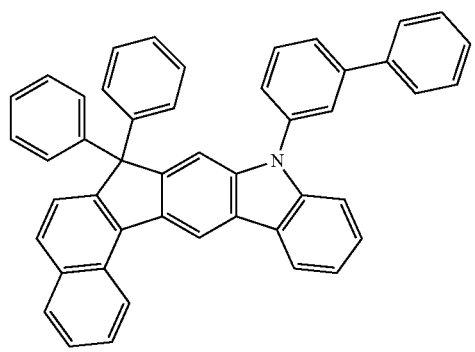
3-57
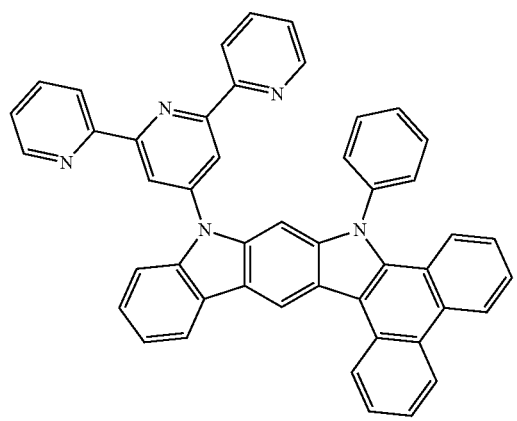
3-58
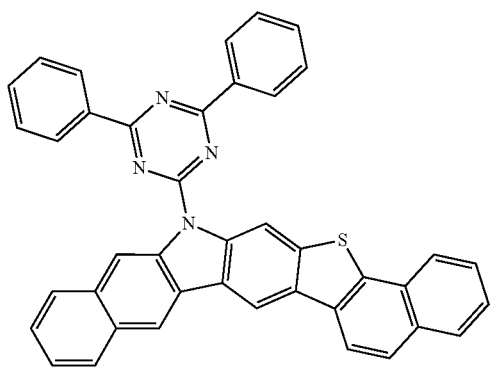
3-59
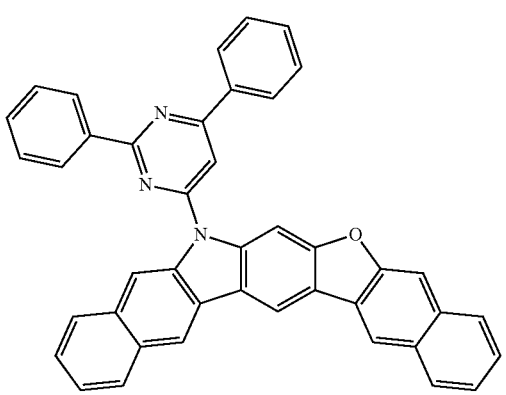
3-60
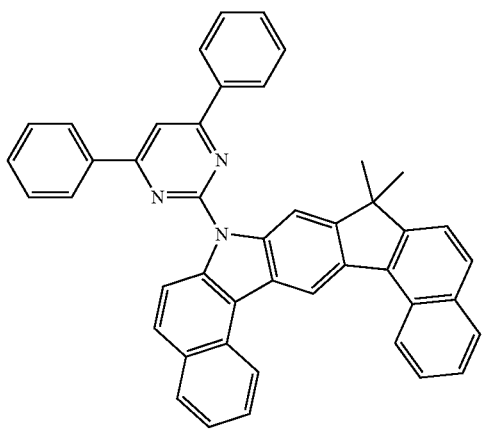
3-61
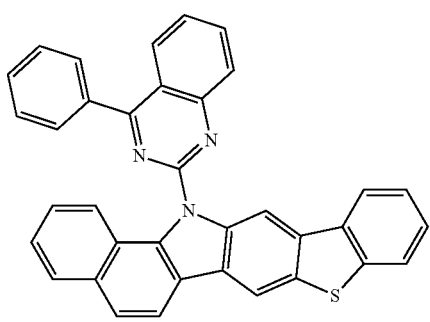
3-62
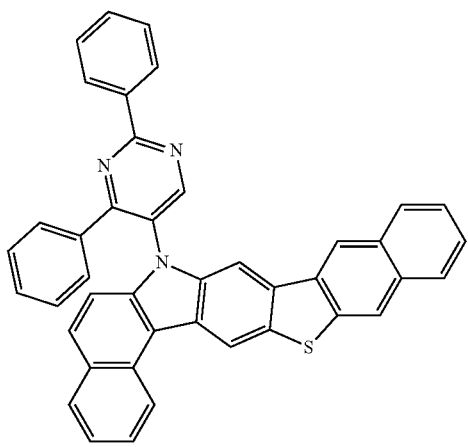
3-63
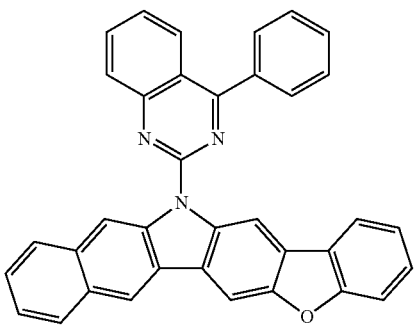

-continued
3-64
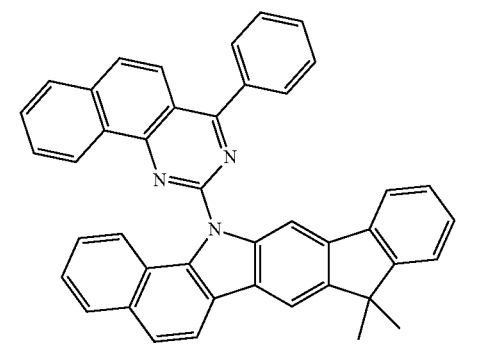
3-65
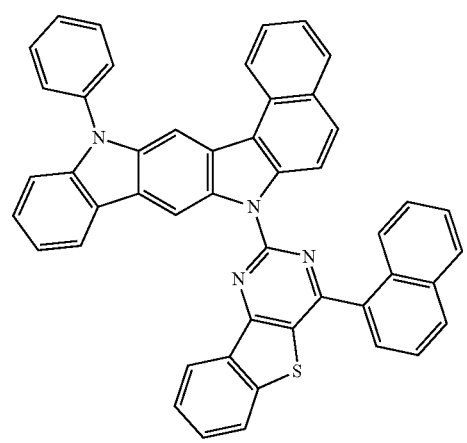
3-66
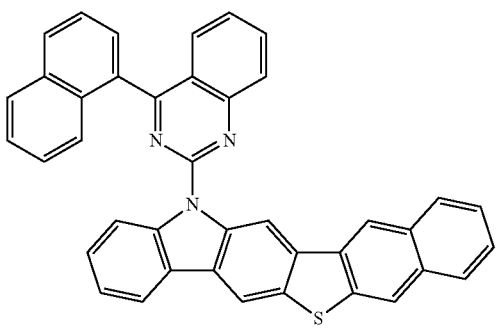
3-67
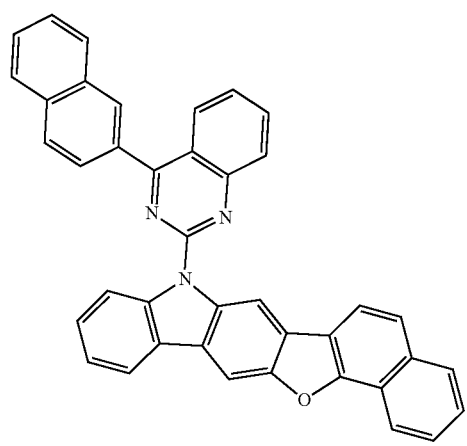
-continued
3-68
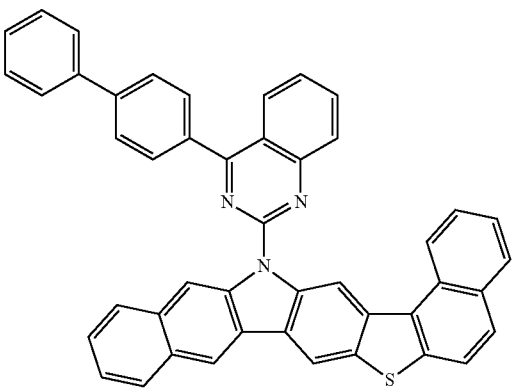
3-69
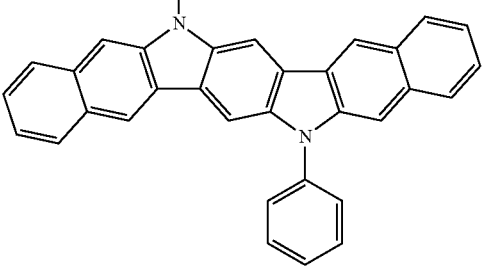
3-70
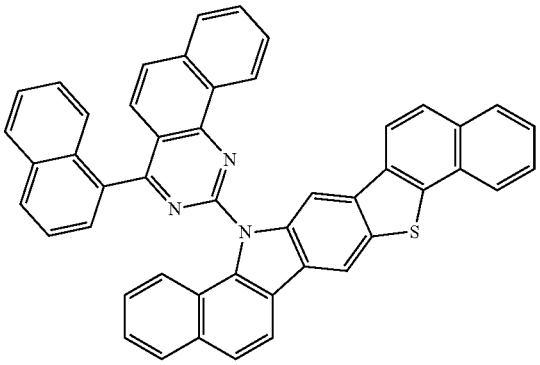

3-71
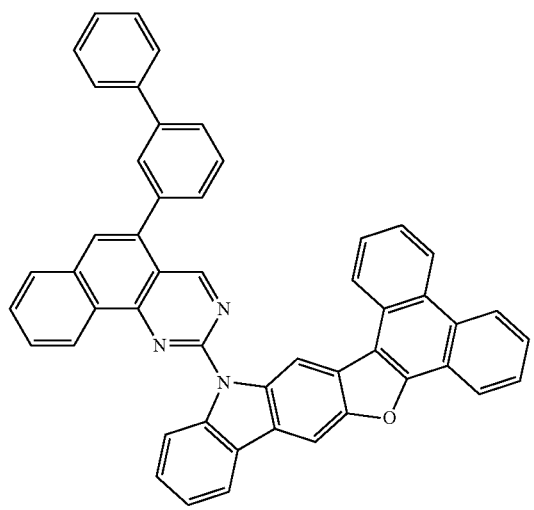
3-72
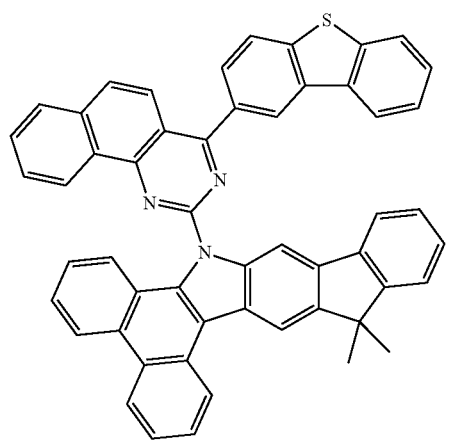
3-73
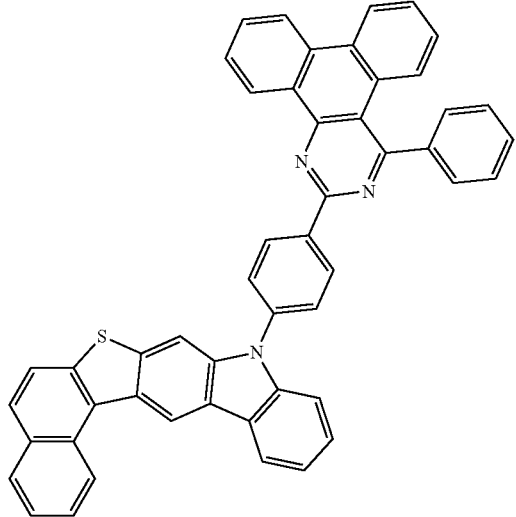
3-74
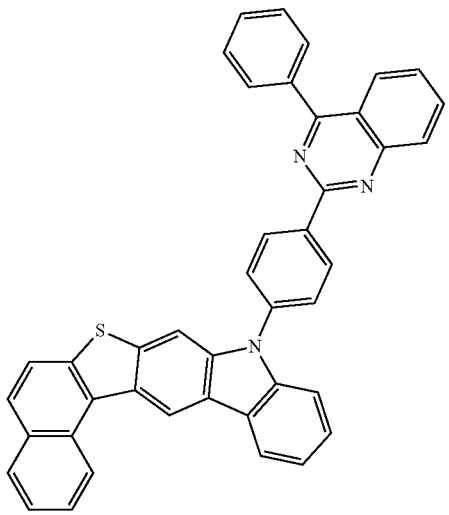
3-75
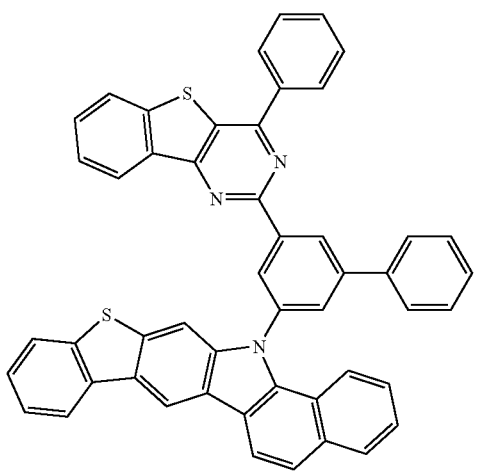
3-76
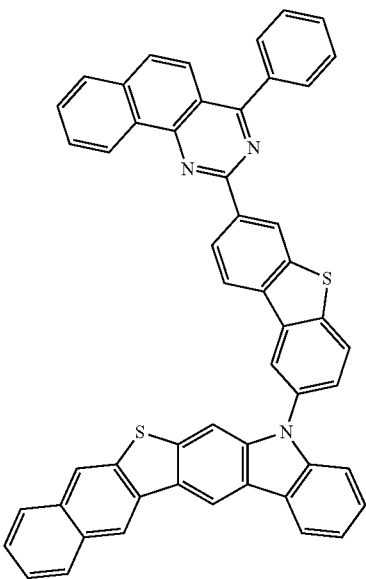

-continued
3-77
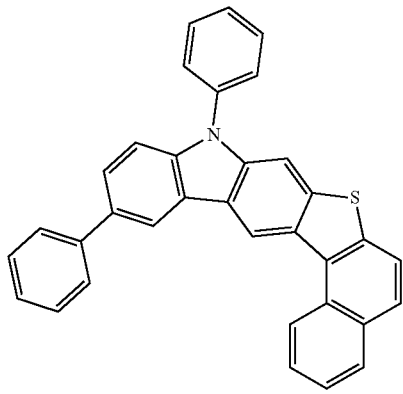
3-78
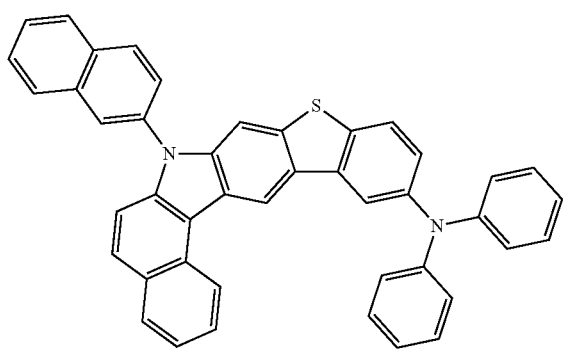
3-79
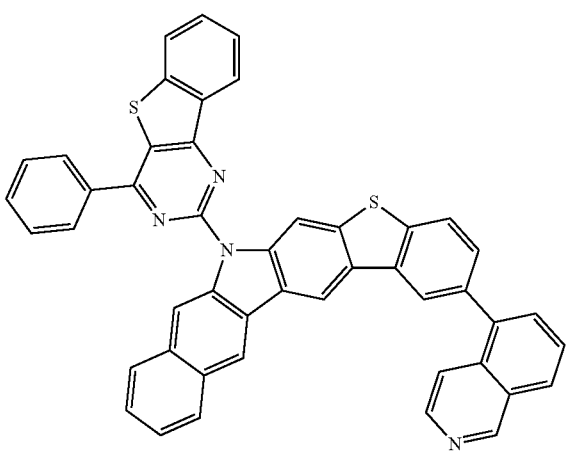
3-80
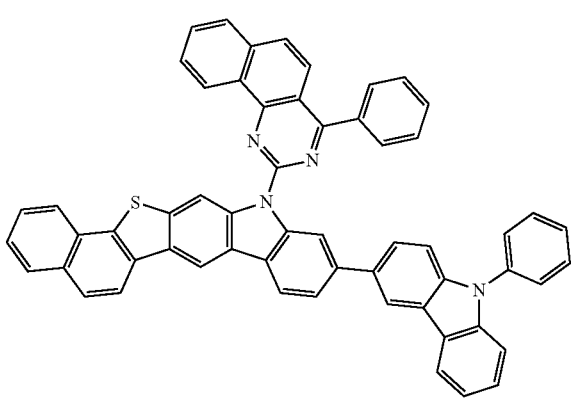
-continued
3-81
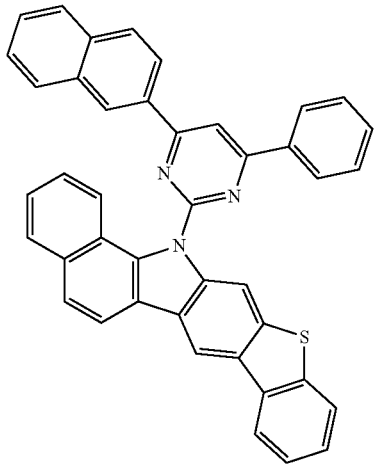
3-82
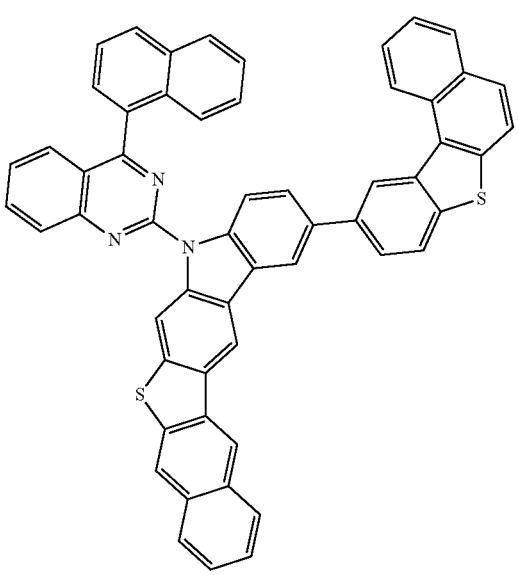
3-83
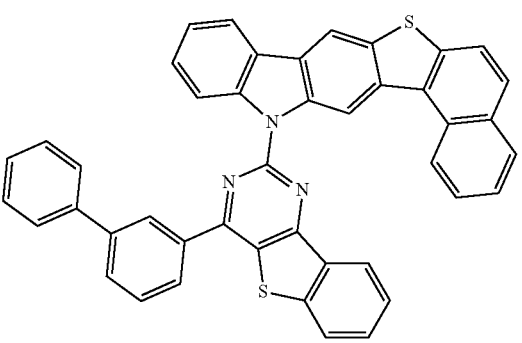

3-84
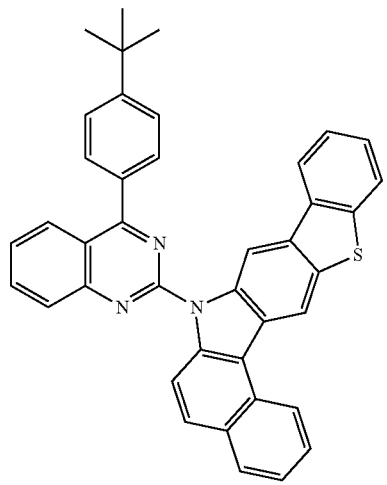
3-87
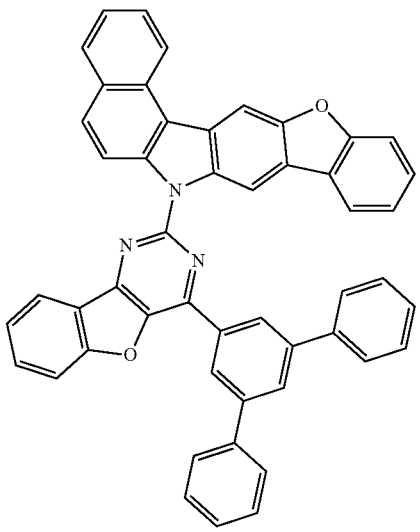
3-85
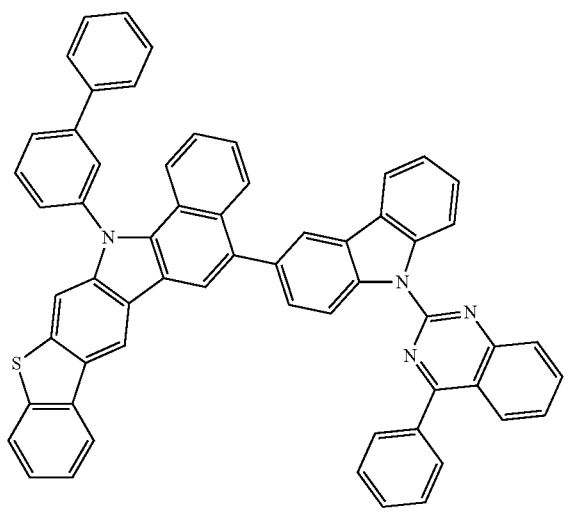
3-88
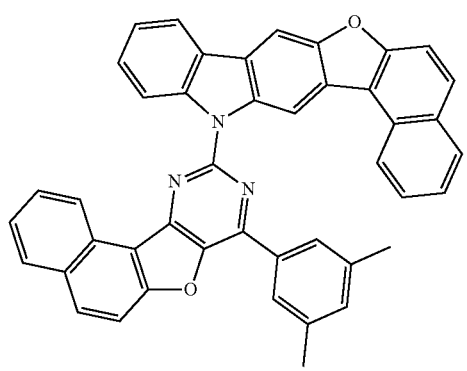
3-86
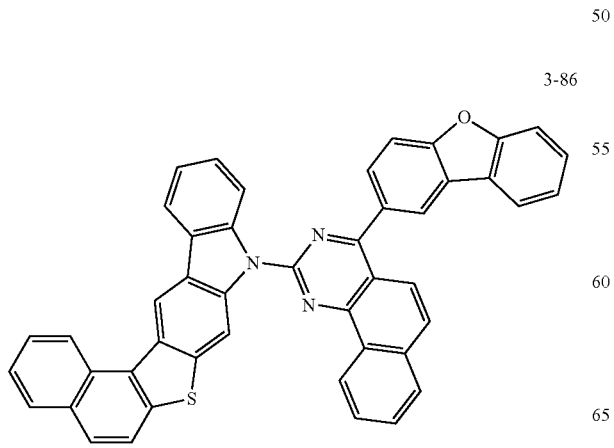
3-89
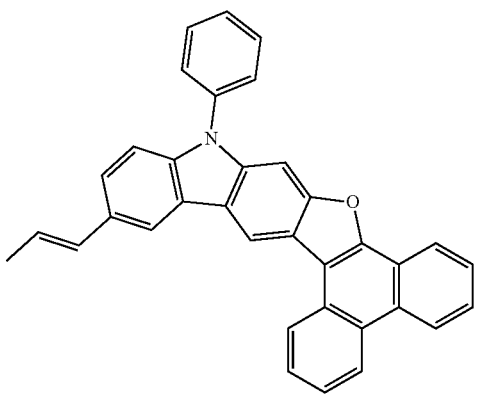

3-90
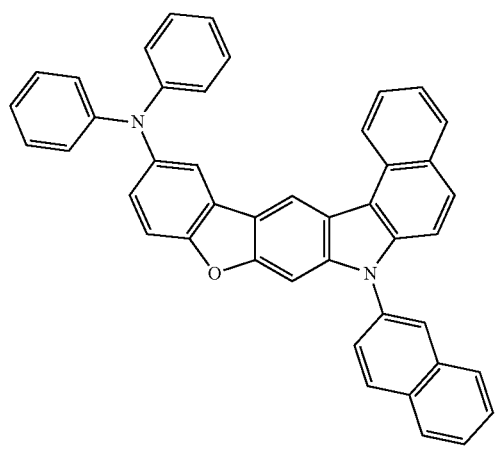
3-91
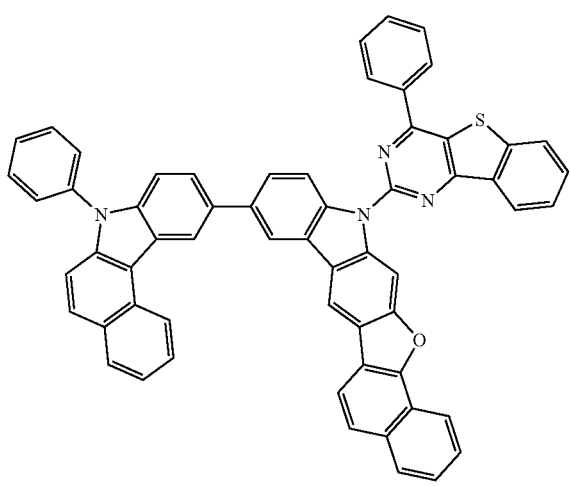
3-92
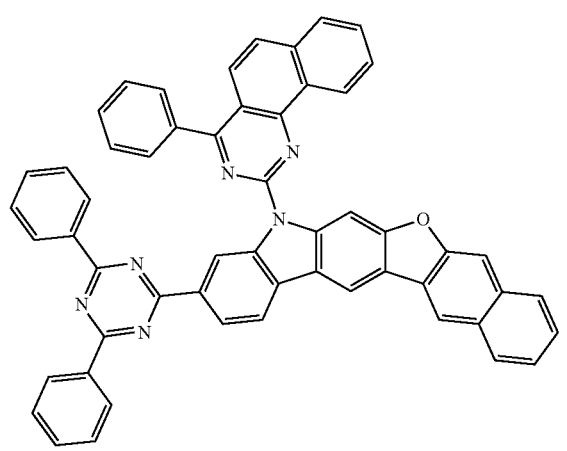
3-93
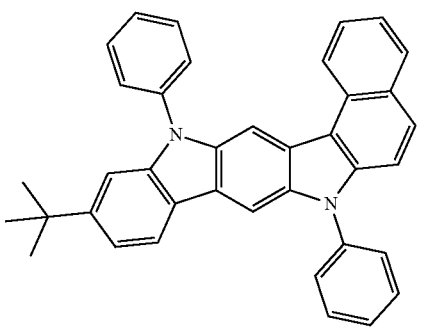
3-94
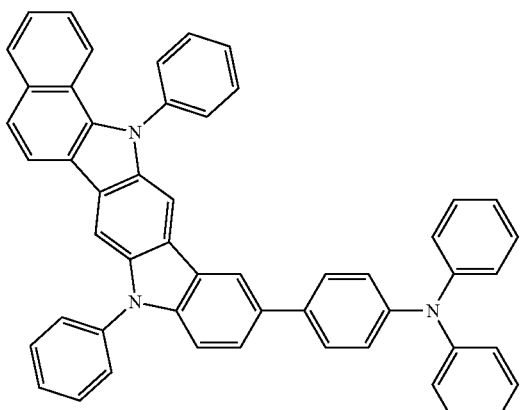
3-95
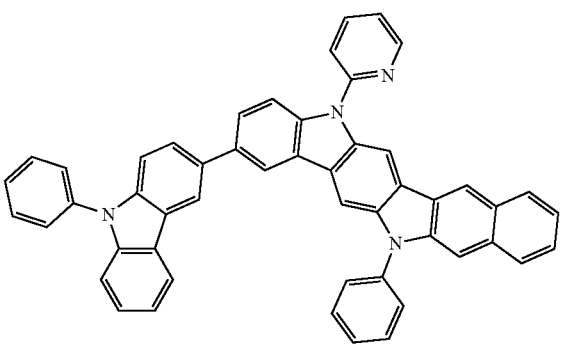
3-96
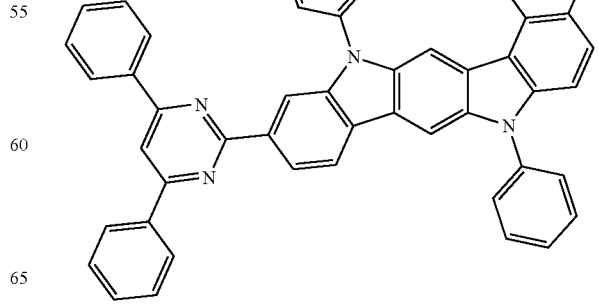

3-97

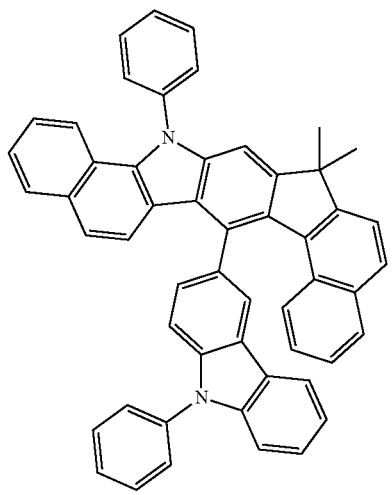

3-98

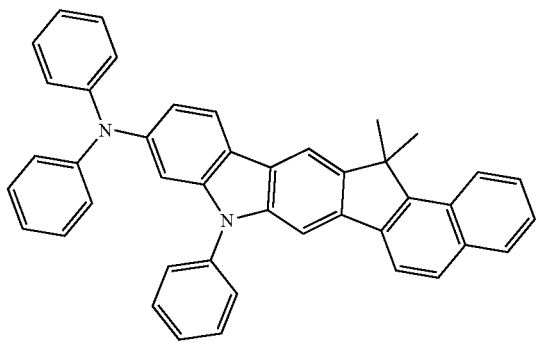

3-99

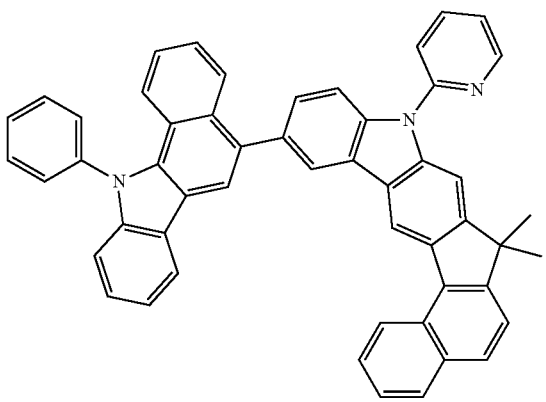

3-100

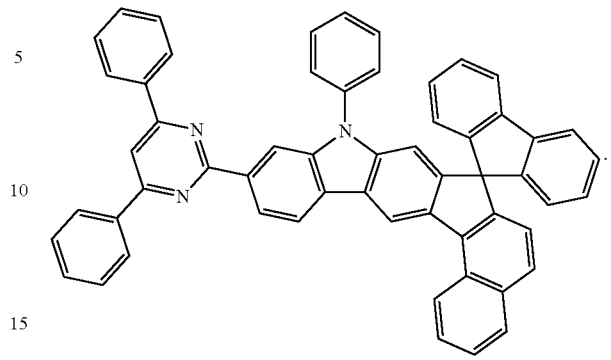

17. The organic electric element according to claim 1, wherein the emitting layer is a phosphorescent light emitting layer.

18. The organic electric element according to claim 1, wherein the compounds represented by Formula 1 and 2 are mixed in a ratio of 1:9 to 9:1 to be included in the emitting layer.

19. The organic electric element according to claim 1, wherein the compound represented by Formula 1 and 2 are mixed in a ratio of 1:9 to 5:5 to be included in the emitting layer.

20. The organic electric element according to claim 1, wherein he compound represented by Formula 1 and 2 are mixed in a ratio of 2:8 or 3:7 to be included in the emitting layer.

21. An electronic device comprising a display apparatus comprising the organic electric element according to claim 1; and a driving part configured to drive the display apparatus.

22. The electronic device according to claim 21, wherein the organic electric element is an OLED, an organic solar cell, an organic photo conductor, an organic transistor, or a device for monochromic or white illumination.

* * * * *